US011517629B2

(12) United States Patent
Luo et al.

(10) Patent No.: US 11,517,629 B2
(45) Date of Patent: Dec. 6, 2022

(54) METHODS OF TREATING CELLS CONTAINING FUSION GENES BY GENOMIC TARGETING

(71) Applicant: UNIVERSITY OF PITTSBURGH—OF THE COMMONWEALTH SYSTEM OF HIGHER EDUCATION, Pittsburgh, PA (US)

(72) Inventors: Jianhua Luo, Wexford, PA (US); Zhanghui Chen, Huzhou (CN); Yanping Yu, Wexford, PA (US); George Michalopoulos, Pittsburgh, PA (US); Joel B. Nelson, Pittsburgh, PA (US); Chien-Cheng Tseng, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 516 days.

(21) Appl. No.: 16/427,212

(22) Filed: May 30, 2019

(65) Prior Publication Data

US 2019/0282708 A1 Sep. 19, 2019

Related U.S. Application Data

(63) Continuation of application No. PCT/US2017/066207, filed on Dec. 13, 2017.

(60) Provisional application No. 62/572,960, filed on Oct. 16, 2017, provisional application No. 62/433,608, filed on Dec. 13, 2016.

(51) Int. Cl.
| | |
|---|---|
| *A61K 48/00* | (2006.01) |
| *A61P 35/00* | (2006.01) |
| *A61K 31/522* | (2006.01) |
| *A61K 31/7088* | (2006.01) |
| *A61K 38/46* | (2006.01) |
| *C12N 9/22* | (2006.01) |
| *C12N 15/11* | (2006.01) |
| *C12Q 1/6886* | (2018.01) |
| *C12N 15/90* | (2006.01) |

(52) U.S. Cl.
CPC .......... *A61K 48/005* (2013.01); *A61K 31/522* (2013.01); *A61K 31/7088* (2013.01); *A61K 38/465* (2013.01); *A61P 35/00* (2018.01); *C12N 9/22* (2013.01); *C12N 15/11* (2013.01); *C12N 15/90* (2013.01); *C12Q 1/6886* (2013.01); *A01K 2217/07* (2013.01); *A01K 2217/206* (2013.01); *A01K 2227/105* (2013.01); *A01K 2267/0331* (2013.01); *C12N 2310/20* (2017.05); *C12N 2750/14143* (2013.01); *C12N 2800/80* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 9,464,327 B1 | 10/2016 | Lo et al. |
| 2011/0027808 A1 | 2/2011 | Van Dongen |

FOREIGN PATENT DOCUMENTS

| | | | |
|---|---|---|---|
| WO | WO 2014/093701 A1 | 6/2014 | |
| WO | WO 2014/165825 A2 | 10/2014 | |
| WO | WO 2015/103057 A1 | 7/2015 | |
| WO | WO 2016/011428 A1 | 1/2016 | |

OTHER PUBLICATIONS

Zhou et al., "Cas12a variants designed for lower genome-wide off-target effect through stringent PAM recongition", Molecular Therapy vol. 30, No. 1, Jan. 2022 pp. 1-12 (2021) (Year: 2021).*
Wan et al.,"Material solutions for delivery of CRISPR/Cas-based genome editing tools: Current Status and future outlook", Materials Today vol. 26, pp. 40-66 Jun. 2019.*
Doudna, J., "The promise and challenge of therapeutic genome editing", Nature, vol. 578, pp. 229-236, Feb. 2020.*
Song et al.,"Delivery of CRISPR/Cas systems for cancer gene therapy and immunotherapy", Advanced Drug Delivery Reviews 168: 158-180 May 2020.*
Anderson et al., "A simple method for the rapid generation of recombinant adenovirus vectors," Gene Therapy 7:1034-1038 (2000).
Baker, "PTEN Enters the Nuclear Age," Cell 128:25-28 (2007).
Bernardino et al., "Characterization of Chromosome Changes in Two Human Prostatic Carcinoma Cell Lines (PC-3 and DU145) Using Chromosome Painting and Comparative Genomic Hybridization," Cancer Genetics Cytogenetics 96:123-128 (1997).
Chen et al., "Human Nopp140, Which Interacts with RNA Polymerase I: Implications for rRNA Gene Transcription and Nucleolar Structural Organization," Molecular and Cellular Biology 19(12):8536-8546 (1999).
Chen et al., "Targeting genomic rearrangements in tumor cells using Cas9-mediated insertion of a suicide gene," Nature Biotechnology 35(6):543-550 (2017).
Cloughesy et al., "Antitumor Activity of Rapamycin in a Phase I Trial for Patients with Recurrent PTEN-Deficient Glioblastoma," PLoS Medicine 5(1):e8 (2008) 13 pages.

(Continued)

*Primary Examiner* — Anand U Desai
(74) *Attorney, Agent, or Firm* — Baker Botts L.L.P.

(57) ABSTRACT

The present invention relates to methods for treating patients having cancer or a premalignant or neoplastic condition. It is based, at least in part, on the discovery that a genome editing technique that specifically targets a fusion gene can induce cell death in a cancer cell other than a prostate cancer cell, e.g., a hepatocellular cancer cell, having the fusion gene. The present invention provides methods for treating cancer patients that include performing a genome editing technique targeting a fusion gene present within one or more cells of a subject to produce an anti-cancer effect.

15 Claims, 67 Drawing Sheets

Figure 1:
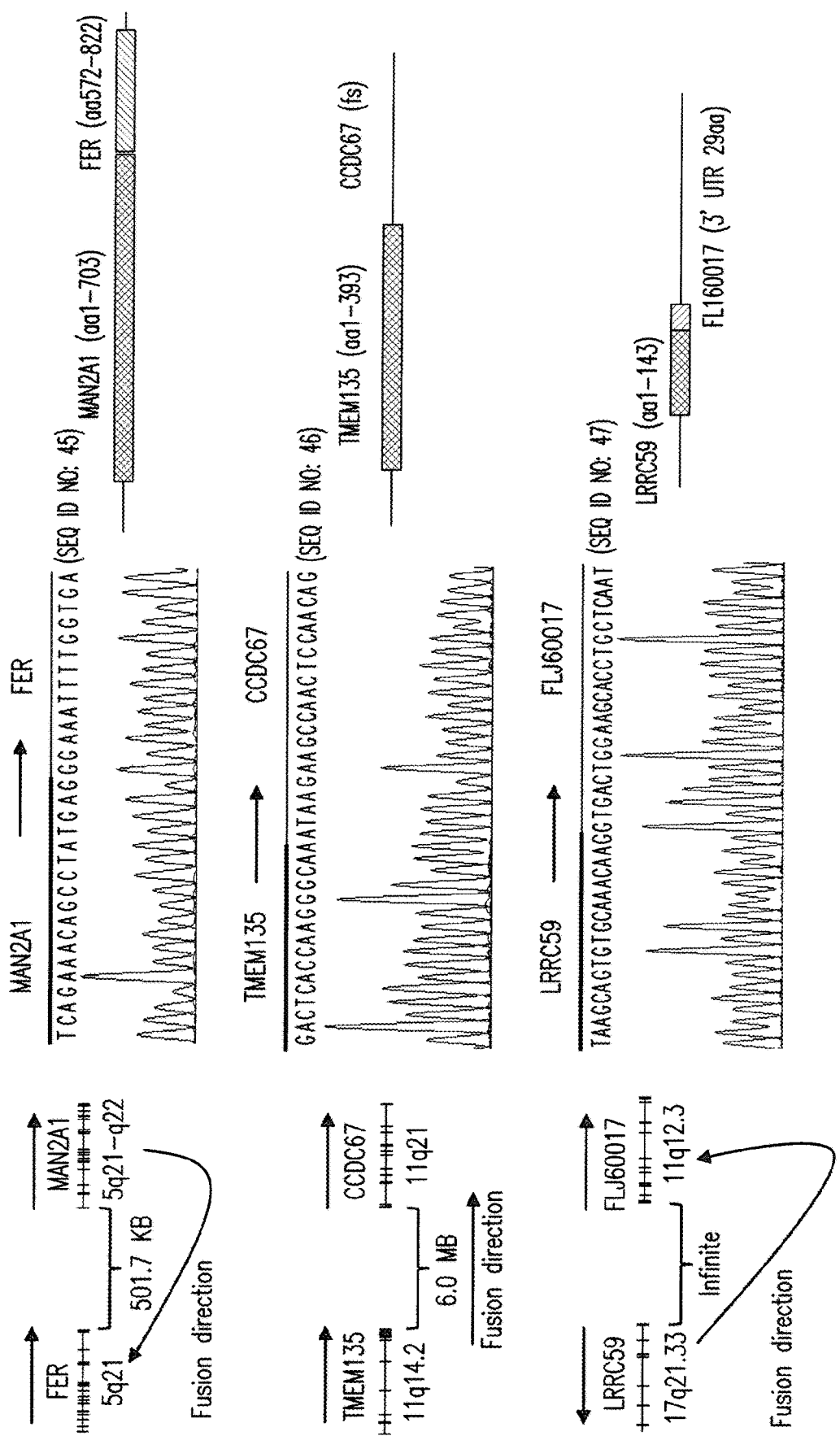
Figure 1:
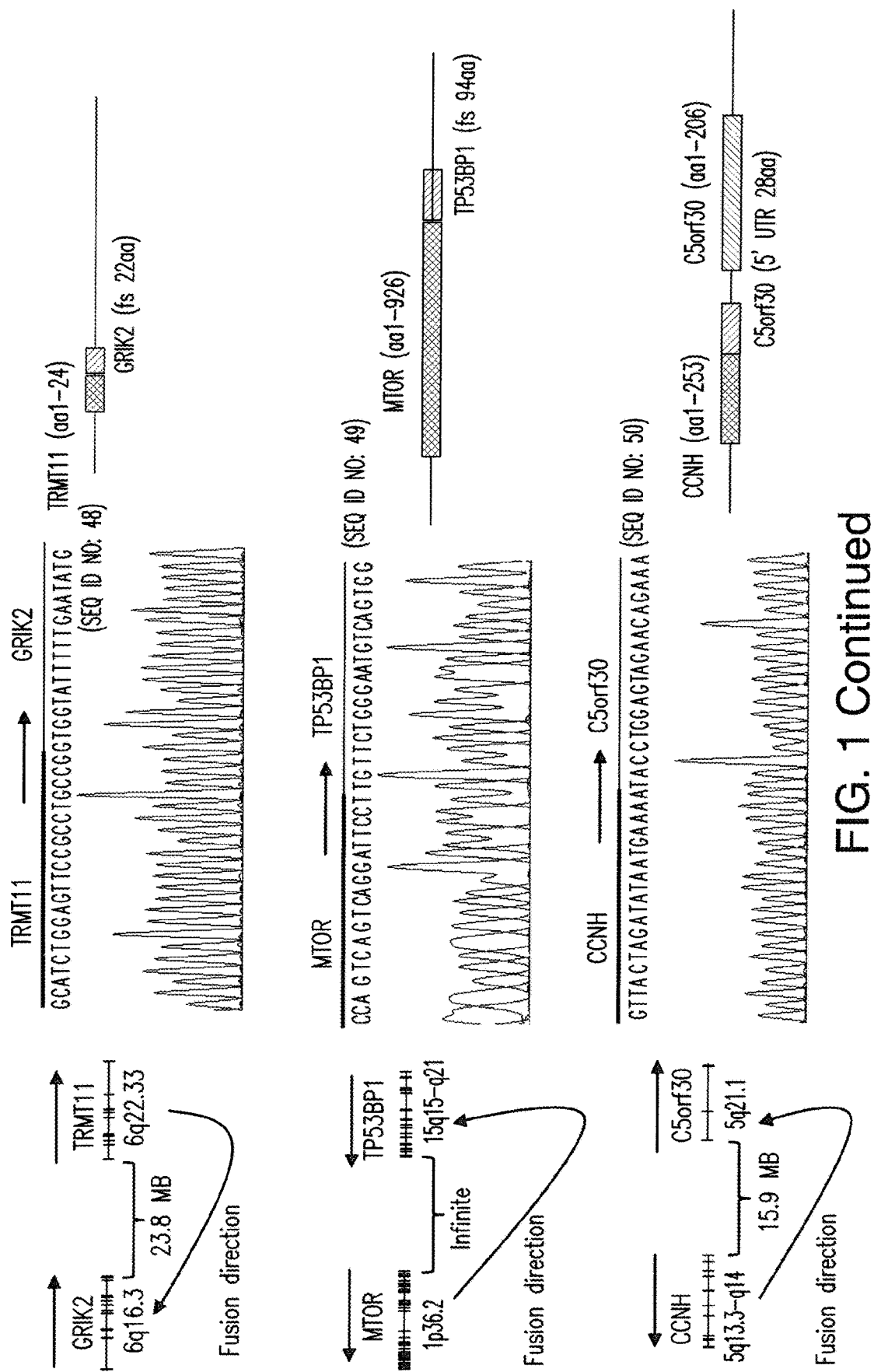
Figure 1:
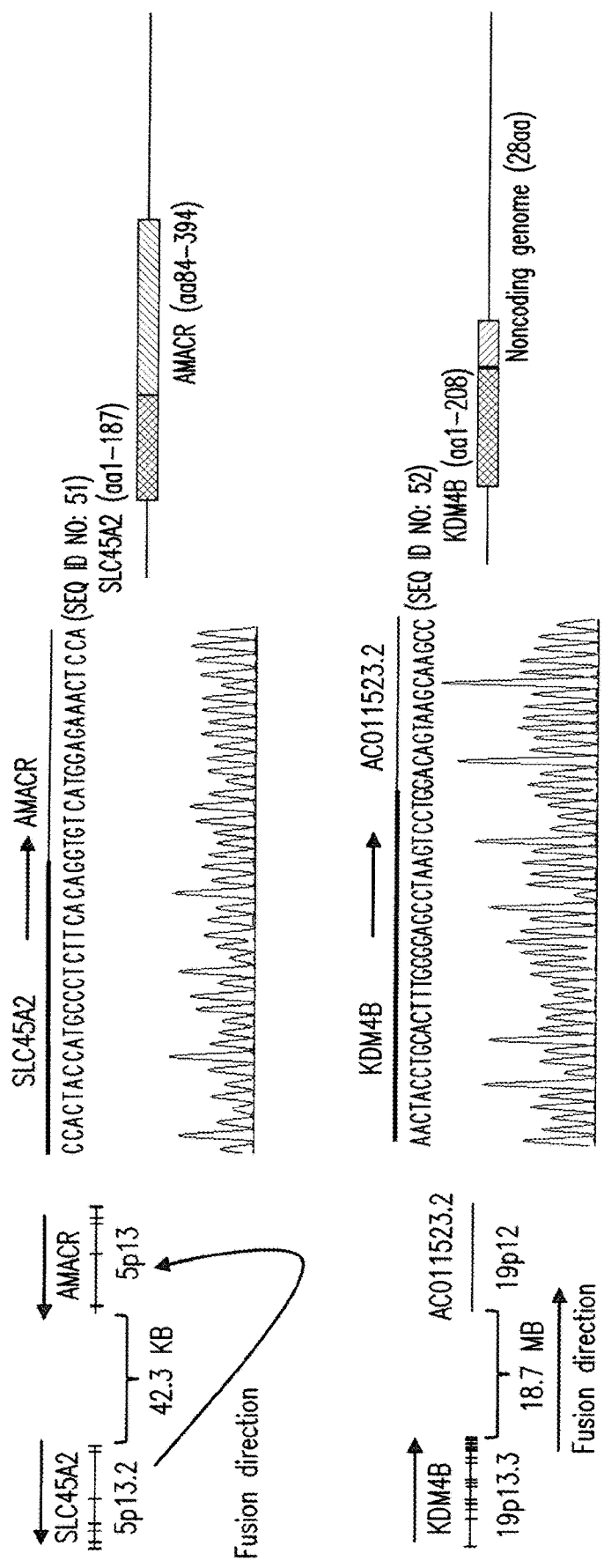

Specification includes a Sequence Listing.

(56) References Cited

OTHER PUBLICATIONS

Cong et al., "Multiplex Genome Engineering Using CRISPR/Cas Systems," Science 339(6121):819-823 (2013).
Courtney et al., "The PI3K Pathway as Drug Target in Human Cancer," J Clin Oncol 28:1075-1083 (2010).
Demetris et al., "Ductular Reaction after Submassive Necrosis in Humans. Special Emphasis on Analysis of Ductular Hepatocytes," The American Journal of Pathology 149(2):439-448 (1996).
Edgren et al., "Identification of fusion genes in breast cancer by paired-end RNA-sequencing," Genome Biol 12:R6 (2011).
Esvelt et al., "Concerning RNA-guided gene drives for the alteration of wild populations," eLife 3:e03401 (2014).
Gasiunas et al., "Cas9—crRNA ribonucleoprotein complex mediates specific DNA cleavage for adaptive immunity in bacteria," PNAS 109:E2579-E2586 (2012).
Han et al., "Fluorescence in situ hybridization study shows association of PTEN deletion with ERG rearrangement during prostate cancer progression," Mod Pathol 22:1083-1093 (2009).
Han et al., "Interaction of integrin linked kinase (ILK) and MCM7 mediating integrin α7 induced cell growth suppression," Cancer Research 70(11):4375-4384 (2010).
Han et al., "Metallothionein 1 h tumour suppressor activity in prostate cancer is mediated by euchromatin methyltransferase 1," The Journal of Pathology 230(2):184-193 (2013).
Hanahan et al., "Hallmarks of Cancer: The Next Generation," Cell 144:646-674 (2011).
Hsu et al., "DNA targeting specificity of RNA-guided Cas9 nucleases," Nature Biotechnology 31(9):827-832 (2013).
Hwang et al., "NOLC 1, an Enhancer of Nasopharyngeal Carcinoma Progression, is Essential for TP53 to Regulate MDM2 Expression," The American Journal of Pathology 175:342-354 (2009).
International Search Report dated May 30, 2018 in International Application No. PCT/US17/66207.
Jinek et al., "A Programmable Dual-RNA—Guided DNA Endonuclease in Adaptive Bacterial Immunity," Science 337:816-821 (2012).
Jing et al., "Expression of Myopodin Induces Suppression of Tumor Growth and Metastasis," The American Journal of Pathology 164(5):1799-1806 (2004).
Kozarsky et al., "Gene therapy: adenovirus vectors," Current Opinion in Genetics & Development 3:499-503 (1993).
Lee et al., "Transcriptional Induction of the Alpha-1 Acid Glycoprotein (AGP) Gene by Synergistic Interaction of Two Alternative Activator Forms of AGP/Enhancer-Binding Protein (C/EBPβ) and NF-κB or Nopp 140," Molecular and Cellular Biology 16(8):4257-4263 (1996).
Li et al., "PTEN, a Putative Protein Tyrosine Phosphatase Gene Mutated in Human Brain, Breast, and Prostate Cancer," Science 275:1943-1947 (1997).
Luo et al., "(—)-Epigallocatechin-3-gallate induces Du145 prostate cancer cell death via downregulation of inhibitor of DNA binding 2, a dominant negative helix-loop-helix protein," Cancer Science 101:707-712 (2010).
Luo et al., "Discovery and Classification of Fusion Transcripts in Prostate Cancer and Normal Prostate Tissue," Am. J Pathol. 185(7):1834-1845 (2015).
Luo et al., "Genome-Wide Methylation Analysis of Prostate Tissues Reveals Global Methylation Patterns of Prostate Cancer," Am J Pathol 182:2028-2036 (2013).
Maehama et al., "The Tumor Suppressor, PTEN /MMAC1, Dephosphorylates the Lipid Second Messenger, Phosphatidylinositol 3,4,5-Trisphosphate," The Journal of Biological Chemistry 273:13375-13378 (1998).
Maruyama et al., "Inhibition of non-homologous end joining increases the efficiency of CRISPR/Cas9-mediated precise [TM: inserted] genome editing," Nature Biotechnology 33(5):538-542 (2015).
McCubrey et al., "Roles of the RAF/MEK/ERK and PI3K/PTEN/AKT pathways in malignant transformation and drug resistance," Adv Enzyme Regul 46:249-279 (2006).
Mojica et al., "Intervening Sequences of Regularly Spaced Prokaryotic Repeats Derive from Foreign Genetic Elements," J. of Molecular Evolution 60:174-182 (2005).
Myers et al., "The lipid phosphatase activity of PTEN is critical for its tumor suppressor function," PNAS USA 95:13513-13518 (1998).
Ohnuki, et al., "Chromosomal Analysis of Human Prostatic Adenocarcinoma Cell Lines," Cancer Research 40:524-534 (1980).
Pai et al., "Cell-cycle-dependent alterations of a highly phosphorylated nucleolar protein p130 are associated with nucleologenesis," Journal of Cell Science 108 (Pt. 5): 1911-1920 (1995).
Prakash et al., "Expression of Conjoined Genes: Another Mechanism for Gene Regulation in Eukaryotes," PLoS One 5(10):e13284 (2010) 9 pages.
Rajab et al., "Suicide Gene Therapy against Cancer," J. of Genetics Syndromes and Gene Therapy 4:9 (2013) 8 pages.
Ran et al., "Double nicking by RNA-guided CRISPR Cas9 for Enhanced Genome Editing Specificity," Cell 154(6):1380-1389 (2013).
Ren et al., "Analysis of Integrin α7 Mutations in Prostate Cancer, Liver Cancer, Glioblastoma Multiforme, and Leiomyosarcoma," J Natl Cancer Inst 99:868-880 (2007).
Ren et al., "MCM7 amplification and overexpression are associated with prostate cancer progression," Oncogene 25:1090-1098 (2006).
Sansai et al., "The Biology and Clinical Relevance of the PTEN tumor suppressor pathway," J Clin Oncol 22(14):2954-2963 (2004).
Shen et al., "Essential Role for Nuclear PTEN in Maintaining Chromosomal Integrity," Cell 128:157-170 (2007).
Shi et al., "Inhibition of prostate cancer growth and metastasis using small interference RNA specific for minichromosome complex maintenance component 7," Cancer Gene Therapy 17(10):694-699 (2010).
Siegel et al., "Cancer Statistics, 2015," CA Cancer J Clin 65:5-29 (2015).
Siegel et al., "Cancer Statistics, 2016," CA Cancer J Clin 66:7-30 (2016).
Steck et al., "Identification of a candidate tumour suppressor gene, MMAC1, at chromosome 10q23.3 that is mutated in multiple advanced cancers," Nature Genetics 15:356-362 (1997).
Trotman et al., "Ubiquitination Regulates PTEN Nuclear Import and Tumor Suppression," Cell 128:141-156 (2007).
Vlietstra et al., "Frequent Inactivation of PTEN in Prostate Cancer Cell Lines and Xenografts," Cancer Research 58:2720-2723 (1998).
Wang et al., "A Mechanism of Cell Survival: Sequestration of Fas by the HGF Receptor Met," Mol Cell 9:411-421 (2002).
Wang et al., "p53-induced Gene 3 Mediates Cell Death Induced by Glutathione Peroxidase 3," The Journal of Biological Chemistry 287(20):16890-16902 (2012).
Wei Zeng et al., "Visualizing Interchange Patterns in Massive Movement Data," Computer Graphics Forum, 32(3):10 pages (2013).
Yin et al., "PTEN: a new guardian of the genome," Oncogene 27:5443-5453 (2008).
Yu et al., "CSR1 Suppresses Tumor Growth and Metastasis of Prostate Cancer," American Journal of Pathology 168(2):597-607 (2006).
Yu et al., "Genome Abnormalities Precede Prostate Cancer and Predict Clinical Relapse," Am J Pathol 180(6):2240-2248 (2012).
Yu et al., "Genomic Copy Number Variations in the Genomes of Leukocytes Predict Prostate Cancer Clinical Outcomes," PLoS One 10(8):e0135982 (2015).
Yu et al., "Glutathione Peroxidase 3, Deleted or Methylated in Prostate Cancer, Suppresses Prostate Cancer Growth and Metastasis," Cancer Research 67(17):8043-8050 (2007).
Yu et al., "Novel Fusion Transcripts Associate with Progressive Prostate Cancer," Am. J. Pathol. 184(10):2840-2849 (2014).
Yu et al., "Small Molecules Enhance CRISPR Genome Editing in Pluripotent Stem Cells," Cell Stem Cell 16:142-147 (2015).
Yu et al., "Whole-Genome Methylation Sequencing Reveals Distinct Impact of Differential Methylations on Gene Transcription in Prostate Cancer," Am J Pathol 183(6):1960-1970 (2013).
Zarogoulidis et al., "Suicide Gene Therapy for Cancer—Current Strategies," J. of Genetics Syndromes and Gene Therapy 4(9):16849 (2013) 29 pages.

(56) References Cited

OTHER PUBLICATIONS

Zhu et al., "CSR1 induces cell death through inactivation of CPSF3," Oncogene 28:41-51 (2009).

Zhu et al., "Integrin Alpha 7 Interacts with High Temperature Requirement A2 (HtrA2) to Induce Prostate Cancer Cell Death," The American Journal of Pathology 177(3):1176-1186 (2010).

Extended European Search Report dated Jun. 29, 2020 in Application No. EP 17880166.

Mitelman, et al., "The impact of translocations and gene fusions on cancer causation", Nature Reviews, Cancer, 7:233-245 (2007).

Wang, et al., "Genetic Screens in Human Cells Using the CRISPR-Cas9 System", Science, 343:80-84 (2014).

Blum et al., "RNA Sequencing Identifies Transcriptionally Viable Gene Fusions in Esophageal Adenocarcinomas," Cancer Research, 76(19):5628-5633 (2016).

McPherson et al., "deFuse: An Algorithm for Gene Fusion Discovery in Tumor RNA-Seq Data," PLoS Computational Biology, 7(5):e1001138, 16 pgs. (2011).

Nome et al., "Common Fusion Transcripts Identified in Colorectal Cancer Cell Lines by High-Throughput RNA Sequencing," Translational Oncology, 6(5):546-553 (2013).

Parker et al., "Fusion genes in solid tumors: an emerging target for cancer diagnosis and treatment," Chinese Journal of Cancer, 32(11):594-603 (2013).

Chung et al., "Identification of a recurrent transforming UBR5-ZNF423 fusion gene in EBV-associated nasopharyngeal carcinoma," Journal of Pathology, 231: 158-167 (2013).

Liu et al., Development and potential applications of CRISPR-Cas9 genome editing technology in sarcoma, Cancer Letters, 373, 109-118 (2016).

Mandal et al., "Efficient Ablation of Genes in Human Hematopoietic Stem and Effector Cells using CRISPR/Cas9," Cell Stem Cell, 15, 643-652 (2014).

Toub et al., "Efficacy of siRNA Nanocapsules Targeted Against the EWS-Fli1 Oncogene in Ewing Sarcoma," Pharmaceutical Research, 23, 5, 892-900 (2006).

Wu et al., "Functional analysis of the TMPRSS2:ERG fusion gene in cisplatin-induced cell death," Molecular Medicine Reports, 13, 4, 3173-3180 (2016).

\* cited by examiner

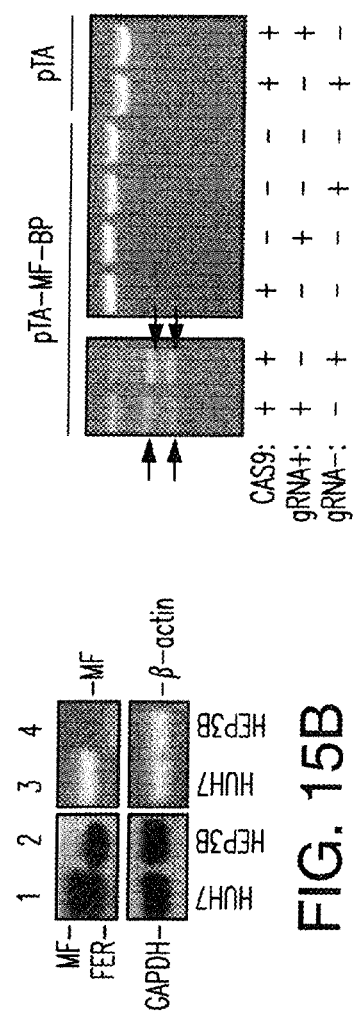
FIG. 15B
FIG. 15C
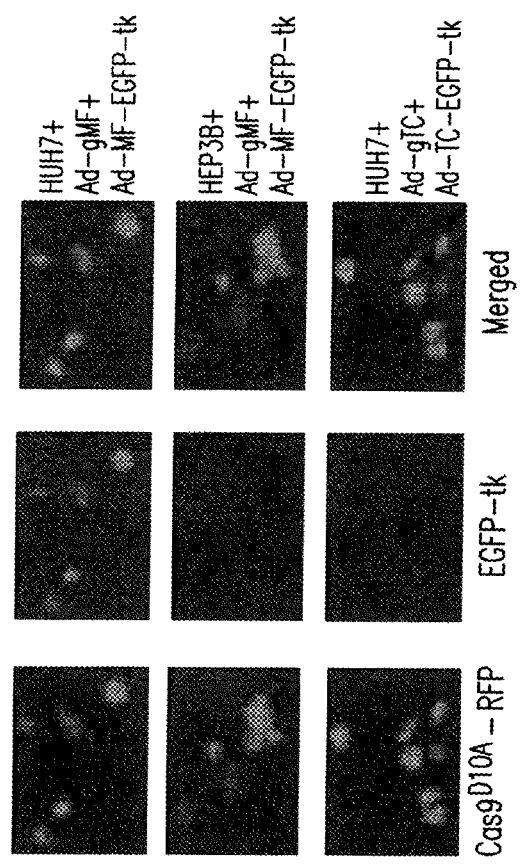
FIG. 15D
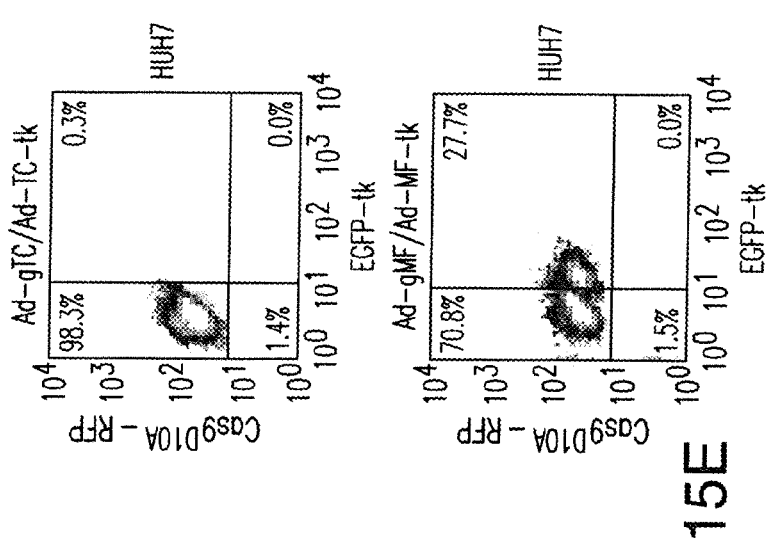
FIG. 15E

FIG. 22A

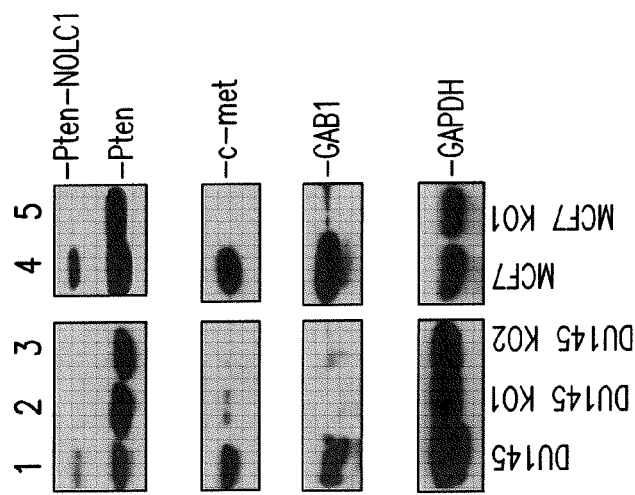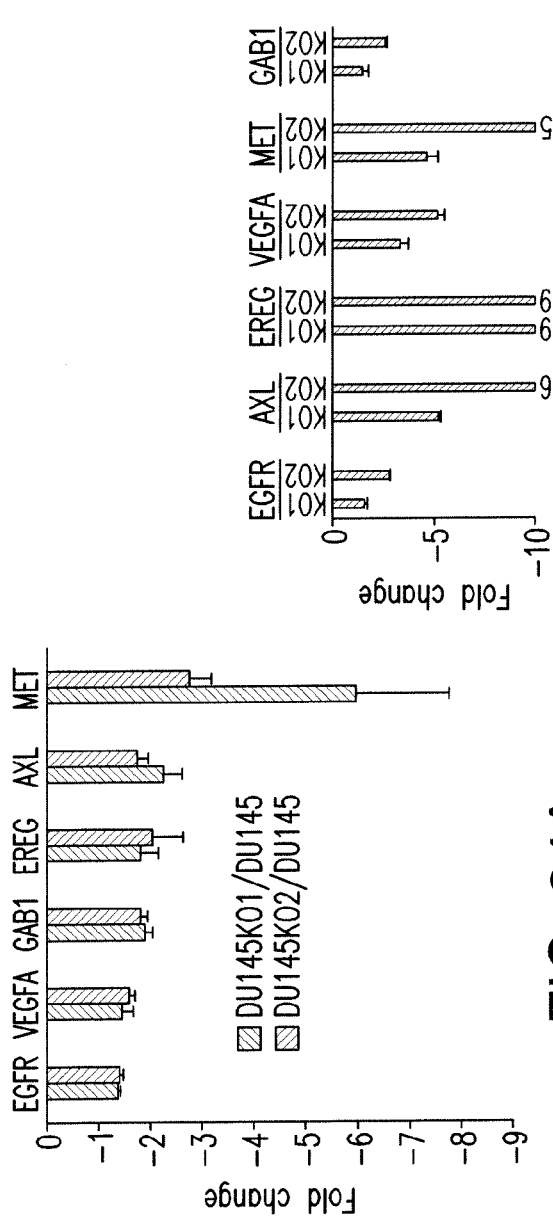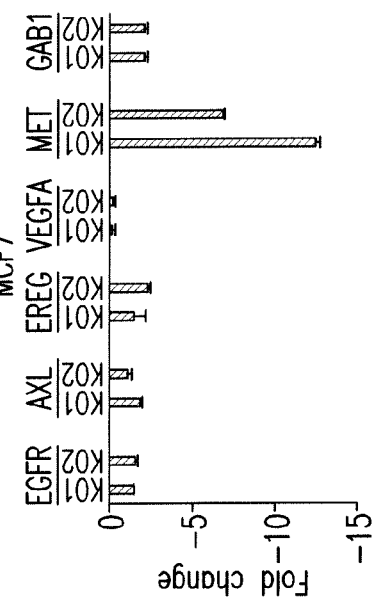
FIG. 24A
FIG. 24B
FIG. 24C

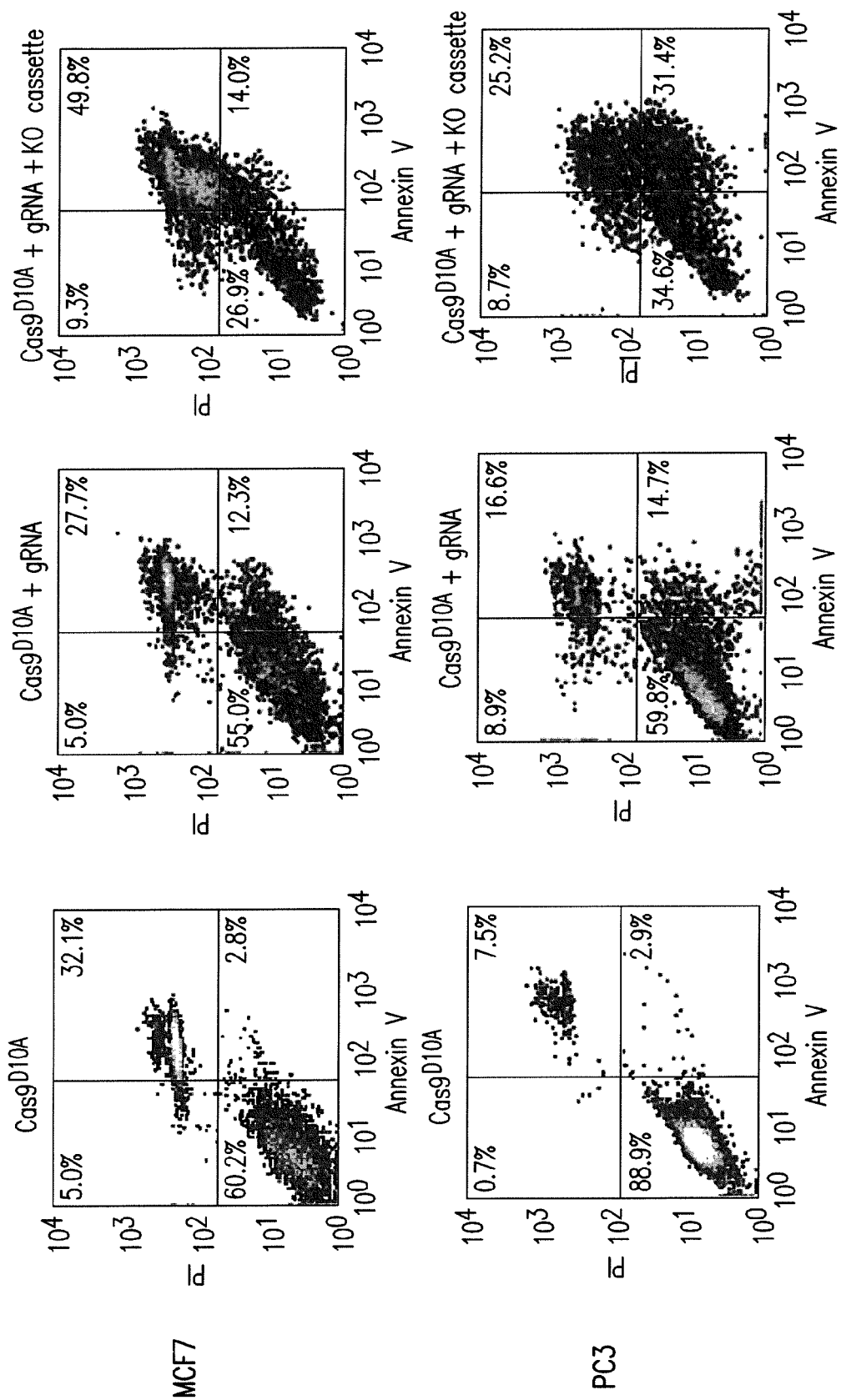

METHODS OF TREATING CELLS CONTAINING FUSION GENES BY GENOMIC TARGETING

PRIORITY INFORMATION

This application is a continuation of International Patent Application No. PCT/US2017/066207, filed Dec. 13, 2017, which claims priority to U.S. Provisional Patent Application Ser. No. 62/433,608, filed Dec. 13, 2016, and U.S. Provisional Patent Application Ser. No. 62/572,960, filed Oct. 16, 2017, the contents of which are herein incorporated by reference in their entireties.

GRANT INFORMATION

This invention was made with government support under Grant Nos. CA098249 and CA190766 awarded by the National Institutes of Health and Grant Nos. W81XWH-16-1-0541 and W81XWH-16-1-0364 awarded by the U.S. Army Medical Research & Materiel Command. The government has certain rights in the invention.

1. INTRODUCTION

The present invention relates to methods of treating patients carrying one or more specific fusion genes by performing a genome targeting technique.

2. BACKGROUND OF THE INVENTION

Clustered regularly interspaced short palindromic repeats (CRISPR)/CRISPR-associated (Cas) were originally discovered to act as immunity defense mechanisms against foreign pathogens in prokaryotic cells (Mojica et al. (2005) J. of Molecular Evolution 60:174-182). Cas9, a protein for the type II CRISPR/Cas system, was found to exhibit DNA cleavage activity. The nuclease activity of Cas9 can be guided by a CRISPR RNA and a trans-activating CRISPR RNA complementary to a targeted sequence of DNA in the genome (Jinek et al. (2012) Science 337:816-821). Since trans-activating CRISPR RNA and CRISPR RNA can be made into a chimeric RNA containing the full function of both RNA species, artificial fusion RNA sequences, also called guide RNAs (gRNAs), were generated to target the activity of Cas9 to a target DNA sequence (Esvelt et al. (2014) eLife:e03401). A D10A mutation present in the catalytic domain of Cas9 converts it to a nickase that produces single nucleotide breaks at the target DNA (Jinek et al. (2012) Science 337:816-821). Double nicking of target DNA can increase genome editing specificity by 50-1500 fold (Ran et al. (2013) Cell 154:1380-1389), with the off-target rate as low as 1/10,000. Such specificity can make somatic genomic targeting a viable approach in treating human diseases.

In the U.S., prostate cancer is one of the most frequent malignancies observed in men. The mortality of prostate cancer reached 27,540 in 2014, the second most lethal cancer for men (Siegel et al. (2015) A Cancer Journal For Clinicians 65:5-29)). As disclosed in WO 2015/103057 and WO 2016/011428, a number of fusion genes generated by chromosomal rearrangement were identified in prostate cancers that have been shown to be recurrent and lethal. The expression of these fusion genes are widespread among aggressive prostate cancers but are absent in normal tissues. WO 2016/011428 discloses the genomic targeting of the chromosomal breakpoint of the fusion gene TMEM135-CCDC67, which resulted in cell death and remission of xenografted prostate cancer in mice.

Cancers, in general, are among the leading causes of death in the U.S. The mortality rate of cancers reached 595,690 in 2015 in the U.S. alone, making it the second most lethal cause of death after cardiovascular diseases (Siegel et al. (2016) A Cancer Journal For Clinicians 66(1):7-30). Treatment of cancers, particularly of those that become metastatic, remains problematic, and cures for cancer remain elusive. Therefore, there remains a need in the art for methods of treating cancer.

3. SUMMARY OF THE INVENTION

The present invention relates to methods for treating patients suffering from cancer or a pre-malignant or neoplastic condition. It is based, at least in part, on the discovery that a genome editing technique that specifically targets a fusion gene can induce cell death in a cancer cell, for example a cancer cell other than a prostate cancer cell, for example a hepatocellular cancer cell, having the fusion gene.

In various non-limiting embodiments, the present invention provides for methods of treating a subject that carries a fusion gene. For example, and not by way of limitation, the subject can have cancer, a pre-malignant condition or a neoplastic condition. In certain embodiments, a method of the present invention comprises performing a genome editing technique that targets a fusion gene present within one or more cancer cells of the subject. Non-limiting examples of such fusion genes include TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In certain embodiments, the fusion gene is PTEN-NOLC1. In certain embodiments, the fusion gene is MAN2A1-FER. In certain embodiments, the cancer is not prostate cancer. In certain embodiments, the cancer is not lung adenocarcinoma, glioblastoma multiforme or hepatocellular carcinoma.

In certain non-limiting embodiments, the present invention further provides kits for performing methods of treating a subject that carries a fusion gene. For example, and not by way of limitation, the subject can have a cancer, a pre-malignant condition or a neoplastic condition. In certain embodiments, a kit of the present invention can comprise one or more vectors or plasmids comprising a nucleic acid encoding a Cas9 protein, e.g., $Cas9^{D10A}$. In certain embodiments, the one or more vectors can further comprise one or more gRNAs specific to a fusion gene, e.g., specific to a breakpoint of a fusion gene and/or sequences flanking the breakpoint of a fusion gene.

In certain embodiments, a kit of the present invention can further include one or more vectors or plasmids comprising a nucleic acid, that when expressed results in cell death. In certain embodiments, the nucleic acid encodes HSV-1 thymidine kinase. In certain embodiments, this vector can further comprise one or more targeting sequences that are complementary to sequences within the fusion gene to promote homologous recombination and insertion of the nucleic acid. In certain embodiments, where the nucleic acid encodes HSV-1 thymidine kinase, the kit can further comprise ganciclovir and/or valganciclovir.

In certain embodiments, the kit can include nucleic acid primers for PCR analysis or nucleic acid probes for RNA in situ analysis to detect the presence of one or more fusion genes in a sample from the subject. In certain non-limiting embodiments, the one or more fusion genes can be selected from the group consisting of TRMT11-GRIK2, SLC45A2-AMACR, MTOR-TP53BP1, LRRC59-FLJ60017, TMEM135-CCDC67, PTEN-NOLC1, CCNH-C5orf30, TRMT11-GRIK2, SLC45A2-AMACR, KDM4B-AC011523.2, MAN2A1-FER, MTOR-TP53BP, ZMP-STE24-ZMYM4, CLTC-ETV1, ACPP-SEC13, DOCK7-OLR1, PCMTD1-SNTG11 and a combination thereof.

4. BRIEF DESCRIPTION OF THE FIGURES

FIG. 1. Unique fusion gene events. Left panel: Miniature diagrams of genome of the fusion genes, the transcription directions, the distances between the joining genes and directions of the fusions. Middle panel: Representative sequencing chromograms of fusion genes. The joining gene sequences were indicated (SEQ ID NOs: 45-52). Right panel: Diagrams of translation products of fusion genes. Blue-driver gene translation product; Red-passenger gene translation product; Orange-novel translation products due to frameshift or translation products from a non-gene region.

Figure 2:
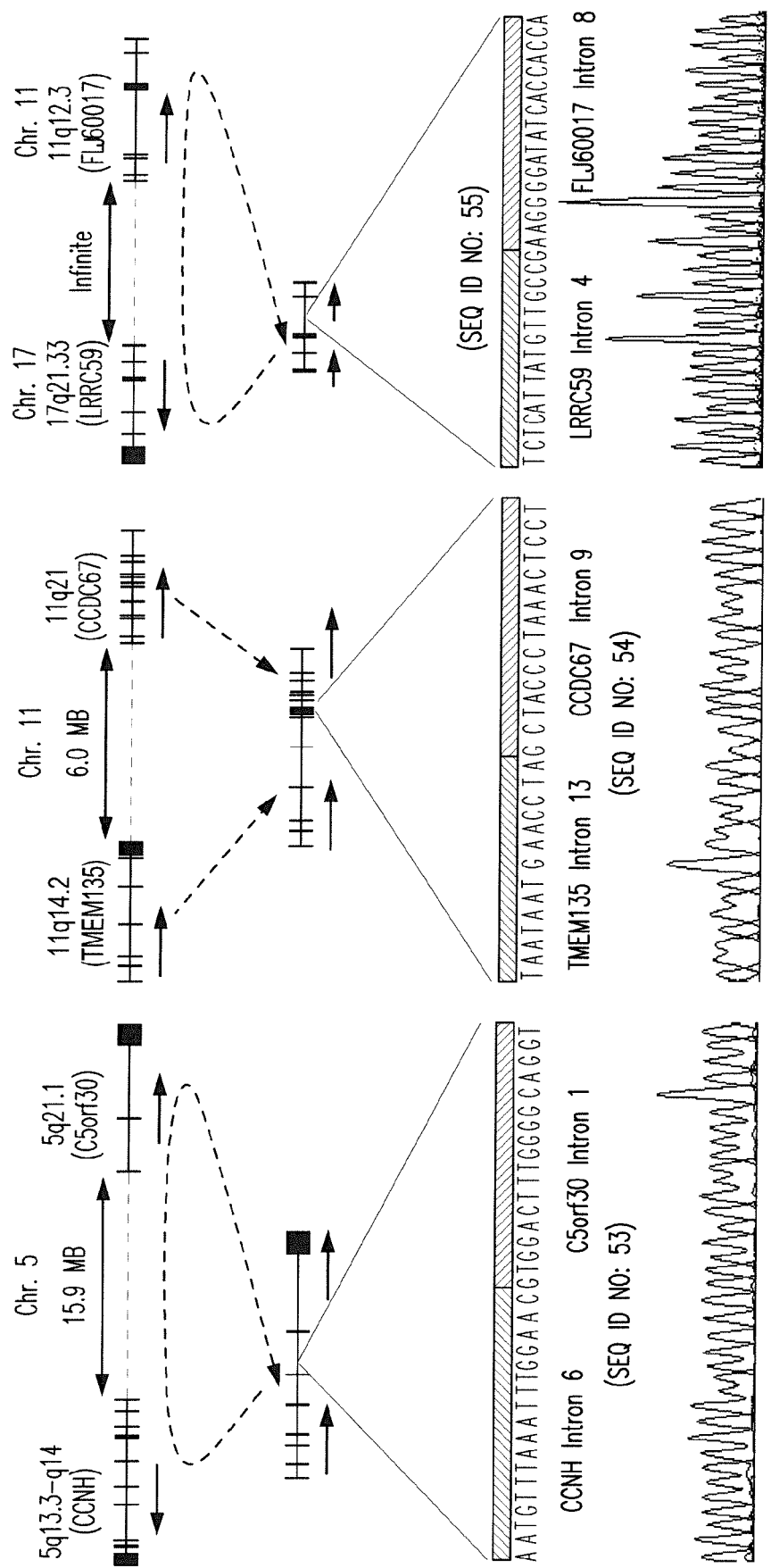

FIG. 2. Genome breakpoint analysis of fusion genes. Top panel: Miniature diagrams of genome of the fusion genes, the transcription directions, the distances between the joining genes and directions of the chromosome joining. Middle panel: Miniature of fusion genome and transcription direction. Bottom: Representative sequencing chromograms encompassing the joining breakpoint of chromosomes (SEQ ID NOs: 53-55).

Figure 3A:
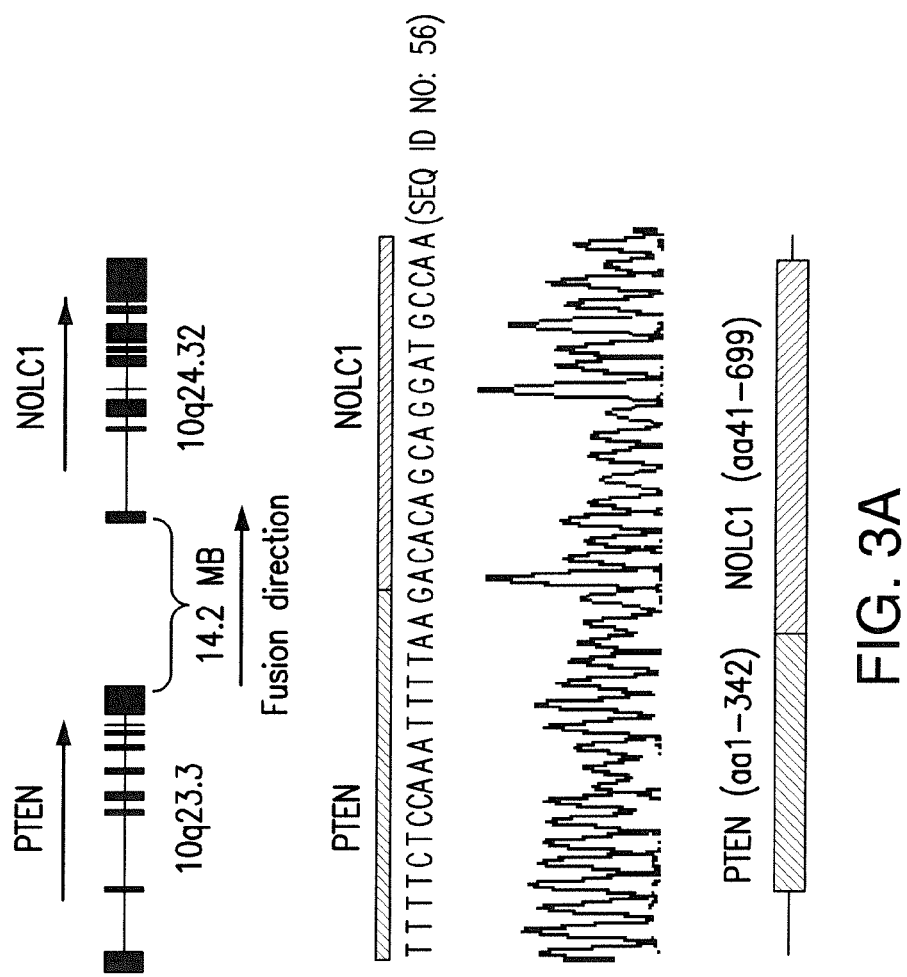
Figure 3B:
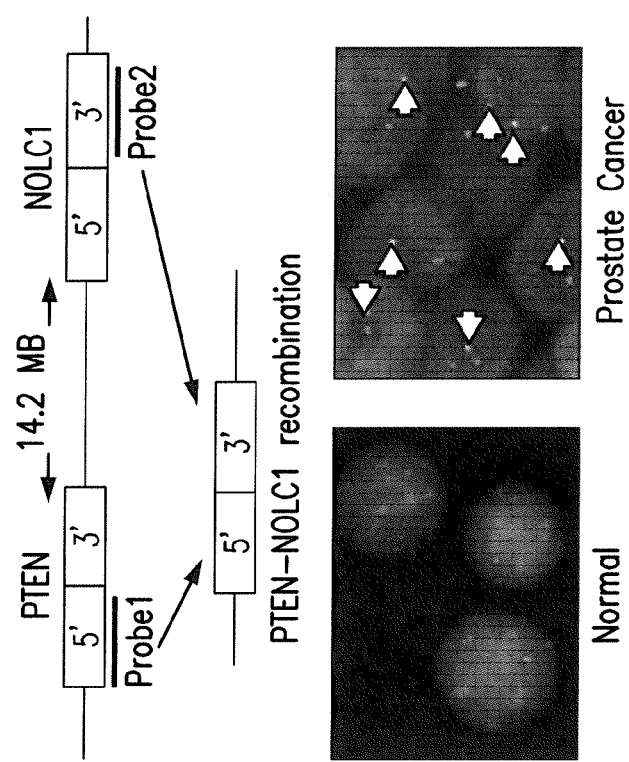

FIG. 3A-B. PTEN-NOLC1 fusion gene (A) PTEN-NOLC1 fusion transcript. Top panel: Miniature diagrams of genome of the PTEN and NOLC1 genes, the transcription direction, the distance between the joining genes and direction of the fusion. Middle panel: Representative sequencing chromogram of PTEN-NOLC1 transcript. The joining gene sequences were indicated. Lower panel: Diagram of translation product of fusion transcript. Blue-head gene translation product; Red-tail gene translation product. (B) Schematic diagram of PTEN and NOLC1 genome recombination and FISH probe positions.

Figure 4:
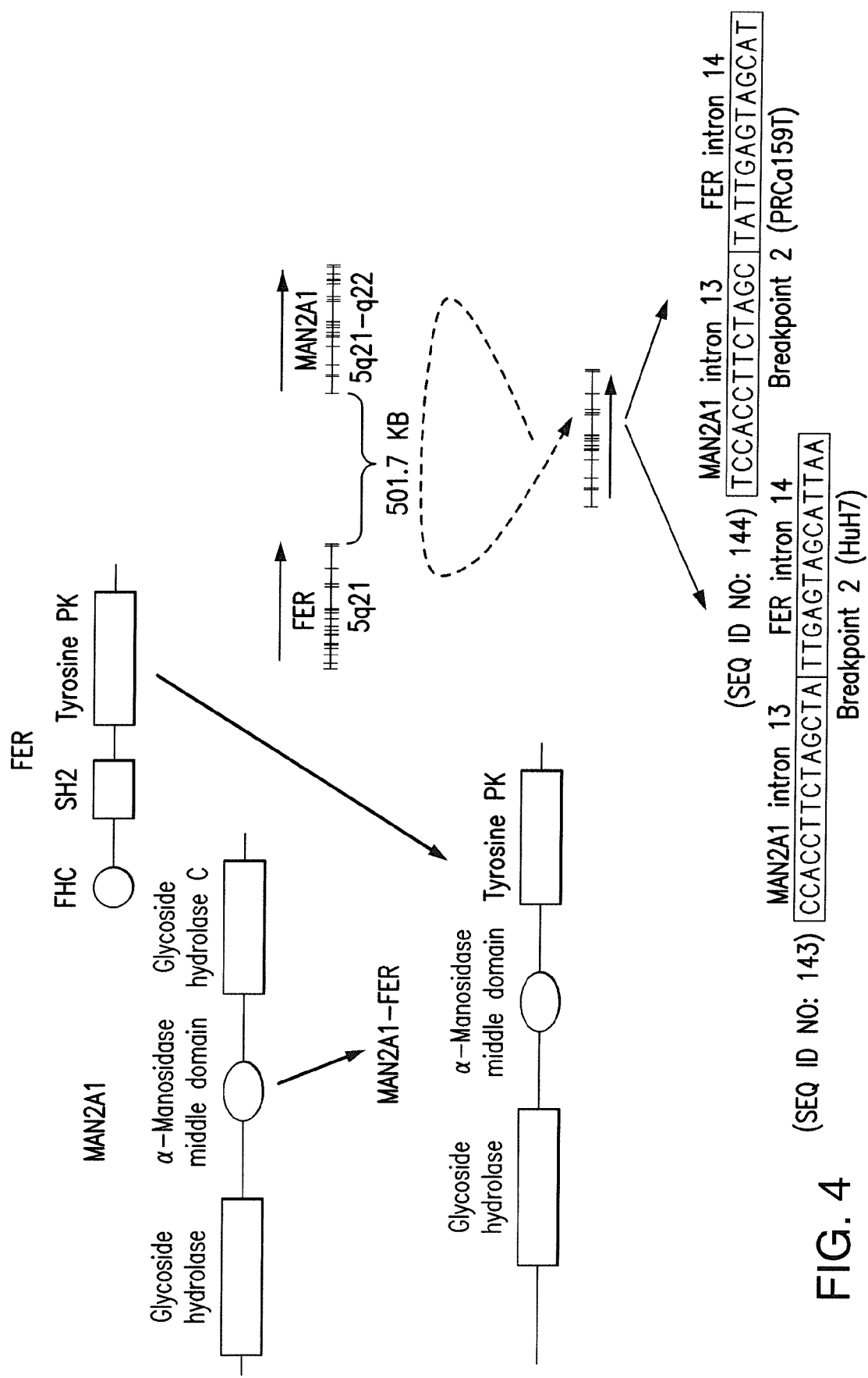

FIG. 4. Motif analysis of MAN2A1-FER. Diagram of functional domains of MAN2A1, FER and MAN2A1-FER fusion proteins and the chromosomal breakpoints observed for the MAN2A1-FER fusion gene in different cell lines. In the fusion gene MAN2A1-FER, the N-terminus of FER suffers a loss of SH2 and FHC domains. These domains were replaced with the glycoside hydrolase and α-mannosidase middle domain from MAN2A1.

Figure 5:
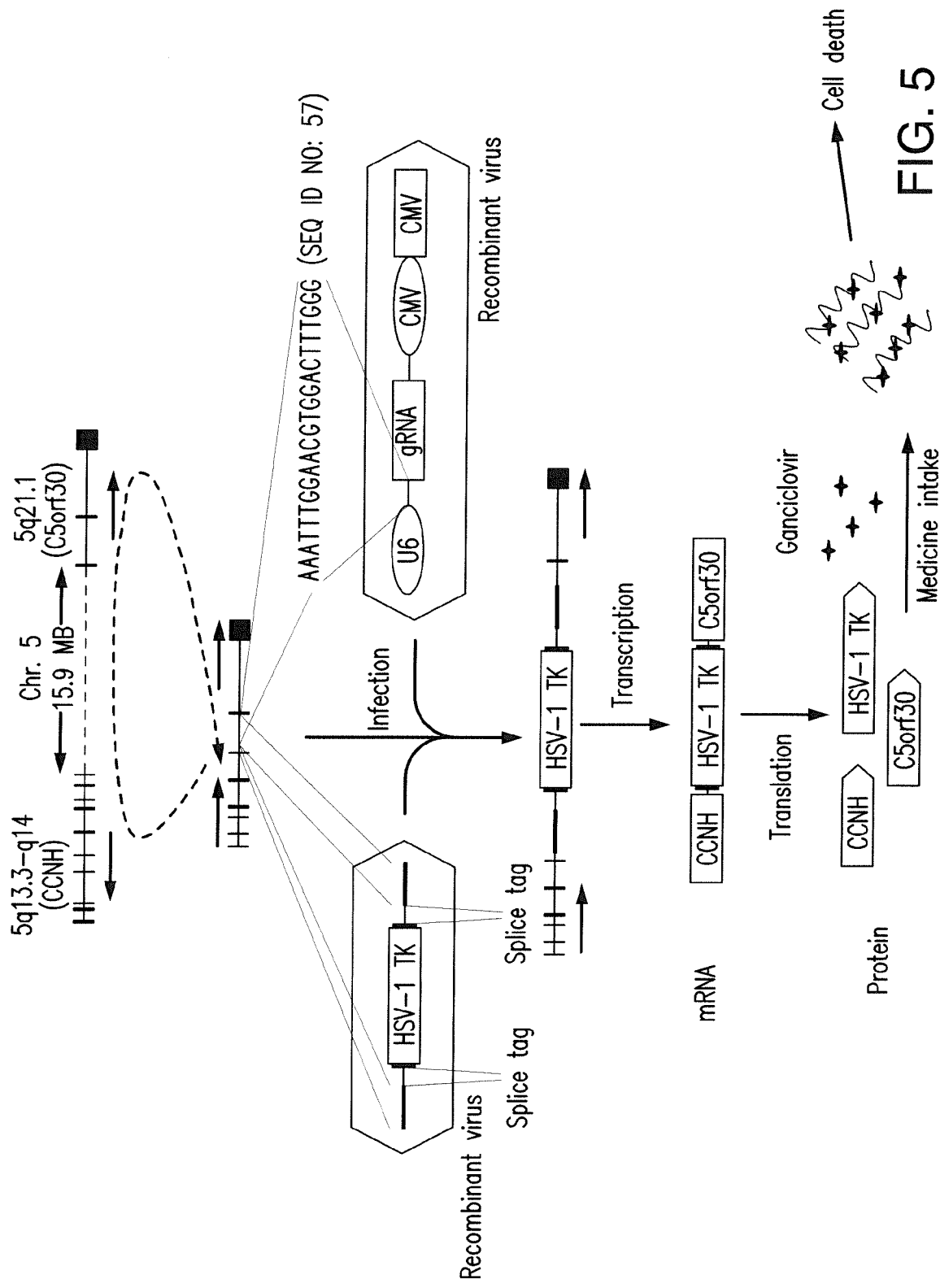

FIG. 5. Schematic diagram of Genome editing targeting at a fusion gene breakpoint in cancer cells positive for CCNH-C5orf30. Genome recombination in prostate cancer case 3T produced a breakpoint in chromosome 5 that connect intron 6 of CCNH with intron 1 of C5orf30. A guide RNA (gRNA) of 23 bp including protospacer adjacent motif (PAM) sequence is designed specific for the breakpoint region. The DNA sequence corresponding to this target sequence is artificially ligated into vector containing the remainder of gRNA and Cas9. This sequence is recombined and packaged into recombinant virus (Adenovirus or *lenti*-virus). A promoterless Herpes Simplex Virus Type 1 (HSV-1) thymidine kinase is constructed into a shuttle vector for adenovirus along with splice tag sequence from intron/exon juncture of CCNH exon 7. A 500 bp sequence surrounding the CCNH-C5orf30 breakpoint from each side is also ligated into the shuttle vector in order to produce efficient homologous recombination to complete the donor DNA construction. The vector is recombined and packaged into AdEasy to generate recombinant viruses. These viruses can be administered to patients or animals that have cancers positive for CCNH-C5orf30 fusion transcript. This leads to insertion of donor DNA into the target site (fusion breakpoint). Since HSV-1 TK in recombinant virus is promoterless, no transcription will occur if HSV-1 TK cDNA does not integrate into a transcription active genome. However, transcription of HSV-1 TK is active if HSV-1 TK is integrated into the target site of CCNH-C5orf30 in the patient, and when ganciclovir or its oral homologue valganciclovir is administered to the patient takes, the homologue is readily converted to triphosphate guanine analogue by HSV-1 TK and incorporated into the genomes of cancer cells. This leads to stoppage of DNA elongation in cells that are positive for CCNH-C5orf30.

Figure 6:
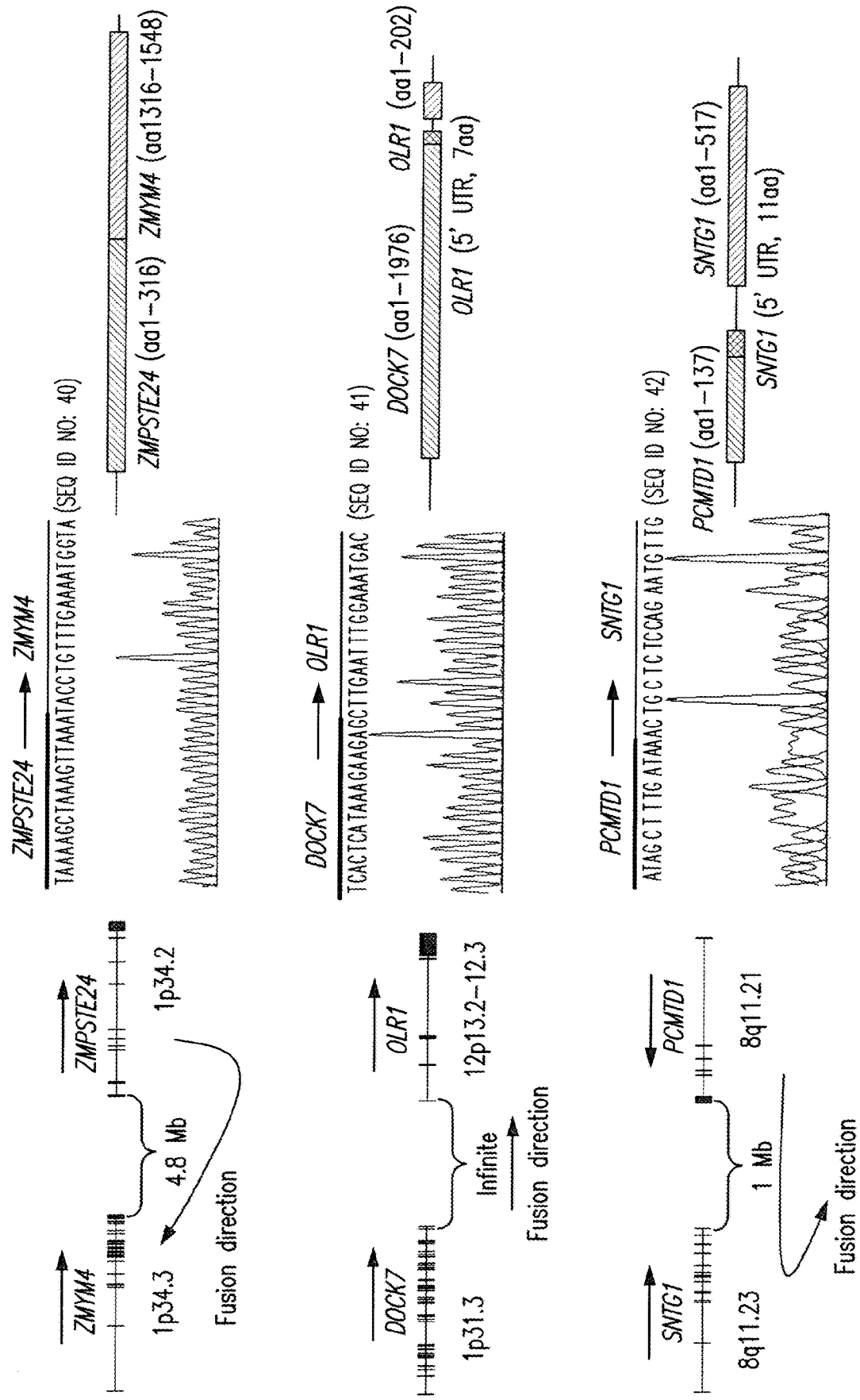
Figure 6:
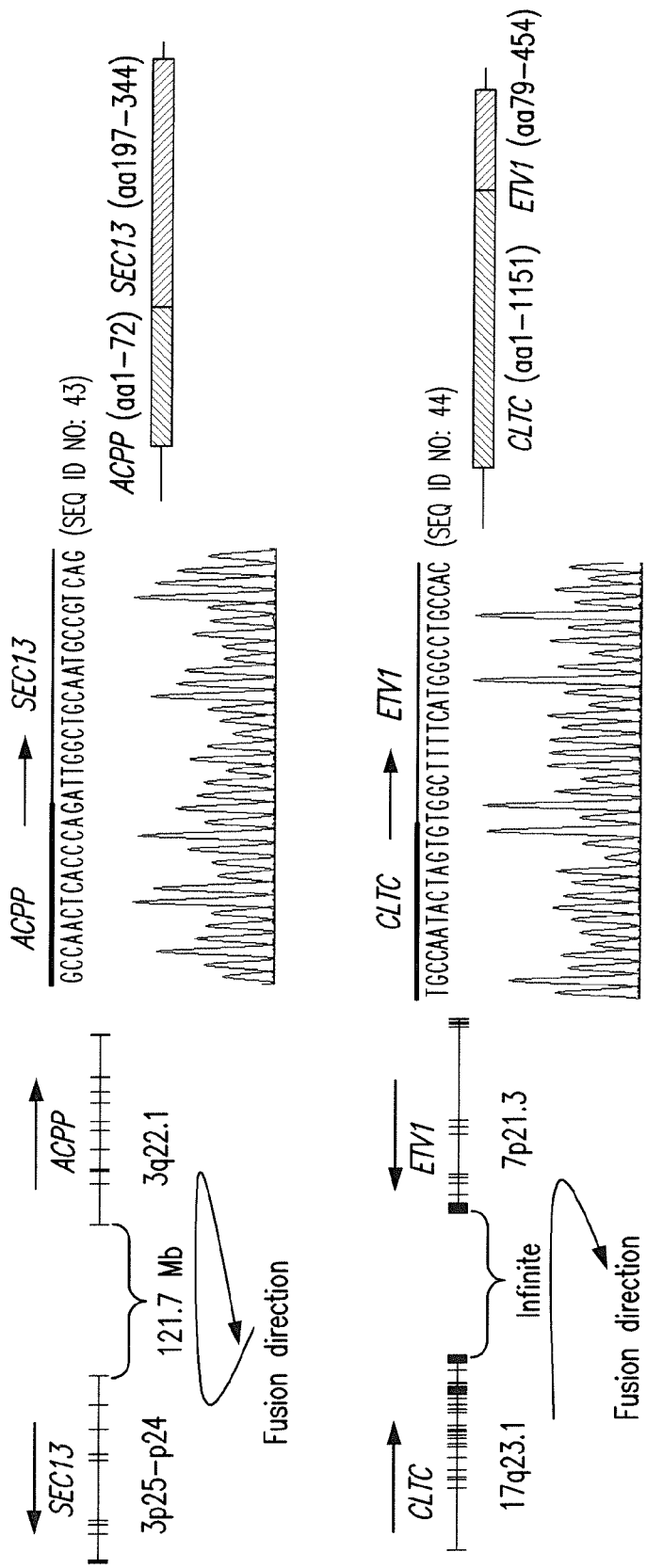

FIG. 6. Schematic diagram of fusion genes. Left panel: Schematic diagram of genome of fusion partners. Genetic locus, distance between partners, transcription direction and fusion direction are indicated. Middle panel: Histogram of Sanger sequencing surrounding the fusion point of each fusion gene (SEQ ID NOs: 40-44). Right panel: Predicted protein products of fusion genes. Blue: Head gene protein; Yellow: frameshift translation; Red: tail.

Figure 7:
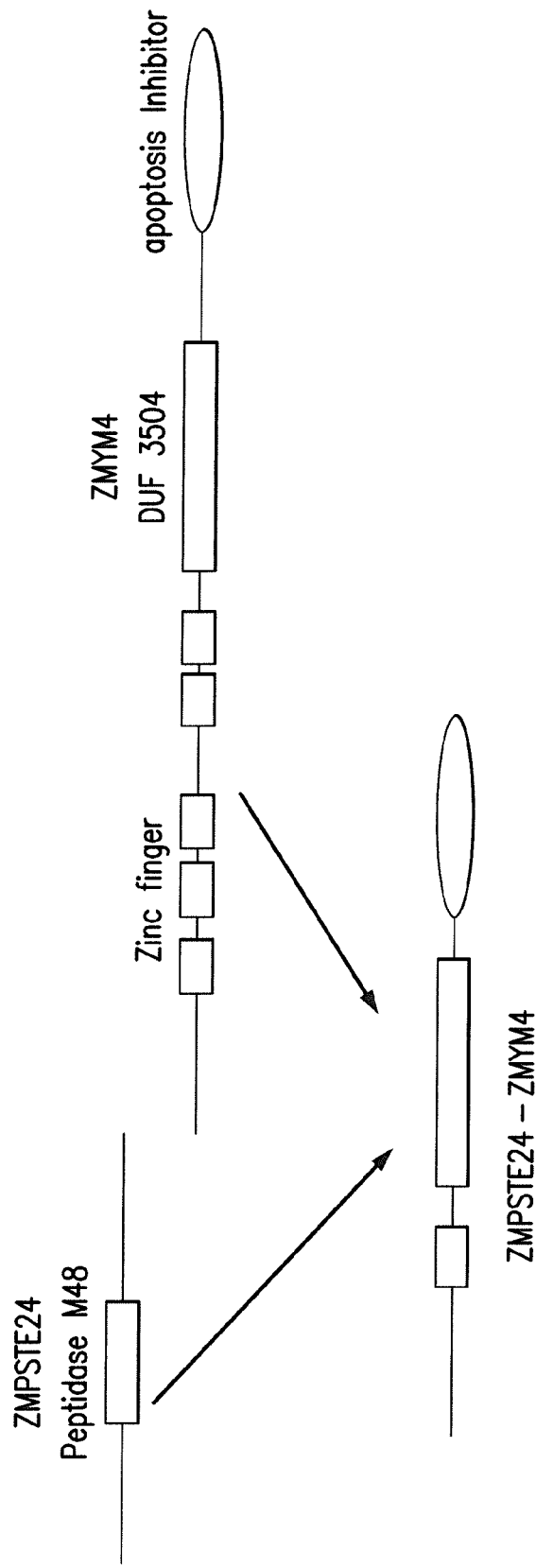

FIG. 7. Schematic diagram of ZMPSTE24-ZMYM5 fusion formation. Functional domains are indicated. The fusion formation between ZMPSTE24 and ZMYM4 produces a truncation of 159 amino acids from the C-terminus of ZMPSTE24 and 1315 amino acids from the N-terminus of ZMYM4. Motif analysis suggests that ZMPSTE24-ZMYM4 fusion will delete about 50% of the peptidase domain from ZMPSTE24 and remove all zinc fingers from ZMYM4, but leave ZUF3504 (domain of unknown function) and apoptosis inhibitor domain intact.

Figure 8:
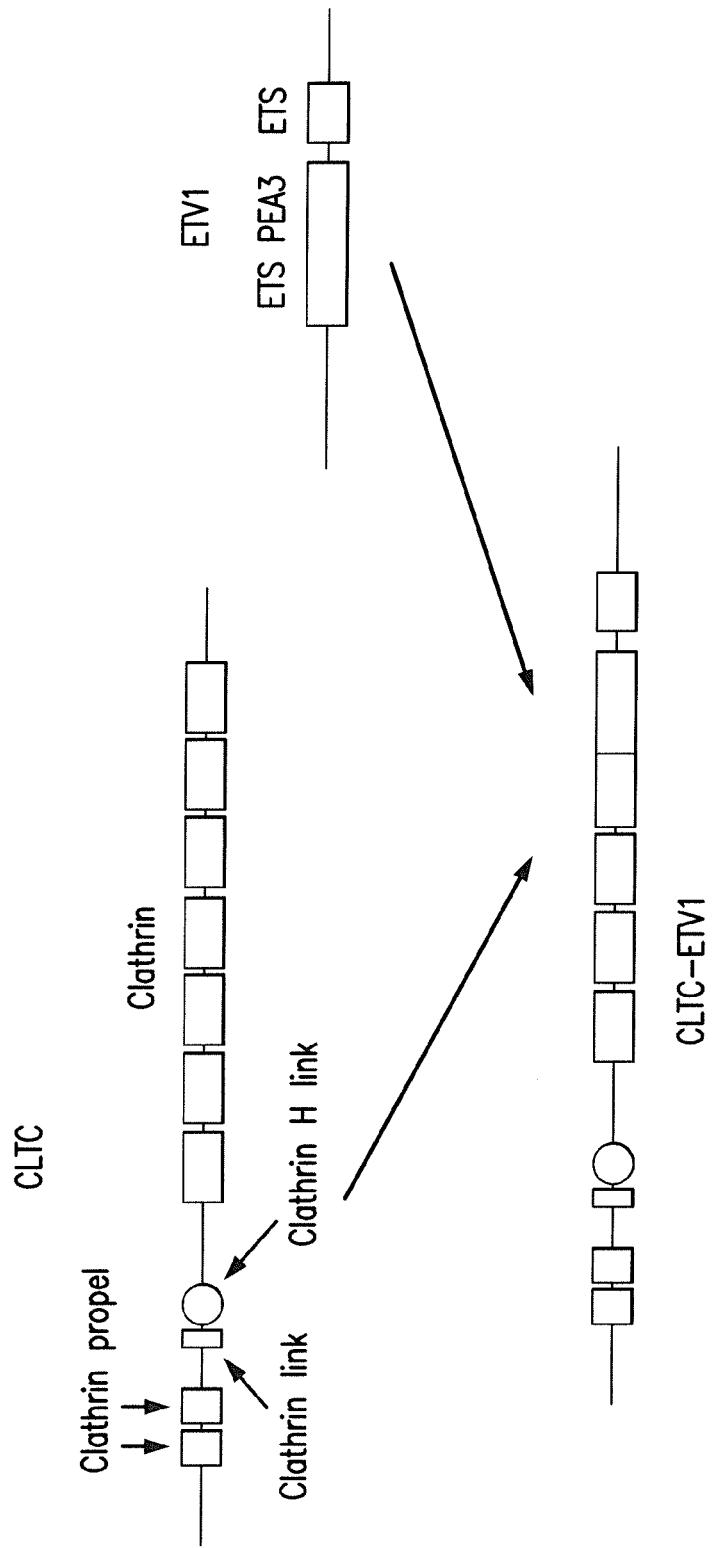

FIG. 8. Schematic diagram of CLTC-ETV1 fusion formation. Functional domains are indicated. CLTC-ETV1 fusion preserves a largely intact transcription domain in ETV1, and deletes 3 clathrin domains from CLTC. Truncation in the N-terminus of ETV1 eliminates all these regulatory elements from ETV1.

Figure 9:
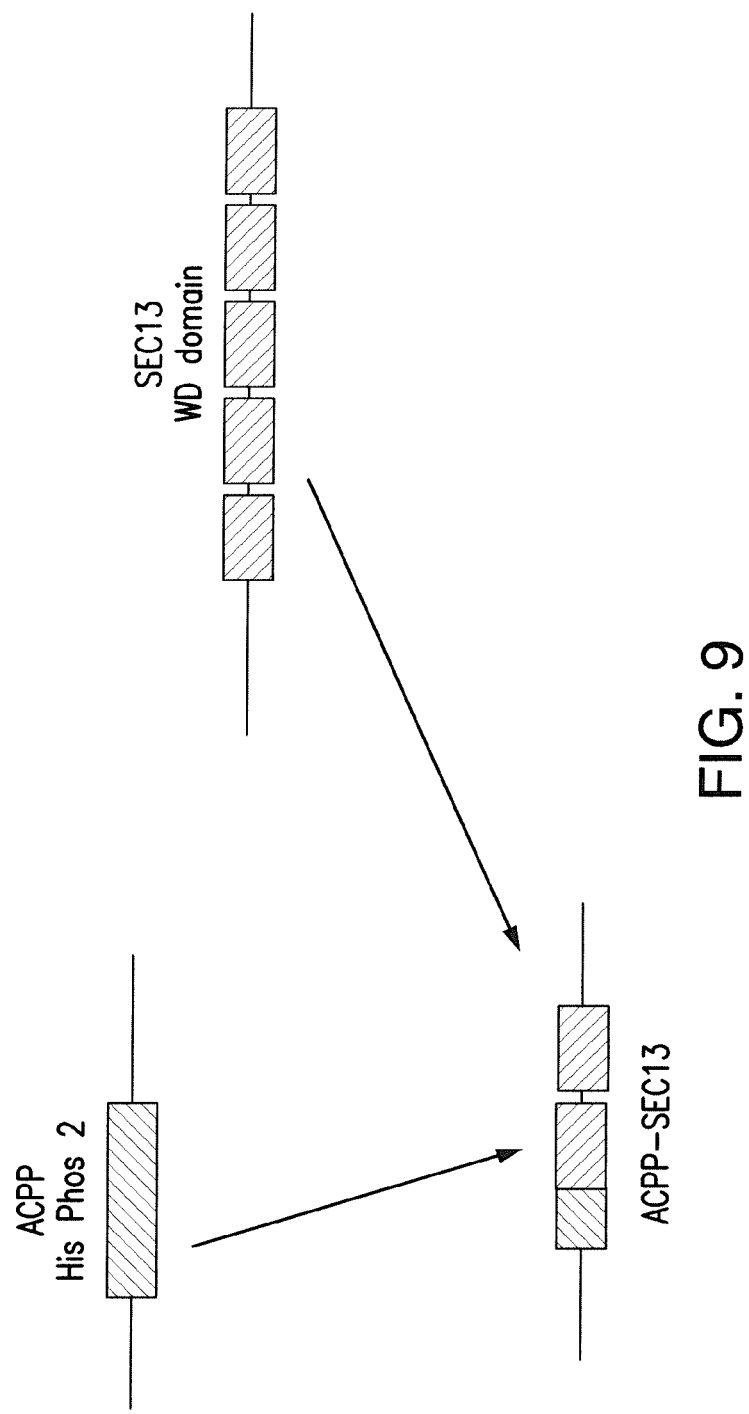

FIG. 9. Schematic diagram of ACPP-SEC13 fusion formation. Functional domains are indicated. In ACPP-SEC13 fusion, only the N-terminus 72 amino acids of ACPP is preserved, and over ⅔ of the phosphatase domain is truncated, while SEC13 loses 196 amino acids from its N-terminus and has 3 WD-repeat domains deleted.

Figure 10:
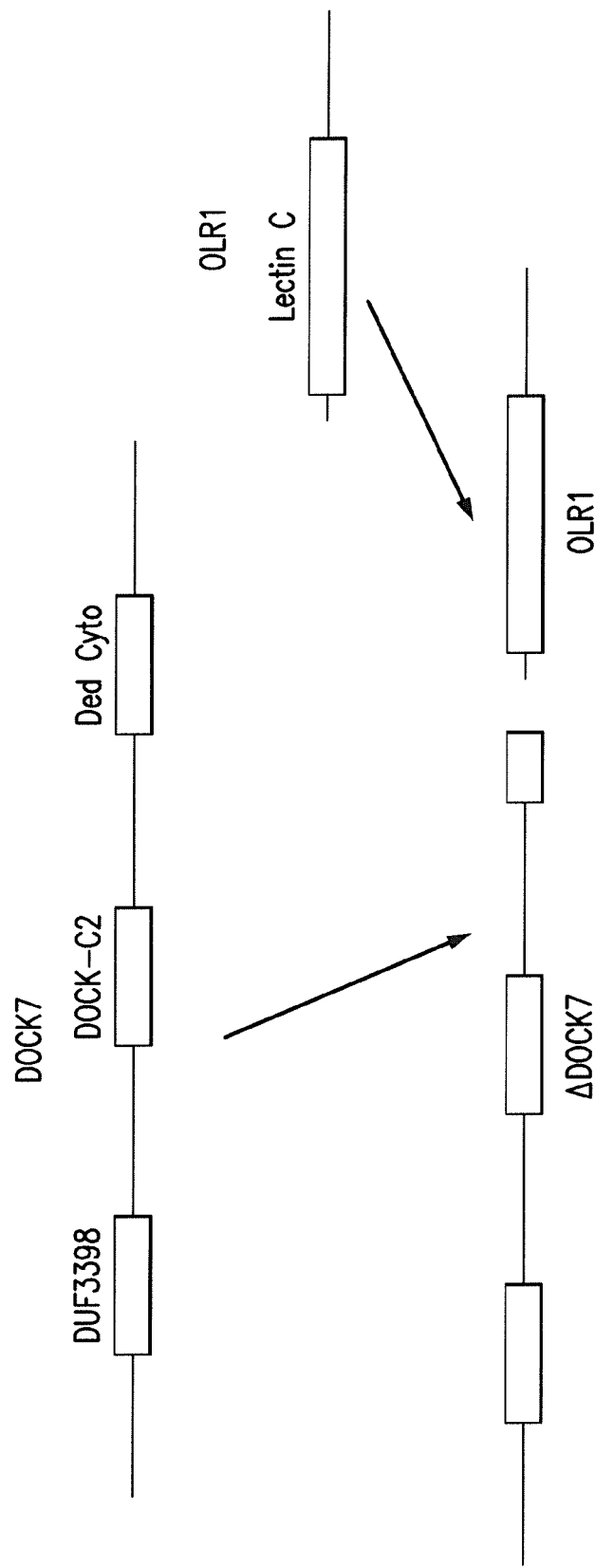

FIG. 10. Schematic diagram of DOCK7-OLR1 fusion formation. Functional domains are indicated. DOCK7-OLR1 does not produce a chimeric protein. Separate translation of DOCK7 and OLR1 occurs from the fusion transcript. The fusion gene deletes a significant portion of cytokinesis domain of DOCK, and the fusion transcript produces an intact OLR1 protein.

Figure 11:
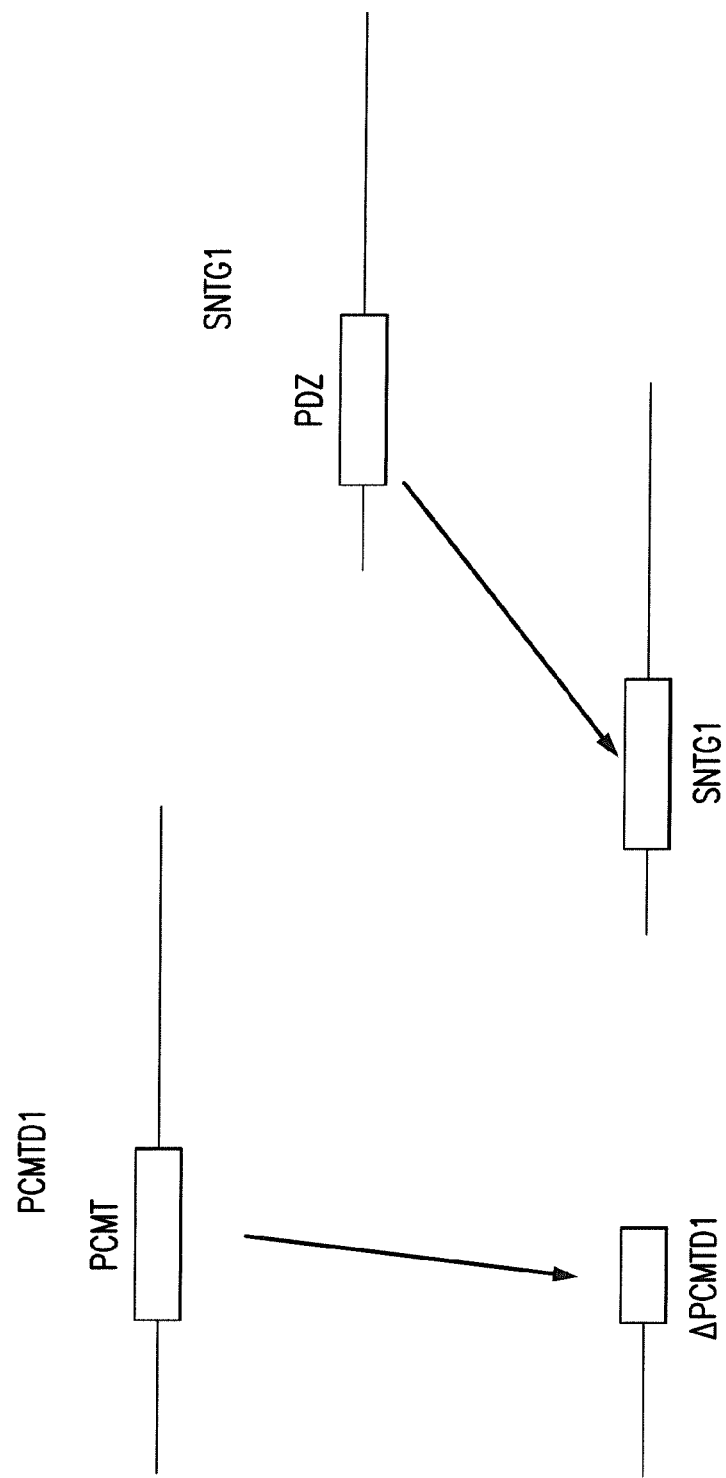

FIG. 11. Schematic diagram of PCMTD1-SNTG1 fusion formation. Functional domains are indicated. PCMTD1-SNTG1 fusion does not produce a chimeric protein. PCMTD1-SNTG1 fusion produces a truncated PCMTD1, which removes half of the methyl-transferase domain of PCMTD1, and SNTG1 remains intact.

Figure 12:
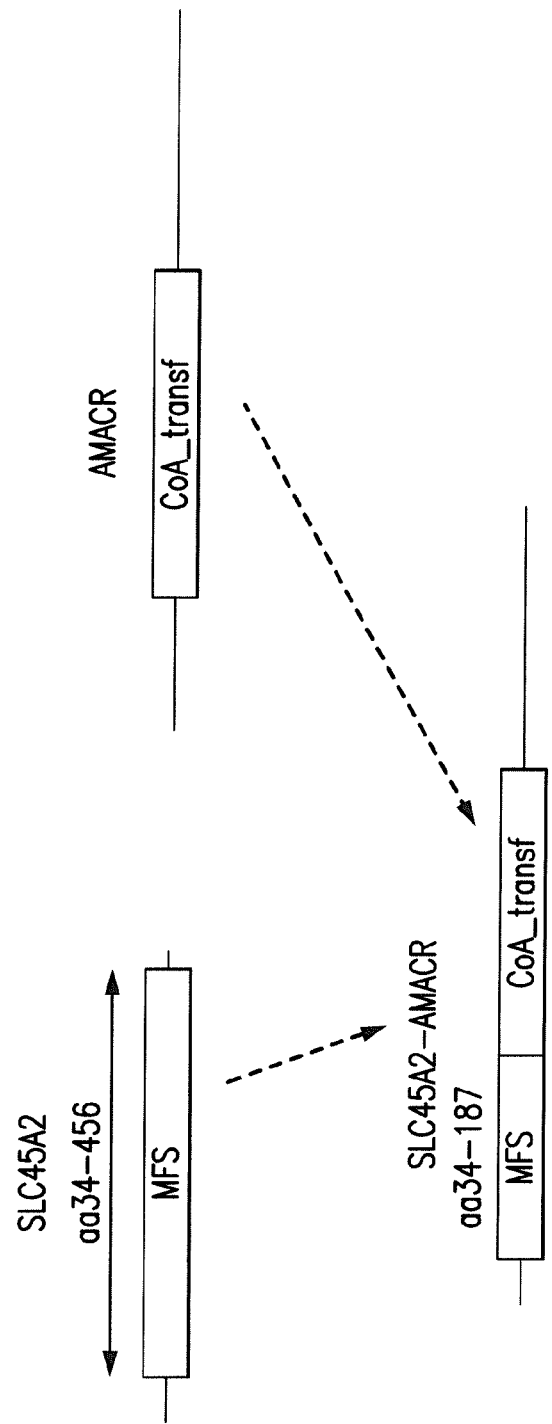

FIG. 12. Schematic diagram of SLC45A2-AMACR chimeric protein. Fusion between SLC45A2 and AMACR results in truncation of two-third of (MFS) domain in SLC45A2, but largely retains CoA-transferase domain of AMACR. SLC45A2-AMACR produces a chimeric protein with the N-terminal 187 amino acids of SLC45A2 and the C-terminal 311 amino acids of AMACR. SLC45A2-AMACR replaces 5 transmembrane and cytosolic domains of SLC45A2 with an intact racemase domain from AMACR, while leaving the extracellular and the N-terminal transmembrane domains intact.

Figure 13A:
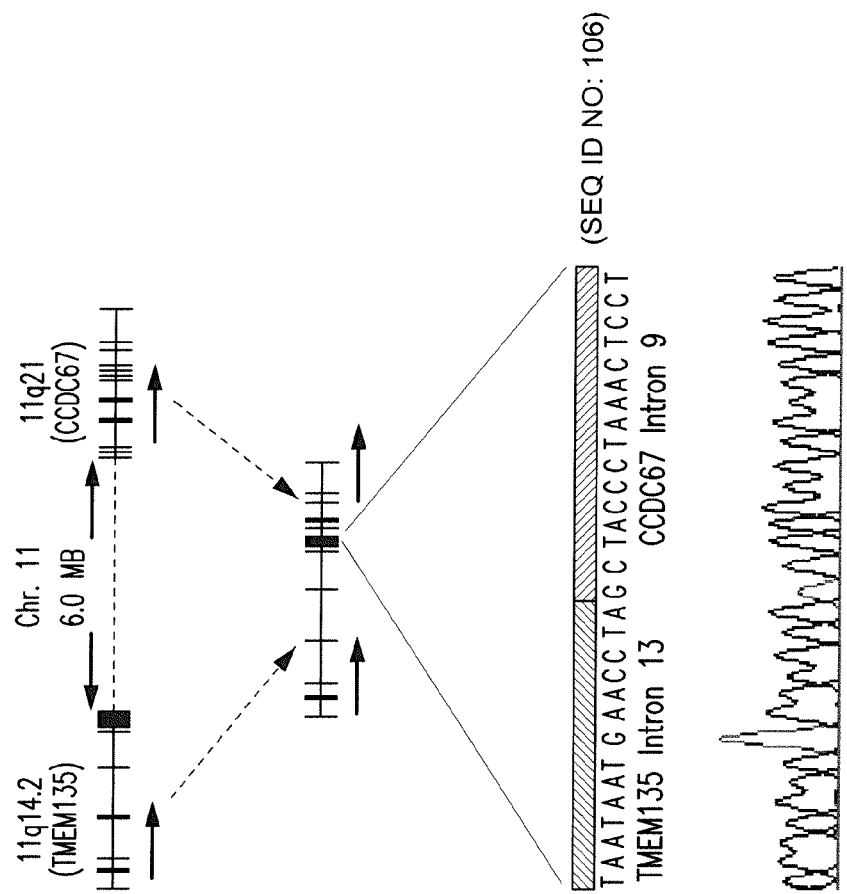
Figure 13B:
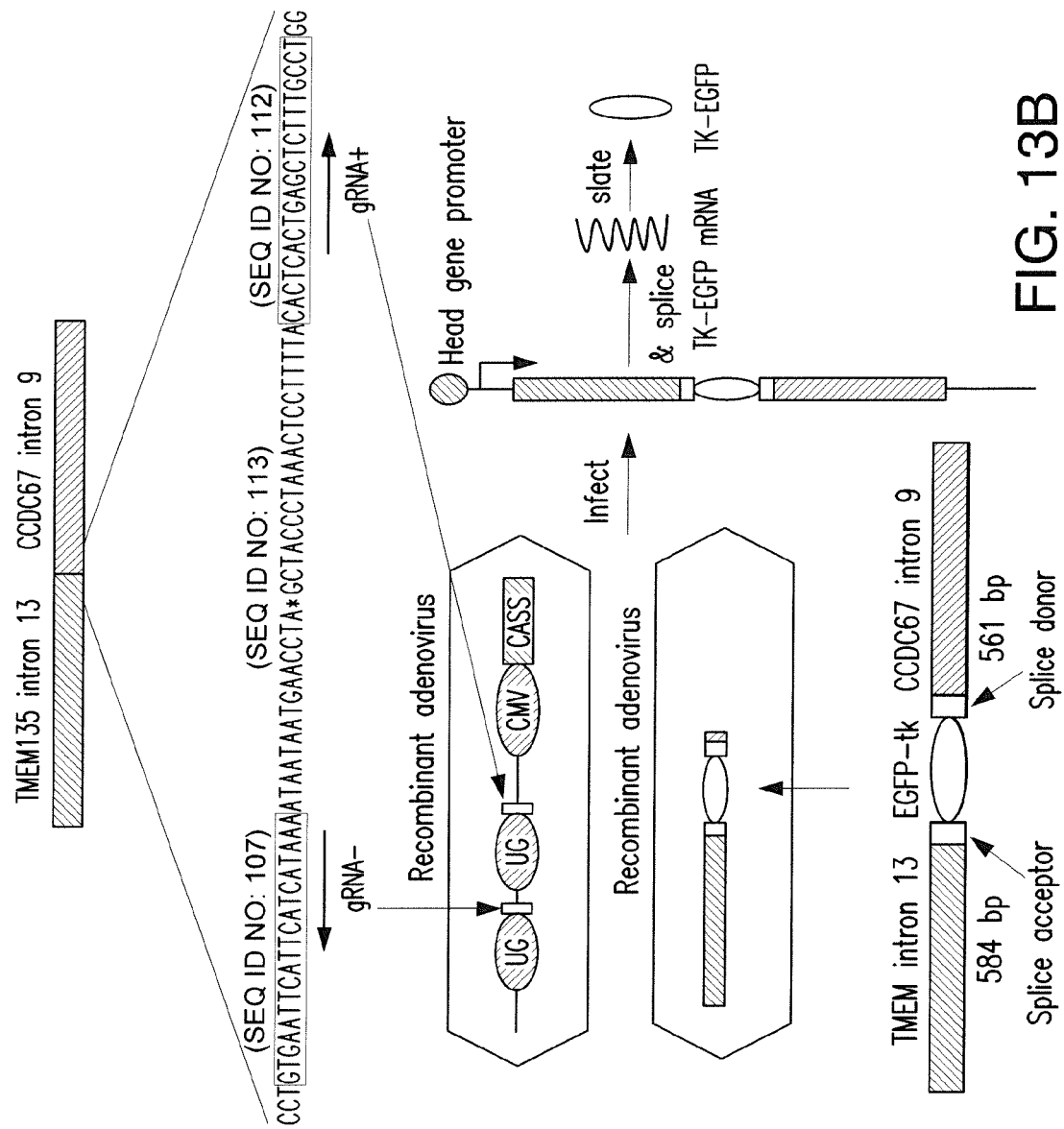
Figure 13C:
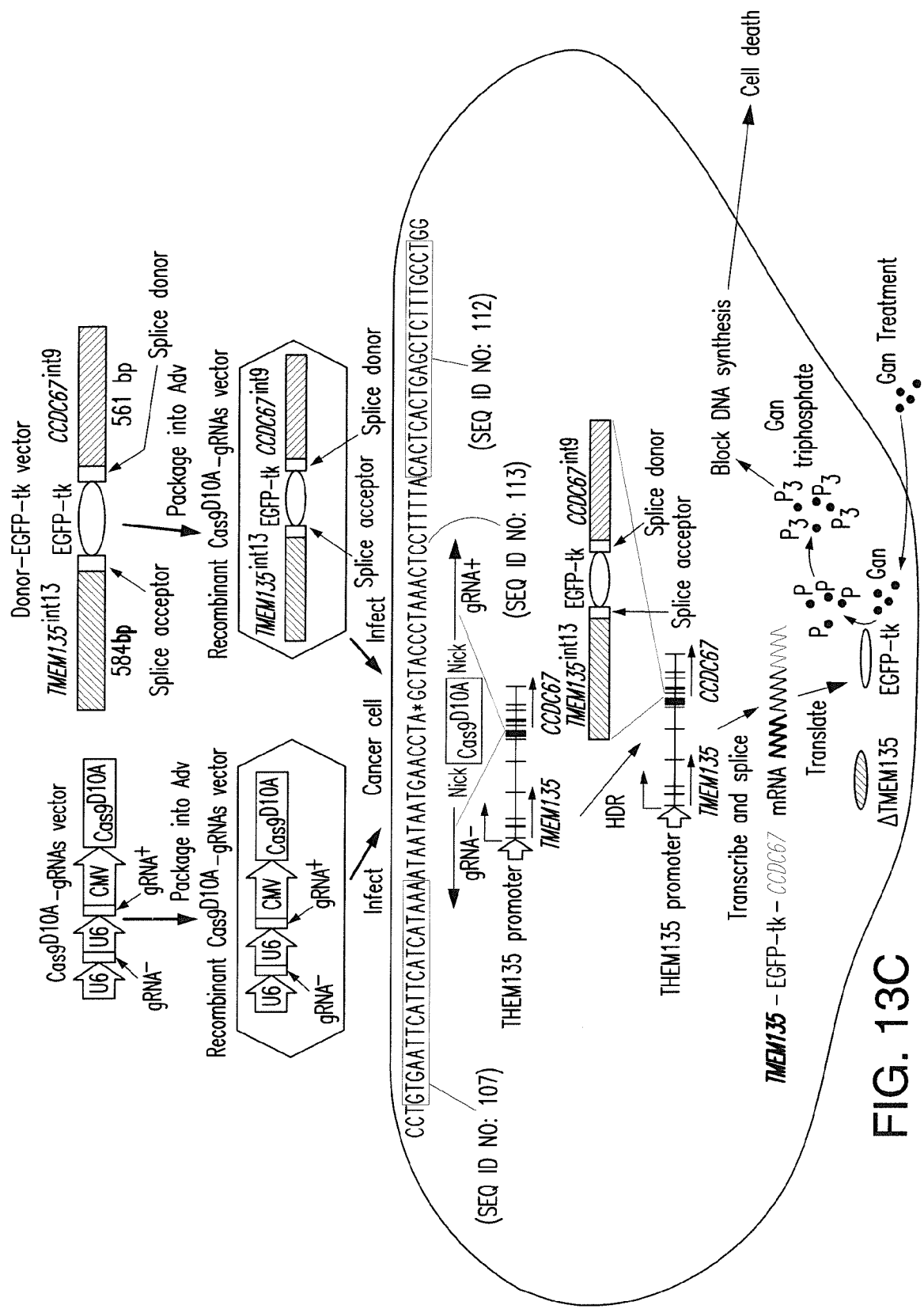

FIG. 13A-C. Schema of strategy to introduce EGFP-tk into the breakpoint of TMEM135-CCDC67 fusion gene. (A) Diagram representation and Sanger sequencing of TMEM135-CCDC67 chromosome breakpoint. Direction of transcription is indicated by the arrows. (B and C) Schematic diagrams of the strategy to introduce EGFP-tk into the breakpoint of TMEM135-CCDC67. The locations of gRNA- and gRNA+ are indicated by boxes. These gRNAs were ligated with $Cas9^{D10A}$ into VQAd5-CMV shuttle vector and recombined into pAd5 virus. Separately, 584 bp of TMEM135 intron 13 sequence and 561 bp of CCDC67 intron 9 sequence were designed to sandwich a promoterless EGFP-tk cDNA, ligated into PAdlox shuttle vector and recombined into adenovirus. A splice acceptor and a splice donor from exon 14 of TMEM135 were inserted between TMEM intron 13 and EGFP-tk, and between EGFP-tk and CCDC67 intron 9, respectively, to allow proper EGFP-tk RNA splicing to occur. Cells containing TMEM135-CCDC67 chromosome breakpoint were infected with these recombinant viruses. The integrated EGFP-tk was transcribed by the fusion head gene promoter in these cells, spliced and translated into protein product of EGFP-tk, which in turn blocks DNA synthesis by converting ganciclovir to ganciclovir triphosphate.

Figure 14:
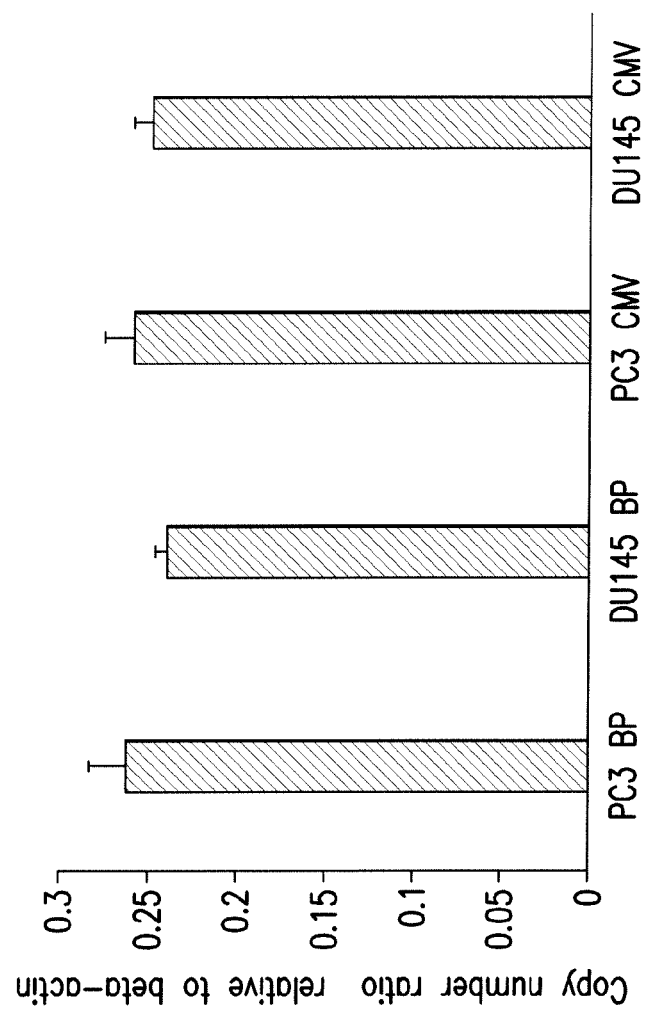

FIG. 14. qPCR to quantify the relative copy number of TMEM135-CCDC67 breakpoint and pCMV vector sequence in the genome of transformed prostate cancer cells. One microgram of genomic DNA of PC3 BP (PC3 cells transformed with pCMV-TMEM135$^{int13}$-CCDC67$^{int9}$), or DU145 BP (DU145 cells transformed with pCMV-TMEM135$^{int13}$-CCDC67$^{int9}$), or PC3 CMV (PC3 cells transformed with pCMVscript) or DU145 CMV (DU145 cells transformed with pCMVscript) was quantified for β-actin or the TMEM135-CCDC67 breakpoint through qPCR using the primers listed in Table 2. The copy numbers of BP and β-actin were fitted with standard curves generated with serial titrations of known copy numbers of BP and β-actin, respectively. The BP/β-actin ratios were plotted.

FIG. 15A-I. Genome therapy targeting at MAN2A1-FER breakpoint. (A) Design of gRNA and recombination donor adenoviruses for MAN2A1-FER fusion gene. Upper panel: Sanger sequencing diagram of MAN2A1-FER chromosome breakpoint of HUH7 cells; Middle panel: Design of gRNA for pAD5-Cas9$^{D10A}$-gRNAMAN2A1$^{int13}$-gRNAFER$^{int14}$; Lower panel: Design of homologous DNA sequences and EGFP-tk for pAD-MAN2A1$^{int13}$-EGFP-tk-FER$^{int14}$. The splicing acceptor and donor sequences correspond to the juncture sequences of intron13-exon 14 of MAN2A1 and exon15-intron 15 of FER. (B) Expression of MAN2A1-FER in HUH7 cells. Lanes 1 and 2: immunoblots of protein extracts from HUH7 and HEP3B cells with antibodies specific for FER or GAPDH. MAN2A1-FER (MF) and FER protein are indicated. Lanes 3 and 4: RT-PCR of RNA from HUH7 and HEP3B cells with primers specific for MAN2A1-FER (MF) or β-actin. (C) In vitro cleavage assays were performed on BamH1 linearized pTAMAN2A1int13-FERint14 vector using recombinant Cas9, S. pyogenes and in vitro transcribed gRNA- or gRNA+ as indicated. The cleavage generated 2446 and 1944 bp fragments of pTAMAN2A1$^{int13}$-FER$^{int14}$ vector for gRNA-, and 2484 and 1906 bp for gRNA+. (D) Infection of HUH7 or HEP3B cells led to expression of EGFP-tk in HUH7 but not HEP3B cells. HUH7 and HEP3B cells were infected with pAD5-Cas9D10A-gRNAMAN2A1$^{int13}$-gRNAFER$^{int14}$ (Ad-MF) and pAD-MAN2A1$^{int13}$-EGFP-tk-FER$^{int14}$ (Ad-MF-EGFP-tk). Expression of Cas9$^{D10A}$-RFP is indicated by red fluorescence, while expression EGFP-tk is indicated by green. HUH7 cells infected with pAD5-Cas9D10A-gRNATMEM135$^{int13}$-gRNACCDC67$^{int9}$ (Ad-gTC) and pADTMEM135$^{int13}$-EGFP-tk-CCDC67$^{int9}$ (Ad-TC-EGFP-tk) were used as specificity control. (E) Quantification of EGFP-tk integration/expression by flow cytometry. (F) Killing of HUH7 cells with ganciclovir. HUH7 or HEP3B cells were infected with pAD5-Cas9D10A-gRNAMAN2A1$^{int13}$-gRNAFER$^{int14}$/pAD-MAN2A1$^{int13}$-EGFP-tk-FER$^{int14}$ (Ad-MF). These cells were then incubated with various concentrations of ganciclovir for 24 hours. Cell deaths were then quantified with phycoerythrin labeled Annexin V through flow cytometer. HUH7 cells infected with pAD5-Cas9$^{D10A}$-gRNATMEM135$^{int13}$-gRNACCDC67$^{int9}$/pAD-TMEM135$^{int13}$-EGFP-tk-CCDC67$^{int9}$ (Ad-TC) were used as specificity controls. (G) HUH7 and HEP3B cells were xenografted into the subcutaneous regions of SCID mice. These tumors were allowed to grow for 2 weeks before the treatment. These mice were treated with the indicated viruses plus ganciclovir (G, 80 mg/kg) or PBS (P). The indicated drugs were applied through peritoneal injections 3 times a week until all the mice from control treatments died off. The tumor volumes were measured weekly. (H) Mice treated with MAN2A1-FER breakpoint therapy are free of cancer metastasis. (I) Mice treated MAN2A1-FER breakpoint therapy had no mortality.

Figure 16A:
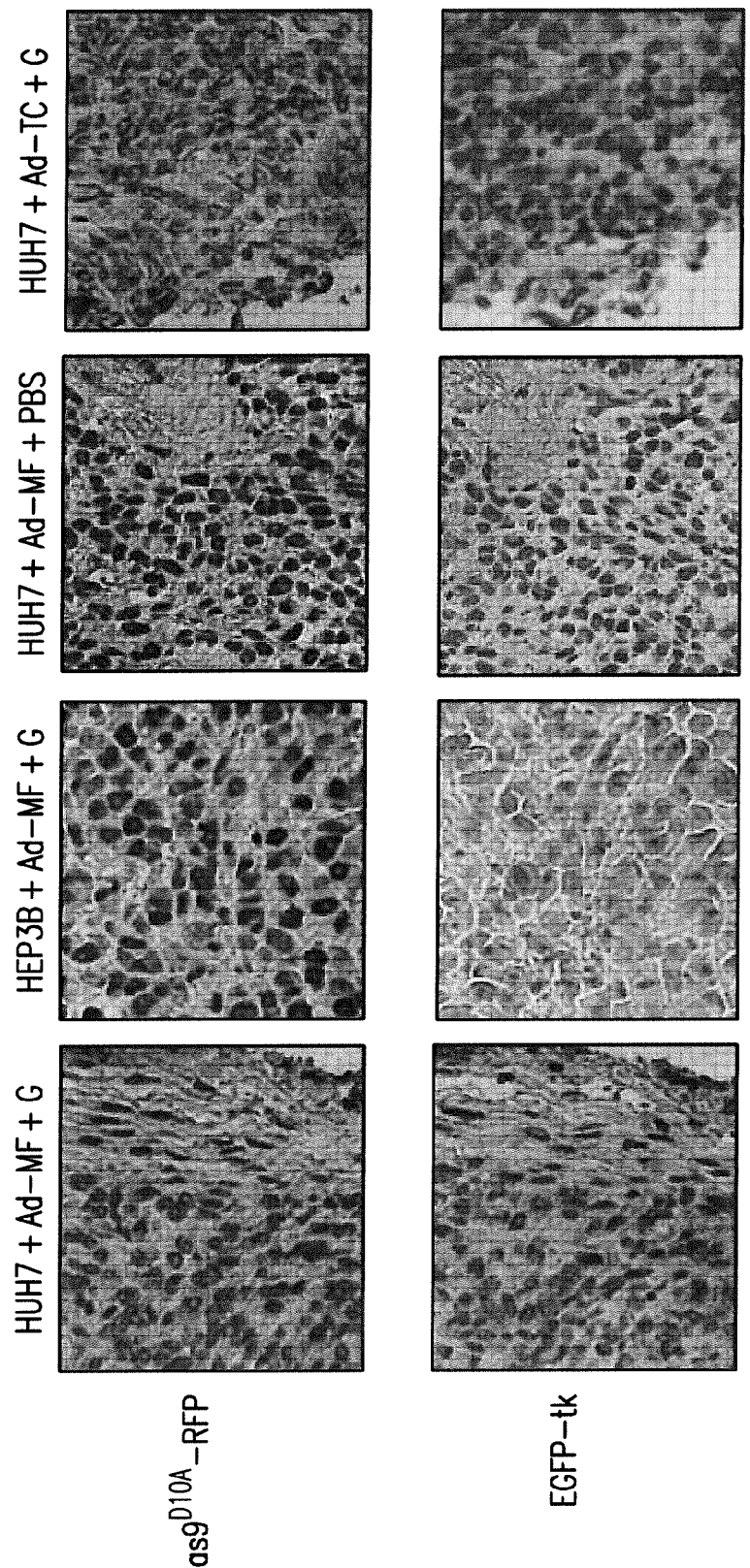
Figure 16B:
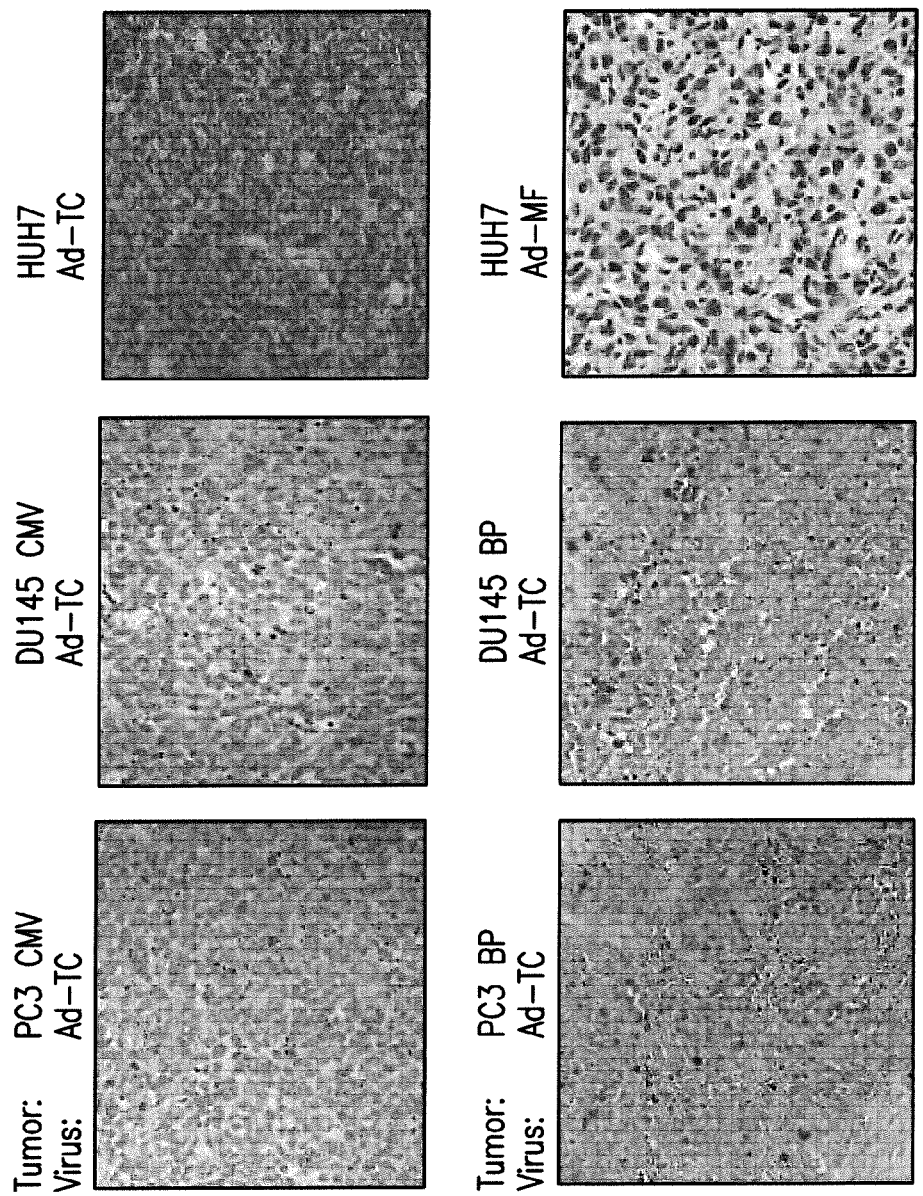

FIG. 16A-B. (A) Expression of Cas9$^{D10A}$ and HSV1-tk in HUH7 or HEP3B tumors treated with Ad-TC or pAD5-Cas9$^{D10A}$-gRNAMAN2A1$^{int13}$-gRNAFER$^{int14}$/pAD-MAN2A1$^{int13}$-EGFP-tk-FER$^{int14}$ (Ad-MF). Green arrows indicate unstained mouse stromal cells. (B) Genome therapy induced apoptosis of xenografted cancers that contain fusion gene breakpoints. Terminal deoxynucleotidyl transferase (TdT) dUTP Nick-End Labeling (TUNEL) assays were performed on the PC3 BP, DU145 BP, PC3 CMV, DU145 CMV, or HUH7 xenografted cancers treated with either Ad-TC or Ad-MF.

Figure 17A:
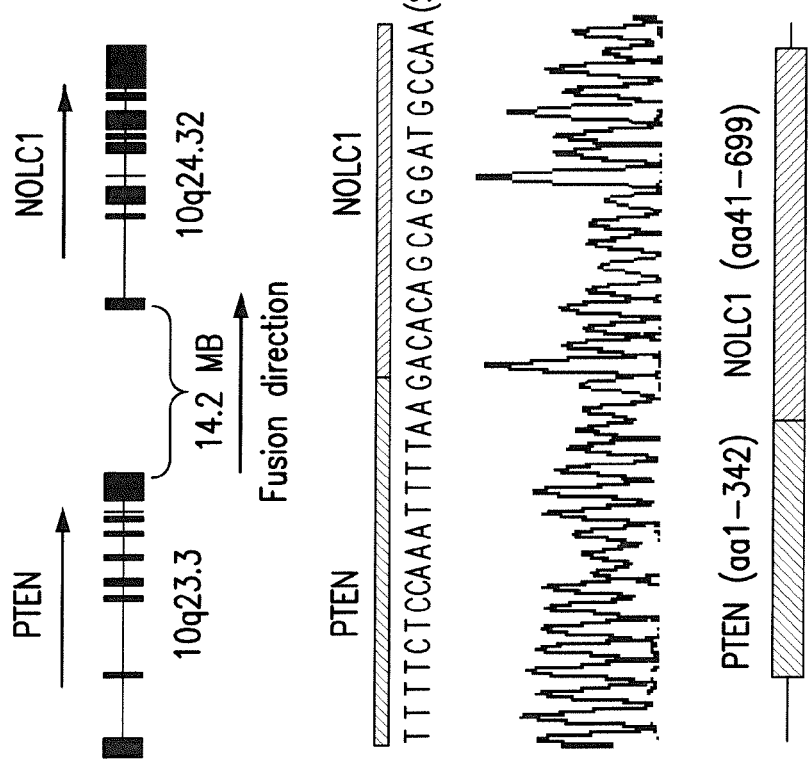
Figure 17B:
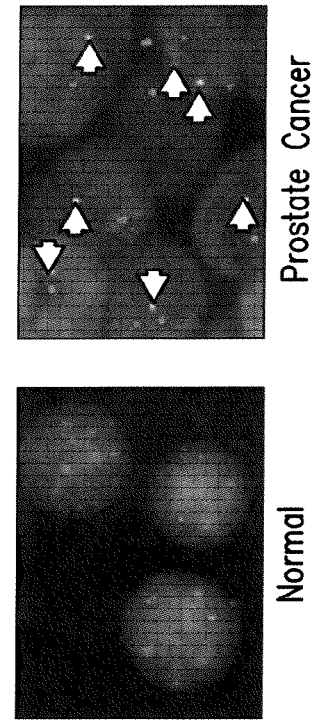
Figure 17C:
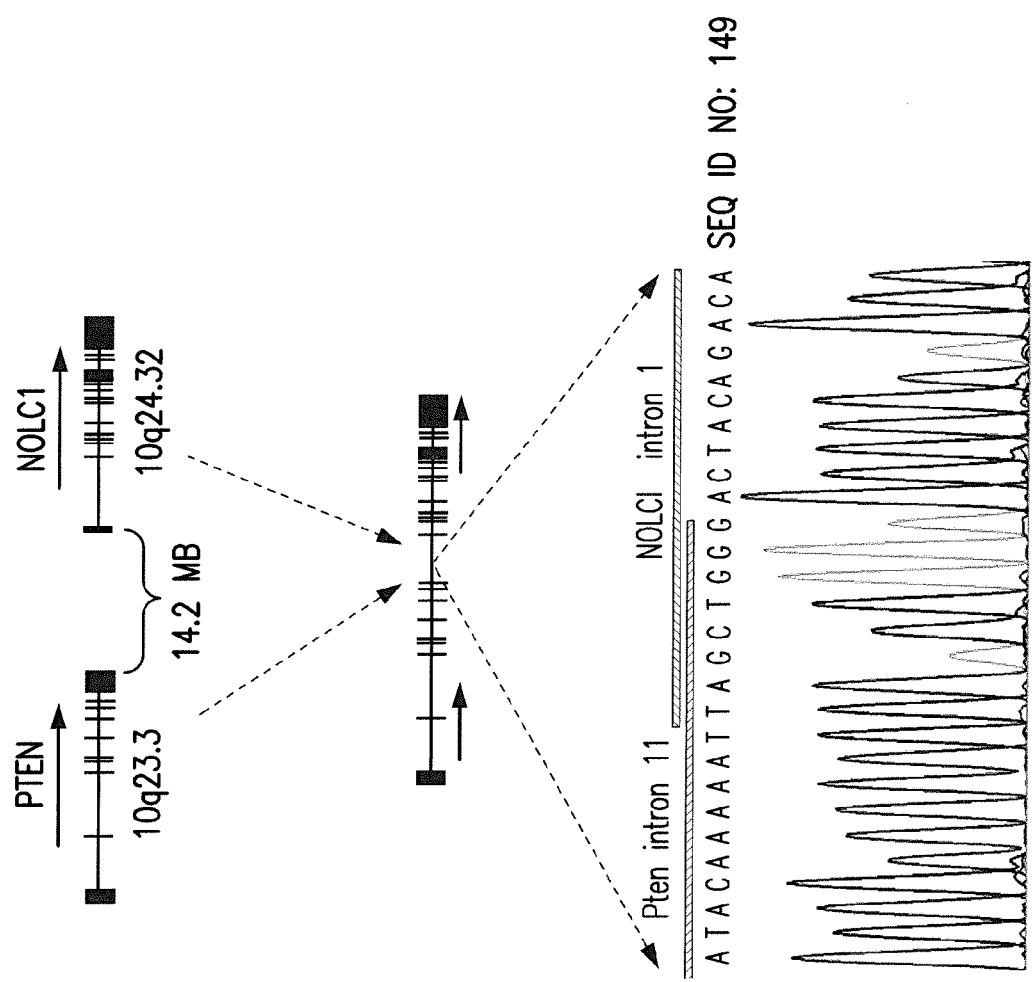

FIG. 17A-C. Pten-NOLC1 fusion. (A) Schematic diagram of Pten-NOLC1 fusion. Top panel: Miniature diagrams of the genome of the fusion gene, the transcription direction, the distance between the joining gene and direction of the fusions. Middle panel: Representative sequencing chromogram of fusion transcript. The joining gene sequences were indicated. Lower panel: Diagrams of translation products of Pten-NOLC1 fusion transcript. Blue-head gene translation product; Red-tail gene translation product. (B) Fluorescence in situ hybridization indicates genome recombination in prostate cancer cells. Schematic diagram of Pten and NOLC1 genome recombination and FISH probe positions. Representative FISH images were shown for normal prostate epithelial cells and cancer cells positive for Pten-NOLC1 fusion. Orange denotes probe 1; Green denotes probe 2. Fusion signals are indicated by green arrows. (C) Genome breakpoint analysis of Pten-NOLC1 fusion. Top panel: Miniature diagrams of the genome of the fusion genes, the transcription directions, the distances between the joining genes and directions of the chromosome joining. Middle panel: Miniature of fusion genome and transcription direction. Bottom panel: Representative sequencing chromogram encompassing the joining breakpoint of chromosomes. Intron 11 of Pten (blue) and intron 1 (red) of NOLC1 are indicated.

Figure 18:
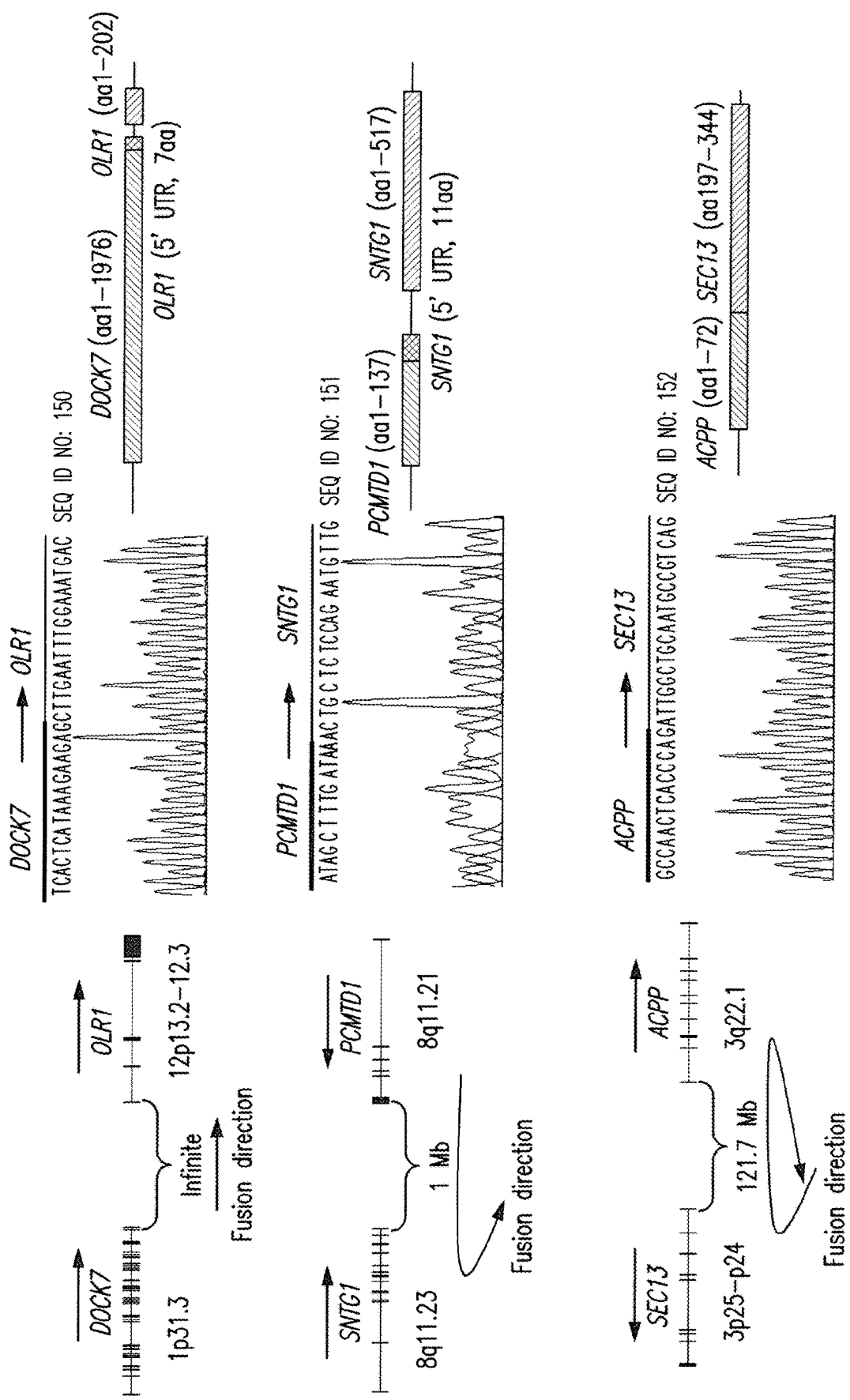
Figure 18:
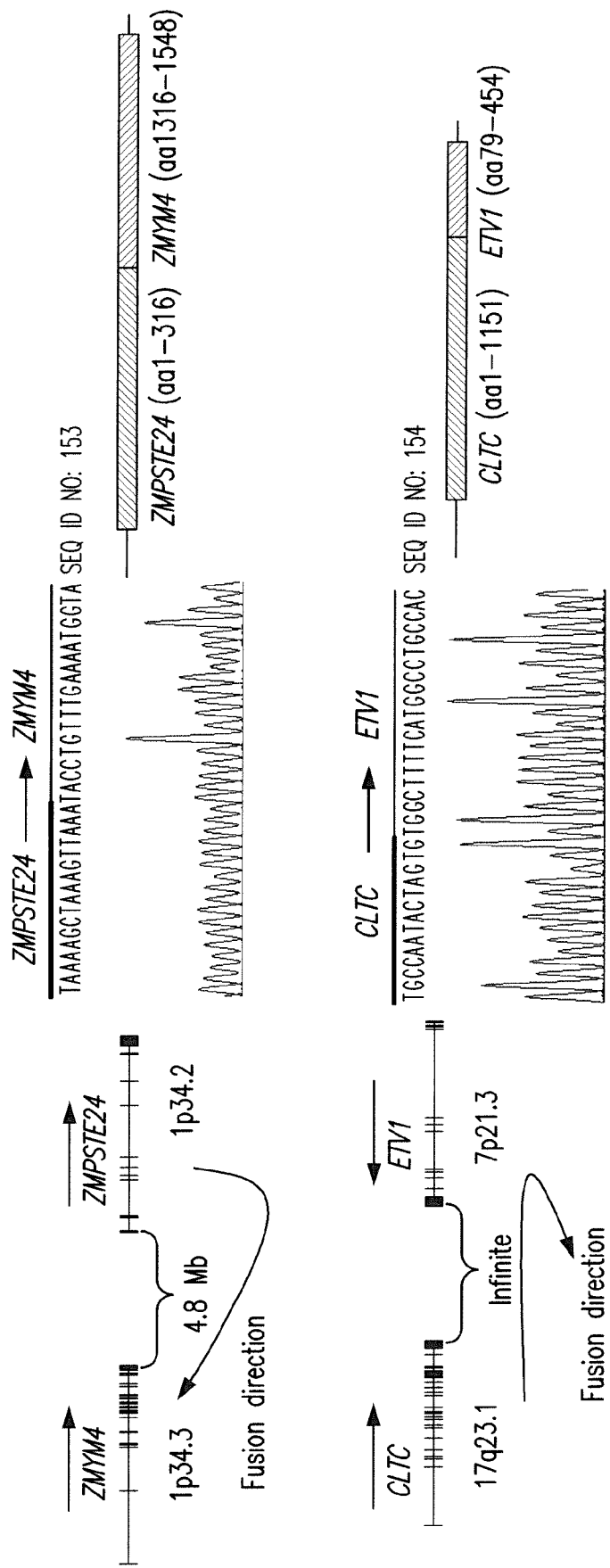
Figure 19B:
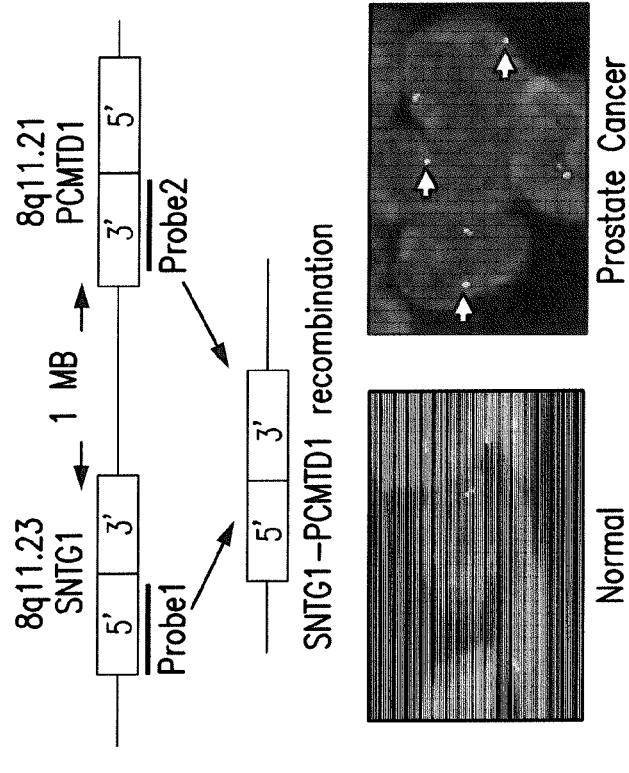
Figure 19A:
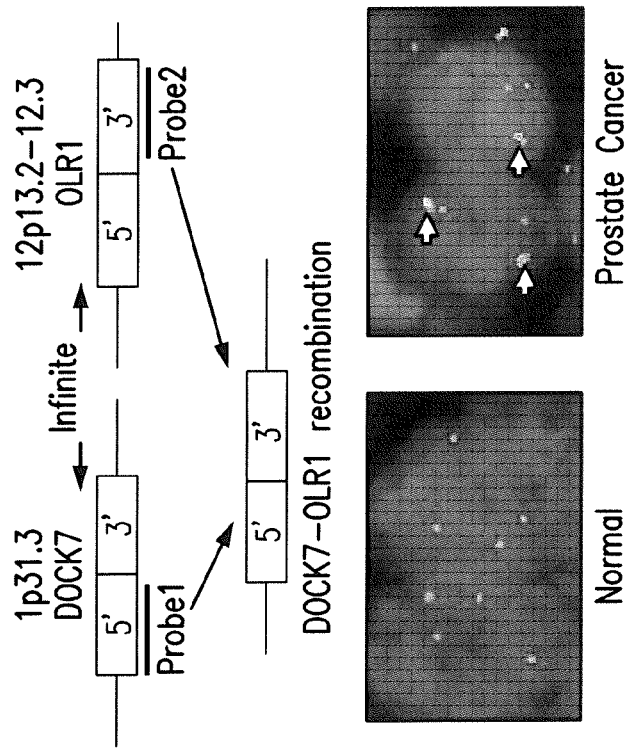
Figure 19D:
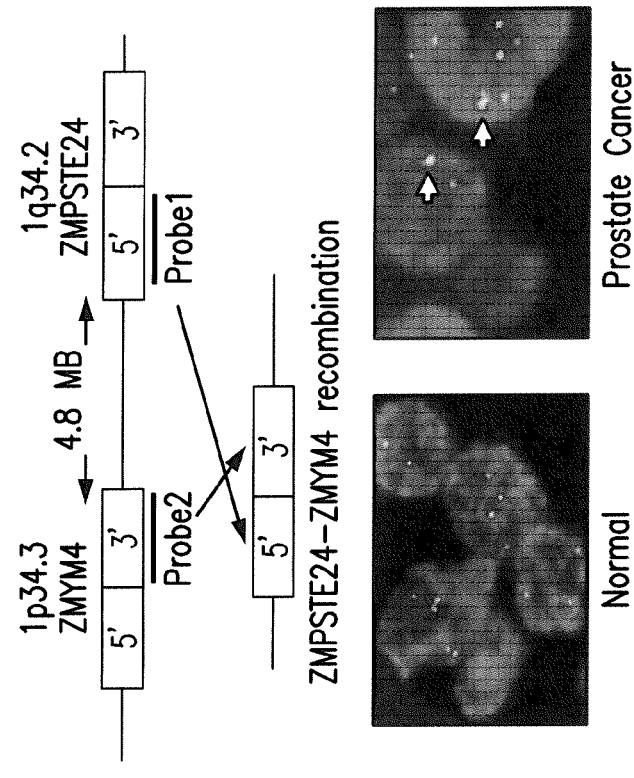
Figure 19C:
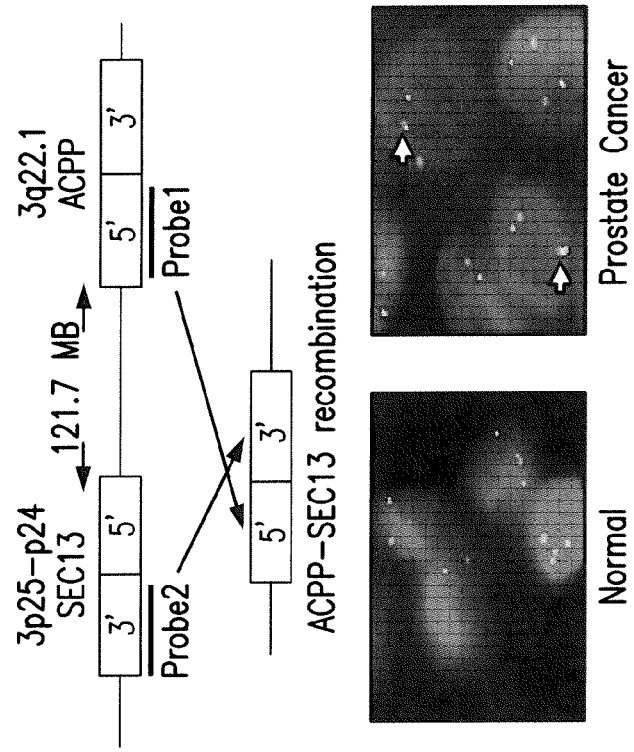
Figure 19E:
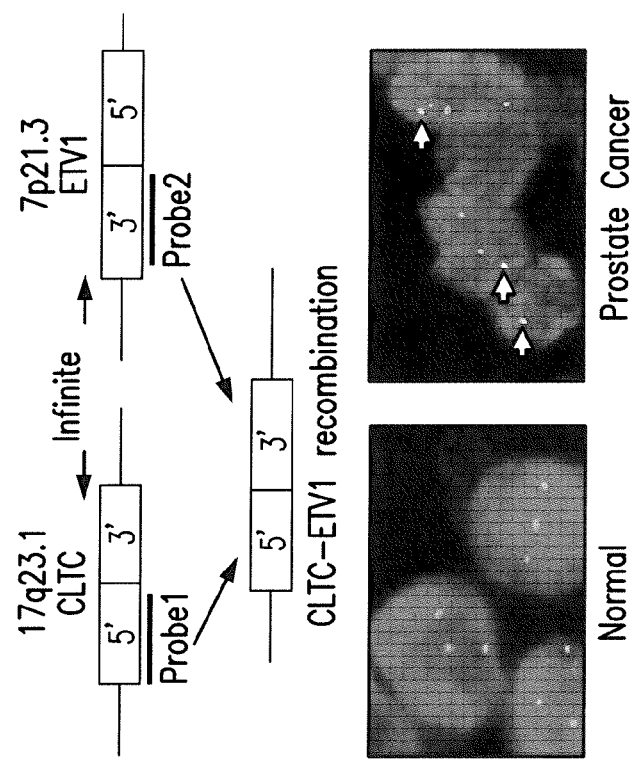

FIG. 18. Unique fusion gene events. Left panel: Miniature diagrams of genome of the fusion genes, the transcription directions, the distances between the joining genes and directions of the fusions. Middle panel: Representative sequencing chromograms of fusion transcripts. The joining gene sequences were indicated. Right panel: Diagrams of translation products of fusion transcripts. Blue-head gene translation product; Red-tail gene translation product; Orange-novel translation products due to frameshift or translation products from a non-gene region.

FIG. 19A-E. Fluorescence in situ hybridization suggests genome recombination in prostate cancer cells. (A) Schematic diagram of DOCK7 and OLR1 genome recombination and FISH probe positions. Representative FISH images were shown for normal prostate epithelial cells and cancer cells positive for DOCK7-OLR1 fusion. Orange denotes probe 1; Green denotes probe 2. Fusion joining signals are indicated by green arrows. (B) Schematic diagram of SNTG1 and PCMTD1 genome recombination and FISH probe positions. Representative FISH images were shown for normal prostate epithelial cells and cancer cells positive for SNTG1-PCMTD1 fusion. Orange denotes probe 1; Green denotes probe 2. Fusion joining signals are indicated by green arrows. (C) Schematic diagram of ACPP and SEC13 genome recombination and FISH probe positions. Representative FISH images were shown for normal prostate epithelial cells and cancer cells positive for ACPP-SEC13 fusion. Orange denotes probe 1; Green denotes probe 2. Fusion joining signals are indicated by green arrows. (D) Schematic diagram of ZMPSTE24 and ZMYM4 genome recombination and FISH probe positions. Representative FISH images were shown for normal prostate epithelial cells and cancer cells positive for ZMPSTE24-ZMYM4 fusion. Orange denotes probe 1; Green denotes probe 2. Fusion joining signals are indicated by green arrows. (E) Schematic diagram of CLTC and ETV1 genome recombination and FISH probe positions. Representative FISH images were shown for normal prostate epithelial cells and cancer cells positive for CLTC-ETV1 fusion. Orange denotes probe 1; Green denotes probe 2. Fusion joining signals are indicated by green arrows.

Figure 20A:
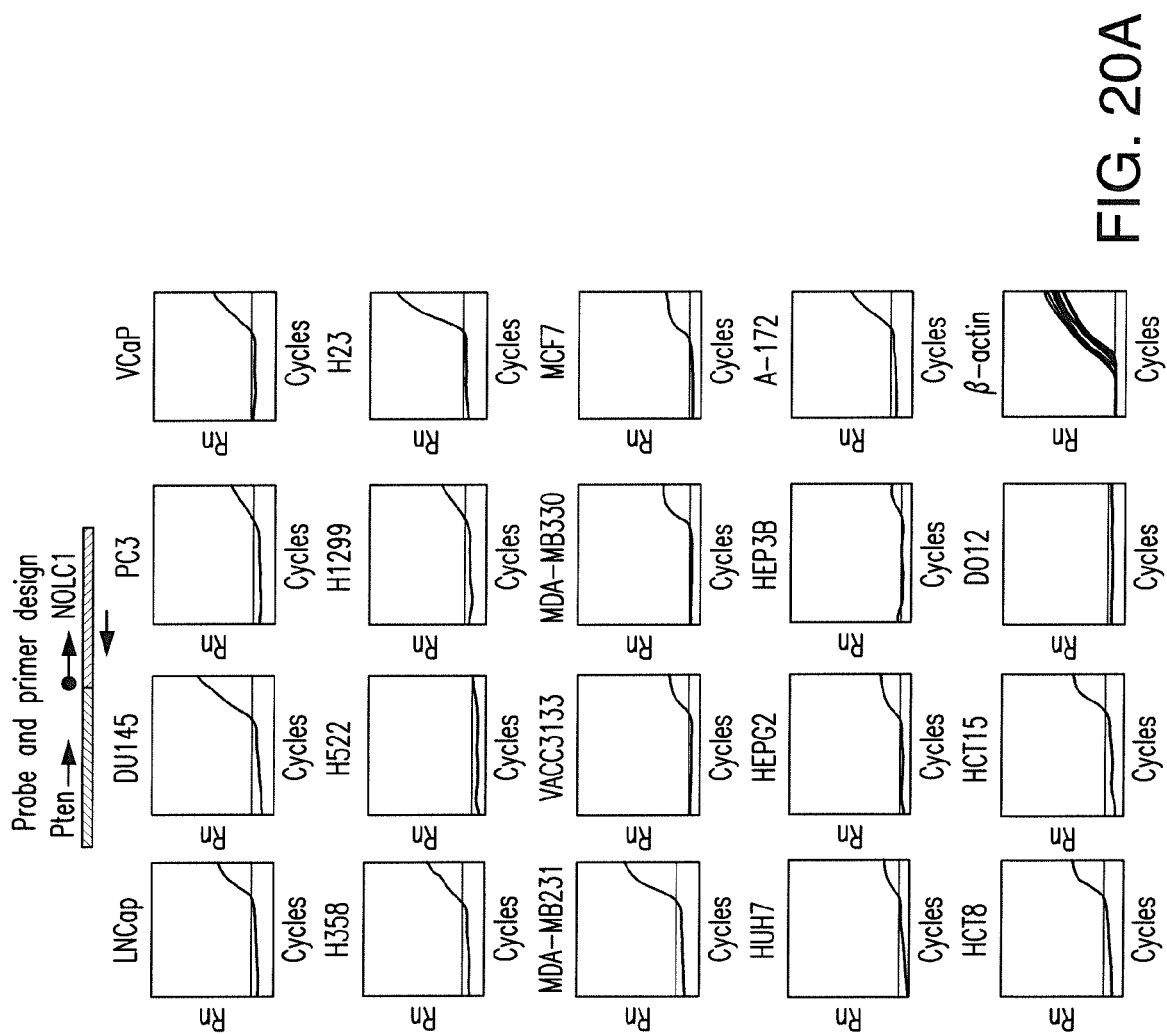
Figure 20B:
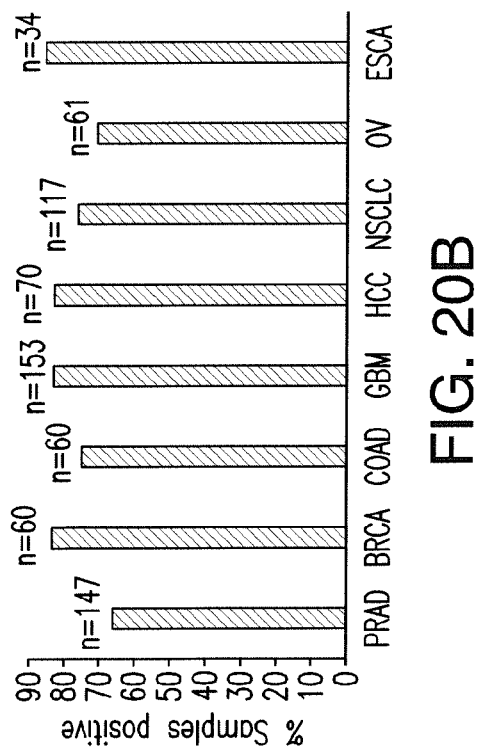
Figure 20C:
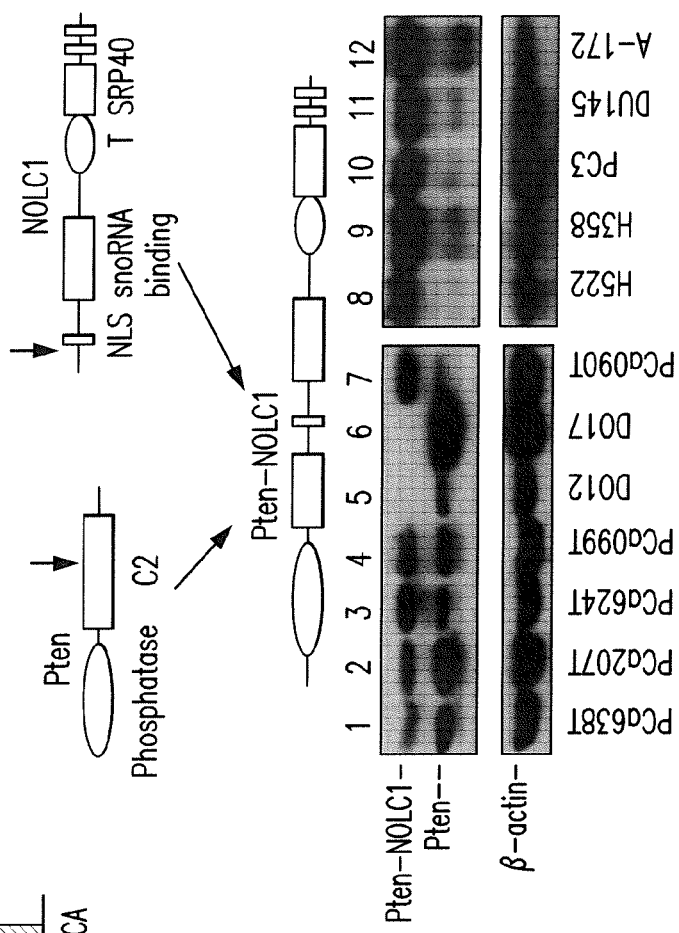

FIG. 20A-C. Pten-NOLC1 in human cancers. (A) Taqman qRT-PCR to detect Pten-NOLC1 in human cancer cell lines and a healthy organ donor prostate sample. (B) The frequency of Pten-NOLC1 in primary human cancers. (C) Expression of Pten-NOLC1 protein. Upper panel: diagram of functional domains of Pten and NOLC1 protein as well as Pten-NOLC1 fusion protein. Truncation sites are indicated by arrows. NLS denotes nuclear localization signal; SRP40 denotes homolog domain to C-terminus of the S. cerevisiae SRP40 protein; snoRNA binding denotes binding site for small nucleolus RNA; T denotes serine-rich sequence homologous to HSV1 transcription factor ICP4. Lower panel: Immunoblotting of Pten and Pten-NOLC1 proteins from primary prostate cancer samples (PCa638T, PCa207T, PCa624T, PCa099T and PCa090T) or healthy organ donor prostate samples (DO12 and DO17), or the indicated cell lines (lanes 8-12).

Figure 21A:
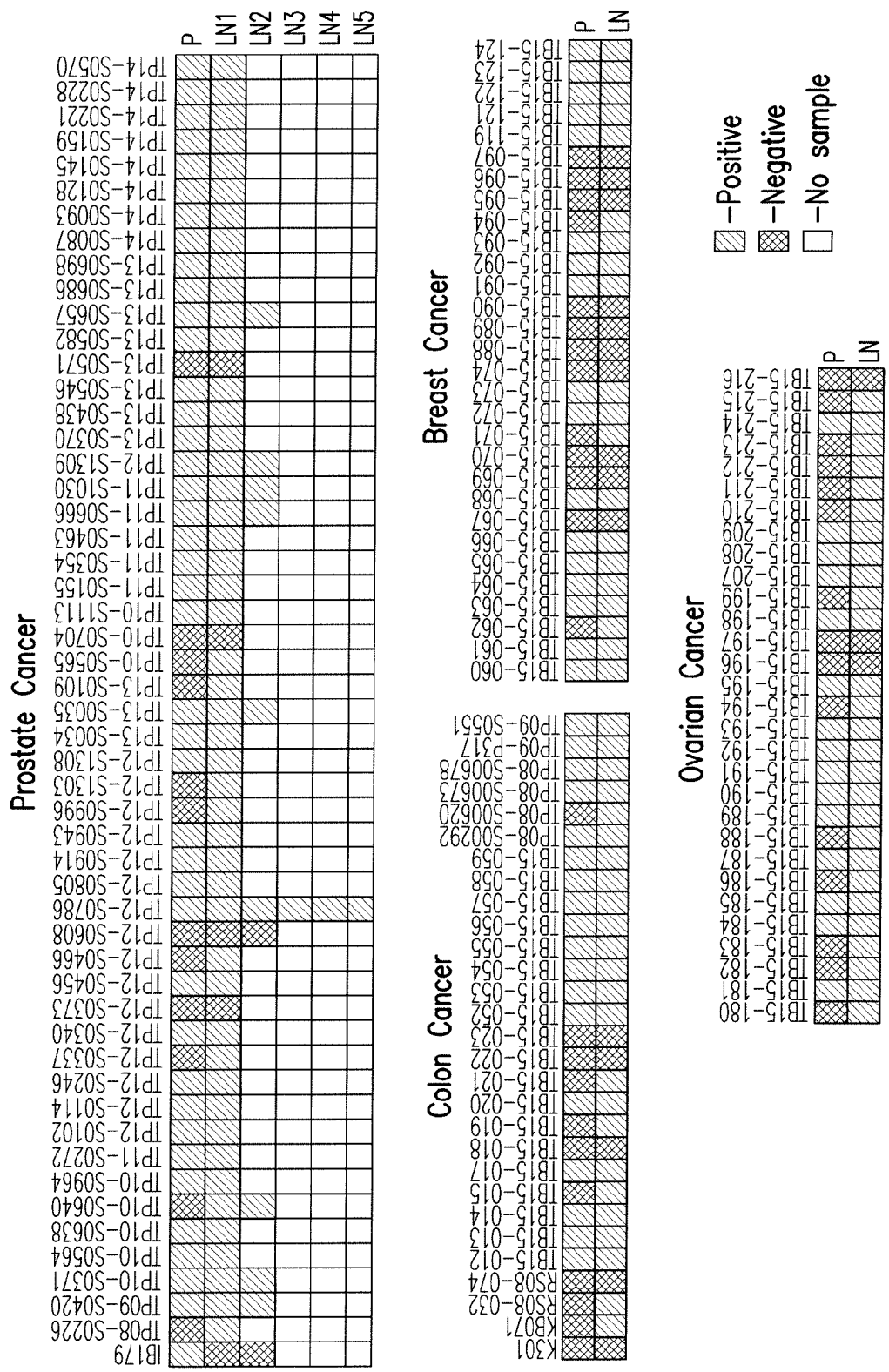
Figure 21B:
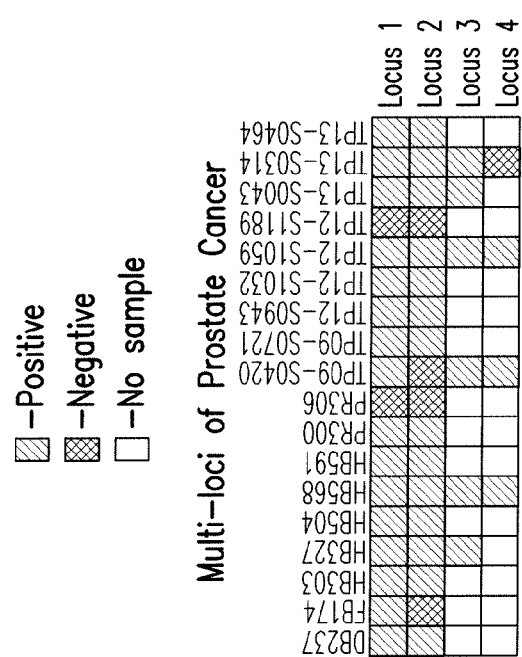

FIG. 21A-B. Pten-NOLC1 in metastasis and multiple loci of human cancers. (A) Pten-NOLC1 in primary cancers (P) and its matched lymph node metastases (LN). Red—positive; Grey—negative; Blank—no sample. (B) Pten-NOLC1 is present in most prostate cancer loci. Red—positive; Grey—negative; Blank—no sample.

Figure 22A:
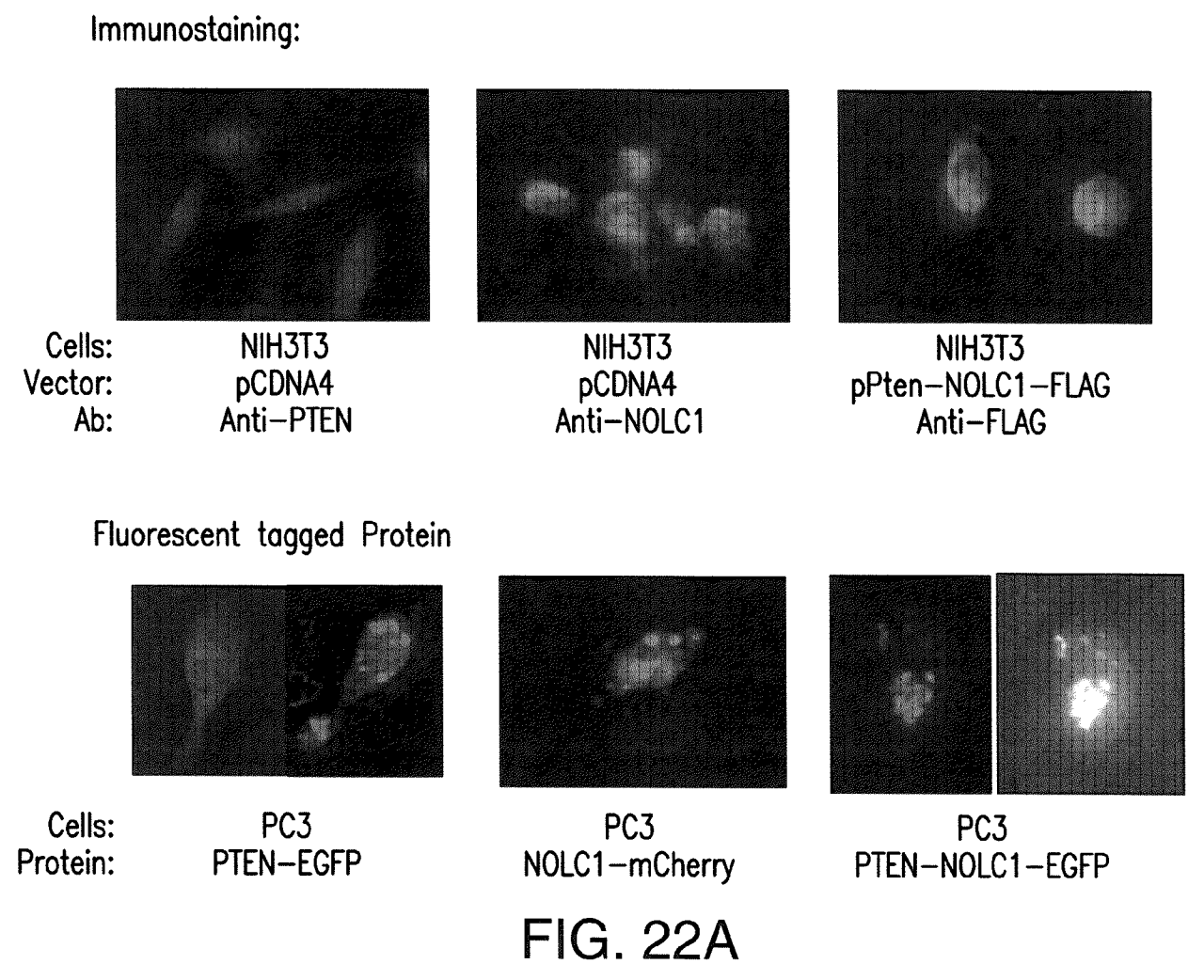
Figure 22C:
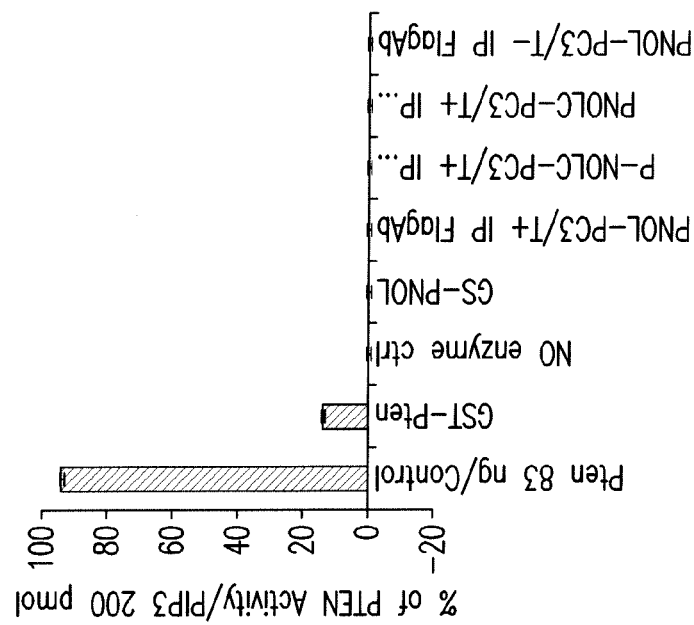
Figure 22B:
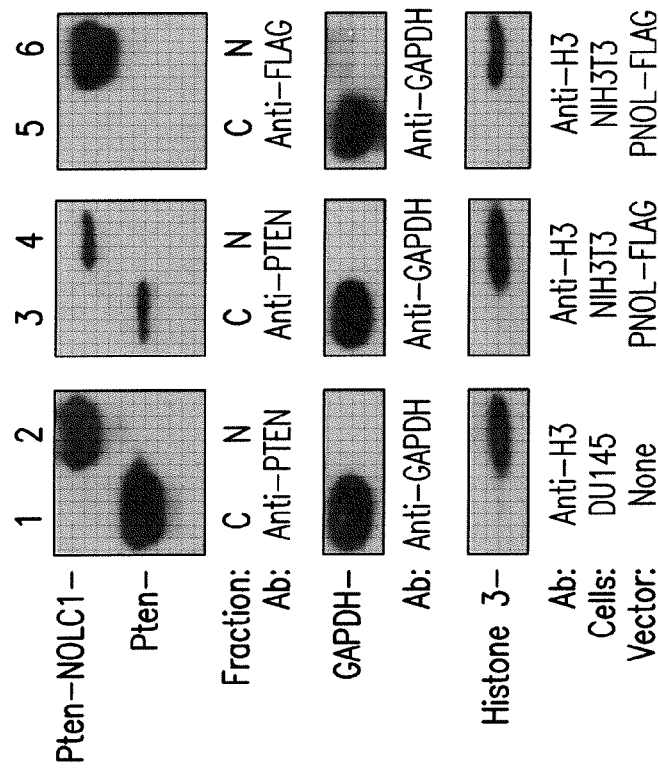

FIG. 22A-C. Pten-NOLC1 is translocated to the nucleus and lacks lipid phosphatase activity. (A) Immunofluorescence analyses of Pten, NOLC1 and Pten-NOLC1 in NIH3T3 and PC3 cells. Top panel: Immunostaining of Pten (left), NOLC1 (middle) and Pten-NOLC1-FLAG (right) in NIH3T3 cells, using antibodies specific for Pten, NOLC1 or FLAG, respectively. Lower panel: PC3 cells were transfected with pPten-EGFP (left), pNOLC1-mCherry (middle) and pPten-NOLC1-EGFP (right). (B) Immunoblotting of Pten and Pten-NOLC1 in nuclear and cytoplasmic fractions of DU145 cells or NIH3T3 cells transfected with Pten-NOLC1-FLAG (PNOL-FLAG). Immunoblotting using antibodies specific for GAPDH and Histone 3 was used as faction purity controls. (C) Pten-NOLC1 lacks PIP3 phosphatase activity in vitro. GST-Glutamate-S-Transferase; PNOL-Pten-NOLC1; IP-immunoprecipitation; T+-tetracycline induced; Ab-antibodies.

FIG. 23A-I. Pten-NOLC1 promotes cancer cell growth and invasion. (A) Schematic diagram of Pten-NOLC1 knockout strategy. Intron 11 sequence of Pten is indicated by blue, while intron 1 sequence of NOLC1 is indicated by red. pCas9$^{D104}$-EGFP and Pten donor-Zeocin-mCherry-NOLC1 donor vectors were cotransfected into DU145 cells. The images represent the co-expression Cas9$^{D104}$-EGFP and integrated zeocin-mCherry, representing knockout of Pten-NOLC1 in DU145KO1 cells. (B) Taqman quantitative RT-PCR on Pten-NOLC1 knockout DU145 and MCF7 cells. Taqman RT-PCRs for β-actin are for RNA quantity controls. (C) Pten-NOLC1 expression promotes cell entry to S phase. Insets are representative images of BrdU labeling of 10,000 cells of DU145, DU145KO1, MCF7 and MCF7KO1. Triplicates experiments were performed. Standard deviations are indicated. (D) Pten-NOLC1 promotes colony formation. Insets are representative crystal violet staining images of colonies of DU145/DU145KO1 and MCF7/MCF7KO1 cells. Triplicates experiments were performed. Standard deviations are indicated. (E) Pten-NOLC1 promotes resistance to UV-induced cell death. Insets are representative images of annexin V and PI staining of cells after exposure to 175 mj UV irradiation. Triplicates experiments were performed. Standard deviations are indicated. (F) Removal of Pten-NOLC1 reduced cancer cell invasion. Matrigel travers analysis was performed on DU145, DU145KO1 and DU145KO2 cells. Triplicates experiments were performed. Standard deviations are indicated. MCF7 cells fail to migrate through matrigel. (G) Removal of Pten-NOLC1 reduced tumor volume of xenografted DU145 cells. (H) Removal of Pten-NOLC1 reduced incidence of metastasis of xenografted DU145 cancers. (I) Removal of Pten-NOLC1 improves survival of animals xenografted with DU145 cancer.

FIG. 24A-C. Pten-NOLC1 promotes expression of pro-growth genes. (A) Removal of Pten-NOLC1 induced down-regulation of EGFR, VEGFA, GAB1 EREG, AXL and c-MET based on microarray analysis of DU145, DU145KO1 and DU145KO2. (B) Taqman quantitative RT-PCR of EGFR, AXL, EREG, VEGFA, c-MET and GAB1. Relative fold changes to parental DU145 cells are shown. Triplicates experiments were performed. Standard deviations are indicated. (C) Removal of Pten-NOLC1 reduced c-MET and GAB1 protein expression.

FIG. 25A-E. Creation of Pten-NOLC1 generates spontaneous liver cancer. (A) Schematic diagram of the process to delete Pten somatically, and hydrodynamic tail vein injection of pT3-Pten-NOLC1-mCherry/pSB. Insets are representative images of PC3 cells transfected with pT3-Pten-NOLC1-mCherry/pSB. (B) Representative images of livers from mice treated with AAV8-cre and pT3-Pten-NOLC1-mCherry/pSB (right) or treated with AAV8-cre and pT3/pSB (left). (C) Representative histology images of liver cancers from AAV8-cre and pT3-Pten-NOLC1-mCherry/pSB treated mice (right), versus histology images for AAV8-cre and pT3/pSB treated mice (left). (D) High frequency of Ki-67 expression in liver cancer cells. The results are the average of number cells positive for Ki-67 per higher field. Seven fields per sample were counted. (E) Pten-NOLC1 promotes expression of c-MET and GAB1 expression in liver cancer cells.

Figure 26:
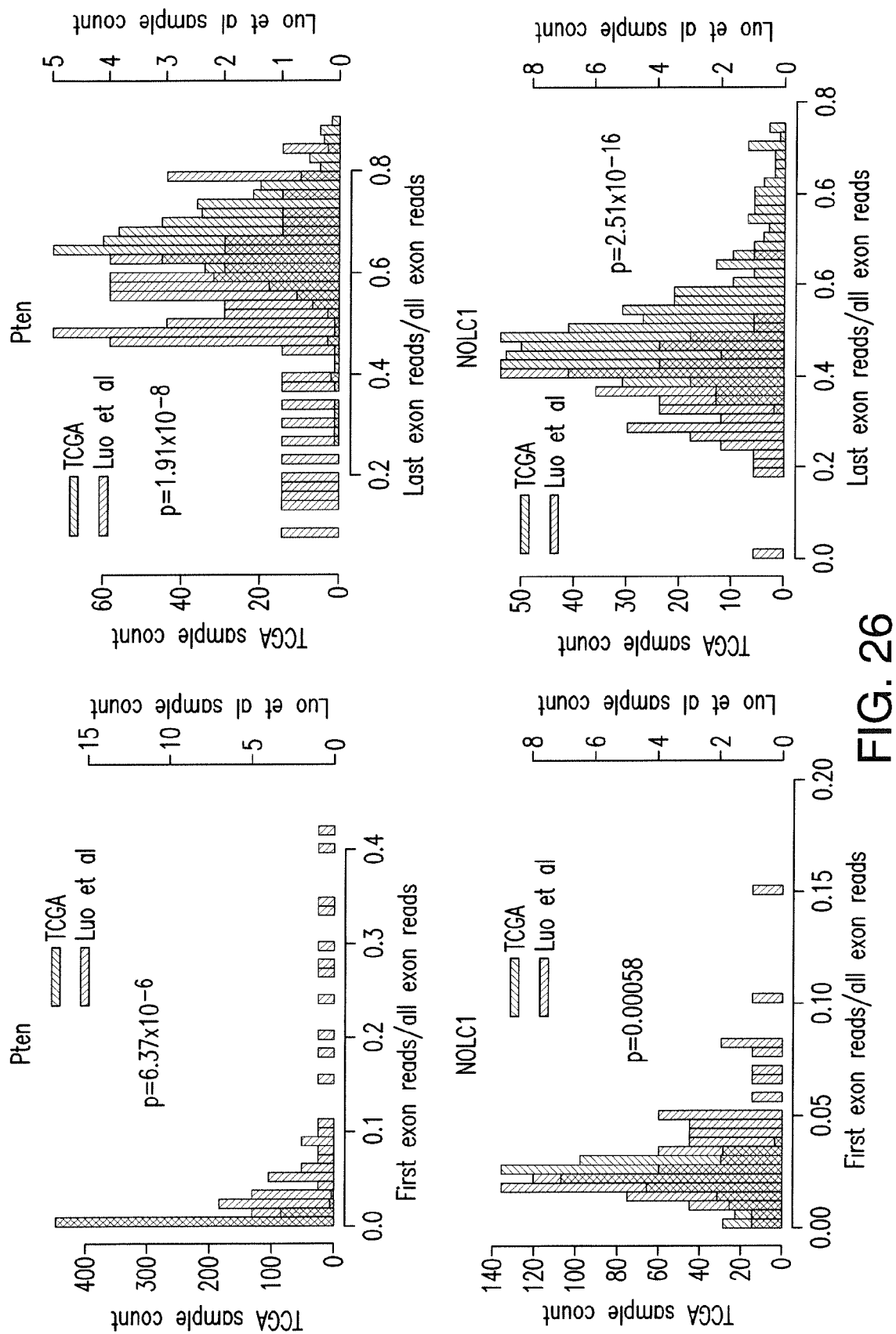

FIG. 26. Transcriptome sequencing read distributions of Pten and NOLC1 genes. The graphs represent distribution of individual sample on the ratio of read counts of first exon to reads of all exons of Pten (top left) or NOLC1 (bottom left) or the ratios of read counts of last exon to reads of all exons of Pten (top right) or NOLC1 (bottom right). Orange-Samples from TCGA data set (550 samples); Blue-Luo et al data set (86 samples). P-values are indicated.

Figure 27A:
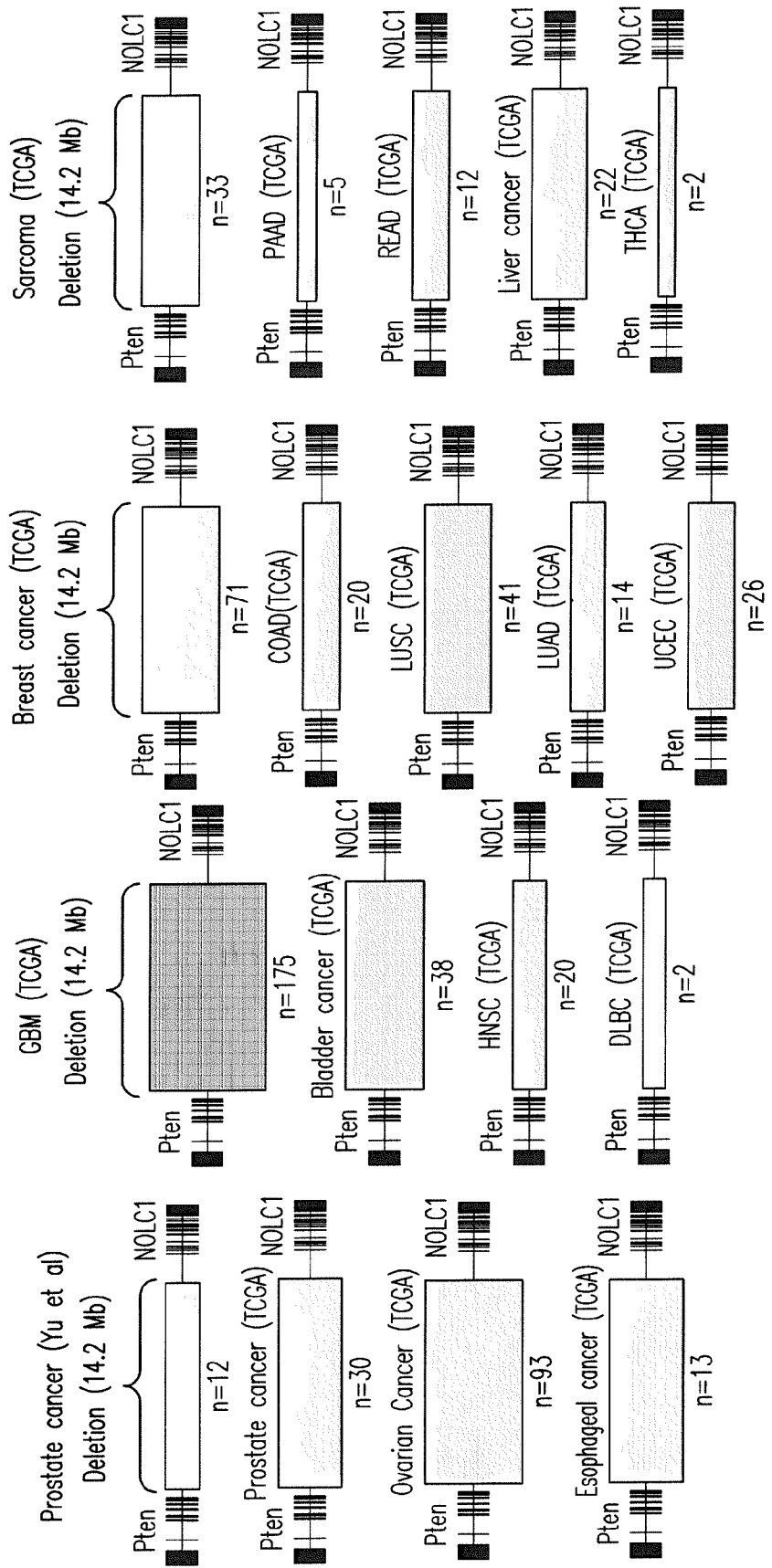
Figure 27C:
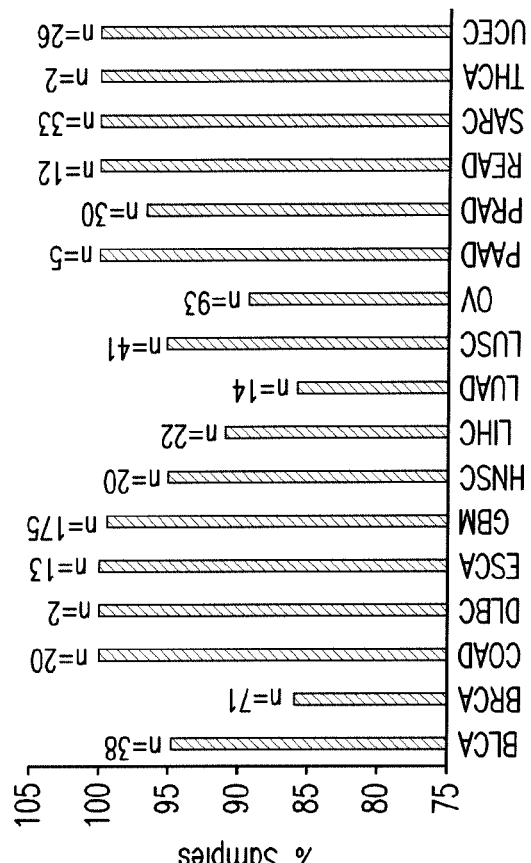
Figure 27B:
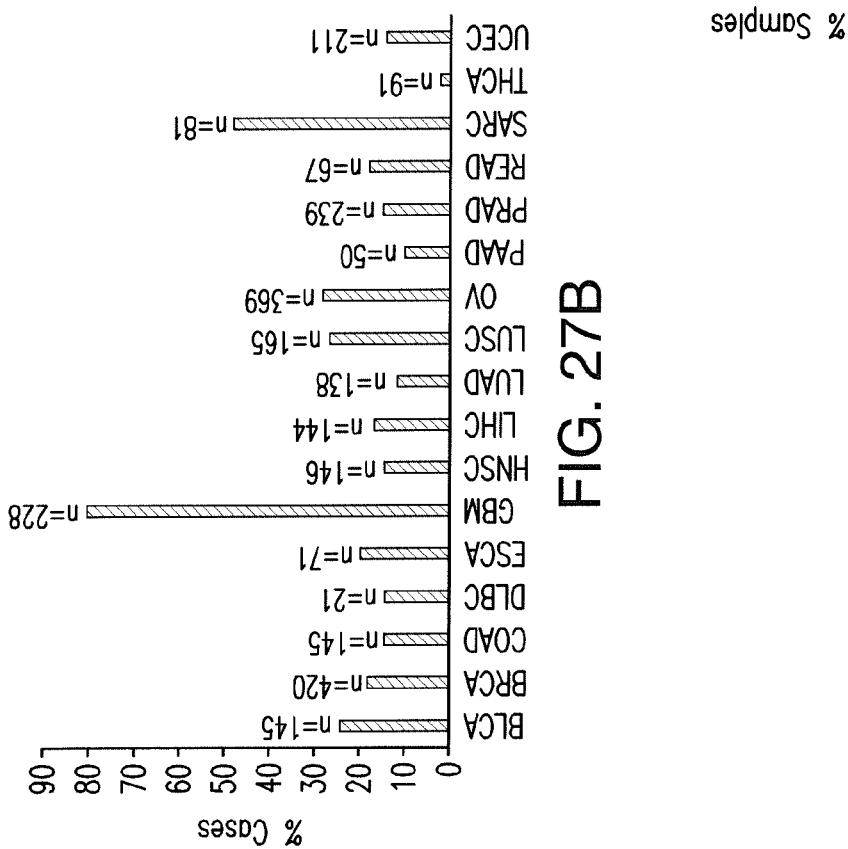

FIG. 27A-C. Spanning deletion between Pten exon 11 and NOLC1 exon 2 in 17 types of human malignancies. (A) Schematic diagram of Pten and NOLC1 minigenomes as well as detection of the spanning deletion between the 2 genes (red line) through copy number analysis of TCGA Affymetrix SNP6.0 data. The number of samples deemed positive for deletion is indicated. (B) Frequency of spanning deletion between Pten and NOLC1 in 17 different types of human malignancies. Total number of samples of each type of human malignancies is indicated. (C) Frequency of Pten deletion in samples with suggestive Pten-NOLC1 fusion. Total number of samples with suggestive Pten-NOLC1 fusion is indicated.

FIG. 28A-D. Pten-NOLC1 interacts with genomic DNA and activates expression of pro-growth genes. (A) Distribution of mapped DNA fragments from ChIP sequencing of DU145 versus DU145 KO1/KO2 (top panel), and MCF7 versus MCF7 KO1/KO2 (bottom panel), using antibodies specific for NOLC1. The distributions of DNA fragments of DU145 or MCF7 cells after subtraction from their knockout counterparts were shown in the right. (B) Taqman Q-PCR quantification of Pten-NOLC1 binding to promoter/enhancer regions of MET, EGFR, RAF1, AXL, GAB1 and VEGFA. (C) Removal of Pten-NOLC1 reduced c-MET, EGFR, RAF1 and GAB1 protein expression, and phosphorylation of STAT3 and RAF1. (D) The signaling pathways of MET, EGF and ECM are impacted by the presence of Pten-NOLC1. Red icons indicate genes that were interacted by Pten-NOLC1 but not by NOLC1 protein.

Figure 29:
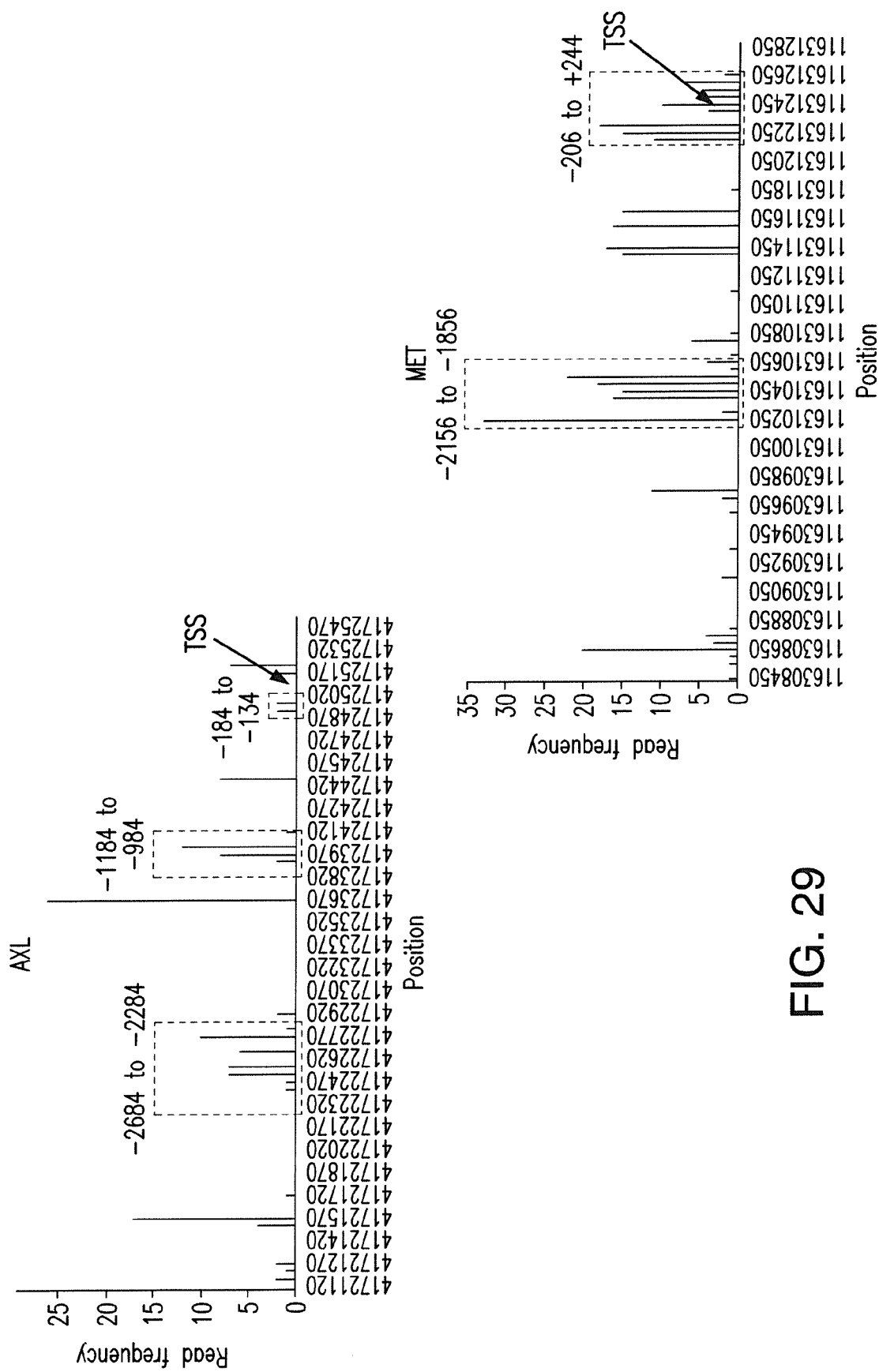
Figure 29:
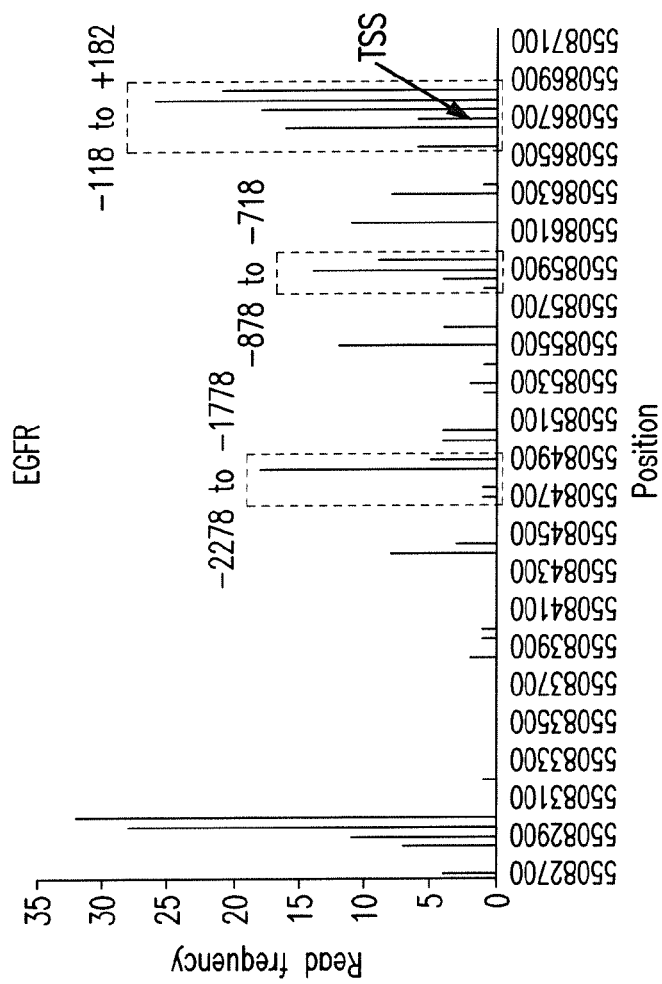
Figure 29:
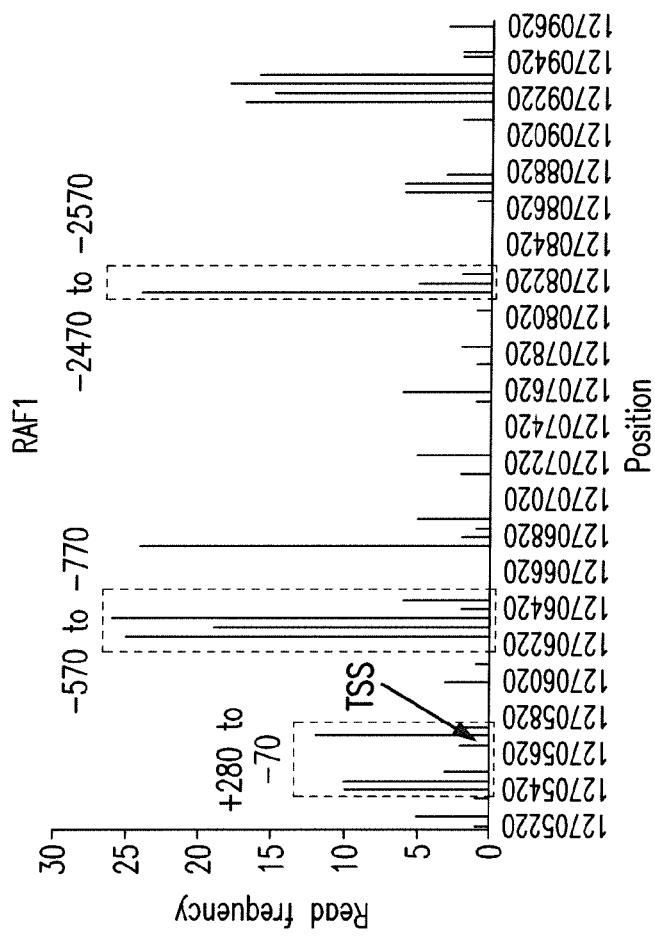
Figure 29:
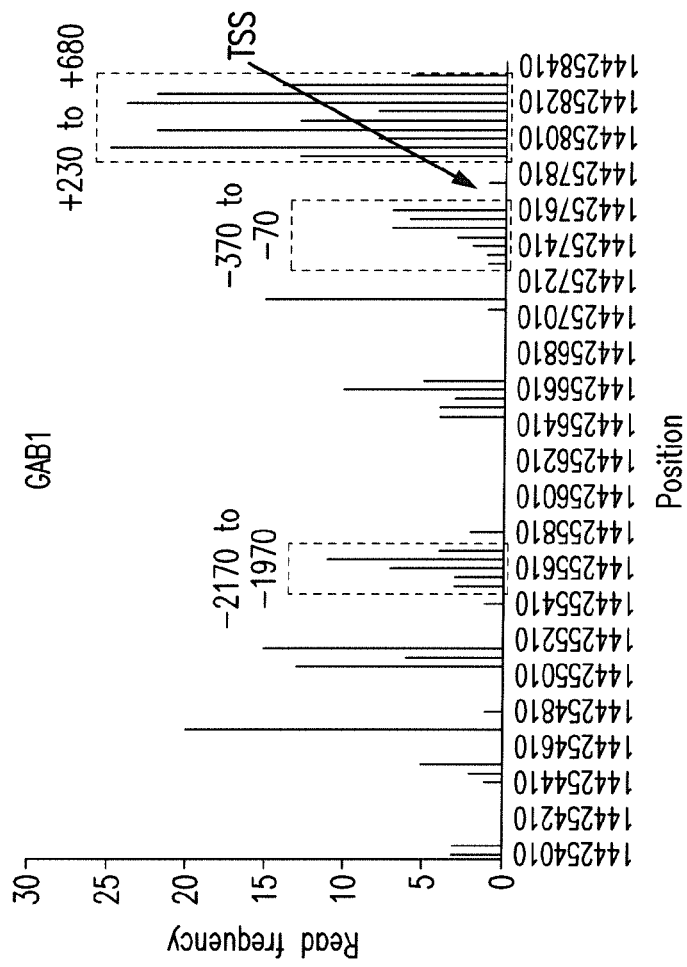
Figure 29:
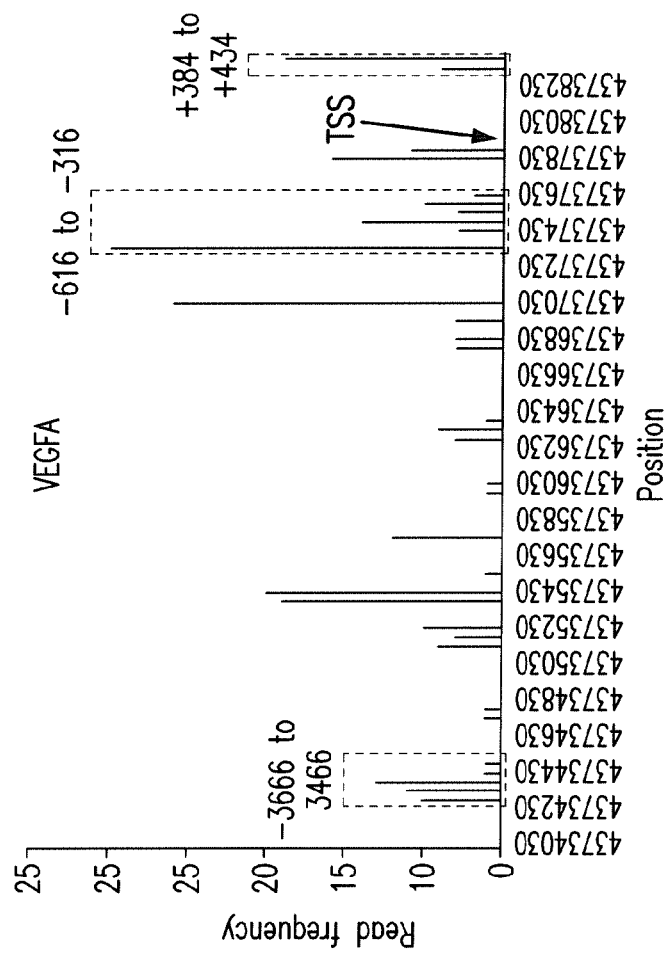

FIG. 29. Pten-NOLC1 binding to promoter regions of MET, EGFR, RAF1, AXL and VEGFA. ChIP sequencing mapped peaks from Pten-NOLC1 positive samples to the promoter regions of these genes are shown in red. Genome positions of the mapped DNA (using HG19 as reference) are indicated. Transcription start sites are indicated by arrows. Box indicates the region enriched with Pten-NOLC1 binding fragments.

Figure 30:
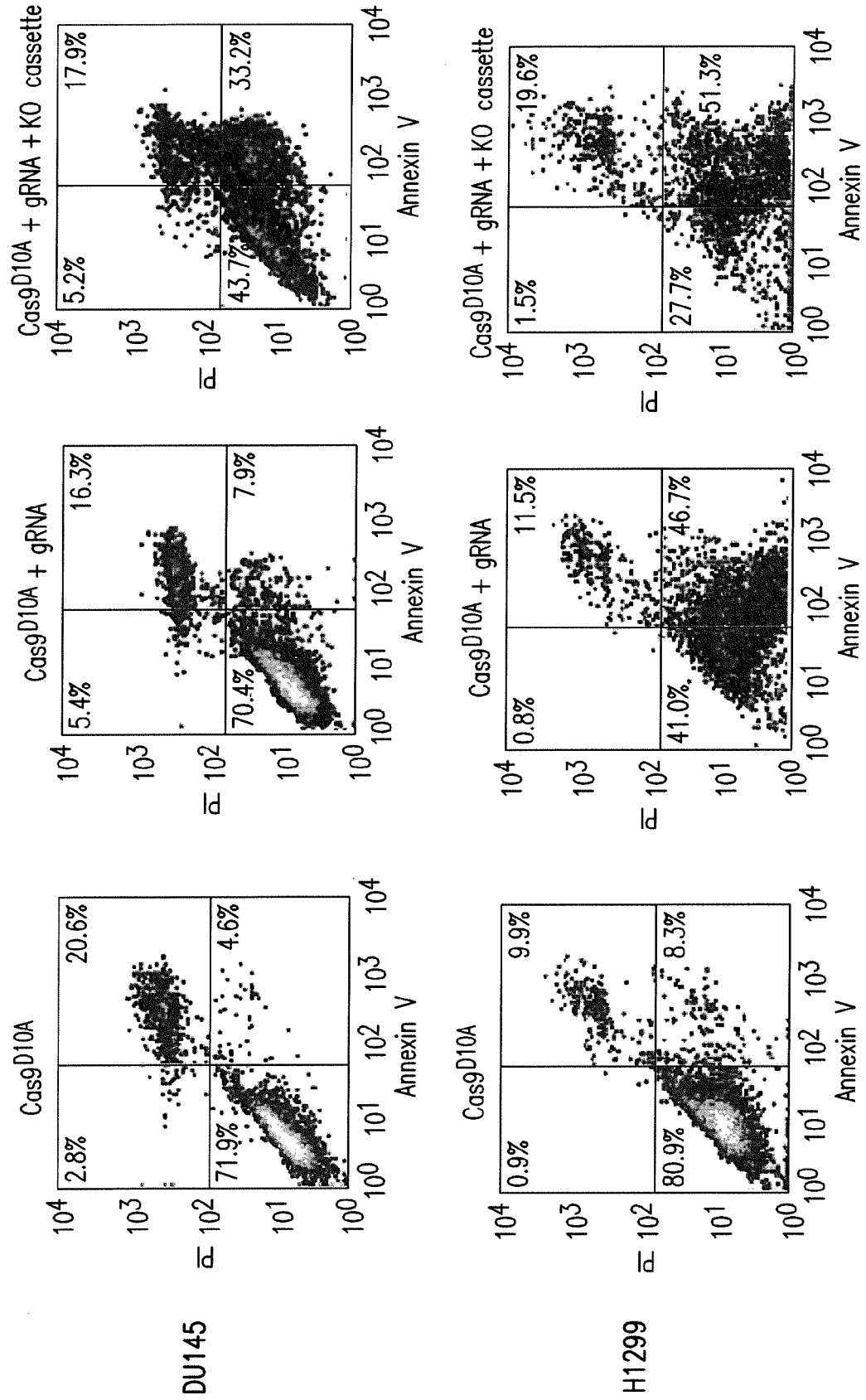
Figure 30:
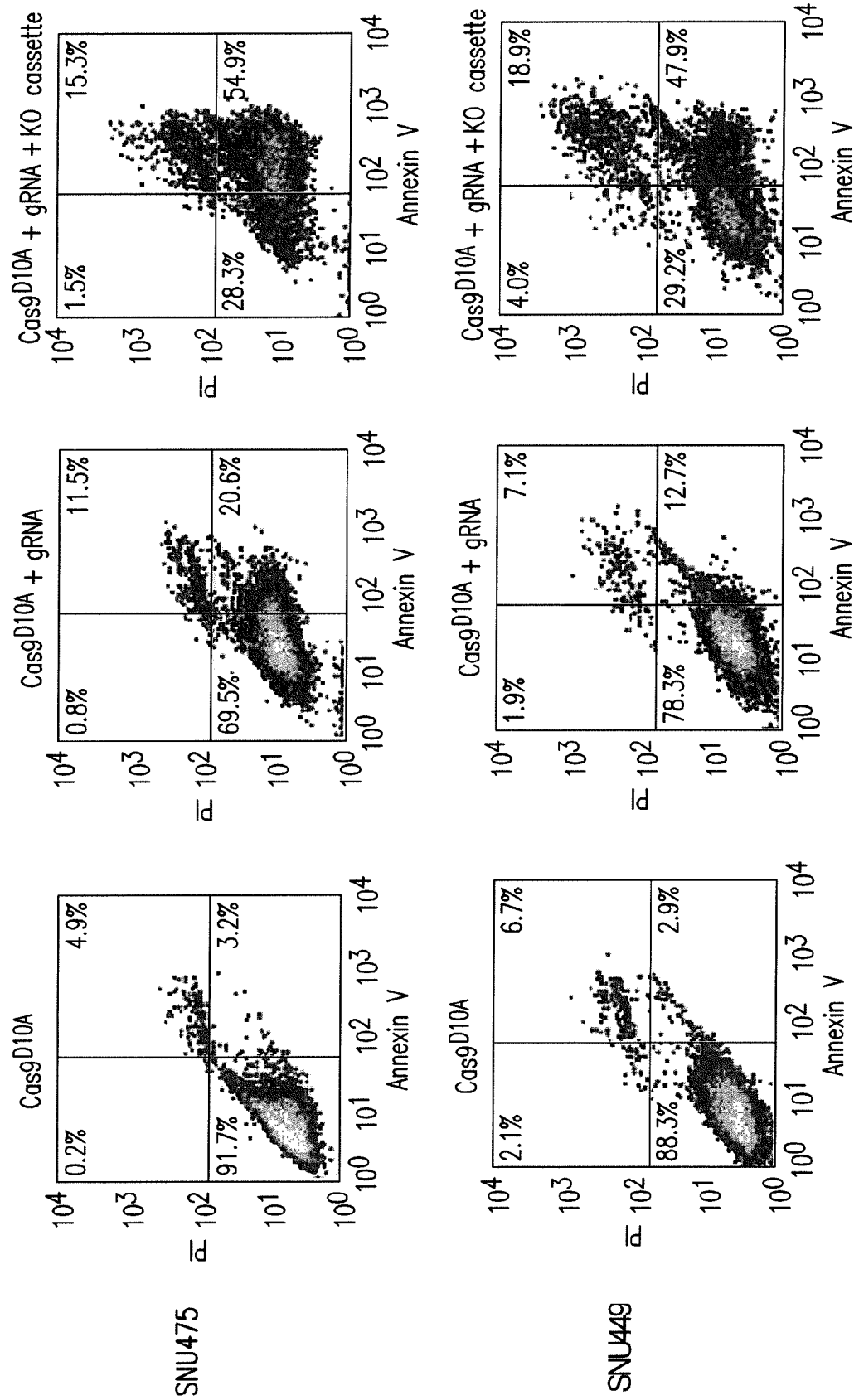
Figure 30:
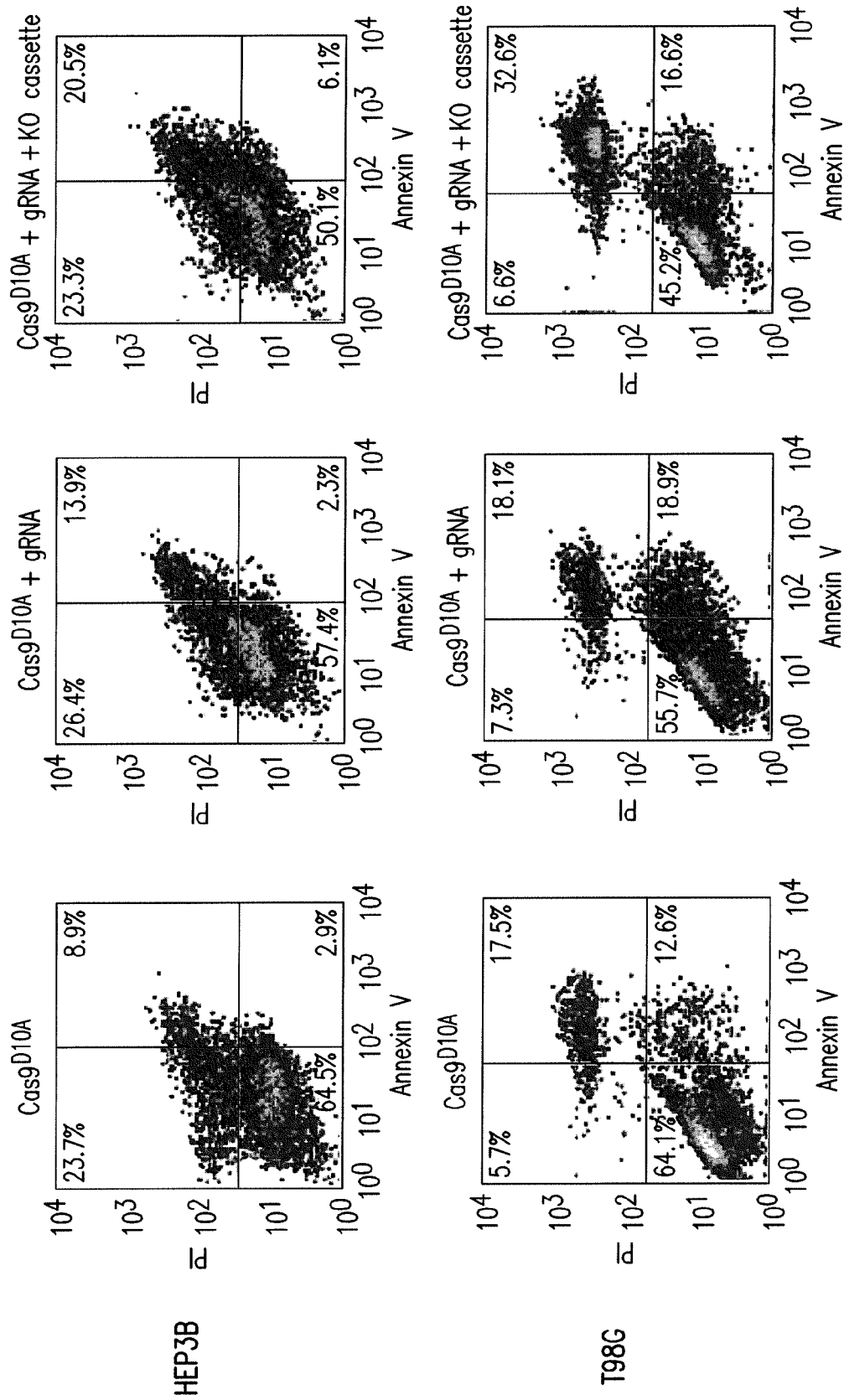
Figure 30:
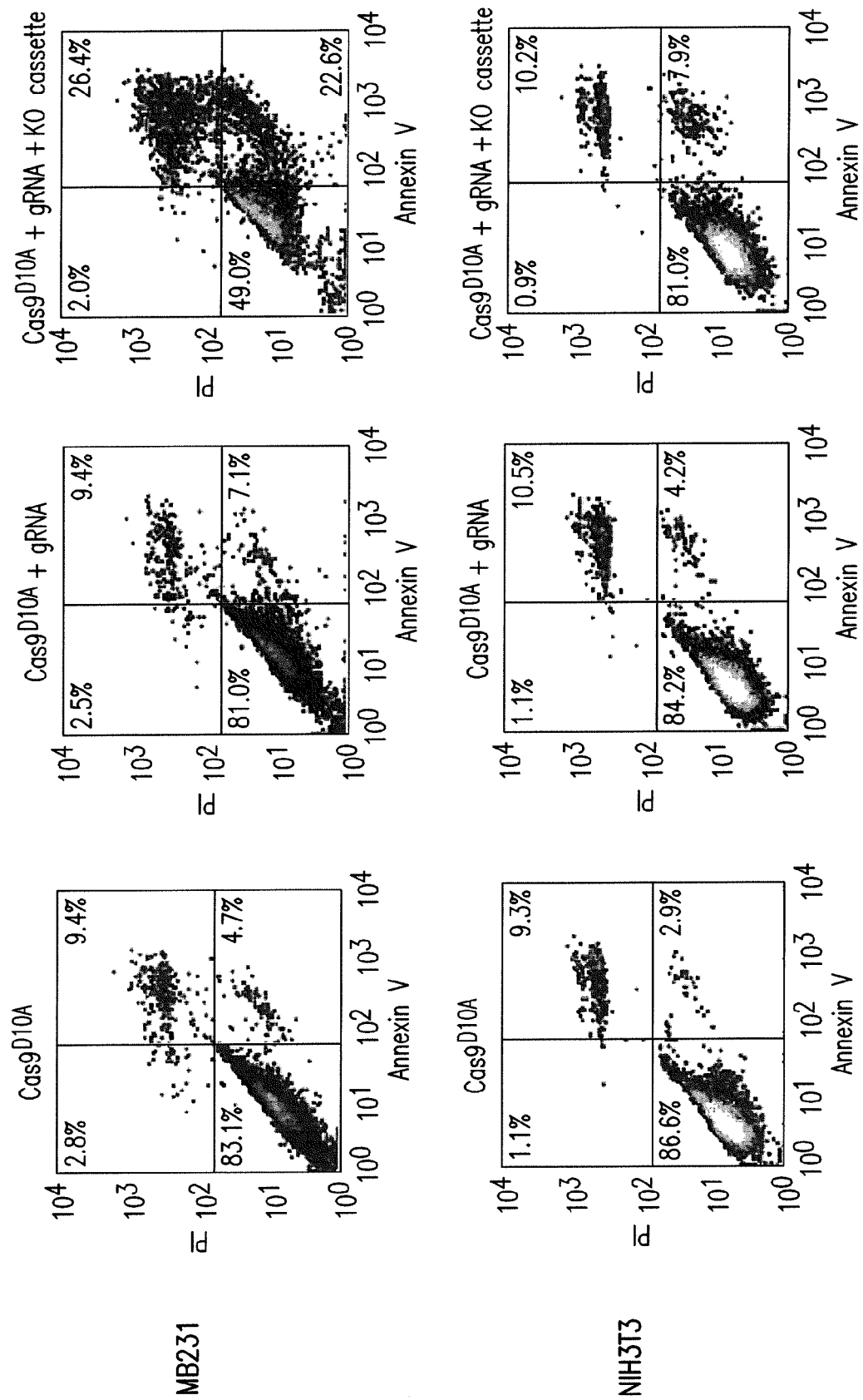

FIG. 30. Cell death induced by genomic interruption of Pten-NOLC1. PC3 (prostate cancer), DU145 (prostate cancer), MCF7 (breast cancer), H1299 (lung cancer), SNU449 (liver cancer), SNU475 (liver cancer), HEP3B (liver cancer), T98G (glioblastoma multiforme), MB231 (breast cancer) and NIH3T3 (mouse immortalized fibroblasts) cells were treated with $Cas9^{D10A}$, or $Cas9^{D10A}$ plus gRNA specific for Pten-NOLC1 or $Cas^{9D10A}$ plus gRNA specific for Pten-NOLC1 plus Pten-NOLC1 knockout cassette. Cell death was then analyzed 2 days after the treatment using Annexin V and propridium iodide staining.

Figure 31:
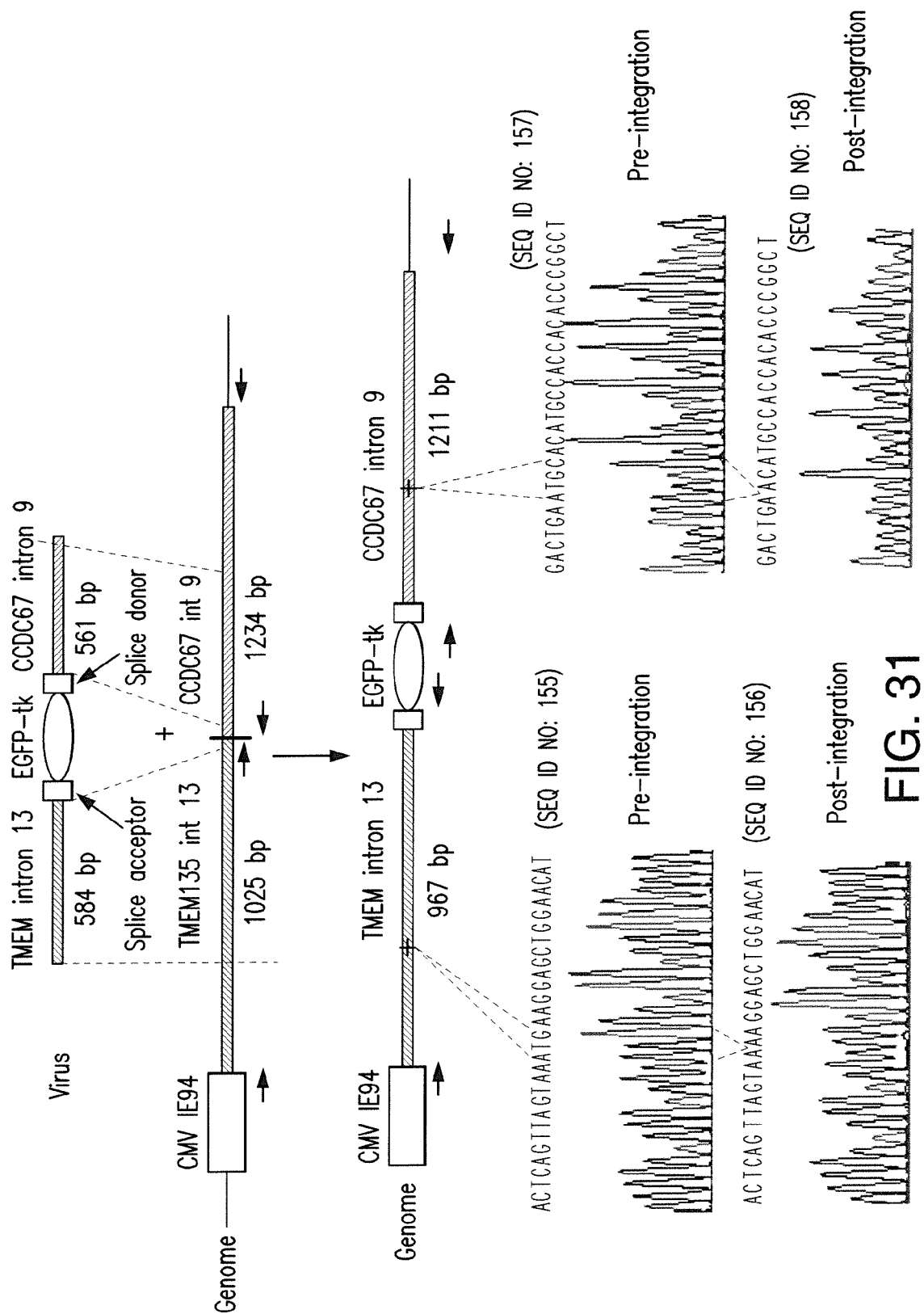

FIG. 31. Schematic diagram for the detection of TMEM135int13-EGFP-tk-CCDC67int9 integration into TMEM135-CCDC67 breakpoint in the PC3 cell genome. Arrows indicate the primer position for PCR. Putative integration sites that generated mutations are indicated by yellow stars. The PCR products obtained from xenografted PC3 cells that contain TMEM135-CCDC67 breakpoint before virus treatment were used as reference control. PCR products obtained after viral (Ad-TC) infections were sequenced. The positions of mutations due to DNA integration were detected through Sanger's sequencing.

5. DETAILED DESCRIPTION OF THE INVENTION

For clarity, and not by way of limitation, the detailed description of the invention is divided into the following subsections:
(i) fusion genes;
(ii) fusion gene detection;
(iii) cancer targets;
(iv) methods of treatment;
(v) genome editing techniques; and
(vi) kits.

5.1 Fusion Genes

The term "fusion gene," as used herein, refers to a nucleic acid or protein sequence which combines elements of the recited genes or their RNA transcripts in a manner not found in the wild type/normal nucleic acid or protein sequences. For example, but not by way of limitation, in a fusion gene in the form of genomic DNA, the relative positions of portions of the genomic sequences of the recited genes is altered relative to the wild type/normal sequence (for example, as reflected in the NCBI chromosomal positions or sequences set forth herein). In a fusion gene in the form of mRNA, portions of RNA transcripts arising from both component genes are present (not necessarily in the same register as the wild-type transcript and possibly including portions normally not present in the normal mature transcript). In non-limiting embodiments, such a portion of genomic DNA or mRNA may comprise at least about 10 consecutive nucleotides, or at least about 20 consecutive nucleotides, or at least about 30 consecutive nucleotides, or at least 40 consecutive nucleotides. In certain embodiments, such a portion of genomic DNA or mRNA may comprise up to about 10 consecutive nucleotides, up to about 50 consecutive nucleotides, up to about 100 consecutive nucleotides, up to about 200 consecutive nucleotides, up to about 300 consecutive nucleotides, up to about 400 consecutive nucleotides, up to about 500 consecutive nucleotides, up to about 600 consecutive nucleotides, up to about 700 consecutive nucleotides, up to about 800 consecutive nucleotides, up to about 900 consecutive nucleotides, up to about 1,000 consecutive nucleotides, up to about 1,500 consecutive nucleotides or up to about 2,000 consecutive nucleotides of the nucleotide sequence of a gene present in the fusion gene. In certain embodiments, such a portion of genomic DNA or mRNA may comprise no more than about 10 consecutive nucleotides, about 50 consecutive nucleotides, about 100 consecutive nucleotides, about 200 consecutive nucleotides, about 300 consecutive nucleotides, about 400 consecutive nucleotides, about 500 consecutive nucleotides, about 600 consecutive nucleotides, about 700 consecutive nucleotides, about 800 consecutive nucleotides, about 900 consecutive nucleotides, about 1,000 consecutive nucleotides, about 1,500 consecutive nucleotides or about 2,000 consecutive nucleotides of the nucleotide sequence of a gene present in the fusion gene. In certain embodiments, such a portion of genomic DNA or mRNA does not comprise the full wildtype/normal nucleotide sequence of a gene present in the fusion gene. In a fusion gene in the form of a protein, portions of amino acid sequences arising from both component genes are present (not by way of limitation, at least about 5 consecutive amino acids or at least about 10 amino acids or at least about 20 amino acids or at least about 30 amino acids). In certain embodiments, such a portion of a fusion gene protein may comprise up to about 10 consecutive amino acids, up to about 20 consecutive amino acids, up to about 30 consecutive amino acids, up to about 40 consecutive amino acids, up to about 50 consecutive amino acids, up to about 60 consecutive amino acids, up to about 70 consecutive amino acids, up to about 80 consecutive amino acids, up to about 90 consecutive amino acids, up to about 100 consecutive amino acids, up to about 120 consecutive amino acids, up to about 140 consecutive amino acids, up to about 160 consecutive amino acids, up to about 180 consecutive amino acids, up to about 200 consecutive amino acids, up to about 220 consecutive amino acids, up to about 240 consecutive amino acids, up to about 260 consecutive amino acids, up to about 280 consecutive amino acids or up to about 300 consecutive amino acids of the amino acid sequence encoded by a gene present in the fusion gene. In certain embodiments, such a portion of a fusion gene protein may comprise no more than about 10 consecutive amino acids, about 20 consecutive amino acids, about 30 consecutive amino acids, about 40 consecutive amino acids, about 50 consecutive amino acids, about 60 consecutive amino acids, about 70 consecutive amino acids, about 80 consecutive amino acids, about 90 consecutive amino acids, about 100 consecutive amino acids, about 120 consecutive amino acids, about 140 consecutive amino acids, about 160 consecutive amino acids, about 180 consecutive amino acids, about 200 consecutive amino acids, about 220 consecutive amino acids, about 240 consecutive amino acids, about 260 consecutive amino acids, about 280 consecutive amino acids or about 300 consecutive amino acids of the amino acid sequence encoded by a gene present in the fusion gene. In certain embodiments, such a portion of a fusion gene protein does not comprise the full wildtype/normal amino acid sequence encoded by a gene present in the fusion gene. In this paragraph, portions arising from both genes, transcripts or proteins do not refer to sequences which may happen to be identical in the wild type forms of both genes (that is to say, the portions are "unshared"). As such, a fusion gene represents, generally speaking, the splicing together or fusion of genomic elements not normally joined together. See WO 2015/103057 and WO 2016/011428, the contents of which are hereby incorporated by reference, for additional information regarding the disclosed fusion genes.

The fusion gene TRMT11-GRIK2 is a fusion between the tRNA methyltransferase 11 homolog ("TRMT11") and glutamate receptor, ionotropic, kainate 2 ("GRIK2") genes. The human TRMT11 gene is typically located on chromosome 6q11.1 and the human GRIK2 gene is typically located on chromosome 6q16.3. In certain embodiments, the TRMT11 gene is the human gene having NCBI Gene ID No: 60487, sequence chromosome 6; NC_000006.11 (126307576 . . . 126360422) and/or the GRIK2 gene is the human gene having NCBI Gene ID No:2898, sequence chromosome 6; NC_000006.11 (101841584 . . . 102517958). In certain embodiments, the junction (also referred to herein as chromosomal breakpoint and/or junction fragment) of a TRMT11-GRIK2 fusion gene comprises a sequence as shown in FIG. 1 and/or Table 1.

The fusion gene SLC45A2-AMACR is a fusion between the solute carrier family 45, member 2 ("SLC45A2") and alpha-methylacyl-CoA racemase ("AMACR") genes. The human SLC45A2 gene is typically located on human chromosome 5p13.2 and the human AMACR gene is typically located on chromosome 5p13. In certain embodiments the SLC45A2 gene is the human gene having NCBI Gene ID No: 51151, sequence chromosome 5; NC_000005.9 (33944721 . . . 33984780, complement) and/or the AMACR gene is the human gene having NCBI Gene ID No:23600, sequence chromosome 5; NC_000005.9 (33987091 . . . 34008220, complement). In certain embodiments, the junction and/or junction fragment of a SLC45A2-AMACR fusion gene comprises a sequence as shown in FIG. 1 and/or Table 1.

The fusion gene MTOR-TP53BP1 is a fusion between the mechanistic target of rapamycin ("MTOR") and tumor protein p53 binding protein 1 ("TP53BP1") genes. The human MTOR gene is typically located on chromosome 1p36.2 and the human TP53BP1 gene is typically located on chromosome 15q15-q21. In certain embodiments, the MTOR gene is the human gene having NCBI Gene ID No:2475, sequence chromosome 1 NC_000001.10 (11166588 . . . 11322614, complement) and/or the TP53BP1 gene is the human gene having NCBI Gene ID No: 7158, sequence chromosome 15; NC_000015.9 (43695262 . . . 43802707, complement). In certain embodiments, the junction and/or junction fragment of a MTOR-TP53BP1 fusion gene comprises a sequence as shown in FIG. 1 and/or Table 1.

The fusion gene LRRC59-FLJ60017 is a fusion between the leucine rich repeat containing 59 ("LRRC59") gene and the "FLJ60017" nucleic acid. The human LRRC59 gene is typically located on chromosome 17q21.33 and nucleic acid encoding human FLJ60017 is typically located on chromosome 11q12.3. In certain embodiments, the LRRC59 gene is the human gene having NCBI Gene ID No:55379, sequence chromosome 17; NC_000017.10 (48458594 . . . 48474914, complement) and/or FLJ60017 has a nucleic acid sequence as set forth in GeneBank AK_296299. In certain embodiments, the junction and/or junction fragment of a LRRC59-FLJ60017 fusion gene comprises a sequence as shown in FIG. 1, FIG. 2 and/or Table 1.

The fusion gene TMEM135-CCDC67 is a fusion between the transmembrane protein 135 ("TMEM135") and coiled-coil domain containing 67 ("CCDC67") genes. The human TMEM135 gene is typically located on chromosome 11q14.2 and the human CCDC67 gene is typically located on chromosome 11q21. In certain embodiments the TMEM135 gene is the human gene having NCBI Gene ID No: 65084, sequence chromosome 11; NC_000011.9 (86748886 . . . 87039876) and/or the CCDC67 gene is the human gene having NCBI Gene ID No: 159989, sequence chromosome 11; NC_000011.9 (93063156 . . . 93171636). In certain embodiments, the junction and/or junction fragment of a TMEM135-CCDC67 fusion gene comprises a sequence as shown in FIG. 1, FIG. 2, FIG. 13 and/or Table 1.

The fusion gene CCNH-C5orf30 is a fusion between the cyclin H ("CCNH") and chromosome 5 open reading frame 30 ("C5orf30") genes. The human CCNH gene is typically located on chromosome 5q13.3-q14 and the human C5orf30 gene is typically located on chromosome 5q21.1. In certain embodiments, the CCNH gene is the human gene having NCBI Gene ID No: 902, sequence chromosome 5; NC_000005.9 (86687310 . . . 86708850, complement) and/or the C5orf30 gene is the human gene having NCBI Gene ID No: 90355, sequence chromosome 5; NC_000005.9 (102594442 . . . 102614361). In certain embodiments, the junction and/or junction fragment of a CCNH-C5orf30 fusion gene comprises a sequence as shown in FIG. 1, FIG. 2 and/or Table 1.

The fusion gene KDM4B-AC011523.2 is a fusion between lysine (K)-specific demethylase 4B ("KDM4B") and chromosomal region "AC011523.2." The human KDM4B gene is typically located on chromosome 19p13.3 and the human AC011523.2 region is typically located on chromosome 19q13.4. In certain embodiments the KDM4B gene is the human gene having NCBI Gene ID NO: 23030, sequence chromosome 19; NC_000019.9 (4969123 . . . 5153609); and/or the AC011523.2 region comprises a sequence as shown in FIG. 1. In certain embodiments, the junction and/or junction fragment of a KDM4B-AC011523.2 fusion gene comprises a sequence as shown in FIG. 1 and/or Table 1.

The fusion gene MAN2A1-FER is a fusion between mannosidase, alpha, class 2A, member 1 ("MAN2A1") and (fps/fes related) tyrosine kinase ("FER"). The human MAN2A1 gene is typically located on chromosome 5q21.3 and the human FER gene is typically located on chromosome 5q21. In certain embodiments, the MAN2A1 gene is the human gene having NCBI Gene ID NO: 4124, sequence chromosome 5; NC_000005.9 (109025156 . . . 109203429) or NC_000005.9 (109034137 . . . 109035578); and/or the FER gene is the human gene having NCBI Gene ID NO: 2241, sequence chromosome 5: NC_000005.9 (1080-83523 . . . 108523373). In certain embodiments, the junction and/or junction fragment of a MAN2A1-FER fusion gene comprises a sequence as shown in FIG. 1, FIG. 4, FIG. 15 and/or Table 1.

The fusion gene PTEN-NOLC1 is a fusion between the phosphatase and tensin homolog ("PTEN") and nucleolar and coiled-body phosphoprotein 1 ("NOLC1"). The human PTEN gene is typically located on chromosome 10q23.3 and the human NOLC1 gene is typically located on chromosome 10q24.32. In certain embodiments, the PTEN gene is the human gene having NCBI Gene ID NO: 5728, sequence chromosome 10; NC_000010.11 (87863438 . . . 87970345) and/or the NOLC1 gene is the human gene having NCBI Gene ID NO: 9221, sequence chromosome 10; NC_000010.11 (102152176 . . . 102163871). In certain embodiments, the junction and/or junction fragment of a PTEN-NOLC1 fusion gene comprises a sequence as shown in FIG. 3, FIG. 17 and/or Table 1.

The fusion gene ZMPSTE24-ZMYM4 is a fusion between zinc metallopeptidase STE24 ("ZMPSTE24") and zinc finger, MYM-type 4 ("ZMYM4"). The human ZMPSTE24 is typically located on chromosome 1p34 and the human ZMYM4 gene is typically located on chromosome 1p32-p34. In certain embodiments, the ZMPSTE24 gene is the human gene having NCBI Gene ID NO: 10269, sequence chromosome 1; NC_000001.11 (40258050 . . . 40294184) and/or the ZMYM4 gene is the human gene having NCBI Gene ID NO: 9202, sequence chromosome 1; NC_000001.11 (35268850 . . . 35421944). In certain embodiments, the junction and/or junction fragment of a ZMPSTE24-ZMYM4 fusion gene comprises a sequence as shown in FIG. 6 and/or FIG. 18.

The fusion gene CLTC-ETV1 is a fusion between clathrin, heavy chain (Hc) ("CLTC") and ets variant 1 ("ETV1"). The human CLTC is typically located on chromosome 17q23.1 and the human ETV1 gene is typically located on chromosome 7p21.3. In certain embodiments, the CLTC gene is the human gene having NCBI Gene ID NO: 1213, sequence chromosome 17; NC_000017.11 (59619689 . . . 59696956) and/or the ETV1gene is the human gene having NCBI Gene ID NO: 2115, sequence chromosome 7; NC_000007.14 (13891229 . . . 13991425, complement). In certain embodiments, the junction and/or junction fragment of a CLTC-ETV1 fusion gene comprises a sequence as shown in FIG. 6 and/or FIG. 18 or a fragment thereof.

The fusion gene ACPP-SEC13 is a fusion between acid phosphatase, prostate ("ACPP") and SEC13 homolog ("SEC13"). The human ACPP is typically located on chromosome 3q22.1 and the human SEC13 gene is typically located on chromosome 3p25-p24. In certain embodiments, the ACPP gene is the human gene having NCBI Gene ID NO: 55, sequence chromosome 3; NC_000003.12 (132317367 . . . 132368302) and/or the SEC13 gene is the human gene having NCBI Gene ID NO: 6396, sequence chromosome 3; NC_000003.12 (10300929 . . . 10321188, complement). In certain embodiments, the junction and/or junction fragment of an ACPP-SEC13 fusion gene comprises a sequence as shown in FIG. 6 and/or FIG. 18.

The fusion gene DOCK7-OLR1 is a fusion between dedicator of cytokinesis 7 ("DOCK7") and oxidized low density lipoprotein (lectin-like) receptor 1 ("OLR1"). The human DOCK7 is typically located on chromosome 1p31.3 and the human OLR1 gene is typically located on chromosome 12p13.2-p12.3. In certain embodiments, the DOCK7 gene is the human gene having NCBI Gene ID NO: 85440, sequence chromosome 1; NC_000001.11 (62454726 . . . 62688368, complement) and/or the OLR1 gene is the human gene having NCBI Gene ID NO: 4973, sequence chromosome 12; NC_000012.12 (10158300 . . . 10172191, complement). In certain embodiments, the junction and/or junction fragment of a DOCK7-OLR1 fusion gene comprises a sequence as shown in FIG. 6 and/or FIG. 18.

The fusion gene PCMTD1-SNTG1 is a fusion between protein-L-isoaspartate (D-aspartate) O-methyltransferase domain containing 1 ("PCMTD1") and syntrophin, gamma 1 ("SNTG1"). The human PCMTD1 is typically located on chromosome 8q11.23 and the human SNTG1 gene is typically located on chromosome 8q11.21. In certain embodiments, the PCMTD1 gene is the human gene having NCBI Gene ID NO: 115294, sequence chromosome 8; NC_000008.11 (51817575 . . . 51899186, complement) and/or the SNTG1gene is the human gene having NCBI Gene ID NO: 54212, sequence chromosome 8; NC_000008.11 (49909789 . . . 50794118). In certain embodiments, the junction and/or junction fragment of a PCMTD1-SNTG1 fusion gene comprises a sequence as shown in FIG. 6 and/or FIG. 18.

5.2 Fusion Gene Detection

Any of the foregoing fusion genes described above in section 5.1 may be identified and/or detected by methods known in the art. The fusion genes may be detected by detecting a fusion gene manifested in a DNA molecule, an RNA molecule or a protein. In certain embodiments, a fusion gene can be detected by determining the presence of a DNA molecule, an RNA molecule or protein that is encoded by the fusion gene. For example, and not by way of limitation, the presence of a fusion gene may be detected by determining the presence of the protein encoded by the fusion gene.

The fusion gene may be detected in a sample of a subject. A "patient" or "subject," as used interchangeably herein, refers to a human or a non-human subject. Non-limiting examples of non-human subjects include non-human primates, dogs, cats, mice, etc. The subject may or may not be previously diagnosed as having cancer.

In certain non-limiting embodiments, a sample includes, but is not limited to, cells in culture, cell supernatants, cell lysates, serum, blood plasma, biological fluid (e.g., blood, plasma, serum, stool, urine, lymphatic fluid, ascites, ductal lavage, saliva and cerebrospinal fluid) and tissue samples. The source of the sample may be solid tissue (e.g., from a fresh, frozen, and/or preserved organ, tissue sample, biopsy, or aspirate), blood or any blood constituents, bodily fluids (such as, e.g., urine, lymph, cerebral spinal fluid, amniotic fluid, peritoneal fluid or interstitial fluid), or cells from the individual, including circulating cancer cells. In certain non-limiting embodiments, the sample is obtained from a cancer. In certain embodiments, the sample may be a "biopsy sample" or "clinical sample," which are samples derived from a subject. In certain embodiments, the sample includes one or more cancer cells from a subject. In certain embodiments, the one or more fusion genes can be detected in one or more samples obtained from a subject, e.g., in one or more cancer cell samples. In certain embodiments, the sample is not a prostate cancer sample or one or more prostate cancer cells. In certain embodiments, the sample is not a lung adenocarcinoma, glioblastoma multiforme or hepatocellular carcinoma sample.

In certain non-limiting embodiments, the fusion gene is detected by nucleic acid hybridization analysis.

In certain non-limiting embodiments, the fusion gene is detected by fluorescent in situ hybridization (FISH) analysis. FISH is a technique that can directly identify a specific sequence of DNA or RNA in a cell or biological sample and enables visual determination of the presence and/or expression of a fusion gene in a tissue sample. In certain non-limiting embodiments, where a fusion gene combines genes not typically present on the same chromosome, FISH analysis may demonstrate probes binding to the same chromosome. For example, and not by way of limitation, analysis may focus on the chromosome where one gene normally resides and then hybridization analysis may be performed to determine whether the other gene is present on that chromosome as well.

In certain non-limiting embodiments, the fusion gene is detected by DNA hybridization, such as, but not limited to, Southern blot analysis.

In certain non-limiting embodiments, the fusion gene is detected by RNA hybridization, such as, but not limited to, Northern blot analysis. In certain embodiments, Northern blot analysis can be used for the detection of a fusion gene, where an isolated RNA sample is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography to detect the presence of a fusion gene in the RNA sample.

In certain non-limiting embodiments, the fusion gene is detected by nucleic acid sequencing analysis.

In certain non-limiting embodiments, the fusion gene is detected by probes present on a DNA array, chip or a microarray. For example, and not by way of limitation, oligonucleotides corresponding to one or more fusion genes can be immobilized on a chip which is then hybridized with labeled nucleic acids of a sample obtained from a subject. Positive hybridization signal is obtained with the sample containing the fusion gene transcripts.

In certain non-limiting embodiments, the fusion gene is detected by a method comprising Reverse Transcription Polymerase Chain Reaction ("RT-PCR"). In certain embodiments, the fusion gene is detected by a method comprising RT-PCR using the one or more pairs of primers disclosed herein (see, for example, Table 5).

In certain non-limiting embodiments, the fusion gene is detected by antibody binding analysis such as, but not limited to, Western Blot analysis and immunohistochemistry.

TABLE 5

Primer sequences for RT-PCR.

| Fusion genes | Sequences |
| --- | --- |
| ACPP-SEC13 | 5'-TCCCATTGACACCTTTCCCAC (SEQ ID NO: 30)/<br>5'-TGAGGCTTCCAGGTACAACAG (SEQ ID NO: 31) |
| CLTC-ETV1 | 5'-GCCCAGTTGCAGAAAGGAATG (SEQ ID NO: 32/<br>5'-CTTGATTTTCAGTGGCAGGCC (SEQ ID NO: 33) |
| DOCK7-OLR1 | 5'-GACTACGTCTCATGCCTTTCC (SEQ ID NO: 34)/<br>5'-TTCTCATCAGGCTGGTCCTTC (SEQ ID NO: 35) |
| PCMTD1-SNTG | 5'-GATGTGGTGGAATATGCCAAGG (SEQ ID NO: 36)/<br>5'-AAATCCATGTGCTGTGGCACC (SEQ ID NO: 37) |
| ZMPSTE24-ZMYM4 | 5'-CGCAATGAGGAAGAAGGGAAC (SEQ ID NO: 38)/<br>5'-CATAAATCTGGAATAGGGCTCAG (SEQ ID NO: 39) |
| TMEM135-CCDC67 | 5'-GAGACCATCTTACTGGAAGTTCC-3' (SEQ ID NO: 58)/<br>5'-TGGTACTCTTCCACCTGTTGG-3' (SEQ ID NO: 59) |
| Mtor-TP53BP1 | 5'-TTGGCATGATAGACCAGTCCC-3' (SEQ ID NO: 60)/<br>5'-CAGCACCAAGGGAATGTGTAG-3' (SEQ ID NO: 61) |
| TRMT11-GRIK2 | 5'-GCGCTGTCGTGTACCCTTAAC-3' (SEQ ID NO: 62)/<br>5'-GGTAAGGGTAGTATTGGGTAGC-3' (SEQ ID NO: 63) |
| CCNH-C5orf30 | 5'-CCAGGGCTGGAATTACTATGG-3' (SEQ ID NO: 64)/<br>5'-AAGCACCAGTCTGCACAATCC-3' (SEQ ID NO: 65) |
| SLC45A2-AMACR | 5'-TTGATGTCTGCTCCCATCAGG-3' (SEQ ID NO: 66)/<br>5'-TGATATCGTGGCCAGCTAACC-3' (SEQ ID NO: 67) |
| KDM4B-AC011523.2 | 5'-AACACGCCCTACCTGTACTTC-3' (SEQ ID NO: 68)/<br>5'-CTGAGCAAAGACAGCAACACC-3' (SEQ ID NO: 69) |

TABLE 5 -continued

Primer sequences for RT-PCR.

| Fusion genes | Sequences |
|---|---|
| MAN2A1-FER | 5'-TGGAAGTTCAAGTCAGCGCAG-3' (SEQ ID NO: 70)/<br>5'-GCTGTCTTTGTGTGCAAACTCC-3' (SEQ ID NO: 71) |
| LRRC59-FLJ60017 | 5'-GTGACTGCTTGGATGAGAAGC-3' (SEQ ID NO: 72)/<br>5'-CCAGCATGCAGCTTTTCTGAG-3' (SEQ ID NO: 73) |
| TMPRSS2-ERG | 5'-AGTAGGCGCGAGCTAAGCAGG-3' (SEQ ID NO: 74)/<br>5'-GGGACAGTCTGAATCATGTCC-3' (SEQ ID NO: 75) |
| β-actin | 5'-TCAAGATCATTGCTCCTCCTGAGC-3' (SEQ ID NO: 76)/<br>5'-TGCTGTCACCTTCACCGTTCCAGT-3' (SEQ ID NO: 77) |

5.3 Cancer Targets

Non-limiting examples of cancers that may be subject to the presently disclosed invention include prostate cancer, breast cancer, liver cancer, hepatocarcinoma, hepatoma, lung cancer, non-small cell lung cancer, cervical cancer, endometrial cancer, pancreatic cancer, ovarian cancer, gastric cancer, thyroid cancer, glioblastoma multiforme, colorectal cancer, diffuse large B cell lymphoma, sarcoma, acute and chronic lymphocytic leukemia, Hodgkin's lymphoma, non-Hodgkin's lymphoma, and adenocarcinoma, e.g., esophageal adenocarcinoma. In certain embodiments, the target of treatment is a premalignant or neoplastic condition involving lung, cervix, endometrium, pancreas, ovary, stomach, thyroid, glia, intestine, esophagus, muscle or B cells. In certain embodiments, the cancer is not prostate cancer. In certain embodiments, the cancer is not lung adenocarcinoma, glioblastoma multiforme or hepatocellular carcinoma. In certain embodiments, the target of treatment is a cell that carries at least one fusion gene, e.g., PTEN-NOLC1 or MAN2A1-FER.

5.4 Methods of Treatment

The present invention provides methods of treating a subject that has one or more cells that carry a fusion gene. In certain embodiments, the subject has, or is suspected of having, cancer or a neoplastic or pre-malignant condition that carries one or more fusion genes (a pre-malignant condition is characterized, inter alia, by the presence of pre-malignant or neoplastic cells). Non-limiting examples of fusion genes are disclosed herein and in section 5.1. In certain embodiments, the methods of treatment include performing a targeted genome editing technique on one or more cancer cells within the subject to produce an anti-cancer or anti-neoplastic or anti-proliferative effect. Non-limiting examples of cancers that can be treated using the disclosed methods are provided in section 5.3. Non-limiting examples of genome editing techniques are disclosed in section 5.5.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer. In certain embodiments, an anti-cancer effect can refer to the induction of cell death, e.g., in one or more cells of the cancer, and/or the increase in cell death within a tumor mass. Similarly, an "anti-neoplastic effect" refers to one or more of a reduction in aggregate neoplastic cell mass, a reduction in neoplastic cell growth rate, a reduction in neoplasm progression (e.g., progressive de-differentiation or epithelial to mesenchymal transition), a reduction in neoplastic cell proliferation, a reduction in neoplasm mass, a reduction in neoplasm volume, and/or a reduction in neoplasm growth rate.

In certain embodiments, a method of treating a subject comprises determining the presence of one or more fusion genes in a sample from the subject, where if one or more fusion genes are present in the sample then performing a targeted genome editing technique on one or more cells within the subject. In certain embodiments, the genome editing technique results in the reduction and/or elimination of the expression of a fusion gene and/or the expression of the protein encoded by the fusion gene in one or more cells of the subject. In certain embodiments, the genome editing technique specifically targets the cells that carry the fusion gene, e.g., by specifically targeting a nucleic acid sequence of the fusion gene. For example, and not by way of limitation, the methods of the current invention specifically target a chromosomal breakpoint of one or more of the fusion genes. In certain embodiments, the methods of the current invention involve the targeting of sequences that flank the breakpoint. In certain embodiments, the methods of the current invention involve the targeting of sequences that flank and partially overlap the breakpoint. Non-limiting examples of techniques for identifying and/or detecting a fusion gene are disclosed in section 5.2.

In certain embodiments, a method of treating a cancer in a subject comprises determining the presence of one or more fusion genes in a cancer cell-containing sample from the subject, where if one or more fusion genes are present in the sample then performing a targeted genome editing technique on one or more cancer cells within the subject to produce an anti-cancer effect or anti-neoplastic effect.

In certain embodiments, the method can include determining the presence or absence of a fusion gene. For example, and not by way of limitation, the method can include determining the presence or absence of one or more, two or more, three or more, four or more, five or more, six or more, seven or more, eight or more, nine or more, ten or more, eleven or more, twelve or more, thirteen or more or all fourteen of the fusion genes disclosed herein. In certain embodiments, the one or more fusion genes can be TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 or a combination thereof.

In certain embodiments, the fusion gene can be TMEM135-CCDC67.

In certain embodiments, the fusion gene can be CCNH-C5orf30.

In certain embodiments, the fusion gene can be MAN2A1-FER.

In certain embodiments, the fusion gene can be PTEN-NOLC1.

In certain embodiments, the fusion gene is not TMEM135-CCDC67 or CCNH-C5orf30.

In certain embodiments, the method of treating a subject comprises determining the presence of one or more fusion genes (e.g., selected from the group consisting MAN2A1-FER, TMEM135-CCDC67, TRMT11-GRIK2, CCNH-C5orf30, LRRC59-FLJ60017, SLC45A2-AMACR, KDM4B-AC011523.2, PTEN-NOLC1, MTOR-TP53BP1 or a combination thereof) in a sample of the subject, where if one or more fusion genes are detected in the sample then performing a targeted genome editing technique on the fusion gene in one or more cancer cells within the subject to produce an anti-cancer effect.

In certain embodiments, the method of treating a subject having a cancer comprises determining the presence, in one or more cancer cell(s) of the subject, of one or more fusion genes selected from the group consisting of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 or a combination thereof, where if one or more fusion genes are detected in the cancer cell(s) then performing a genome editing technique targeting the fusion gene present within one or more cancer cells of the subject to produce an anti-cancer effect. In certain embodiments, the normal or non-cancerous cells that are adjacent to the cancer are not subjected to a genome editing technique as the gRNAs are specific for the sequences of the fusion gene, e.g., specific to the sequence of the breakpoint.

In certain embodiments, the method of treating a subject having a cancer comprises determining the presence, in one or more cancer cell(s) of the subject, of one or more fusion genes selected from the group consisting of ZMPSTE24-ZMYM4, CLTC-ETV1, ACPP-SEC13, DOCK7-OLR1, PCMTD1-SNTG1 or a combination thereof, where if one or more fusion genes are detected in the cancer cell(s) then performing a targeted genome editing technique on one or more cancer cells within the subject to produce an anti-cancer effect.

In certain embodiments, the method of treating a subject comprises determining the presence, in one or more cell(s) of the subject, of one or more fusion genes selected from the group consisting of CCNH-C5orf30, TMEM135-CCDC67, PTEN-NOLC1, MAN2A1-FER and a combination thereof, where if one or more fusion genes are detected in the cell(s) then performing a targeted genome editing technique on one or more cells within the subject, e.g., to reduce and/or eliminate the expression of the fusion gene and/or reduce and/or eliminate the expression of the protein encoded by the fusion gene in the one or more cells of the subject.

In certain embodiments, the method of treating a subject having a cancer comprises determining the presence, in one or more cancer cell(s) of the subject, of one or more fusion genes selected from the group consisting of CCNH-C5orf30, TMEM135-CCDC67, PTEN-NOLC1, MAN2A1-FER and a combination thereof, where if one or more fusion genes are detected in the cancer cell(s) then performing a targeted genome editing technique on one or more cancer cells within the subject to produce an anti-cancer effect.

In certain embodiments, the present invention provides a method of producing an anti-cancer effect in a subject having a cancer comprising performing a targeted genome editing technique on one or more cancer cells that contain a fusion gene within the subject, e.g., by targeting the fusion gene, to produce an anti-cancer effect.

The present invention further provides a method of preventing, minimizing and/or reducing the growth of a tumor comprising determining the presence of one or more fusion genes in a sample of the subject, where if one or more fusion genes are present in the sample then performing a genome editing technique targeting the fusion gene present within the tumor of the subject to prevent, minimize and/or reduce the growth of the tumor.

The present invention provides a method of preventing, minimizing and/or reducing the growth and/or proliferation of a cancer cell comprising determining the presence of one or more fusion genes in a sample of the subject, where if one or more fusion genes are present in the sample then performing a genome editing technique targeting the fusion gene, e.g., by targeting the chromosome breakpoint, present within the cancer cell of the subject to prevent, minimize and/or reduce the growth and/or proliferation of the cancer cell. In certain embodiments, the sequences that flank the breakpoint can be targeted by the genome editing technique.

In certain non-limiting embodiments, the present invention provides for methods of treating and/or inhibiting the progression of cancer and/or tumor and/or neoplastic growth in a subject comprising determining the presence of one or more fusion genes in a sample of the subject, where if one or more fusion genes are present in the sample then performing a targeted genome editing technique on one or more cells from the cancer and/or tumor of the subject to treat and/or inhibit the progression of the cancer and/or the tumor.

In certain embodiments, the present invention provides a method for lengthening the period of survival of a subject having a cancer. In certain embodiments, the method comprises determining the presence of one or more fusion genes in a sample of the subject, where if one or more fusion genes are present in the sample then performing a targeted genome editing technique on one or more cancer cells within the subject to produce an anti-cancer effect. In certain embodiments, the period of survival of a subject having cancer can be lengthened by about 1 month, about 2 months, about 4 months, about 6 months, about 8 months, about 10 months, about 12 months, about 14 months, about 18 months, about 20 months, about 2 years, about 3 years, about 5 years or more using the disclosed methods.

In certain embodiments, the present invention provides a method for treating a subject that comprises determining that at least one fusion gene is present in a sample obtained from a subject and then performing a genome editing technique targeting the fusion gene within one or more cells of the subject to achieve an anti-neoplastic effect, wherein the subject does not have prostate cancer.

In certain embodiments, the present invention provides an agent, or a composition comprising an agent, capable of targeted genome editing for use in a method to treat a subject. For example, and not by way of limitation, the present invention provides an agent capable of targeted genome editing for use in a method to treat or prevent cancer in a subject, wherein the method comprises performing a targeted genome editing procedure using the agent on one or more cells, e.g., cancer cells, that contain a fusion gene within the subject. In certain embodiments, the invention provides an agent, or a composition thereof, capable of targeted genome editing for use in a method to treat or prevent cancer in a subject, wherein the method comprises (i) determining the presence of one or more fusion genes in a cancer sample of the subject and (ii) where the sample contains a fusion gene, performing a targeted genome editing procedure using the agent on one or more cancer cells within the subject. In certain embodiments, the agent targets a specific chromosomal breakpoint of one or more of the fusion genes. In certain embodiments, the methods of the current invention involve the targeting of sequences that flank the breakpoint. In certain embodiments, the agent is an endonuclease. For example, and not by way of limitation, the endonuclease is a Cas9 protein. In certain embodiments, the endonuclease is a mutated form of Cas9, e.g., Cas9$^{D10A}$. In certain embodiments, the agent is an endonuclease, e.g., Cas9, in complex with one or more gRNAs (e.g., a ribonucleoprotein). In certain embodiments, the agent is an siRNA molecule.

In certain embodiments, the present invention provides a method of determining a treatment for a subject having one or more cells that contains one or more fusion genes. In certain embodiments, the method can include i) providing a sample from the subject; ii) determining whether one or more cells of the subject contains one or more fusion genes selected from the group consisting of TMEM135-CCDC67, TRMT11-GRIK2, SLC45A2-AMACR, MTOR-TP53BP1, LRRC59-FLJ60017, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 and a combination thereof; and iii) instructing a genome editing technique to be performed if one or more fusion genes are detected in the one or more cells, wherein the genome editing technique targets the one or more of the fusion genes detected in the one or more cells, and wherein the subject does not have prostate cancer. In certain embodiments, the genome editing technique is performed using the CRISPR/Cas 9 system.

In certain embodiments, the sample in which the one or more fusion genes are detected is prostate cancer, breast cancer, liver cancer, hepatocarcinoma, adenocarcinoma, hepatoma, lung cancer, non-small cell lung cancer, cervical cancer, endometrial cancer, pancreatic cancer, ovarian cancer, gastric cancer, thyroid cancer, glioblastoma multiforme, colorectal cancer, sarcoma, diffuse large B-cell lymphoma, acute lymphocytic leukemia, chronic lymphocytic leukemia, Hodgkin's lymphoma, non-Hodgkin's lymphoma and esophageal adenocarcinoma.

In certain embodiments, the sample is a glioblastoma sample, a breast cancer sample, a lung cancer sample, a liver cancer sample, an ovarian cancer sample, an adenocarcinoma or a colon cancer sample.

In certain embodiments, the sample in which the one or more fusion genes are detected is a breast cancer sample, a lung cancer sample or a colon cancer sample.

In certain embodiments, the sample in which the one or more fusion genes are detected is not a prostate cancer sample.

In certain embodiments, the sample is not a lung adenocarcinoma, glioblastoma multiforme or hepatocellular carcinoma sample.

In certain embodiments, the fusion gene in a sample is detected by genome sequencing. In certain embodiments, the fusion gene in a sample is detected by RNA sequencing. For example, and not by way of limitation, RNA sequencing can be performed using the primers disclosed in Table 5. In certain embodiments, the fusion gene in a sample is detected by FISH.

In certain embodiments, the methods of treating a subject, e.g., a subject that has a cancer that carries a fusion gene disclosed herein, can further comprise administering a therapeutically effective amount of an anti-cancer agent or agent that results in an anti-neoplastic effect. A "therapeutically effective amount" refers to an amount that is able to achieve one or more of the following: an anti-cancer effect, an anti-neoplastic effect, a prolongation of survival and/or prolongation of period until relapse. An anti-cancer agent can be any molecule, compound chemical or composition that has an anti-cancer effect. Anti-cancer agents include, but are not limited to, chemotherapeutic agents, radiotherapeutic agents, cytokines, anti-angiogenic agents, apoptosis-inducing agents or anti-cancer immunotoxins. In certain non-limiting embodiments, a genome-editing technique, disclosed herein, can be used in combination with one or more anti-cancer agents. "In combination with," as used herein, means that the genome-editing technique and the one or more anti-cancer agents (or agents that are that results in an anti-neoplastic effect) are part of a treatment regimen or plan for a subject.

5.5 Genome Targeting/Editing Techniques

Genome editing is a technique in which endogenous chromosomal sequences present in one or more cells within a subject, can be edited, e.g., modified, using targeted endonucleases and single-stranded nucleic acids. The genome editing method can result in the insertion of a nucleic acid sequence at a specific region within the genome, the excision of a specific sequence from the genome and/or the replacement of a specific genomic sequence with a new nucleic acid sequence. In certain embodiments, the genome editing technique can results in the repression of the expression of a gene, e.g., fusion gene. For example, and not by way of limitation, a nucleic acid sequence can be inserted at a chromosomal breakpoint of a fusion gene. A non-limiting example of a genome editing technique for use in the disclosed methods is the CRISPR system, e.g., CRISPR/Cas 9 system. Non-limiting examples of such genome editing techniques are disclosed in PCT Application Nos. WO 2014/093701 and WO 2014/165825, the contents of which are hereby incorporated by reference in their entireties.

In certain embodiments, the genome editing technique can include the use of one or more guide RNAs (gRNAs), complementary to a specific sequence within a genome, e.g., a chromosomal breakpoint associated with a fusion gene, including protospacer adjacent motifs (PAMs), to guide a nuclease, e.g., an endonuclease, to the specific genomic sequence. In certain embodiments, the genome editing technique can include the use of one or more guide RNAs (gRNAs), complementary to the sequences that are adjacent to and/or overlap the chromosomal breakpoint (see, e.g., FIGS. 13, 15 and 23), to guide one or more nucleases.

In certain embodiments, the one or more gRNAs can include a targeting sequence that is complementary to a sequence present within the fusion gene, e.g., complementary to the sequences that are adjacent to and/or overlap the chromosomal breakpoint. In certain embodiments, the one or more gRNAs used for targeting the fusion gene can comprise a sequence that is at least partially complementary to the breakpoint sequence of the fusion gene and at least partially complementary to a sequence of one of the genes that comprises the fusion gene. In certain embodiments, the targeting sequences are about 10 to about 50 nucleotides in length, e.g., from about 10 to about 45 nucleotides, from about 10 to about 40 nucleotides, from about 10 to about 35 nucleotides, from about 10 to about 30 nucleotides, from about 10 to about 25 nucleotides, from about 10 to about 20 nucleotides, from about 10 to about 15 nucleotides, from about 15 to about 50 nucleotides, from about 20 to about 50 nucleotides, from about 25 to about 50 nucleotides, from about 30 to about 50 nucleotides, from about 35 to about 50 nucleotides, from about 40 to about 50 nucleotides or from about 45 to about 50 nucleotides in length. In certain embodiments, the targeting sequence is greater than about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length.

In certain embodiments, the one or more gRNAs comprise a pair of offset gRNAs complementary to opposite strands of the target site. In certain embodiments, the one or more gRNAs comprises a pair of offset gRNAs complementary to opposite strands of the target site to generate offset nicks by an endonuclease. In certain embodiments, the offset nicks are induced using a pair of offset gRNAs with a nickase, e.g., a Cas9 nickase such as Cas9$^{D10A}$. In certain embodiments, the pair of offset gRNAs are offset by at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 88, 89, 90, 91, 92, 93, 94, 95, 96, 97, 98, 99, or at least 100 nucleotides. In certain embodiments, the pair of offset sgRNAs are offset by about 5 to about 100 nucleotides, about 10 to about 50 nucleotides, about 10 to about 40 nucleotides, about 10 to about 30 nucleotides, about 10 to about 20 nucleotides or about 15 to 30 nucleotides.

In certain non-limiting embodiments, a PAM can be recognized by a CRISPR endonuclease such as a Cas protein. Non-limiting examples of Cas proteins include, but are not limited to, CasI, CasIB, Cas2, Cas3, Cas4, Cas5, Cas6, Cas7, Cas8, Cas9 (also known as Csnl or Csxl2), CasIO, Csyl, Csy2, Csy3, Cse1, Cse2, Csc1, Csc2, Cse5, Csn2, Csm2, Csm3, Csm4, Csm5, Csm6, Cmrl, Cmr3, Cmr4, Cmr5, Cmr6, Csbl, Csb2, Csb3, Csxl7, Csxl4, CsxlO, Csxl6, CsaX, Csx3, Csxl, CsxlS, Csfl, Csf2, CsO, Csf4, Cpfl, c2cl, c2c3, Cas9HiFi, homologues thereof or modified versions thereof.

In certain embodiments, the endonuclease can be the clustered, regularly interspaced short palindromic repeat (CRISPR) associated protein 9 (Cas9) endonuclease. In certain embodiments, the Cas9 endonuclease is obtained from *Streptococcus pyogenes*. In certain embodiments, the Cas9 endonuclease is obtained from *Staphylococcus aureus*. In certain embodiments, the endonuclease can result in the cleavage of the targeted genome sequence and allow modification of the genome at the cleavage site through nonhomologous end joining (NHEJ) or homologous recombination. In certain embodiments, the Cas9 endonuclease can be a mutated form of Cas9, e.g., that generates a single-strand break or "nick." For example, and not by way of limitation, the Cas9 protein can include the D10A mutation, i.e., Cas9$^{D10A}$ (see Cong et al. Science. 339:819-823 (2013); Gasiunas et al. PNAS 109:E2579-2586 (2012); and Jinek et al. Science. 337:816-821 (2012), the contents of which are incorporated by reference herein).

In certain embodiments, the genome editing method and/or technique can be used to target one or more sequences of a fusion gene present in a cell, e.g., in a cancer cell, to promote homologous recombination to insert a nucleic acid into the genome of the cell. For example, and not by way of limitation, the genome editing technique can be used to target the region where the two genes of the fusion gene are joined together (i.e., the junction and/or chromosomal breakpoint).

In certain embodiments, the genome editing method and/or technique can be used to knockout the fusion gene, e.g., by excising out at least a portion of the fusion gene, to disrupt the fusion gene sequence. For example, and not by way of limitation, an endonuclease, e.g., a wild type Cas9 endonuclease, can be used to specifically cleave the double-stranded DNA sequence of a fusion gene, and in the absence of a homologous repair template non-homologous end joining can result in indels to disrupt the fusion gene sequence.

In certain embodiments, the genome editing method and/or technique can be used to repress the expression of the fusion gene, e.g., by using a nuclease-deficient Cas9. For example, and not by way of limitation, mutations in a catalytic domain of Cas9, e.g., H840A in the HNH domain and D10A in the RuvC domain, inactivates the cleavage activity of Cas9 but do not prevent DNA binding. In certain embodiments, Cas9$^{D10A\ H840A}$ (referred to herein as dCas9) can be used to target the region where the two genes of the fusion gene are joined together without cleavage, and by fusing with various effector domains, dCas9 can be used to silence the fusion gene.

As normal, non-cancerous cells do not contain the fusion gene, and therefore do not contain the chromosomal breakpoint associated with the fusion gene, cells can be specifically targeted using this genome editing technique. In certain embodiments, the genome editing technique can be used to target the junction (i.e., breakpoint) of a fusion gene including, but not limited to, TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1.

In certain embodiments, the one or more gRNAs that can be used in the disclosed methods can target the breakpoints that comprise the nucleotide sequences set forth in SEQ ID NOs: 40-56, 106 and 113 and/or the breakpoints that comprise the nucleotide sequences disclosed in FIGS. 4, 15, 17 and 18, e.g., SEQ ID NOs: 143-145 and 148-154. In certain embodiments, the one or more gRNAs used in the disclosed methods can be about 80%, about 85%, about 90%, about 91%, about 92%, about 93%, about 94%, about 95%, about 96%, about 97%, about 98% or about 99% homologous and/or complementary to the chromosomal breakpoints disclosed herein.

In certain embodiments, the gRNAs can be designed to target (e.g., be complementary to) the sequences flanking the chromosomal breakpoint region (see, for example, FIGS. 13, 15, 23 and 31) to guide an endonuclease, e.g., Cas9$^{D10A}$, to the chromosomal breakpoint region or a region surrounding the breakpoint. Non-limiting examples of the sequences of the gRNAs that can be used in the disclosed methods are detailed in FIG. 13B, FIG. 15A and FIG. 23A (e.g., SEQ ID NOs: 107, 112, 146, 147, 272 and 274). In certain embodiments, the one or more gRNAs used in the disclosed methods can be about 80%, about 85%, about 90%, about 91%, about 92%, about 93%, about 94%, about 95%, about 96%, about 97%, about 98% or about 99% homologous to the gRNAs disclosed herein. In certain embodiments, the disclosed gRNAs can include about 1, about 2, about 3, about 4 or about 5 nucleotide substitutions and/or mutations.

In certain embodiments, the one or more gRNAs can target intron 13 of TMEM135 and intron 9 of CCDC67, e.g., one gRNA can target intron 13 of TMEM135 and the second gRNA can target intron 9 of CCDC67, which flank the breakpoint of the TMEM135-CCDC67 fusion gene. In certain embodiments, one or more gRNAs used to target TMEM135-CCDC67 fusion gene can have a nucleotide sequence that comprises one or more of the nucleotide sequences set forth in FIG. 13B or 13C. In certain embodiments, the one or more gRNAs for targeting TMEM135-CCDC67 can be about 80%, about 85%, about 90%, about 91%, about 92%, about 93%, about 94%, about 95%, about 96%, about 97%, about 98% or about 99% homologous to the gRNAs disclosed in FIG. 13.

In certain embodiments, the one or more gRNAs can target intron 13 and/or exon 14 (or the splicing acceptor site of intron 13 and exon 14) of MAN2A1 and intron 14 of FER, which flank the breakpoint of the MAN2A1-FER fusion gene. In certain embodiments, one or more gRNAs used to target MAN2A1-FER fusion gene can have a nucleotide sequence that comprises one or more of the nucleotide sequences set forth in FIG. 15A. In certain embodiments, the one or more gRNAs for targeting MAN2A1-FER can be about 80%, about 85%, about 90%, about 91%, about 92%, about 93%, about 94%, about 95%, about 96%, about 97%, about 98% or about 99% homologous to the gRNAs disclosed in FIG. 15.

In certain embodiments, the one or more gRNAs can target intron 11 of PTEN and intron 1 of NOLC1, which flank the breakpoint of the PTEN-NOLC1fusion gene. In certain embodiments, one or more gRNAs used to target PTEN-NOLC1fusion gene can have a nucleotide sequence that comprises one or more of the nucleotide sequences set forth in FIG. 17A or FIG. 23A. In certain embodiments, the one or more gRNAs can target intron 11 of PTEN and intron 1 of NOLC1, which flank the breakpoint of the PTEN-NOLC1 fusion gene. In certain embodiments, the one or more gRNAs for targeting PTEN-NOLC1 can be about 80%, about 85%, about 90%, about 91%, about 92%, about 93%, about 94%, about 95%, about 96%, about 97%, about 98% or about 99% homologous to the gRNAs disclosed in FIGS. 17 and 23.

In certain embodiments, the fusion gene is CCNH-C5orf30.

In certain embodiments, the fusion gene is TMEM135-CCDC67.

In certain embodiments, the fusion gene is MAN2A1-FER.

In certain embodiments, the fusion gene can be PTEN-NOLC1.

In certain embodiments, the fusion gene is not CCNH-C5orf30 or TMEM135-CCDC67.

In certain embodiments, the disclosed genome editing technique can be used to promote homologous recombination with a sequence of a fusion gene, e.g., at a chromosomal breakpoint (junction) of a fusion gene, in one or more cells of a subject to allow the insertion of a nucleic acid sequence that when expressed results in the death, e.g., apoptosis, of the one or more cells. For example, and not by way of limitation, the nucleic acid sequence (also referred to herein as a donor nucleic acid) can encode the Herpes Simplex Virus 1 (HSV-1) thymidine kinase, Exotoxin A from *Pseudomonas aeruginosa*, Diphtheria toxin from *Corynebacterium* diphtheri, Ricin or abrin from *Ricinus communi* (castor oil plant), Cytosine deaminase from bacteria or yeast, Carboxyl esterase or Varicella Zoster virus (VZV) thymidine kinase. Additional non-limiting examples of nucleic acids and/or genes that can be inserted into the genome of a cell carrying a fusion gene to induce cell death are disclosed in Rajab et al. (2013) (J. of Genetics Syndromes and Gene Therapy, 4(9):187) and Zarogoulidis et al. (2013) (J. of Genetics Syndromes and Gene Therapy, 4(9):pii: 16849). In certain non-limiting embodiments, the nucleic acid sequence, e.g., the HSV-1 thymidine kinase nucleic acid sequence, is not operably linked to a regulatory sequence promoter (e.g., a promoter) and requires integration into the genome for expression. For example, and not by way of limitation, the promoter of the head gene of the fusion gene can promote the expression of the donor nucleic acid sequence.

In certain embodiments where a nucleic acid encoding HSV-1 thymidine kinase is inserted in the genome of one or more cells of a subject, a therapeutically effective amount of the guanine derivative, ganciclovir, or its oral homolog, valganciclovir, can be administered to the subject. HSV-1 thymidine kinase can phosphorylate and convert ganciclovir and/or valganciclovir into the triphosphate forms of ganciclovir and/or valganciclovir in the one or more cells of the subject. The triphosphate form of ganciclovir and/or valganciclovir acts as competitive inhibitor of deoxyguanosine triphosphate (dGTP) and is a poor substrate of DNA elongation, and can result in the inhibition of DNA synthesis. The inhibition of DNA synthesis, in turn, can result in the reduction and/or inhibition of growth and/or survival and/or cell death of cancer cells that contain the targeted chromosomal breakpoint and the integrated HSV-1 thymidine kinase nucleic acid sequence. This genome editing method can be used to produce an anti-cancer effect in a subject that has been determined to have a fusion gene.

In certain embodiments, a genome editing technique of the present disclosure can include the introduction of an expression vector comprising a nucleic acid sequence that encodes a Cas protein or a mutant thereof, e.g., Cas9$^{D10A}$, into one or more cells of the subject, e.g., cancer cells, carrying a fusion gene. In certain embodiments, the cells are not prostate cancer cells. In certain embodiments, the vector can further comprise one or more gRNAs for targeting the Cas9 protein to a specific nucleic acid sequence within the genome. In certain embodiments, the expression vector can be a viral vector.

In certain embodiments, the one or more gRNAs can hybridize to a target sequence within a fusion gene. For example, and not by way of limitation, the one or more gRNAs can target the chromosomal breakpoint of a fusion gene and/or target the one or more sequences that flank the chromosomal breakpoint region. Non-limiting examples of sequences of fusion gene chromosomal breakpoints are disclosed herein and within the Figures (see, for example, Table 1). In certain embodiments, one gRNA can be complementary to a region within one of the genes of the fusion gene and another gRNA can be complementary to a region within the other gene of the fusion gene. For example, and not by way of limitation, one gRNA can be complementary to a region within the TMEM135 gene of the TMEM135-CCDC67 fusion gene and another gRNA can be complementary to a region within the CCDC67 gene. In certain embodiments, one gRNA can be complementary to a region within the MAN2A1 gene of the MAN2A1-FER fusion gene and another gRNA can be complementary to a region within the FER gene. In certain embodiments, one gRNA can be complementary to a region within the PTEN gene of the PTEN-NOLC1 fusion gene and another gRNA can be complementary to a region within the NOLC1 gene. In certain embodiments, one gRNA can be complementary to a region upstream of the chromosomal breakpoint of a fusion gene and another gRNA can be complementary to a region downstream of the chromosomal breakpoint. In certain embodiments, genome sequencing can be performed to determine the regions of the fusion gene that can be targeted by the gRNAs. In certain embodiment, the regions of the genes that are targeted by the gRNAs can be introns and/or exons.

In certain embodiments, the nucleic acid sequence encoding the Cas protein, e.g., Cas9, can be operably linked to a regulatory element, and when transcribed, the one or more gRNAs can direct the Cas protein to the target sequence in the genome and induce cleavage of the genomic loci by the Cas protein. In certain embodiments, the Cas9 protein cut about 3-4 nucleotides upstream of the PAM sequence present adjacent to the target sequence. In certain embodiments, the regulatory element operably linked to the nucleic acid sequence encoding the Cas protein can be a promoter, e.g., an inducible promoter such as a doxycycline inducible promoter. The term "operably linked," when applied to DNA sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

In certain embodiments, the Cas9 enzyme encoded by a vector of the present invention can comprise one or more mutations. The mutations may be artificially introduced mutations or gain- or loss-of-function mutations. Non-limiting examples of such mutations include mutations in a catalytic domain of the Cas9 protein, e.g., the RuvC and HNH catalytic domains, such as the D10 mutation within the RuvC catalytic domain and the H840 in the HNH catalytic domain. In certain embodiments, a mutation in one of the catalytic domains of the Cas9 protein results in the Cas9 protein functioning as a "nickase," where the mutated Cas9 protein cuts only one strand of the target DNA, creating a single-strand break or "nick." In certain embodiments, the use of a mutated Cas9 protein, e.g., Cas9$^{D10A}$, allows the use of two gRNAs to promote cleavage of both strands of the target DNA. Additional non-limiting examples of Cas9 mutations include VP64, KRAB and SID4X, FLAG, EGFP and RFP. In certain embodiments, the genome editing technique of the present disclosure can further include introducing into the one or more cells an additional vector comprising a nucleic acid, that when expressed results in the death, e.g., apoptosis, of the one or more cells. In certain embodiments, this vector can further comprise one or more targeting sequences that are complementary (e.g., can hybridize) to the same and/or adjacent to the genomic sequences targeted by the gRNAs to allow homologous recombination to occur and insertion of the nucleic acid sequence (i.e., donor nucleic acid sequence) into the genome. In certain embodiments, the additional vector can further comprise one or more splice tag sequences of an exon/intron junction of a gene that makes up the fusion gene. In certain embodiments, the targeting sequences can be complementary to an intron, exon sequence and/or intron/exon splicing sequence within a gene of the fusion gene. In certain embodiments, one targeting sequence can be complementary to a region within one of the genes of the fusion gene targeted by the gRNAs and a second targeting sequence can be complementary to a region within the other gene of the fusion gene, to allow homologous recombination between the vector comprising the donor nucleic acid and the genome sequence cleaved by the Cas9 protein. For example, and not by way of limitation, one targeting sequence can be complementary to a region within the TMEM135 gene of the TMEM135-CCDC67 fusion gene and another targeting sequence can be complementary to a region within the CCDC67 gene. In certain embodiments, one targeting sequence can be complementary to a region within the MAN2A1 gene of the MAN2A1-FER fusion gene and another targeting sequence can be complementary to a region within the FER gene. In certain embodiments, one targeting sequence can be complementary to a region within the PTEN gene of the PTEN-NOLC1 fusion gene and another targeting sequence can be complementary to a region within the NOLC1 gene. In certain embodiments, one targeting sequence can be complementary to a region upstream of the cleavage site generated by the Cas9 protein and another targeting sequence can be complementary to a region downstream of the chromosomal breakpoint. Non-limiting examples of the types of nucleic acid sequences that can be inserted into the genome are disclosed above. In certain embodiments, the nucleic acid that is to be inserted into the genome encodes HSV-1 thymidine kinase. Additional non-limiting examples of nucleic acids and/or genes that can be inserted into the genome of a cell carrying a fusion gene to induce cell death are set forth above.

The vectors for use in the present disclosure can be any vector known in the art. For example, and not by way of limitation, the vector can be derived from plasmids, cosmids, viral vectors and yeast artificial chromosomes. In certain embodiments, the vector can be a recombinant molecule that contains DNA sequences from several sources. In certain embodiments, the vector can include additional segments such as, but not limited to, promoters, transcription terminators, enhancers, internal ribosome entry sites, untranslated regions, polyadenylation signals, selectable markers, origins of replication and the like. In certain embodiments, the vectors can be introduced into the one or more cells by any technique known in the art such as by electroporation, transfection and transduction. In certain embodiments, the vectors can be introduced by adenovirus transduction.

TABLE 1

Fusion gene junction sequences and siRNA sequences targeting the fusion gene junctions.

MAN2A1-FER

MAN2A1                          FER
GCAAATACTATTTCAGA AACAGCCTATGAGGGAAATTTTGGTGAAGTATATAAGGGCACA
(SEQ ID NO: 1)
siRNA sequence for MAN2A1-FER:
Sense Strand: 5' RCrArGrCrCrUrArUrGrArGrGrGrArArArUrUrUrUrGrGrUGA
(SEQ ID NO: 2)
Antisense Strand: 5' RUrCrArCrCrArArArArUrUrUrCrCrCrUrCrArUrArGr
GrCrUrGrUrU (SEQ ID NO: 3)

TABLE 1 -continued

Fusion gene junction sequences and siRNA sequences targeting the fusion genejunctions.

SLC45A2-AMACR
```
           SLC45A2              AMACR
TCCACTAC CATGCCCTCTTCACAGGTGTCATGGAGAAACTCCAGCTGGGCCCAGAGA
(SEQ ID NO: 4)
siRNA sequence for SLC45A2-AMACR:
Sense Strand: 5' RUrGrCrCrCrUrCrUrUrCrArCrArGrGrUrGrUrCrArUrGrGAG
(SEQ ID NO: 5)
Antisense Strand: 5' RCrUrCrCrArUrGrArCrArCrCrUrGrUrGrArArGrArGr
GrGrCrArUrG (SEQ ID NO: 6)
```

MTOR-TP53BP1
```
           MTOR                       TP53BP1
TGTCAGAATCC AAGTCAAGTCAGGATTCCTTGTTCTGGGAATGTCAGTGGAATCTGCT
CCTGC (SEQ ID NO: 7)
siRNA sequence for MTOR-TP53BP1:
Sense Strand: 5' RGrUrCrArGrGrArUrUrCrCrUrUrGrUrUrCrUrGrGrGrArATG
(SEQ ID NO: 8)
Antisense Strand: 5' RCrArUrUrCrCrCrArGrArArCrArArGrGrArArUrCrCr
UrGrArCrUrU (SEQ ID NO: 9)
```

TMEM135-CCDC67
```
           TMEM135                    CCDC67
TTTT AAGACTCACCAAGGGCAAATAAGAAGCCAACTCCAACAGGTGGAAGAGTACCA
(SEQ ID NO: 10)
siRNA sequence for TMEM135-CCDC67:
Sense Strand: 5' RGrArCrUrCrArCrCrArArGrGrGrCrArArArUrArArGrArAGC
(SEQ ID NO: 11)
Antisense Strand: 5' RGrCrUrCrUrUrArUrUrUrGrCrCrCrUrUrGrGrUrGr
ArGrUrCrUrU (SEQ ID NO: 12)
```

CCNH-C5orf30
```
           CCNH                       C5ORF30
TGTCACAGTTACTAGATA TAATGAAAATACCTGGAGTAGAACAGAAAAATTATTATGT
CT (SEQ ID NO: 13)
siRNA sequence for CCNH-C5orf30:
Sense Strand: 5' RArUrGrArArArArUrArCrCrUrGrGrArGrUrArGrArArCrAGA
(SEQ ID NO: 14)
Antisense Strand: 5' RUrCrUrGrUrUrCrUrArCrUrCrCrArGrGrUrArUrUrUrUr
CrArUrUrA (SEQ ID NO: 15)
```

KDM4B-AC011523.2
```
           KDM4B                      AC011523.2
AACTACCTGCACTTTG GGGAGCCTAAGTCCTGGACAGTAAGCAAGCCTGGATCTGAG
AGA (SEQ ID NO: 16)
siRNA sequence for KDM4-AC011523.2:
Sense Strand: 5' RGrArGrCrCrUrArArGrUrCrCrUrGrGrArCrArGrUrArArGCA
(SEQ ID NO: 17)
Antisense Strand: 5' RUrGrCrUrUrArCrUrGrUrCrCrArGrGrArCrUrUrArGrGr
CrUrCrCrC (SEQ ID NO: 18)
```

TRMT11-GRIK2
```
           TRMT11                     GRIK2
AGCATCTGGAG TTCCGCCTGCCGGTGGTATTTTTGAATATGTGGAATCTGGCCCAA
ATGGGAGCTG (SEQ ID NO: 19)
siRNA sequence for TRMT11-GRIK2:
Sense Strand: 5' RCrCrGrCrCrUrGrCrCrGrGrUrGrGrUrArUrUrUrUrUrGrAAT
(SEQ ID NO: 20)
Antisense Strand: 5' RArUrUrCrArArArArUrArCrCrArCrCrGrGrCrArGrGr
CrGrGrArA (SEQ ID NO: 21)
```

LRRC59-FLJ60017
```
           LRRC69                     FLJ60017
CTGCTTGGATGAGAAGCAGTGTAAGCAGTGTGC AAACAAGGTGACTGGAAGCACC
TGCTCAATGGCTG (SEQ ID NO: 22)
siRNA sequence for LRRC59-FLJ60017:
Sense Strand: 5' RArCrArArGrGrUrGrArCrUrGrGrArArGrCrArCrCrUrGrCTC
(SEQ ID NO: 23)
Antisense Strand: 5' RGrArGrCrArGrGrUrGrCrUrUrCrCrArGrUrCrArCrCr
UrUrGrUrU (SEQ ID NO: 24)
```

TABLE 1 -continued

Fusion gene junction sequences and siRNA sequences targeting the fusion gene junctions.

```
PTEN-NOLC1
              PTEN                    NOLC1
AAGCCAACCGATACTT TTCTCCAAATTTTAAGACACAGCAGGATGCCAATGCCTCTT
CCCTCTTAGAC (SEQ ID NO: 25)
siRNA sequence for PTEN-NOLC1:
Sense Strand: 5' RCrUrCrCrArArArUrUrUrUrArArGrArCrArCrArGrCrArGGA
(SEQ ID NO: 26)
Antisense Strand: 5' RUrCrCrUrGrCrUrGrUrGrUrCrUrUrArArArArUrUrUr
GrGrArGrArA (SEQ ID NO: 27)
```

The head gene is indicated by italic font.
Targeted sequences are underlined and bolded.

5.5.1 Particular Non-Limiting Examples

In certain embodiments, a genome editing technique of the present invention comprises introducing into one or more cells, e.g., cancer cells, of a subject: (i) a vector comprising a nucleic acid sequence that encodes a Cas9 protein, or mutant thereof; (ii) a vector comprising one or more gRNAs that are complementary to one or more target sequences of a fusion gene, that when expressed induce Cas9-mediated DNA cleavage within the fusion gene; and (iii) a vector comprising a donor nucleic acid sequence, that when expressed results in cell death, and one or more targeting sequences that are complementary to one or more sequences of the fusion gene to promote homologous recombination and the insertion of the donor nucleic acid sequence into the fusion gene. In certain embodiments, the cancer cell is not a prostate cancer cell.

In certain embodiments, a genome editing technique of the present invention comprises introducing into one or more cells of a subject: (i) a vector comprising a nucleic acid sequence that encodes a Cas9 protein, or mutant thereof (e.g., Cas9$^{D10A}$), and one or more gRNAs that are complementary to one or more target sequences of a fusion gene, wherein when transcribed, the one or more gRNAs direct sequence-specific binding of one or more Cas9 proteins to the one or more target sequences of the fusion gene to promote cleavage of the fusion gene; and (ii) a vector comprising a donor nucleic acid sequence, that when expressed results in cell death, and one or more targeting sequences that are complementary to one or more sequences of the fusion gene to promote homologous recombination and the insertion of the donor nucleic acid sequence into the fusion gene. In certain embodiments, the one or more targeting sequences can include the chromosomal breakpoint of a fusion gene and/or the one or more sequences that flank the chromosomal breakpoint region or a combination thereof. For example, and not by way of limitation, the target sequence can comprise at least a part of the breakpoint sequence of the fusion gene and at least a part of a sequence of one of the genes that comprises the fusion gene.

In certain embodiments, a genome editing technique of the present invention comprises introducing into one or more cells of a subject: (i) a vector comprising a nucleic acid sequence that encodes Cas9 protein, or mutant thereof, and one or more gRNAs that are complementary to one or more target sequences of a fusion gene, wherein when transcribed, the one or more gRNAs direct sequence-specific binding of a Cas9 protein to the one or more target sequences of the fusion gene to promote cleavage of the fusion gene; and (ii) a vector comprising a donor nucleic acid sequence encoding HSV-1 thymidine kinase and one or more targeting sequences that are complementary to one or more sequences of the fusion gene to promote homologous recombination and the insertion of the donor nucleic acid sequence encoding HSV-1 thymidine kinase into the fusion gene. In certain embodiments, the genome editing technique further comprises the administration of a therapeutically effective amount of ganciclovir and/or valganciclovir.

5.6 Kits

The present invention further provides kits for treating a subject that carries one or more of the fusion genes disclosed herein and/or for carrying out any one of the above-listed detection and therapeutic methods. In certain embodiments, the present disclosure provides kits for performing a targeted genome editing technique on one or more cancer cells within the subject that carries one or more of the fusion genes disclosed herein. In certain embodiments, the one or more cancer cells are not prostate cancer cells.

Types of kits include, but are not limited to, packaged fusion gene-specific probe and primer sets (e.g., TaqMan probe/primer sets), arrays/microarrays, antibodies, which further contain one or more probes, primers, or other reagents for detecting one or more fusion genes and/or can comprise means for performing a genome editing technique.

In certain embodiments, the kit can include means for performing the genome editing techniques disclosed herein. For example, and not by way of limitation, a kit of the present disclosure can include a container comprising one or more vectors or plasmids comprising a nucleic acid encoding a Cas protein or a mutant thereof, e.g., Cas9$^{D10A}$. In certain embodiments, the nucleic acid encoding the Cas protein can be operably linked to a regulatory element such as a promoter. In certain embodiments, the one or more vectors can further comprise one or more gRNAs specific to a fusion gene, e.g., specific to a breakpoint of a fusion gene and/or sequences flanking the breakpoint of a fusion gene.

In certain embodiments, a kit of the present invention can include, optionally in the same container as the vector comprising the nucleic acid encoding a Cas protein or in another container, one or more vectors or plasmids comprising a nucleic acid, that when expressed (in the presence of absence of a compound) results in cell death. For example, and not by way of limitation, the nucleic acid sequence can encode the Herpes Simplex Virus 1 (HSV-1) thymidine kinase, Exotoxin A from *Pseudomonas aeruginosa*, Diphtheria toxin from *Corynebacterium* diphtheri, Ricin or abrin from *Ricinus* communi (castor oil plant), Cytosine deaminase from bacteria or yeast, Carboxyl esterase or Varicella Zoster virus (VZV) thymidine kinase. In certain embodiments, this vector can further comprise one or more targeting sequences that are complementary to sequences within the fusion gene to promote homologous recombination and insertion of the donor nucleic acid.

In certain embodiments, where the donor nucleic acid encodes HSV-1 thymidine kinase, the kit can further comprise ganciclovir and/or valganciclovir.

In certain non-limiting embodiments, a kit of the present disclosure can further comprise one or more nucleic acid primers or probes and/or antibody probes for use in carrying out any of the above-listed methods. Said probes may be detectably labeled, for example with a biotin, colorimetric, fluorescent or radioactive marker. A nucleic acid primer may be provided as part of a pair, for example for use in polymerase chain reaction. In certain non-limiting embodiments, a nucleic acid primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length. An nucleic acid probe may be an oligonucleotide probe and/or a probe suitable for FISH analysis. In specific non-limiting embodiments, the kit comprises primers and/or probes for analysis of at least two, at least three, at least four, at least five, six, seven, eight, nine, ten, eleven, twelve, thirteen, fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1. In certain embodiments, the kit comprises primers for analysis of TMEM135-CCDC67, MAN2A1-FER, PTEN-NOLC1 and CCNH-C5orf30.

In certain non-limiting embodiments, the nucleic acid primers and/or probes may be immobilized on a solid surface, substrate or support, for example, on a nucleic acid microarray, wherein the position of each primer and/or probe bound to the solid surface or support is known and identifiable. The nucleic acid primers and/or probes can be affixed to a substrate, such as glass, plastic, paper, nylon or other type of membrane, filter, chip, bead, or any other suitable solid support. The nucleic acid primers and/or probes can be synthesized directly on the substrate, or synthesized separate from the substrate and then affixed to the substrate. The arrays can be prepared using known methods.

In non-limiting embodiments, a kit provides nucleic acid probes for FISH analysis to determine the presence of one or more fusion genes in a sample obtained from a subject. In certain embodiments, the one or more fusion genes are selected from the group consisting of: TRMT11-GRIK2, SLC45A2-AMACR, MTOR-TP53BP1, LRRC59-FLJ60017, TMEM135-CCDC67, CCNH-C5orf30, TRMT11-GRIK2, SLC45A2-AMACR, KDM4B-AC011523.2, MAN2A1-FER, PTEN-NOLC1, MTOR-TP53BP1, ZMPSTE24-ZMYM4, CLTC-ETV1, ACPP-SEC13, DOCK7-OLR1, PCMTD1-SNTG1 and a combination thereof. In non-limiting embodiments, a kit provides nucleic acid probes for FISH analysis of one or more fusion genes. In certain embodiments, the one or more fusion genes can include TRMT11-GRIK2, SLC45A2-AMACR, MTOR-TP53BP1, LRRC59-FLJ60017, TMEM135-CCDC67, PTEN-NOLC1 and CCNH-C5orf30, and TRMT11-GRIK2, SLC45A2-AMACR, KDM4B-AC011523.2, MAN2A1-FER, MTOR-TP53BP1 or combinations thereof. In specific non-limiting embodiments, probes to detect a fusion gene may be provided such that separate probes each bind to the two components of the fusion gene or a probe may bind to a "junction" that encompasses the boundary between the spliced genes. For example, and not by way of limitation, the junction is the region where the two genes are joined together. In specific non-limiting embodiments, the kit comprises said probes for analysis of at least two, at least three, at least four or all five of ZMPSTE24-ZMYM4, CLTC-ETV1, ACPP-SEC13, DOCK7-OLR1 or PCMTD1-SNTG1.

In non-limiting embodiments, a kit provides nucleic acid primers for PCR analysis to determine the presence of one or more fusion genes in a sample obtained from a subject. In certain embodiments, the one or more fusion genes are selected from the group consisting of: TRMT11-GRIK2, SLC45A2-AMACR, MTOR-TP53BP1, LRRC59-FLJ60017, TMEM135-CCDC67, PTEN-NOLC1, CCNH-C5orf30, TRMT11-GRIK2, SLC45A2-AMACR, KDM4B-AC011523.2, MAN2A1-FER, MTOR-TP53BP1 and a combination thereof. In non-limiting embodiments, a kit provides nucleic acid primers for PCR analysis of one or more fusion gene selected from the group consisting of: ZMPSTE24-ZMYM4, CLTC-ETV1, ACPP-SEC13, DOCK7-OLR1 or PCMTD1-SNTG1. In specific non-limiting embodiments, the kit comprises said primers for analysis of at least two, at least three, at least four, at least five, six, seven, eight, nine, ten, eleven, twelve, thirteen, fourteen of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1 and PCMTD1-SNTG1.

The following Examples are offered to more fully illustrate the disclosure, but are not to be construed as limiting the scope thereof.

6. Example 1: Genome Therapy Targeting at the Chromosome Breakpoints of Fusion Genes Resulted in Remission of Xenografted Human Cancers 6.1 Introduction In this Example, a genome intervention approach was developed to kill cancer cells based on unique sequences resulting from genome rearrangement. The chromosome breakpoints from MAN2A1-FER and TMEM135-CCDC67 fusion genes were exploited as therapeutic targets. The MAN2A1-FER and TMEM135-CCDC67 fusion genes have been previously determined to be present in prostate cancer (see WO 2016/011428, the contents of which are hereby incorporated by reference in its entirety). Additionally, the MAN2A1-FER fusion gene has been shown to be present in glioblastoma multiforme, non-small cell lung cancer, ovarian cancer, esophagus adenocarcinoma and liver cancer, in percentages ranging from 2-25.9%. MAN2A1-FER fusion gene has been shown to be present in 16.8% of non-small cell lung cancer, 15.7% of liver cancer, 7.1% GBM, 25.9% of esophagus adenocarcinoma, 5.2% of prostate cancer and 1.7% of ovarian cancer.

Clustered regularly interspaced short palindromic repeats (CRISPR)/CRISPR-associated (Cas) was originally discovered as one of the immunity defense mechanisms against foreign pathogens in prokaryotic cells[2]. Cas9, a critical protein for type II of CRISPR/Cas system, was found to contain DNA cleavage activity. The nuclease activity of Cas9 was guided by a 20-base complementary sequence from CRISPR RNA and trans-activating CRISPR RNA to the targeted DNA[3]. Since trans-activating CRISPR RNA and CRISPR RNA can be made into a chimeric RNA containing the full function of both RNA species, guide RNA (gRNA) was coined for the artificial fusion RNA[4]. The D10A mutation in the catalytic domain of Cas9 converts it to a nickase that produces a single nucleotide break at the target DNA[4]. Nicking genomic DNA can be used to precisely introduce sequences into a specific genomic locus by using the cellular homology-directed repair (HDR) pathway. Introducing two nicks in proximity (double nicking) in target DNA increases the efficiency of introducing sequences 50- to 1,500-fold[5] over natural homologous-recombination rates, with an off-target rate as low as 1/10,000. Such specificity makes somatic genomic targeting a viable approach in treating human diseases, especially neoplasms carrying fusion genes that do not exist in normal cells.

Herpes Simplex Virus 1 thymidine kinase (HSV1-tk) phosphorylates thymidine and forms thymidine monophosphate, a building block for DNA synthesis. However, the substrate specificity of HSV1-tk is different from that of its mammalian counterpart in that it also phosphorylates the synthetic nucleoside homolog ganciclovir (prodrug)[7], which is not recognized by mammalian thymidine kinase. This phosphorylation results in accumulation of ganciclovir monophosphate in mammalian cells that express HSV1-tk after treatment with ganciclovir. Ganciclovir monophosphate is converted to its triphosphate form by two other kinases[8]. Ganciclovir triphosphate blocks DNA synthesis through elongation termination. Mammalian cells negative for HSV1-tk, in contrast, are immune from this effect, owing to their inability to phosphorylate ganciclovir.

In this Example, we show that by using $Cas9^{D10A}$ mediated genome editing, we have successfully inserted HSV1-tk into the chromosomal breakpoints of fusion gene, MAN2A1-FER. Treatment of tumors harboring this chromosome breakpoint with ganciclovir led to cell death in cell culture and remission of xenografted prostate and liver cancers in Severe Combined Immunodeficiency (SCID) mice.

6.2 Materials and Methods

Materials and vector construction. PC3 (prostate cancer), Du145 (prostate cancer) and the hepatocellular carcinoma cell lines, HUH7 and HEP3B cells, were purchased from American Type Cell Culture (Manassas, Va.). PC3 cells were cultured with F12K medium supplemented with 10% fetal bovine serum (InVitrogen, Carlsbad, Calif.). Du145 cells were cultured with modified Eagle medium supplemented with 10% fetal bovine serum (Invitrogen). HEP3B cells were cultured with modified Eagle medium supplemented with 10% fetal bovine serum (InVitrogen). HUH7 cells were cultured with Dulbecco's modified eagle medium supplemental with 10% fetal bovine serum. The genomes of these cell lines were tested for a short tandem repeat (STR) DNA profile on eight different loci (CSF1PO, D13S317, D16S539, D5S818, D7S820, THO1, TPDX, and vWA) of the genomes by PCR using the following sets of primers

```
CSF1PO:
                                      (SEQ ID NO: 78)
AACCTGAGTCTGCCAAGGACTAGC/

(SEQ ID NO: 79)
TTCCACACACCACTGG CCATCTTC;

D13S317:
                                      (SEQ ID NO: 80)
ACAGAAGTCTGGGATGTGGA/

(SEQ ID NO: 81)
GCCCAAAAAGACAGACAGAA,

D16S539:
                                      (SEQ ID NO: 82)
GATCCCAAGCTCTTCCTCTT/
```

```
                                      (SEQ ID NO: 83)
ACGTTTGTGTGTGCATCTGT;

D5S818:
                                      (SEQ ID NO: 84)
GGGTGATTTTCCTCTTTGGT/

(SEQ ID NO: 85)
TGATTCCAATCATAGCCACA;

D7S820:
                                      (SEQ ID NO: 86)
TGTCATAGTTTAGAACGAACTAACG/

(SEQ ID NO: 87)
CTGAGGTATCAAAAACTC AGAGG;

TH01:
                                      (SEQ ID NO: 88)
GTGGGCTGAAAAGCTCCCGATTAT/

(SEQ ID NO: 89)
ATTCAAAGGGTATCTGGGCTCTGG;

TPDX:
                                      (SEQ ID NO: 90)
ACTGGCACAGAACAGGCACTTAGG/

(SEQ ID NO: 91)
GGAGGAACTGGGAACCACACAGGT;

vWA:
                                      (SEQ ID NO: 92)
CCCTAGTGGATGATAAGAATAATCAGTATG/

(SEQ ID NO: 93)
GGACAGATGATAAATACATAGGATGGATGG.
```

These cell lines were authenticated because the STR profiles of the cell lines perfectly matched those published by ATCC. Rabbit polyclonal anti-Cas9 antibodies were purchased from Clontech Inc., CA. Rabbit anti-HSV-1 TK polyclonal antibodies were purchased from Sigma Inc., OH.

Construction of vector. To construct the gRNA expression vector, sequences flanking the breakpoint region of TMEM135-CCDC67 were analyzed and gRNAs were designed using DNA 2.0 tool: www.dna20.com/eCommerce/cas9/input. Both gRNA- and gRNA+ were ligated into All-in-One NICKASENINJA® vector that also contains $Cas9^{D10A}$. The insert was then released by restriction with XbaI, and ligated into similarly restricted VQAd5 shuttle vector to create VQAd5-$Cas9^{D10A}$-$gRNA^{TMEM135int13}$-$gRNA^{CCDC67int9}$. The recombinant shuttle vector was then recombined with pAD5 virus to generate pAD5-$Cas9^{D10A}$-$gRNA^{TMEM135int13}$-$gRNAc^{CDC67int9}$ using a method previously described (14).

To construct donor DNA recombinant virus, PCR was performed on pEGFP-N1 using the following primers: GTACTCACGTAAGCTTTCGCCACCATGGTGAGCA-AGG (SEQ ID NO:94); and GACTCAGATGGG-CGCCCTTGTACAGCTCGTCCATGCC (SEQ ID NO:95). The PCR product was restricted with KasI and HindIII, and ligated into similarly restricted pSELECT-zeo-HSV1tk vector to create pEGFP-HSV1-tk.

PCR was performed on the genome DNA from sample where TMEM135-CCDC67 fusion was discovered to obtain intron 13 sequence of TMEM135 using the following primers: GACTCAGATGGCGGCCGCCTGTATTCTTTGTTT-ACAGATTTGCTGTCAGGGG TTAGATAGCTTGCCAG (SEQ ID NO:96)/GTACTCACGTAAGCTTGAGCTAA-CATTACCAATGAGGC (SEQ ID NO:97). The PCR products were then restricted with NotI and HindIII, and ligated into similarly restricted pEGFPtk vector to create pTMEM135$^{int13}$-EGFP-tk. Subsequently, PCR was performed on the genome DNA from the sample where TMEM135-CCDC67 fusion was discovered to obtain intron 9 sequence of CCDC67 using the following primers: GACTCAGATGGCTAGCAGTTCACTGAGTGTGC-CATGC (SEQ ID NO:98)/GTACTCACGTGAATTCCTAT-TCTGCCTGCTTGCATACCTTTTGTTTTGGTTGCA GTATAGTGGGCTGAG (SEQ ID NO:99). The PCR was then restricted with NheI and EcoRI, and ligated into the similarly restricted pTMEM135$^{int13}$-EGFP-tk vector to create pTMEM135$^{int13}$-EGFP-tk-CCDC67$^{int9}$. The vector was then restricted with EcoR1 and NotI and ligated into the similarly restricted pAdlox to create pAdlox-pTMEM135$^{int13}$-EGFP-tk-CCDC67$^{int9}$. The recombinant shuttle vector was then recombined with adenovirus to create pAd-TMEM135$^{int13}$-EGFP-tk-CCDC67$^{int9}$. For the construction of pCMV-TMEM135-CCDC67bp vector, PCR was performed on genome DNA from a prostate cancer sample that are positive for TMEM135-CCDC67 fusion using the following primers: GACTCAGATGAAGCT-TAAGAGCATGGGCTTTGGAGTC (SEQ ID NO:100)/ GTACTCACGTTCTAGACTGGAATCTAGGACTCTT-GGC (SEQ ID NO:101). The PCR product was then sequenced to confirm the presence of TMEM135-CCDC67 breakpoint. The PCR product was digested with HindIII and XbaI, and ligated into similarly digested pCMVscript vector. The construct was subsequently transfected into PC3 and DU145 cells using lipofectamine 3000. Cells stably expressing TMEM135-CCDC67 breakpoint transcripts were selected by incubation of the transfected cells in medium containing G418 (200 µg/ml).

The construction of pAD5-Cas9D$^{10A}$-gRNAM-AN2A1$^{int13}$-gRNAFER$^{int14}$ followed the similar procedure of constructing the gRNA for targeting the TMEM135-CCDC67 fusion gene as described above. For construction of pAdlox-MAN2A1$^{int13}$-EGFP-tk-FER$^{int14}$, extended long PCR was performed on 1 µg genome DNA from HUH7 cells using the following primers: GACTCAGATGGCGG-CCGCGAACATCAGAACTGGGAGAGG(SEQ ID NO: 102)/GTACTCACGTAAGCTTCAGGAGAATCACTT-GAACCCG (SEQ ID NO:103). The PCR product was then digested with HindIII and Not1, and ligated into similarly digested pEGFP-tk vector to create pMAN2A1$^{int13}$-EGFP-tk. A synthetic sequence corresponding to splicing acceptor site of MAN2A1 intron 13/exon 14 (TAATGTTGGTTT-TACCAAAAATATAAATGGTTTGCCTCTCAGTAGA-TAACAT TTATCTTTAATAAATTCCCTTCCCTATCTTT-TAAAGATCTCTTTTCGAGCACAT AT (SEQ ID NO:104)/TAATATGTGCTCGAAAAGAGATCTTTAAA AGATAGGGAAGGGAATTTATTAA AGATAAATGTTA TCTACTGAGAGGCAAACCATTTATATTTTGGTAA AACCA ACAT(SEQ ID NO:105)) was ligated to ASE1 restricted pMAN2A1$^{int13}$-EGFP-tk. Separately, a PCR was performed on HUH7 genome DNA using primers GACTCAGATGGAATTCAAGGTGGAACACAGAAG GAGG (SEQ ID NO: 121)/GTACTCACGTGAATTCGAT-TACTTTAAATAACTCACTTGGCTTCTTG CAGAGG TAGAGCTGAGAGAAG (SEQ ID NO:122) to generate a 1984 bp sequence corresponding to intron 14 of FER including 31 bp splice donor site sequence corresponding to FER exon 15/intron 15. The PCR was then restricted with EcoR1, and ligated into similarly restricted pMAN2 A1int13-EGFP-tk-FERint14 to create pMAN2A1$^{int13}$-EGFP-tk-FER$^{int14}$. The vector was then restricted with NotI, and bluntended with T4 DNA polymerase. The product was then restricted with XmaI. Separately, pAdlox vector was restricted with HindIII, and blunt-ended with T4 DNA polymerase. The product was restricted with XmaI, and ligated with the digestion product of pMAN2A1$^{int13}$-EGFP-tk-FER$^{int14}$. The recombinant shuttle vector was then recombined with adenovirus to create pAd-MAN2A1$^{int13}$-EGFP-tk-FER$^{int14}$.

In vitro Cas9 target cleavage assays. gRNA DNA sequence plus scaffold DNA sequence for + or − DNA strand were amplified from the all-in-one vector with the following primers: GGCCAGTGAATTGTAATACGACTCACTAT AGGGAGGCGGTAGCATTAAGGG CCCCCTAAGTTT-TAGAGCTAGAAATAGCAAG (SEQ ID NO:108) for gRNA+ template of MAN2A1-FER, and GGCCAGT-GAATTGTAATACGACTCACTATAGGGAGGCGGAT AGCTAGAAGG TGGATCACGTTTTAGAGCTAGA AATAGCAAG (SEQ ID NO:109) for gRNA− template of MAN2A1-FER. The PCR products were in vitro transcribed using In Vitro Transcription kit from Ambion, CA, to obtain gRNA+ and gRNA− products. Cleavage assays were performed at 25° C. for 10 min and then 37° C. for 1 hour under the following condition: 1×Cas9 nuclease reaction buffer, 30 nM gRNA 3 nM DNA template and 30 nM Cas9 Nuclease, S. pyogenes. The cleaved DNA was visualized in 1% agarose gel electrophoresis.

Fluorescence activated cell sorting (FACS) analysis of apoptotic cells. The assays were previously described (8,9). Briefly, the cells treated with pAD5-Cas9$^{D10A}$-gRNAMAN2A1$^{int13}$-gRNAFER$^{int14}$/pAD-MAN2A1$^{int13}$-EGFP-tk-FER$^{int14}$ and various concentrations of ganciclovir were trypsinized and washed twice with cold PBS. The cells were then resuspended in 100 µl of annexin binding buffer (Invitrogen), and incubated with 5 µl of phycoerythrin (PE)-conjugated annexin V and 1 µl of 100 µg/ml propidium iodide for 15 min in dark at room temperature. The binding assays were terminated by addition of 400 µl of cold annexin binding buffer. FACS analysis was performed using a BD-LSR-II flow cytometer (BD Science, San Jose, Calif.). The fluorescence stained cells were analyzed at the fluorescence emission at 533 nm (FL2). The negative control, cells with neither PE nor PI in the incubation medium, was used to set the background for the acquisition. UV treated cells were used as a positive control for apoptosis. For each acquisition, 10,000 to 20,000 cells were analyzed and sorted based on the fluorescence color of the cells. For HUH7 and HEP3B FACS analysis, similar procedures were performed except these cells were treated with 1 µM scr-7 along with viral infections to improve genome editing efficiency (10).

Tumor Growth and Spontaneous Metastasis. The xenografting procedure was described previously (11,12). For HUH7 and HEP3B xenografted tumor treatment, a similar procedure was applied as previously described in Example 7 of WO 2016/011428, except that the treatment was started 2 weeks after the tumor xenografting due to rapid growth of the cancers. The breakdown of the treated groups is the following: 5 mice xenografted with HUH7 cells were treated with pAD5-Cas9$^{D10A}$-gRNAMAN2A1$^{int13}$-gRNAFE$^{int14}$/pAD-MAN2A1$^{int13}$-EGFP-tk-FER$^{int14}$ and ganciclovir; 5 mice xenografted with HUH7 cells were treated with pAD5-Cas9$^{D10A}$-gRNATMEM135$^{int13}$-gRNACCDC67$^{int9}$/pAD-TMEM135int13-EGFP-tk-CCDC67$^{int9}$ and ganciclovir (control); 5 mice xenografted with HUH7 cells were treated with pAD5-Cas9$^{D10A}$-gRNAMAN2A1$^{int13}$-gRNAFER$^{int14}$/pAD-MAN2A1$^{int13}$-EGFP-tk-FER$^{int14}$ and PBS (control); 5 mice xenografted with HEP3B cells were treated with pAD5-Cas9$^{D10A}$gRNAMAN2A1$^{int13}$-gRNAFER$^{int14}$/pAD-MAN2A1$^{int13}$-EGFP-tk-FER$^{int14}$ and ganciclovir (control). All animals were treated scr-7 (10 mg/kg) along with viruses. All animal procedures were approved by the University of Pittsburgh Institutional Animal Care and Use Committee.

Immunohistochemistry. Immunohistochemistry was performed as described previously 6 with antibodies specific for HSV-1 TK (1:100 dilution) or for Cas9 (1:100 dilution). The antibody was omitted in negative controls. The sections were then incubated with horseradish peroxidase conjugated anti-rabbit IgG for 30 minutes at room temperature (ABC kit from Vector Labs, Inc). Slides were then exposed to a 3,3'-diaminobenzidine solution to visualize immunostaining. Counterstaining was performed by incubating the slides in 1% Hematoxylin solution for 2 minutes at room temperature. The slides were then rinsed briefly in distilled water to remove excessive staining. The procedure of TUNEL assays is similar to that previously described (13).

6.3 Results

One recurring fusion gene discovered in prostate cancer is located between the genes encoding transmembrane protein 135 (TMEM135) and coiled-coil domain containing 67 (CCDC67), i.e., TMEM135-CCD67$^{6,16}$. The fusion gene is created by a 6-Mb deletion in the region of chromosome 11q14.2-21. The deletion joins intron 13 of TMEM135 with intron 9 of CCDC67 in chromosome 11 (FIG. 13A) and creates a unique sequence breakpoint not present in normal tissues, thus providing a unique target in cancer cells for therapeutic intervention.

To target this joining sequence, two sgRNAs were designed, each complementary to one of the regions flanking the chromosomal breakpoint on opposite strands (FIG. 13B). These guide RNAs (gRNAs) and a Cas9$^{D10A}$ sequence were ligated into the VQAd5-CMV shuttle vector and recombined into pAD5 adenovirus to create pAD5-Cas9$^{D10A}$-gRNA$^{TMEM135int13}$-gRNA$^{CCDC67int9}$. To provide a potential lethal gene for targeted cancer cells, cDNA of HSV-1 tk was ligated with EGFP cDNA in frame, thus yielding the chimeric gene EGFP-tk. The chimeric cDNA was promoterless but contained a full open reading frame and ribosome-binding site for independent translation initiation. To provide homologous sequences to engage the HDR pathway, the construct was then ligated with 584 bp of the intron 13 sequence of TMEM135 at the 5' end and 561 bp of the intron 9 sequence of CCDC67 at the 3' end. These sequences were subsequently ligated into the PAdlox shuttle vector and recombined into adenovirus, thus yielding pAD-TMEM135int13-EGFP-tk-CCDC67int9 (FIG. 13C). Integration of TMEM135int13-EGFP-tk-CCDC67int9, expression of EGFP-tk and apoptosis were detected in PC3 or DU145 cells that contained the TMEM135-CCDC67 breakpoint and were treated with the recombinant viruses (FIG. 31). Genetic targeting of the TMEM135-CCD67 in prostate cancer is disclosed in WO 2016/011428, the contents of which are hereby disclosed in their entirety (see FIGS. 30, 31 and 32 of WO 2016/011428, and accompanying text).

Figure 15A:
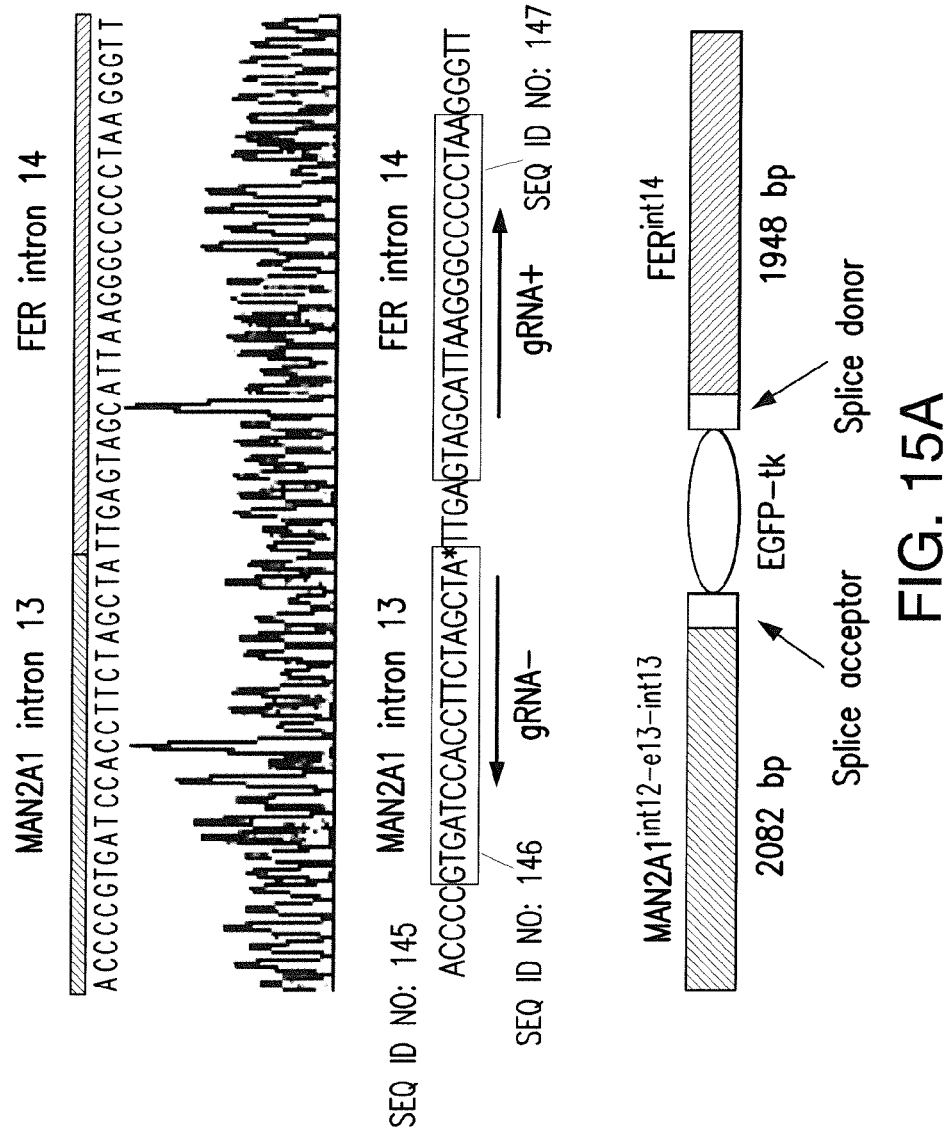
Figure 15G:
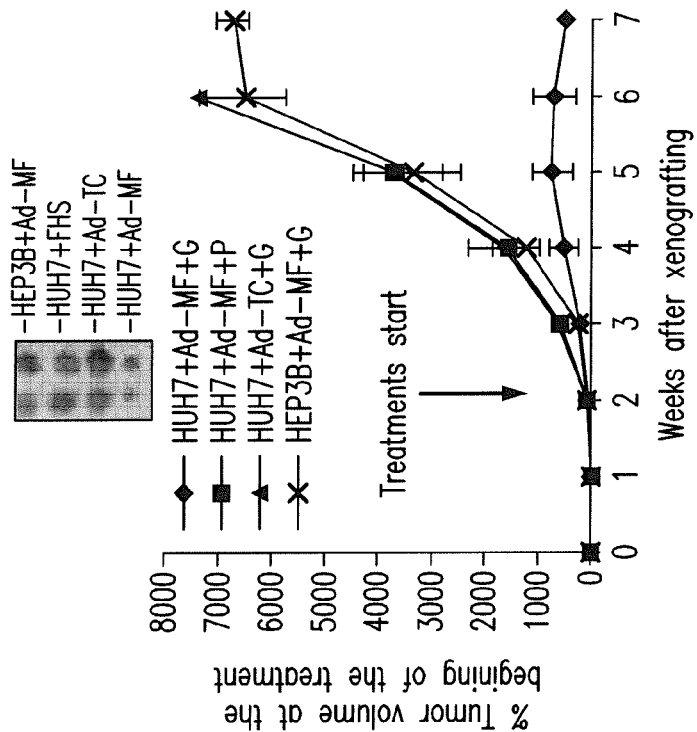
Figure 15F:
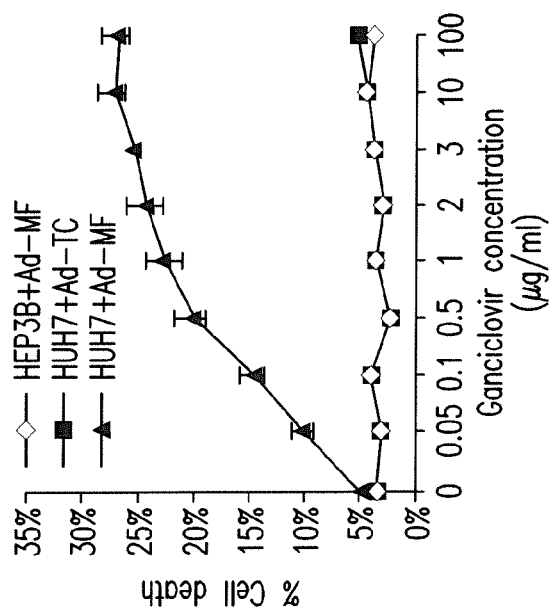
Figure 15I:
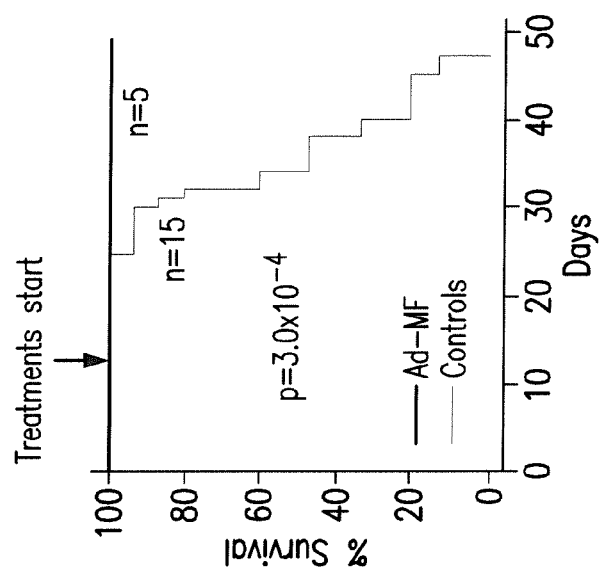
Figure 15H:
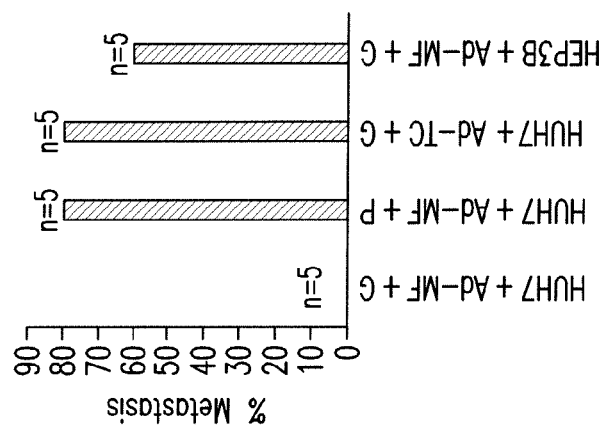

Additional cancers were analyzed for fusion gene expression. Screening of human hepatocellular carcinoma cell line HUH7 showed that it expresses one of the fusion genes, MAN2A1-FER (FIGS. 15A and B). Both MAN2A1-FER mRNA and protein were detected in this cell line (FIGS. 15A and B). A genome breakpoint was identified between intron 13 of MAN2A1 and intron 14 of FER in HUH7 cells. The chimeric protein retains intact tyrosine kinase domain from FER but loses the SH2 domain that regulates the kinase activity. To evaluate the applicability of genome therapy targeting at cancer cells with a native fusion gene breakpoint, we designed a pair of gRNAs specific for intron 13 of MAN2A1 and intron 14 of FER (FIG. 15A). The gRNAs and Cas9$^{D10A}$ was packaged into adenovirus to create pAD5-Cas9$^{D10A}$gRNAMAN2A1$^{int13}$-gRNAFER$^{int14}$. This recombinant virus was co-infected with a "donor" recombinant adenovirus containing the sequences flanking the nick-sites (pAD-MAN2A1$^{int13}$-EGFP-tk-FER$^{int14}$). This "donor" virus also contains splicing sequences corresponding to acceptor of intron 14 of MAN2A1 and donor of intron 15 of FER, respectively, so that EGPF-tk is interrupted into the mRNA of MAN2A1-FER. The results showed that up to 27% of HUH7 cells infected with these viruses expressed EGFP-tk (FIGS. 15D and E; FIG. 16A), while similar infection of HEP3B cells, which are negative for MAN2A1-FER fusion, with these viruses induced minimal fluorescent protein expression. When HUH7 cells, which are negative for TMEM135-CCDC67 fusion, were infected with adenoviruses specific for TMEM135-CCDC67 breakpoint, there is little expression of EGFP-tk (FIGS. 15D and E; FIG. 16A). These results confirm the specificity of this genome targeting technique.

TABLE 2

Primer sequences for PCR and RT-PCR.

| Forward primer/reverse primer | Forward primer/reverse primer |
|---|---|
| Genome BP PCR | GCCCATATATGGAGTTCCGCG (SEQ ID NO: 28)/<br>TCTGGCAAGCTATCTAACCCC (SEQ ID NO: 29) |
| RNA BP RT-PCR | AGCACAGAGACCCAGAAGGTC (SEQ ID NO: 123)/<br>AGGAGGAGGAGGAGGAGAAAG (SEQ ID NO: 124) |
| Genome β-actin PCR | TCTTTGCACTTTCTGCATGTCCCC (SEQ ID NO: 110)/<br>GTCCATCACGATGCCAGTGGTAC (SEQ ID NO: 111) |
| RNA β-actin RT-PCR | ATGATGATATCGCCGCGCTC (SEQ ID NO: 125)/<br>CACGATGGAGGGGAAGACG (SEQ ID NO: 126) |
| Pre-integration 5' end | GCCCATATATGGAGTTCCGCG (SEQ ID NO: 114)/<br>AGGCAAAGAGCTCAGTGAGTG (SEQ ID NO: 115) |
| Pre-integration 3' end | TGCCTCATTGGTAATGTTAGCTC (SEQ ID NO: 116)/<br>GGCGAATTGGGTACACTTACC (SEQ ID NO: 117) |
| CMV-EGFP PCR | ACTCACGGGGATTTCCAAGTC (SEQ ID NO: 118)/<br>AAGTCGTGCTGCTTCATGTGG (SEQ ID NO: 119) |
| HSV1-tk-CMV PCR | TGTTCTAGCCAAGAGGCTGAG (SEQ ID NO: 120)/<br>GGCGAATTGGGTACACTTACC (SEQ ID NO: 121) |

When HUH7 cells were infected with pAD5-Cas9$^{D10A}$-gRNAMAN2A1$^{int13}$-gRNAFER$^{int14}$/pADMAN2A1$^{int13}$-EGFP-tk-FER$^{int14}$ (Ad-MF) and treated with various concentrations of ganciclovir, up to 27% cells died at 10 µg/ml of ganciclovir, while HEP3B cells infected with the same viruses had minimal cell death even at high concentrations of ganciclovir (Table 3). When HUH7 cells were infected with Ad-TC and treated with ganciclovir, there is no appreciable increase of cell death, clearly indicating that cell death induced by ganciclovir is MAN2A1-FER breakpoint dependent compared to the PC3 BP clone and DU145 BP clone that contain the TMEM135-CCDC67 breakpoint (Table 3; FIG. 16B). As shown in FIG. 14, clones of transformed PC3 cells were selected to quantify for the copy number of TMEM135-CCDC67 breakpoint relative to that of β-actin in the genome. The PC3 BP clone was estimated to contain one copy of TMEM135-CCDC67 breakpoint per genome and was selected based on its ratio (~1:4, PC3 cells are hyperploid for the chromosome region containing β-actin) to β-actin (FIG. 14)[15]. Similar selection was also applied to DU145 clone (DU145 BP) that contains the TMEM135-CCDC67 breakpoint. PC3 BP and DU145 BP clones treated with ganciclovir exhibited significant cell death as observed by tunel staining (FIG. 16B).

To examine the effectiveness of genome therapy targeting at MAN2A1-FER in vivo, SCID mice were xenografted with HUH7 and HEP3B cells, and treated with recombinant viruses and ganciclovir 2 weeks after the xenografting (~400 mm$^3$ in average). The mice xenografted with HUH7 cells and treated with Ad-MF and ganciclovir experienced up to 29% reduction of tumor size from the peak, and had no notable metastasis or mortality in the treatment period. In contrast, the mice xenografted with HUH7 cells treated with ganciclovir and Ad-TC, the adenoviruses specific for the TMEM135-CCDC67 breakpoint not carried by the HUH7 cells, experienced 73 fold increase of tumor size. Four of 5 of these mice had metastasis in lung and liver. All 5 mice died in 40 days after xenografting. Similar rates of death, metastases and increase of tumor volume also occurred in mice treated with AD-MF and PBS. Treatment of mice xenografted with HEP3B, a hepatocellular cancer cell line negative for MAN2A1-FER fusion, with Ad-MF and ganciclovir was similarly ineffective. These results indicate that therapy targeting at cancer genome is highly specific and effective.

In addition, our approach appears highly specific, with average functional off-target rates being less than 1% for HEP3B cells and HUH7 cells (EGFP-tk+ cells/Cas9$^{D10A}$-RFP+ cells treated with adeno-MF, Table 4). These off-target rates were largely confirmed by quantitative sequencing methods: the off-target rates ranged from <0.1% to 2.5% in 100 million reads, including samples from in vitro tissue culture experiments, xenografted cancers and liver samples from mice that were treated with the recombinant viruses (Table 18-21). On-target integration rates in vitro, on the basis of sequencing, ranged from 15.9% to 25.5%, whereas rates for xenografted tumors ranged from 21.1% to 33.5%. The higher integration rates in xenografted tumors probably reflect repeated application of the recombinant adenoviruses.

TABLE 3

Chromosome breakpoint dependent cancer cell killing by Ganciclovir

| Samples | Treatment | % Apoptosis |
| --- | --- | --- |
| HUH7 | Ad-MF + Gan** | 26.9% ± 1.3 |
| HUH7 | Ad-TC + Gan* | 2.6% ± 0.41 |
| HEP3B | Ad-MF-Gan** | 2.8% ± 0.16 |

*Treatment of Adeno + Gan includes pAD5-Cas9$^{D10A}$-gRNAT$^{MEM135int13}$-gRNA$^{CCDC67int9}$ and pAD-TMEM135int13-EGFP-tk-CCDC67int9 at 10 multiplicity of infection and Ganciclovir at 10 μg/ml.
**Treatment of Adeno + Gan includes pAD5-Cas9$^{D10A}$-gRNAT$^{MEM135int13}$-gRNA$^{FERint14}$ and pAD-MAN2A1$^{int13}$-EGFP-tk-FER$^{int9}$ at 10 multiplicity of infection and Ganciclovir at 10 μg/ml.

TABLE 4

Chromosome breakpoint dependent integration and expression of EGFP-tk

| Samples | Treatment | Cas9$^{D10A}$-RFP+/ EGFP-tk+ | Cas9$^{D10A}$-RFP+/ EGFP-tk− | Cas9$^{D10A}$-RFP−/ EGFP-tk+ | Cas9$^{D10A}$-RFP−/ EGFP-tk− |
| --- | --- | --- | --- | --- | --- |
| HUH7 | Ad-MF** | 2.73% ± 2.8 | 69.8% ± 3.3 | 0.1% ± 0.1 | 1.6% ± 0.2 |
| HEP3B | Ad-MF** | 0.4% ± 0.1 | 98% ± 1.6 | 0.1% ± 0.1 | 1.5% ± 0.3 |
| HUH7 | Ad-TC* | 0.5% ± 0.1 | 97.8% ± 1.7 | 0.1% ± 0.1 | 1.4% ± 0.2 |

*Treatment includes pAD5-Cas9$^{D10A}$-gRNA$^{TMFM135int13}$-gRNA$^{CCDC67int9}$ and pAD-TMEM135$^{int13}$-EGFP-tk-CCDC67$^{int9}$ at 10 multiplicity of infection.
**Treatment includes pAD5-Cas9$^{D10A}$-gRNA$^{MAN2A1int13}$-gRNA$^{FERint14}$ and pAD-MAN2A1$^{int13}$-EGFP-tk-FER$^{int14}$ at 10 multiplicity of infection.

6.4 Discussion

The impact of fusion genes on the function of genes that are involved could be dramatic due to creation of a new protein or generation of a large truncation of a protein domain. For example, without being limited to a particular theory, it appears that the elimination of SH2 domain of FER in the MAN2A1-FER fusion gene may lead to constitutive activation of FER tyrosine kinase.

Our gRNA target designs would produce two nicks at different strands 37 bp apart for MAN2A1-FER breakpoint. It is unlikely that these nicks would generate a complete break of double stranded DNA. As a result, these DNA damages would likely be repaired by homologous recombination process rather than by non-homologous end joining. Our results are consistent with several other studies that CRISPR/Cas mediated homologous recombination rates can reach between 20-30%[7].

To our knowledge, this is the first report to show that such system can be applied to specifically target a cancer genome and to have a recombination rate sufficient to achieve remission of xenografted cancers. The precision specificity and integration rate of EGFP-tk in genome therapy might make it possible to apply this approach to clinical settings. Future developments that enhance the integration rate of the targeting cassette into the genome target site may be helpful in enhancing the efficiency of genome therapy. Notably the donor sequences of the adenoviral GFP-tk genome are outside the gRNA target sites, and thus the viruses do not contain target sequences recognizable by gRNA-Cas9 activity. The recombination rate between the two viruses is probably low. In over 300,000 integrated EGFP-tk sequencing reads (Tables 20-22), we did not find any reads indicating recombination between EGPFP-tk and Cas9.

The current therapeutic approach to human cancer heavily relies on interception of signaling pathways that drive cancer growth. However, such an approach invariably leads to drug tolerance and resistance to drug treatment as the cancer genome adjusts its gene expression patterns and, through new mutations that bypass the signaling blockade, develops new pathways to support growth. The subsequent application of second-tier chemotherapy may affect both cancer and normal tissues and thus may generally produce poor therapeutic outcomes. The genome approach may have substantial advantages over chemotherapy because it is specific for the cancer genome sequence, and it kills cancer cells regardless of whether the mutations are cancer drivers. It is possible that additional new mutations and fusion genes will be generated under the pressure of cancer therapy. In principle, additional vectors may be designed to target these genomic lesions and might even increase the integration rate, owing to multiple integrations per cell (Table 22). It remains to be determined whether such an adaptive strategy might be feasible in the clinic. For cancers comprising multiple populations of cancer cells with several different fusion-gene targets, these targets can be simultaneously targeted through the genome targeting scheme. Furthermore, our approach is not limited to using HSV-tk in the therapeutic cassette but instead can use a wide spectrum of gene devices, such as immunogens from viruses or toxins from plants or bacteria. The well-documented 'bystander' effect of several prodrugs on tumor cell killing may enhance the therapeutic effects of this genome targeting strategy[17]. When necessary, genome targeting can be combined with other cancer therapeutic treatments, such as tumor immunotherapy or signaling-molecule targeting, to achieve better therapeutic results.

TABLE 18

On- and off-target sequences (SEQ ID NOs: 159-182, in order)

| Fuseion gene | gRNA target | Sequences | Chr. | Position** |
|---|---|---|---|---|
| TMEM135-CCDC67 | On target | CACTCACTGAGCTCTTTGCC | 11 | 99392884 |
| | Human Off-target 1 | CACTGACTGAGCTCTCTGAC | 8 | 91349869 |
| | Human Off-target 2 | CACTCACTGTCCTCTTTGCC | 8 | 96221899 |
| | Human Off-target 3 | AACTCAGCGAGCTCTTTGCC | 8 | 139832573 |
| | Human Off-target 4 | CACTCACTGAGATCTGTGCC | 8 | 141885129 |
| | Human Off-target 5 | GACTCACTGAACTCTTTGGC | 12 | 3670848 |
| | Human Off-target 6 | CCCTGAATGAGCTCTTTGCC | 12 | 48777427 |
| | Mouse Off-target 1 | CACTGACTCAGTTCTTTGCC | 3 | 6691415 |
| | Mouse Off-target 2 | CACTCCATCAGCTCTTTGCC | 3 | 89547973 |
| | Mouse Off-target 3 | CACTCACTGGCCCCTTTGCC | 7 | 143419761 |
| | Mouse Off-target 4 | TACCCACTGAGCTCTTTCCC | 4 | 30920272 |
| | Mouse Off-target 5 | CACTCACTGAGCACTGTGTC | 4 | 124329371 |
| | Mouse Off-target 6 | CACTGACTGAGTCCTTTGCC | 4 | 129431496 |
| MAN2A1-FER | On target | TAGCATTAAGGGCCCCCTAA | 5 | 109041116 |
| | Human Off-target 1 | TAGCACTGAAGGCCCCCTAA | 8 | 132195439 |
| | Human Off-target 2 | TAGCATTAAGGGCCCCACTTG | 4 | 146731371 |
| | Human Off-target 3 | TAGCACTGAGGGCCCCCAAA | 22 | 36767388 |
| | Human Off-target 4 | TAGTATTCAGGGCCCCACTAA | 14 | 84999796 |
| | Human Off-target 5 | TGGGATTAGGGGCCCCCTAA | 11 | 71081076 |
| | Mouse Off-target 1 | TAGCTTTAAGTGCCTCCTAA | 7 | 12534542 |
| | Mouse Off-target 2 | TACCATTAAGTGCCCCCAAA | 4 | 37770804 |
| | Mouse Off-target 3 | TGGCATTAAGGGCCCATTAA | 4 | 98401470 |
| | Mouse Off-target 4 | TTGCATTCAGGGTCCCCTAA | 5 | 36160205 |
| | Mouse Off-target 5 | TAGCATTAAGTGCCCTCTTA | 16 | 53887183 |

**Alignment to GRCh38.p7 primary assembly database for human genome or to GRCm38.p4 C57BL/6J for mouse genome.
Chr-Chromosome.

TABLE 19

On- and off-target sequencing primers for Illumina HiSEQ2500 (SEQ ID NOs: 182-223, in order)

| Fusion gene | Genome sequencing primer | Sequence | Chr | Position** |
|---|---|---|---|---|
| TMEM135-CCDC67 | On target | CCCTGTTTTACATATGAGGAAAC | 11 | 87320212 |
| | Human Off-target 1 | CCCACAAAAGGGTACATGCC | 8 | 92362003 |
| | Human Off-target 2 | TTTGGATTCAGCACAGTGGCC | 8 | 96221823 |
| | Human Off-target 3 | AGGAGGACCATGCCATTTCCC | 8 | 139832521 |
| | Human Off-target 4 | ACAGGCTCCAGACGCATTGTG | 8 | 141885030 |
| | Human Off-target 5a | TCAGTGCCCTGCTCAAAACAG | 12 | 3670781 |
| | Human Off-target 5b | CTCAGTCAGTATCCCTGCCAG | 12 | 3670938 |
| | Human Off-target 6a | TGGGAAGGAATTGGAGGGAAG | 12 | 48777257 |
| | Human Off-target 6b | GCTGTCATCTACAGCATCCTG | 12 | 48777515 |
| | Mouse Off-target 1 | CAGGGAAGCTGCTTTAGAATG | 3 | 6691355 |
| | Mouse Off-target 2a | TGAAATCCCTGACCCCCAATC | 3 | 89547888 |
| | Mouse Off-target 2b | CAGACTGGACAAGGTGCTGCG | 3 | 89548055 |
| | Mouse Off-target 3a | CACAGAGTATGCTAGGGGAAG | 7 | 143419665 |
| | Mouse Off-target 3b | GTGAATGCCCTCTCTCTTTGC | 7 | 143419851 |
| | Mouse Off-target 4 | AGGGTATTGTGGAGGTCACAG | 4 | 30920176 |
| | Mouse Off-target 5 | CTTACTACTTAAGCCGCCCAG | 4 | 124329281 |
| | Mouse Off-target 6 | ATCATCTAAGGGGAGTCTTGG | 4 | 129431411 |
| | EGFP-tk | CAGCTCCTCGCCCTTGCTCAC | N/A | N/A |

TABLE 19 -continued

On- and off-target sequencing primers for Illumina HiSEQ2500
(SEQ ID NOs: 182-223, in order)

| Fusion gene | Genome sequencing primer | Sequence | Chr | Position** |
|---|---|---|---|---|
| MAN2A1-FER | On target | GACAGTCTGGCAGAGTTATGC | 5 | 109816105 |
| | Human Off-target 1a | GAGCACGGGAGGCAAATAAAC | 8 | 132195341 |
| | Human Off-target 1b | GTGAAGGGCACACTCTTCCAG | 8 | 132195532 |
| | Human Off-target 2 | GGAGGAGGTATTGGAGGGTTG | 4 | 146731272 |
| | Human Off-target 3 | AAGGCATCACTCACCACACTG | 22 | 36767292 |
| | Human Off-target 4a | TCTATCATGTAGCCTCAGCTC | 14 | 84999745 |
| | Human Off-target 4b | GTGGCATTTGCTTACCCTGGA | 14 | 84999892 |
| | Human Off-target 5a | ATGGGGCTGTATGTGAAGAGG | 11 | 71081020 |
| | Human Off-target 5b | CTGCATCTTCACAGGGTCGTC | 11 | 71081153 |
| | Mouse Off-target 1a | AGAGCTTTCAGGTGTGCTGTC | 7 | 12534489 |
| | Mouse Off-target 1b | TTGCCCACCTGCGACTAGAGA | 7 | 12534619 |
| | Mouse Off-target 2a | TGGGTTGATCTAGCTGATGGAG | 4 | 37770705 |
| | Mouse Off-target 2b | CTCAACCAACCTCTAATACTGTAC | 4 | 37770882 |
| | Mouse Off-target 3a | GTCTGCTCCCTAAACGAGATG | 4 | 98401370 |
| | Mouse Off-target 3b | CCAAACCAAAGAGTGGTGGAG | 4 | 98401543 |
| | Mouse Off-target 4a | AAGGGATGCTACAGCCTGTCC | 5 | 36160146 |
| | Mouse Off-target 4b | TGGGCACGGAGATAGGTTGTC | 5 | 36160275 |
| | Mouse Off-target 5a | GCTTCTGTTAGGGCTTTCATGC | 16 | 53887121 |
| | Mouse Off-target 5b | CACAGCATAGCCAAAGTTATGG | 16 | 53887237 |
| | EGFP-tk | CAGCTCCTCGCCCTTGCTCAC | N/A | N/A |
| TMEM135-CCDC67 BP | Primer 1 | GCCTCATTGGTAATGTTAGCTC | 11 | 87320809 |
| | Primer 2 | AGCATGGCACACTCAGTGAAC | 11 | 93392861 |
| MAN2A1-FER BP | Primer 1 | CTCCTGACCCCGTGATCCACCT | 5 | 109818361 |
| | Primer 2 | AAACCATAATCATGCTGACTG | 5 | 109041166 |

**Alignment to GRCh38.p7 primary assembly database for human genome or to GRCm38.p4 C57BL/6J fot mouse genome.
Chr-chromosome.

TABLE 20

Quantification of on- and off-target reads of TMEM135-
CCD67 and MAN2A-FER genome therapy in vitro.

| Therapy target | Target cells | Total reads | On-target | Off-targets | Off/On |
|---|---|---|---|---|---|
| TMEM135-CCDC67 | DU145 BP in vitro | 3101148 | 88256 | 1 | <0.1% |
| | PC3 BP in vitro | 6566408 | 134573 | 12 | <0.1% |
| | DU145 BP tumor | 3495728 | 140292 | 6 | <0.1% |
| | PC3 BP tumor | 3080992 | 146217 | 0 | <0.1% |
| MAN2A1-FER | HUH7 in vitro | 1180122 | 84241 | 116 | 0.14% |
| | HUH7 tumor | 1312056 | 240178 | 522 | 0.22% |

DU145 BP—DU145 cell line harboring TMEM135-CCDC67 breakpoint.
PC3 BP—PC3 cell line harboring TMEM135-CCDC67 breakpoint.
Du145 BP in vitro—DU145 BP cell culture treated with Ad-TC.
PC3 BP in vitro—PC3 BP cell culture treated with Ad-TC.
DU145 BP tumor—DU145 BP xenografted tumor treated with Ad-TC.
PC3 BP tumor—PC3 BP xenografted tumor treated with Ad-TC.
HUH7 in vitro—HUH7 cell culture treated with Ad-MF.
HUH7 tumor—HUH7 xenografted tumor treated with Ad-MF.
On-target—Pair-end reads mapped to the correct on-target genome sequence at one end and EGFP-tk sequence at the paired end.
Off-target—Pair-end reads mapped to the off-target genome sequence at one end and EGFP-tk sequence at the paired end.
Off/On: % Off-target rate.
Total reads—Total number of reads including unmapped and mapped reads.

TABLE 21

Quantification of genome EGFP-tk reads in cells without fusion gene breakpoint.

| Therapy viruses | Target cells | Total reads | gEGFP-tk reads | Mapped reads | % Off |
|---|---|---|---|---|---|
| Ad-TC | DU145 CMV in vitro | 10955122 | 2751 | 1093412 | 2.5% |
| | PC3 CMV in vitro | 12621946 | 1128 | 934299 | 1.2% |

TABLE 21-continued

Quantification of genome EGFP-tk reads in cells without fusion gene breakpoint.

| Therapy viruses | Target cells | Total reads | gEGFP-tk reads | Mapped reads | % Off |
|---|---|---|---|---|---|
| Ad-MF | DU145 CMV tumor | 15165454 | 739 | 1401619 | <0.1% |
| | PC3 CMV tumor | 19036426 | 3 | 1469784 | <0.1% |
| | mLiver (DU145 BP) | 2364468 | 7 | 229881 | <0.1% |
| | mLiver (PC3 BP) | 5658462 | 15 | 218017 | <0.1% |
| | HEP3B in vitro | 5864746 | 2 | 53544 | <0.1% |
| | HEP3B tumor | 6235391 | 9 | 52789 | 0.2% |
| | mLiver (HUH7) | 4362937 | 15 | 476025 | <0.1% |

Ad-TC—AD5-Cas9$^{D10A}$-gRNA$^{TMFM135int13}$-gRNA$^{CCDC67int9}$ and AD-TMEM135$^{int13}$-EGFP-tk-CCDC67$^{int9}$
Ad-MF—AD5-Cas9$^{D10A}$-gRNA$^{MAN2A1int13}$-gRNA$^{FERint14}$ and AD-MAN2A1$^{int13}$-EGFP-tk-FER$^{int14}$
gEGFP-tk reads—Pair-end reads mapped to correct on-target or off-target genome sequence at one end and EGFP-tk sequence at the paired end.
Mapped reads—Pair-end reads mapped to the correct genome sequence adjacent to the sequencing primers.
Total reads—Total number of reads including unmapped and mapped reads.
mLiver—mouse liver cells from animals xenografted with cancer cells, and treated with recombinant adenoviruses.
% Off—gEGFP-tk/Mapped reads
DU145 CMV—DU145 cells harboring pCMVscript.
PC3 CMV—PC3 cells harboring pCMVscript.
DU145 CMV in vitro—DU145 CMV cell culture treated with Ad-TC.
PC3 CMV in vitro—PC3 CMV cell culture treated with Ad-TC.
DU145 CMV tumor—DU145 CMV xenografted tumor treated with Ad-TC.
PC3 CMV tumor—PC3 CMV xenografted tumor treated with Ad-TC.
mLiver (DU145 BP)—mLiver from mice xenografted with DU145 BP cells and treated with Ad-TC.
mLiver PC3 BP)—mLiver from mice xenografted with PC3 BP cells and treated with Ad-TC.
HEP3B in vitro—HEP3B cell culture treated with Ad-MF.
HEP3B tumor—HEP3B xenografted tumor treated with Ad-MF.
mLiver (HUH7)—mLiver from mice xenografted with HUH7 cells and treated with Ad-MF.

TABLE 22

Integration rates of EGFP-tk in genome therapy in vitro and in vivo.

| Therapy target | Samples | genome-EGFP-tk reads | BP reads | Integration rates |
|---|---|---|---|---|
| TMEM135-CCDC67 | DU145 BP in vitro | 56245 | 297751 | 15.9% |
| | DU145 BP tumor | 67779 | 164207 | 29.2% |
| | PC3 BP in vitro | 58961 | 255898 | 18.7% |
| | PC3 BP tumor | 77464 | 289594 | 21.1% |
| MAN2A-FER | HUH7 in vitro | 21884 | 63838 | 25.5% |
| | HUH7 tumor | 19074 | 37920 | 33.5% |

DU145 BP in vitro—DU145 BP cell culture treated with Ad-TC.
DU145 BP tumor—DU145 BP xenografted tumor treated with Ad-TC.
PC3 BP in vitro—PC3 BP cell culture treated with Ad-TC
PC3 BP tumor—PC3 BP xenografted tumor treated with Ad-TC.
HUH7 in vitro—HUH7 cell culture treated with Ad-MF.
HUH7 tumor—HUH7 xenografted tumor treated with Ad-MF.
genome-EGFP-tk reads—Pair-end reads mapped to the correct on-target genome sequence at one end and EGFP-tk sequence at the paired end.
BP reads—Pair-end reads mapped to the left side of the chromosome breakpoint at one end and the right side of the chromosome breakpoint at the paired end, or any mapped read containing the chromosomal breakpoint.
Integration rate—genome-EGFP-tk reads/BP reads

6.5 REFERENCES

1. R. L. Siegel, K. D. Miller, and A. Jemal, CA: a cancer journal for clinicians 66 (1), 7 (2016).
2. F. J. Mojica, C. Diez-Villasenor, J. Garcia-Martinez et al., Journal of molecular evolution 60 (2), 174 (2005).
3. M. Jinek, K. Chylinski, I. Fonfara et al., Science (New York, N.Y 337 (6096), 816 (2012).
4. K. M. Esvelt, A. L. Smidler, F. Catteruccia et al., eLife, e03401 (2014).
5. F. A. Ran, P. D. Hsu, C. Y. Lin et al., Cell 154 (6), 1380 (2013).
6. Y. P. Yu, S. Liu, Z. Huo et al., PloS one 10 (8), e0135982 (2015).
7. C. Yu, Y. Liu, T. Ma et al., Cell stem cell 16 (2), 142 (2015); P. D. Hsu, D. A. Scott, J. A. Weinstein et al., Nature biotechnology 31 (9), 827; L. Cong, F. A. Ran, D. Cox et al., Science (New York, N.Y 339 (6121), 819. 13 K. F. Kozarsky and J. M. Wilson, Current opinion in genetics & development 3 (3), 499 (1993).
8. H. Wang, K. Luo, L. Z. Tan et al., The Journal of biological chemistry 287 (20), 16890 (2012); Z. H. Zhu, Y. P. Yu, Z. L. Zheng et al., The American journal of pathology 177 (3), 1176 (2010); K. L. Luo, J. H. Luo, and Y. P. Yu, Cancer science 101 (3), 707 (2010); Y. C. Han, Y. P. Yu, J. Nelson et al., Cancer research 70 (11), 4375 (2010); Z. H. Zhu, Y. P. Yu, Y. K. Shi et al., Oncogene 28 (1), 41 (2009).
9. Y. K. Shi, Y. P. Yu, G. C. Tseng et al., Cancer gene therapy 17 (10), 694 (2010); Y. P. Yu, G. Yu, G. Tseng et al., Cancer research 67 (17), 8043 (2007); B. Ren, Y. P. Yu, G. C. Tseng et al., Journal of the National Cancer Institute 99 (11), 868 (2007); G. Yu, G. C. Tseng, Y. P. Yu et al., American Journal of Pathology 168 (2), 597 (2006).

10. T. Maruyama, S. K. Dougan, M. C. Truttmann et al., Nature biotechnology 33 (5), 538 (2015).
11. Y. C. Han, Z. L. Zheng, Z. H. Zuo et al., The Journal of pathology 230 (2), 184 (2013); B. Ren, G. Yu, G. C. Tseng et al., Oncogene 25 (7), 1090 (2006).
12. L. Jing, L. Liu, Y. P. Yu et al., The American journal of pathology 164 (5), 1799 (2004).
13. A. J. Demetris, E. C. Seaberg, A. Wennerberg et al., The American journal of pathology 149 (2), 439 (1996).
14. Anderson, R. D., Haskell, R. E., Xia, H., Roessler, B. J., & Davidson, B. L. (2000) A simple method for the rapid generation of recombinant adenovirus vectors. Gene therapy 7: 1034-1038.
15. Y. Ohnuki, M. M. Mamell, M. S. Babcock et al., Cancer research 40 (3), 524 (1980); J. Bernardino, C. A. Bourgeois, M. Muleris et al., Cancer genetics and cytogenetics 96 (2), 123 (1997).
16. Yu, Y. P. et al. Novel fusion transcripts associate with progressive prostate cancer. Am. J. Pathol. 184, 2840-2849 (2014); Luo, J. H. et al. Discovery and classification of fusion transcripts in prostate cancer and normal prostate tissue. Am. J. Pathol. 185, 1834-1845 (2015).
17. Hanahan, D. & Weinberg, R. A. Hallmarks of cancer: the next generation. Cell 144, 646-674 (2011).

7. Example 2: Nuclear PTEN-NOLC1 Fusion is Oncogenic in Human Cancers

7.1 Introduction

In this Example, a genome intervention approach was developed to kill cancer cells based on unique sequences resulting from genome rearrangement. The chromosome breakpoints from the Pten-NOLC1 fusion gene were exploited as therapeutic targets. The Pten-NOLC1 fusion gene has been previously determined to be present in prostate cancer (see WO 2016/011428, the contents of which are hereby incorporated by reference in its entirety).

Phosphatase and tensin homolog (Pten) (1, 2), a phosphatase for PIP3 (3, 4), maintains the homeostatic Akt/PI3K signaling and is a crucial regulator of cell survival and growth (5, 6). Poly-ubiquitination of Pten leads to inactivation of Pten in the cytosol, while mono-ubiquitination of Pten translocates the protein into the nucleus (7, 8). The nuclear Pten regulates DNA repair activity of Rad51 and maintains the chromosome stability (9). Deletion of Pten may be associated with genome rearrangement (10). Pten deletion or mutation has been reported in a variety of human malignancies and is considered one of the most important driver events for human cancer development (11). However, whether a sole unchecked Akt/PI3K signaling or nuclear function of Pten is sufficient for cancer development, remains unclear.

Here, a novel Pten related fusion protein is characterized, identified through a high coverage (600-1500×) transcriptome sequencing analyses on 87 prostate samples including 20 organ donor prostate samples from healthy individuals, 3 benign prostate tissues adjacent to cancer, and 64 prostate cancers. Through Fusion-Catcher screening and multiple filtering, 96 cancer-specific fusion transcripts were identified (Table 6). Six of these fusion genes were validated through Sanger sequencing and fluorescence in situ hybridization (FISH, FIGS. 17-19). One of these fusion genes involves Pten and NOLC1. Pten, a tumor suppressor gene (1), is fused with NOLC1 (12, 13), a nucleolar and coiled-body phosphoprotein for nucleolar organogenesis (13), in frame to produce a chimera protein of Pten-NOLC1.

Deletion or mutation of PTEN is frequent in a variety of human cancers, and is one of the mechanisms underlying human cancer development. Here, we report a fusion protein between Pten and nucleolar organogenesis protein NOLC1 in human malignancies.

Pten-NOLC1 fusion is highly recurrent in 8 types of human malignancies (66-85%). Gene fusion between Pten-NOLC1 leads to loss of C2 domain of Pten protein, and translocation of the fusion gene product to the nucleus. Targeted interruption of Pten-NOLC1 genome breakpoint of DU145 and MCF7 cells impeded tumor cell growths, retarded S phase entry, and delayed cell migration and invasiveness, and was prone to the UV-induced apoptosis. Knockout of Pten-NOLC1 blocks xenografted DU145 tumor growth in SCID mice, while forced expression of Pten-NOLC1 through hydrodynamic injection into the mice led to the development of hepatocellular carcinoma. Up-regulation of C-Met/HGFR signaling was detected in the Pten-NOLC1 induced tumor. These results indicate that Pten-NOLC1 fusion produces a gain of function, and converts a tumor suppressor gene into an oncogene.

7.2 Materials and Methods

Tissue Samples:

Total 815 tissue specimens used in the study consisted of 268 prostate cancers, 10 matched blood samples, 20 donor prostates, 102 non-small cell lung cancers, 61 ovarian cancers, 60 colon cancers, 70 liver cancers, 156 glioblastoma, 60 breast cancers, and 34 esophageal adenocarcinomas, and were obtained from University of Pittsburgh Tissue Bank in compliance with institutional regulatory guidelines (Table 7, and 12). Procedures of microdissection of PCa samples and DNA extraction were previously described (21-23). The protocols of tissue procurement and procedure were approved by Institution Board of Review of University of Pittsburgh. All cell lines were purchased from American Type Cell Culture, Inc (ATCC). The procedures of cell cultures followed the manuals from the manufacturer.

Cancer tissues were also obtained from other institutes: 16 non-small cell lung cancer samples obtained from University of Kansas; 28 samples of non-small cell lung cancer from University of Iowa; 3 samples of glioblastoma multiforme from Northwestern University; 50 samples of prostate cancer from Stanford University; and 163 samples from University of Wisconsin Madison; All protocols were approved by the Institution Review Board. The cell lines used in the study were purchased from American Type Cell Culture (ATCC), and were cultured and maintained following the recommendations of manufacturer.

Construction of vector: To construct cDNA for Pten-NOLC1, a PCR was performed on the cDNA template of Pten using primers AGGGGCATCAGCTACCCTTAAG TCCAGAGCCATTTC (SEQ ID NO: 127)/GGCATTGG-CATCCTGCTGTGT CTTAAAATTTGGAGAAAAGTA (SEQ ID NO: 128) to obtain cDNA corresponding to 5' end of Pten, under the following condition: 94° C. for 2 min, then 94° C. for 30 seconds, 61° C. for 30 second, 72° C. for 30 second for 35 cycles. Separately, a PCR was performed on the cDNA template of NOLC1 using primers TACTTTTCTCCAAATTTTAAGACACAGCAGGATGC-CAATGCC (SEQ ID NO: 129)/ACCGAAGATG GCCTCTCTAGACTCGCTGTCAAACTT (SEQ ID NO: 130) to obtain 3' end of NOLC1 under the same condition. The PCR products of the 2 reactions were pooled. A PCR was performed using AGGGGCATCAGCTACCCT- TAAGTCCAGAGCCATTTC (SEQ ID NO: 131)/ACCGAAGATGGCCTCTCTAGACTCGCTGTCAAACTT (SEQ ID NO: 132) in the same condition to obtain full length Pten-NOLC1 cDNA. The PCR product was then restricted with AflII and XbaI, and ligated into similarly digested pCDNA4-FLAG vector to create pPten-NOLC1-FLAG vector.

To construct Pten-EGFP vector, a PCR was performed on the cDNA template of Pten using primers: CTTAAAAT-TTGGAGATCTAGATCGGTTGGCTTTGTC (SEQ ID NO: 133)/ACCGAAGATGGCCTCTCTAGAGACTTTTGTAATTTGTGTATGCTGATC (SEQ ID NO: 134). The PCR product was restricted with NdeI and XbaI, and ligated into similarly restricted pEGFP vector to create pPten-EGFP. To construct pNOLC1-cherry, a PCR was performed on the cDNA template of NOLC1 using primers: TCAGC-TACCCTTAAGCGGTAGTGACGCGTATTGC (SEQ ID NO: 135)/ACCGAAGATGGCCTCTCTAGACTCGCTGT-CAAACTT (SEQ ID NO: 136). The PCR product was restricted with AflII and XbaI, and ligated into similarly restricted pCNDA4-Cherry vector.

To construct pGST-Pten vector, a PCR was performed using primers GTGGGATCCACATGACAGCCATCAT-CAAAGAG (SEQ ID NO: 137)/CATACACAAATTA-CAAAAGTCTGAGGATCCCCAGGAATTCCCGGGT CGACTC (SEQ ID NO: 138) under the following condition: 94° C. for 2 min, then 94° C. for 30 seconds, 60° C. for 30 second, 72° C. for 30 second for 35 cycles. The PCR product was restricted with BamH1, and ligated to similarly restricted pGEX5T vector to create pGST-Pten.

To construct pGST-Pten-NOLC1 vector, a PCR was performed on Pten-NOLC1 cDNA template using primers GTGGGATCCACATGACAGCCATCATCAAAGAG (SEQ ID NO: 139)/CGAGTCGACCCGGGAATTCCT GGGGATCCTCACTCGCTGTCAAACTTAATAG (SEQ ID NO: 140) was restricted with BamH1, and ligated into similarly restricted pGEX5T vector to create pGST-Pten-NOLC1.

To construct pPT3-EF1α-Pten-NOLC1, a PCR was performed on pcDNA4-Pten-NOLC1-Cherry as a template using primers 5'CTCCGGACTCTAGCGTCGACACTTAA GTCCAGAGCC (SEQ ID NO: 224)/5' ATGGTGATGGT-GATGGCGGCCGCTTAACTAGATCCGG (SEQ ID NO: 225) to obtain the full length of Pten-NOLC1-cherry containing Sal1 and Not1 restriction sites. The PCR product was then restricted with Sal1 and Not1, and ligated into similarly restricted pENTR 1A dual vector (Invitrogen) to create pENTR-attL1-Pten-NOLC1-attL2. Using Gateway® LR Clonase™ II enzyme mix (Invitrogen), pENTR-attL1-Pten-NOLC1-attL2 was then recombined with destination vector pPT3-EF1α to generate Pten-NOLC1-cherry expression vector.

Genome and transcriptome sequencing library preparation and sequencing: The prostate samples were fresh-frozen and stored in –80° C. They were obtained from University of Pittsburgh Tissue Bank. The protocol was approved by University of Pittsburgh Institutional Review Board. For transcriptome sequencing, total RNA was extracted from samples of 20 organ donor prostates from individuals free of urological disease, 3 benign prostate tissues adjacent to cancer and 64 prostate samples, using Trizol, and treated with DNAse1. Ribosomal RNA was then removed from the samples using RIBO-Zero™ Magnetic kit (Epicentre, Madison, Wis.). The RNA was reverse-transcribed to cDNA and amplified using TruSeq™ RNA Sample Prep Kit v2 from Illumina, Inc (San Diego, Calif.). The library preparation process such as adenylation, ligation and amplification was performed following the manual provided by the manufacturer. The quality of transcriptome libraries was then analyzed with qPCR using Illumina sequencing primers and quantified with Agilent 2000 Bioanalyzer. The procedure of 200 cycle paired-end sequencing in Illumina HiSeq2500 followed the manufacturer's manual.

Detection of genome breakpoint of Pten-NOLC1 genome rearrangement: To detect the breakpoint of genome between Pten and NOLC1, multiple primers were designed. The forward primers were designed annealing to the region of exon 11 and intron 11 of Pten, and the reverse primers to the region of intron 1 and exon 2 of NOLC1 (Table 16). Multiple nested-PCRs were performed with various primer combinations using AccuPrime™ Pfx DNA Polymerase (Invitrogen) with 35 heat cycles of 95° C. for 15 seconds, 65° C. for 30 seconds, and 72° C. for 10 minutes. The intron primer pair, 5'ATTCACCACACTCGTTTCTTTCTC (SEQ ID NO: 226)/5'CCTGCCTGCCAATCTATATTGATC (SEQ ID NO: 227) was proven to produce a PCR product. The direct sequencing of the purified PCR product confirmed the genome intron breakpoint sequence of Pten-NOLC1.

Knockout Pten-NOLC1 with CRISP/Cas9 genome editing. Vector pSPCAS9N(BB)-2A-GFP was obtained from Addgene, inc (Addgene #PX461). Target sequences for gRNA was analyzed with software CRISPR gRNA design tool-DNA2.0™, and selected, as CGGTTATACC GCTTTGGGATcaaa (Pten) (SEQ ID NO: 228)/caccGAGA TGGGGTTTCACCATGT (NOLC1) (SEQ ID NO: 229) flanking the breaking juncture of Pten and NOLC1. Synthetic oligonucleotides corresponding to gRNA(Pten) and gRNA(NOLC1) were constructed into Bbs1 site of modified pSPCAS9N(BB)-2A-GFP and pX330s-2 vector, respectively. Both vectors were then restricted with Bsa1, and gRNA(NOLC1) released from pX330s-2 vector with Bsa1 cut was subsequently inserted into Bsa1 site of gRNA(Pten)-pSPCAS9n (BB)-2A-GFP. T7 ligase was used in the cloning. For homologous directed recombination of an insert gene at the breakpoint, a donor vector was constructed: mCherry vector (Clontech inc, CA) was used as backbone to construct a cDNA of Zeocin to the upstream of mCherry coding region. The promoter sequence of mCherry vector was removed; a homologous arm sequence identical to the segment of 952 bp sequence of Pten intron 11 upstream to gRNA(Pten) sequence plus a 55 bp of splice acceptor sequence was inserted to the upstream of ribosomal RNA binding kozak sequence for zeocin. The second homologous arm sequence of 845 bp segment of NOLC1 intron 1 downstream from gRNA(NOLC1) was inserted into region downstream of SV40 poly-A for mcherry coding sequence. The donor vector was co-transfected with gRNA-Cas9D10A vector into DU145 and MCF7 cell lines using lipofectamine 3000 (Invitrogen). Integration of insert gene was recognized by mCherry expression and zeocin resistance. Loss of Pten-NOLC1 expression was confirmed by Taqman qRT-PCR with the primers for Pten-NOLC1 fusion detection and immunoblotting for dKO1 and dKO2, mKO1 and mKO2 clones with antibodies against N-terminus of Pten or Cterminus of NOLC1.

Fusion transcript detection: To identify fusion transcript events, the Fusioncatcher (v0.97) algorithm (24) was applied to the RNA sequencing samples. Embedded in fusioncatcher, BOWTIE and BLAT were used to align sequences to the reference genome. The preliminary list of candidate fusion transcripts are filtered in Fusioncatcher based on the existing biological knowledge of the literature including: (1) If the genes are known to be the other's paralog in Ensembl;

(2) If one of the fusion transcripts are the partner's pseudogene; (3) If one of the fusion transcripts are micro/transfer/small-nuclear RNA; (4) If the fusion transcript is known to be a false positive event (e.g., Conjoin gene database (25)); (5) If it has been found in healthy samples (Illumina Body Map 2.0 [www.ebi.ac.uk/arrayexpress/experiments/E-MTAB-513/]); (6) If the head and tail genes are overlapping with each other on the same strand. Fusion genes were visualized with CIRCOS software (26).

TCGA SNP 6.0 data analysis: The CNV segmentation data were downloaded from TCGA level 3 data (cancergenome.nih.gov/). CNVs with less than 10 markers are filtered out. Only the segments overlapping with the between exon 11 of Pten and exon 2 of NOLC1 region (89728532-89728532/hg19) were selected. CNVs with segment_mean value smaller than −0.23 are defined as deletions. For each sample, spanning deletion between Pten and NOLC1 is defined as the length of deletion segments over the whole length of the region between Pten and NOLC1 equal to or greater than 0.8 (illustrated in FIG. 23). Seventeen types of cancers were analyzed for spanning deletion between Pten and NOLC1: bladder cancer (BLCA), breast cancer (BRCA), colon cancer (COAD), diffuse large B-cell lymphoma (DLBC), esophageal carcinoma (ESCA), glioblastoma multiforme (GBM), head and neck squamous cell carcinoma (HNSC), liver cancer (LIHC), lung adenocarcinoma (LUAD), lung squamous cell carcinoma (LUSC), ovarian cancer (OV), pancreatic adenocarcinoma (PAAD), prostate cancer (PRAD), rectal adenocarcinoma (READ), sarcoma (SARC), thyroid cancer (THCA) and uterine endometrium carcinoma (UCEC).

Fluorescence In-situ Hybridization: Similar procedure was previously described (12-14). Briefly, tissue slides (4 microns) were placed in 0.2 N HCl for 20 minutes then Pretreatment Solution (32-801200, Vysis), 80 degrees for 30 minutes. Tissues were then digested in protease solution at 37° C. for 36 minutes, and air dried. The FISH probe was prepared by combining 7 ml of SpectrumOrange-labeled Bacterial artificial chromosome (BAC) sequence containing Pten 5'end (RP11-124B18, InVitrogen, Inc, Grand Island, N.Y.)/50% formamide with 1 ml of BAC sequence (CTD-3082D22) containing 3'end of NOLC1 labeled with SpectrumGreen. The probe was denatured for 5 min at 75° C. Sections of formalin-fixed tissues were denatured in 70% formamide for 3 min, and dehydrated in 70%, 85%, and 100% ethanol for 2 min each at room temperature. The denatured probe was placed on the slide, cover-slipped, sealed with rubber cement, placed in a humidified chamber and hybridized overnight at 37° C. Coverslips were removed and the slides were washed in 2×SSC/0.3% Igepal (Sigma) at 72° C. for 2 min. Slides were air-dried in the dark. The slides were counterstained with DAPI. Analysis was performed using a Olympus BX61 with CytoVision equipped with Chroma Technology 83000 filter set with single band exitors for SpectrumOrange, SpectrumGreen and DAPI (uv 360 nm). Only individual and well delineated cells with two hybridization signals were scored. Overlapping cells were excluded from the analysis. Fifty to 100 cells per sample were scored to obtain an average of signals. The cutoff for gain of MCM8 is an average of at least 2.5 copies per genome Samples with more than 10% cells with merged Pten and NOLC1 signals were considered positive for Pten-NOLC1 fusion.

RNA extraction, cDNA synthesis and Taqman RT-PCR: microdissection was performed on slides of FFPE samples to obtain at least 50% cancer cells. Total RNA was extracted from epithelial cells with the Trizol method (InVitrogen, CA). The extraction procedure was performed according to manufacturer's recommendation. Random hexamer was used in the first strand cDNA synthesis with 1 µg of total RNA and Superscript II™ (InVitrogen, Inc, CA). This was followed by Taqman PCR (94° C. for 2 min, then 94° C. for 30 seconds, 61° C. for 30 second, 72° C. for 30 second for 50 cycles) in Eppendorf Realplex™ cycler using primers GAGCGTGCAGATAATGACAAGG (SEQ ID NO: 141)/GCCAGAAGCTATAGATGTCTAAGAG (SEQ ID NO: 142) and Taqman probe: 5'-/56-FAM/CAG GAT GCC/ZEN/AAT GCC TCT TCC C/31ABkFQ/-3'. Ct threshold of Pten-NOLC1 detection: 38 5 cycles for formalin-fixed paraffin-embedded tissues, 35 cycles for frozen tissues. No template negative control and Pten-NOLC1 cDNA templates were used as negative and positive controls in each batch, respectively.

Immunoblot Analysis and Immunoprecipitation. Pten-NOLC1 expression was examined in H522, H358, PC3 DU145 and A-172 cells. First, cells were washed with PBS and lysed by RIPA buffer (50 mM Tris-HCl at pH 7.4, 1% Nonidet P-40, 0.25% sodium deoxycholate, 150 mM NaCl, 1 mM EDTA, 1 mM phenylmethylsulfonyl fluoride, Aprotinin at 1 µg/mL, leupeptin at 1 µg/mL, pepstatin at 1 µg/mL, and 1 mM $Na_3VO_4$). The lysates were sonicated and centrifuged at 12,000 g at 4° C. for 30 minutes to remove the insoluble materials. The proteins were separated by sodium dodecyl sulfate-polyacrylamide gel electrophoresis (SDS-PAGE) in 8.5% polyacrylamide gels, and bands were blotted onto a polyvinylidene difluoride (PVDF) membrane. The membrane was blocked with 5% powdered skim milk in Tris-Tween 20 buffer (0.1 M Tris-HCl and 0.1% Tween-20, pH 7.4) for 1 hour at room temperature, followed by a 2-hour incubation with primary anti-Pten antibodies (1:1000 dilution, Santa Cruz), anti-NOLC1 antibodies (1:1000 dilution; Santa Cruz, Calif.), anti-FLAG (Santa Cruz), anti-β-actin antibodies (1:500 dilution; Santa Cruz) or antibodies for C-MET, GAB1 C-RAF, Akt, MAPK, p-MAPK, Stat3, pStat3 (Cell Signaling). The membrane was then washed three times with Tris-Tween 20 buffer and incubated with a horseradish peroxidase-conjugated secondary antibody specific for rabbit (anti-β-actin, 1:1000 dilution), mouse (anti-Pten, 1:1000 dilution), or goat (anti-NOLC1, 1:1000 dilution) for 1 hour at room temperature. The protein expression was detected with the ECL system (Amersham Life Science) according to the manufacturer's protocols. Similar immunoblotting was also performed on protein extracts from prostate cancer samples PCa638T, PCa207T, PCa624T, PCa099T, PCa090T, and organ-donor prostates from individual free of urological disease DO12 and DO17. To immunoprecipitate, the cell lysates were incubated with the A/G magnetic bead (Millipore) for 20 minutes to remove non-specific binding. The supernatants were incubated with 4-6 µg primary antibody at 4° C. overnight, and the A/G magnetic beads were added to the immune-complex and continue to rock the reaction at 4° C. for 2 hours. The magnetic beads were collected on magnetic stand and washed with 1×PBS containing proteinase inhibitor for 3 times. The SDS-PAGE loading buffer was directly used to re-suspend and elude the proteins from the beads.

Phosphatidylinositol 3,4,5-triphosphate $(PI(3,4,5)P_3)$ phosphatase assay of Pten and Pten-NOLC1. To quantify the phosphatase activity on $PI(3,4,5)P_3$ of the purified GST-Pten, Pten-NOLC1-FLAG or GST-Pten-NOLC1. Pten-NOLC1-FLAG was immunopurified with FLAG antibody and GST-Pten-NOLC1 was purified with GST column. The phosphatase of purified Pten-NOLC1 were subjected to a competitive ELISA assay: 2 to 10 pmol of purified a protein was incubated with 8 μM PI(3,4,5)P$_3$ for 37° C. for 1 hour. The reaction was then stopped by heating to 95° C. for 3 min. The reaction was then transferred to "Detection Pate" (Echelon, Inc, UT), and incubated at 37° C. for 60 min. This was followed by washing the "Detection plate" with PBS-tween 20 3 times. The plate was added with 100 μl secondary detector provided by Echelon, Inc, and incubated at room temperature for 30 min, followed by washing with PBS-tween 20 3 times. The color was then developed by adding 100 μl TMB solution provided by Echelon for 15 min. The amount of PI(3,4)P$_2$ was quantified through reading of absorbance at 450 nm in a spectrophotometer and fitting with a standard curve of known amount of PI(3,4)P$_2$. The purified Pten protein (Echelon) in the reaction was used as a positive control and GST only protein or Flag only or IgG only were used as negative controls.

Cell growth and cell cycles analysis. DU145 or its Pten-NOLC1 knockout counterparts were used in the colony formation analyses, and 1000 cells of each clone were plated on each well in triplicates. Individual single cell was allowed to grow to form colony for 7-10 days. The colonies were then fixed with ice cold methanol for 10 minutes and stained with 0.025% Crystal violet for 15 minutes. The numbers of colonies were counted and imaged. In cell cycle analysis, FITC BrdU flow kit (BD Biosciences) was used. DU145, or DU145 KO1 or KO2 were synchronized by removing FBS in culture for 48 hours, followed by feeding back 10% FBS and BrdU for 4 hours. The cells were then harvested for analysis with FITC-BrdU antibody and propridium iodide nuclei staining (BD bioscience). The cells in different cell cycle phases were analyzed by flow cytometry (BD Facscalibur). Similar analyses were also performed for MCF7 cells versus mKO1 or mKO2, PC3-PNOL(T+) versus PC3-PNOL (T−), N1H3T3-PNOL(T+) versus NIH3T3-PNOL (T−).

UV-induced cell deaths. The cultured cells of Du145, dKO1, dKO2, MCF7 or mKO1 at 60-70% confluence were irradiated with UV ranging from 50 mj to 200 mj. Seventeen hours later, these cells were harvested for apoptosis analysis. Alexa Fluor 488-annexin V apoptosis assay kit (BD Biosciences) was used, and apoptotic cells were quantified in flow cytometry (BD Facscalibur). The same apoptosis analysis was also applied to PC3-PNOL(T+), PC3-PNOL (T−), NIH3T3-PNOL(T+) and NIH3T3-PNOL (T−) clones.

Pten-NOLC1 knockout cell death analysis. Cancer cell lines carrying breakpoint of Pten-NOLC1 were used. Cells were treated with recombinant adenoviruses containing Cas9$^{D10A}$ with gRNAs for Pten and mCherry-knockout cassette, or viruses containing Cas9 D10A with gRNAs for Pten donor cassette or viruses containing Cas9$^{D10A}$ only as a control. These viruses were applied to the cell cultures when they reached 70-80% confluence for 18-24 hours. The culture medium was then changed. The cells were incubated for 3 days for Pten-NOLC1 disruption to occur. The cells were then harvested for cell death analysis. PE-annexin V apoptosis assay kit (BD Biosciences) was used: The cells were re-suspended in 100 μl of annexin binding buffer (Invitrogen), and incubated with 5 μl of PE-conjugated annexin V and 5 μl of propidium iodide for 20 min in dark at room temperature. The binding assays were terminated by addition of 400 μl of annexin binding buffer. FACS analysis was performed using a BD Facscalibur (BD Sciences, San Jose, Calif.). Ten thousands cells were acquired and sorted. WinMDI 2.9 software (freeware from Joseph Trotter) was used to analyze the data.

Cell motility and invasion assays. Estimated 5×10$^4$ cells were plated in each matrix gel chamber (24-well), and the control well without matrigel membrane. Twenty-two hours later, the cells on top of the membrane were wiped away and the cells migrated through the chamber membrane or dividers of the controls were stained with H&E and the numbers of cells were counted. The cell numbers invaded through the membrane were normalized with the cells migrated through the divider in control. Triplicates of each clone were included and the comparisons were made between clones of DU145 and DU145KO1 or DU145KO2; MCF7 or MCF7KO1 or KO2; PC3-PNOL(T+) and PC3-PNOL (T−); NIH3T3-PNOL(T+) and NIH3T3-PNOL (T−).

Sleeping beauty/transposon mediated hydrodynamic transfection of Pten-NOLC1. The pPt3-EF1α-Pten-NOLC1-Cherry was transfected into PC3 cells and the expression of Pten-NOLC1-Cherry protein was confirmed by the expression of mCherry fluorescent tag. pT3-EF1α-Pten-NOLC1-Cherry (20 μg) and SB (1 μg) were then pooled in 2 ml saline. The hydrodynamic injections of the pooled plasmids were performed for transfection of Pten-NOLC1-mCherry in the liver (Chen et al., 2017a; Liu et al., 1999). The loxP-Pten mice aged at 4 to 6 weeks were used for peritoneal injection of 1010 of AAV8-Cre (Penn Vector Core, University of Pennsylvania) before the transfection.

Chromatin immunoprecipitation (ChIP). The Pten-NOLC1 knockout clones, dKO1, dKO2, mKO1, mKO2 and their parental cells, Du145 and MCF7, were used for ChIP analysis. MagnaChIP A/G kit (Millipore, USA) was used and the manufacturer's protocol was followed. Briefly, 2-3× 105 cells at 80% confluence in culture were incubated in cold 4% formaldehyde at room temperature for 10 minutes to cross-link proteins and DNA, followed by quenching with glycine for 5 minutes at room temperature, washing 3 times with ice cold 1×PBS, and spinning down the cell pellets. The cells were then lysed with lysis buffer containing protease inhibitors on ice for 15 minutes and centrifuged at 800 g in 4° C. for 5 minutes. The pellet was further lysed with nuclear lysis buffer. The nuclear lysates (protein/DNA) were then sheared to the DNA fragment with size of 100-800 bps by sonication. A Focused ultrasonicator M220 (COVARIS) was used with setting at power 7.5, 200 burst/cycle and factor 10%. The fragmented and crosslinked chromatin was immunoprecipitated with antibodies against the C-terminus of NOLC1 or the N-terminus of Pten. The A/G magnetic beads were used to collect the immune complex including DNA fragments. The DNA were then eluded and purified for library preparation (Illumina, CA). Similar assays were also performed on lysates from PC3-PNOL-Flag, RWPE1-PNOL-Flag and their control PC3-Flag and RWPE1-Flag; and PC3 by using antibodies specific for FLAG tag.

ChIP sequencing: The manufacturer recommended procedure was followed (Illumina): Quantity and size of fragment DNAs were analyzed in a Bio-analyzer (Agilent); the DNA was first blunt-ended with the end repairing reagents, followed by 3' end adenylation and ligation with indexing adaptor; the modified DNA was purified with Ampure XP magnetic beads, and resolved in 2% agarose with SYBR Gold gel. The DNA sizes of 250 to 300 bps were excised, purified with MinElute Gel Extraction Kit, and enriched with 17 heat cycles of PCR with TruSeq™ reagents (Illumina). Each library was quantified again in Agilent Bioanalyzer and normalized to 2 nM for each sample for loading. The process of sequencing in Illumina Highseq 2500 followed the manufacturer's standard protocol. Two lanes of 70 G sequencing capacity were used for sequencing 15 ChIP samples. Identification of peaks of ChIP-enriched reads. The Chip-Seq data were aligned to Human Genome reference hg19 by Burrows-Wheeler Aligner (BWA)(Li and Durbin, 2009). Peaks were called from each individual sample by tool Model-based Analysis of ChIP-Seq (MACS)(Zhang et al., 2008). Significant peaks are defined as the DNA regions where reads are enriched compared to local background alignment. The p-values were adjusted by Benjamini-Hochberg procedure because of multiple hypothesis testing, and FDR was set to be 0.05 to define significance (Benjamini and Hochberg 1995). Significant peaks were further compared between pairwise samples to detect differential peaks (supplementary table 1). Reads aligned to a given peak regions were extracted by SAMtools for further analysis (Li et al., 2009).

All programming for plotting and statistical analysis was implemented in R package. Both the global Manhattan plot and local plot of reads around the upstream of transcription start site (TSS) of specific genes (supplemental FIG. 4) were generated. The global Manhattan plot was generated using the R package "qqman" (bioRxiv DOI: 10.1101/005165). Subtraction results were obtained by subtracting overlapped peaks (extending the peaks by a range of +/−2 kb while matching) in knock-out samples from wild type samples. Peaks from the subtraction results (specially "DU145-(DKOR1+DKOR2)"+"MCF7-(MKO1+MKO2)") were annotated to genes and analyzed through Ingenuity Pathway Analysis (IPA®, QIAGEN Redwood City, www.qiagen.com/ingenuity) and the top enriched pathways were reported. As differentially enriched reads in wildtype Du145 were reached and annotated, the reads in the promoter regions of several identified genes, MET, EGFR, AXL, VGEFA, RAF1 and GAB1 were further analyzed. All the reads of each gene, such as MET, identified in 8 wildtype samples and 7 knockout or other negative controls were plotted along the promoter candidate region, −4 kb to +500 bps of tss site. The reads from different wild type samples were frequently mapped to the closely genome location. Two or more reads mapped to the close location within 100 bp distance were combined as 2 to 3 or more reads in the same location in the plot. The read sequences in the densely distributed region for wildtype group samples were used to design Taqman PCR primers and probes as listed in Table 17. The enriched DNA elements were validated through Taqman PCR using the ChIP samples and resolved on 3% agarose gel.

7.3 Results

Pten-NOLC1 Fusion is the Result of Chromosome 10 Rearrangement.

To investigate the mechanism underlying Pten-NOLC1 fusion transcription formation, fluorescence in situ hybridization (FISH) analysis was performed on the prostate cancer samples where Pten-NOLC1 fusion transcript was detected, using two probes corresponding to the 5' end of Pten genome (spectrum red) and to the 3' end of NOLC1 (spectrum green). The results showed that the signals of Pten and NOLC1 were overlapped to form a single hybridization signal (yellowish) in the cancer cells. An independent NOLC1 signal (green) was also clearly identified, but the wild type Pten signal (red) was absent in this prostate cancer case. This is in contrast to the distinct two pair of separate signals for Pten (red) and NOLC1 (green) visualized in normal organ donor prostate tissue. The co-existence of Pten-NOLC1 genome recombination and hemizygous Pten deletion in the cancer genome suggests a complete functional loss of Pten alleles in this cancer.

To identify the location of the chromosomal breakpoint for Pten-NOLC1, a series of nested-long-extended PCR was performed on the genomic DNA of this prostate cancer sample, using primers corresponding to the genome sequences adjacent to the exons flanking the breakpoint juncture.

The PCR product was purified and subjected to Sanger sequencing. The sequencing results of these PCR products showed (FIG. 17C) indicated that the genome breakpoint of Pten-NOLC1 was located at the sequences between intron 11 of Pten and intron 1 of NOLC1, with an 8 bp (TAGCTGGG) overlapped sequence shared by both Pten and NOLC1 introns. In the subsequent Pten-NOLC1 breakpoint analysis, we found that the genomes of cancer cell lines LNCaP, DU145, VCaP, HEP3B, MCF7 and PC3 contain the identical breakpoint sequence, even though they are from different types of malignancies with diverse biological features. These results suggest a common recombination mechanism that underlies Pten-NOLC1 fusion formation in human cancer genomes.

Pten-NOLC1 is Highly Recurrent in Human Malignancies.

To investigate whether Pten-NOLC1 fusion is frequent in human cancers, Taqman RT-PCR analyses were performed on 26 cancer cell lines of 6 different of human cancers using primers and probe shown in FIG. 20A, and Pten-NOLC1 fusion transcript were found present in most tumor cell lines tested, including 4 prostate cancer cell lines tested (PC3, DU145, LNCaP and VCaP), lung cancer cell lines (H358, H1299, H522 and H23), breast cancer cell lines (MDAMB231, VACC3133, MDA-MB330, MCF7), liver cancer cell lines (HUH7, HEP3B, SNU449, SNU475, SNU375, SNU182 and HEPG2), and glioblastoma cell lines (A-172, LN229, T98G, U138 and U118), and colon cancer cell lines (HCT8 and HCT15). Pten-NOLC1 fusion was not detected in 20 normal organ donor prostate samples and 10 blood samples from prostate cancer patients. To investigate whether Pten-NOLC1 is present in primary human cancer samples, Taqman RT-PCR analyses were performed on 1030 cancer samples from 8 different types of human malignancies. The results showed that Pten-NOLC1 is extensively present in these cancers: 70.1% (337 of 481) PCa, 83% (50 of 60) breast cancer, 75% (45 of 60) colon cancer, 83% (127 of 153) GBM, 82.9% (58 of 70) liver cancer, 75.2% (109 of 145) NSCLC, 70.5% (43 of 61) ovarian cancer and 85% (29 of 34) esophageal adenocarcinoma (FIGS. 20B, 18 and 19 and Table 7-12).

To investigate whether this widely present transcript of Pten-NOLC1 was translated to a protein in cancer cells or tissues, the western blots on tumor samples with antibodies specific for Pten were performed. Pten-NOLC1 fusion has a projected molecular weight of ~120 Kd, and the size is significantly bigger than Pten (48.3 Kd). While in the blotting of protein extracts from cell lines H522, H358, PC3, DU145 and A-172, a 110 kDa band was readily detected in cancer line samples by antibodies against Pten (FIG. 20C, line 8-12). Pten-NOLC1 protein was also detected in primary cancer tissue samples that were positive for Pten-NOLC1 mRNA, while was negative in healthy organ donor prostate samples where Pten-NOLC1 fusion was absent (FIG. 20C, line 1-7). Taken together, Pten-NOLC1 was a somatic genome rearrangement product and was recurrently detected as a fusion transcript and chimeric protein in human cancers of different origins.

Pten-NOLC1 Only is Located in Nucleus and Contains No Phosphatase Function.

Cytoplasmic PIP3 is the specific target of Pten phosphatase, while NOLC1 is exclusively a nucleolar protein. Thus, it is of interest to identify the subcellular location of Pten-NOLC1 fusion protein since it has a significant implication on the function of the fusion protein. A cDNA of Pten-NOLC1 was created and constructed into a mammalian expression vector to create pCNDA4-Pten-NOLC1-Flag and transfected into N1H3T3 cell lines for analyzing the location of Pten-NOLC1 with immunostaining. As shown in FIG. 22, using an antibody specific for FLAG tag to analyze the NIH3T3 cells transfected with pCDNA4-Pten-NOLC1-FLAG, signal of Pten-NOLC1 was exclusively localized in the nucleus, similar to the cell nucleus staining with NOLC1 antibody, while Pten antibody showed a diffuse distribution of Pten in NIH3T3 cells covering both cytoplasm and nucleus. Similar results were also observed in PC3 cells transfected with pCNDA4-Pten-NOLC1-FLAG (data not shown). In addition, pCNDA4 expressing proteins with fluorescent tag were created to trace the chimeric Pten-NOLC1-EGFP, truncated Pten$^{del343-403}$-EGFP and truncated NOLC1$^{dell-40}$-mCherry, expression in PC3 cells. When the vector was separately transfected into PC3 cells, respectively, both Pten-NOLC1-EGFP and NOLC1-mCherry proteins were exclusively localized in the nucleus, while Pten-EGFP is mostly in the cytoplasm, rarely (but one cell) in the nucleus in the mitotic stage. Further, when nuclear or cytoplasmic fractions of Du145 lysates were blotted with Pten antibodies, Pten band (48 kDa) was found exclusively in cytoplasmic fraction, and while Pten-NOLC protein was detected in the nuclear fraction (FIG. 22B) as evidenced by the detection of the same protein band with antibodies against Pten and FLAG, respectively, during Western Blot analysis.

Since the phosphatase domain of Pten is intact in Pten-NOLC1 fusion protein while the lipid-binding C2 domain of Pten is truncated, it is unclear whether Pten-NOLC1 has phospholipid phosphatase activity. An ELISA assay was performed (Echelon Pten Activity Elisa kit) to test the capability of purified recombinant GST-Pten or GST-Pten-NOLC1 to convert $PI(3,4,5)P_3$ to $PI(4,5)P_2$. The results showed that GST-Pten had 28 pmol of PIP2 produced (per ng of GST-Pten). In contrast, GST-Pten-NOLC1 failed to produce measurable PIP2 (FIG. 22C). Similar results were found for cellular produced Pten or Pten-NOLC1: The antibodies specific for Pten or NOLC1 or FLAG were used in the immunoprecipitation to purify the Pten-NOLC1 or Pten related proteins in Pten-NOLC1 expressing PC3 clones, but none of these immuno-purified proteins had shown any phosphatase activities. The failure of endogenous Pten in PC3 cells to show PIP3 phosphatase activity probably reflects mutated enzyme in the cancer cell line (14). In conclusion, Pten-NOLC1 resides exclusively in the nucleus, but possesses no wildtype of Pten lipid phosphatase function.

Pten-NOLC1 Promotes Tumor Growth and Increases Tumor Survival.

Following, testing of whether the expression of Pten-NOLC1 has impact on the tumor growth was performed. Most cancer cell lines of different organ origin have been tested to contain weak to moderate expression of Pten-NOLC1 (FIG. 20A). Specific knockdown of Pten-NOLC1 fusion by siRNA may be used to investigate the impact of Pten-NOLC1 on cell growth. However, such approach may not be feasible due to share sequence between Pten-NOLC1 and Pten, or between Pten-NOLC1 and NOLC1.

Figure 23A:
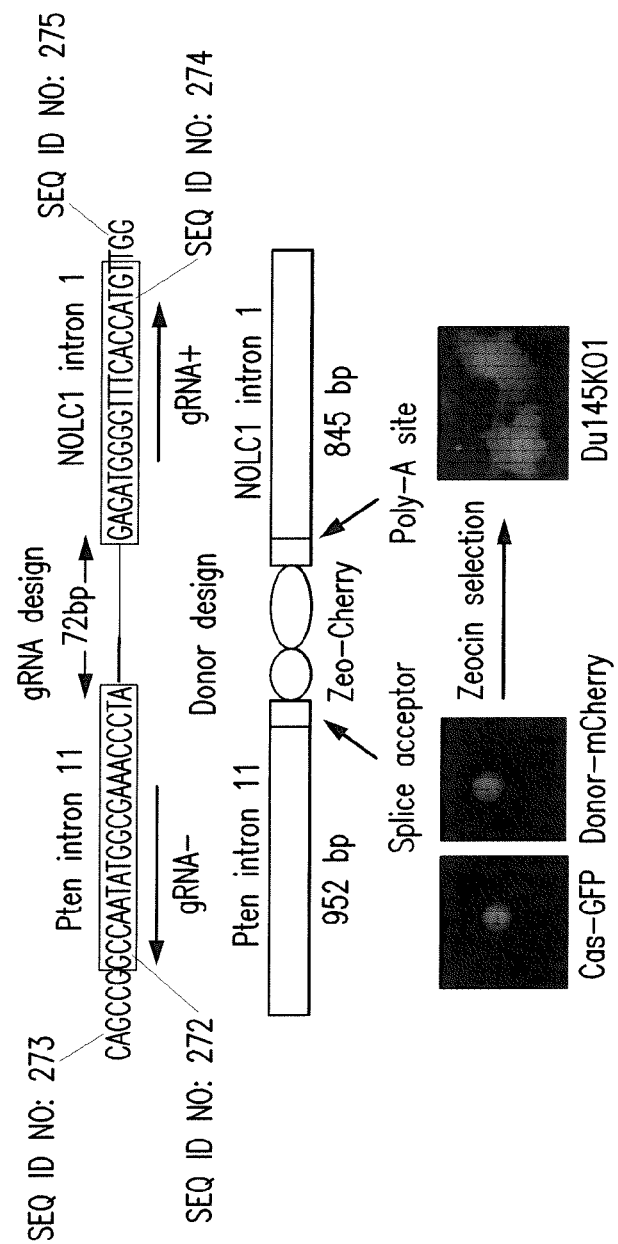
Figure 23B:
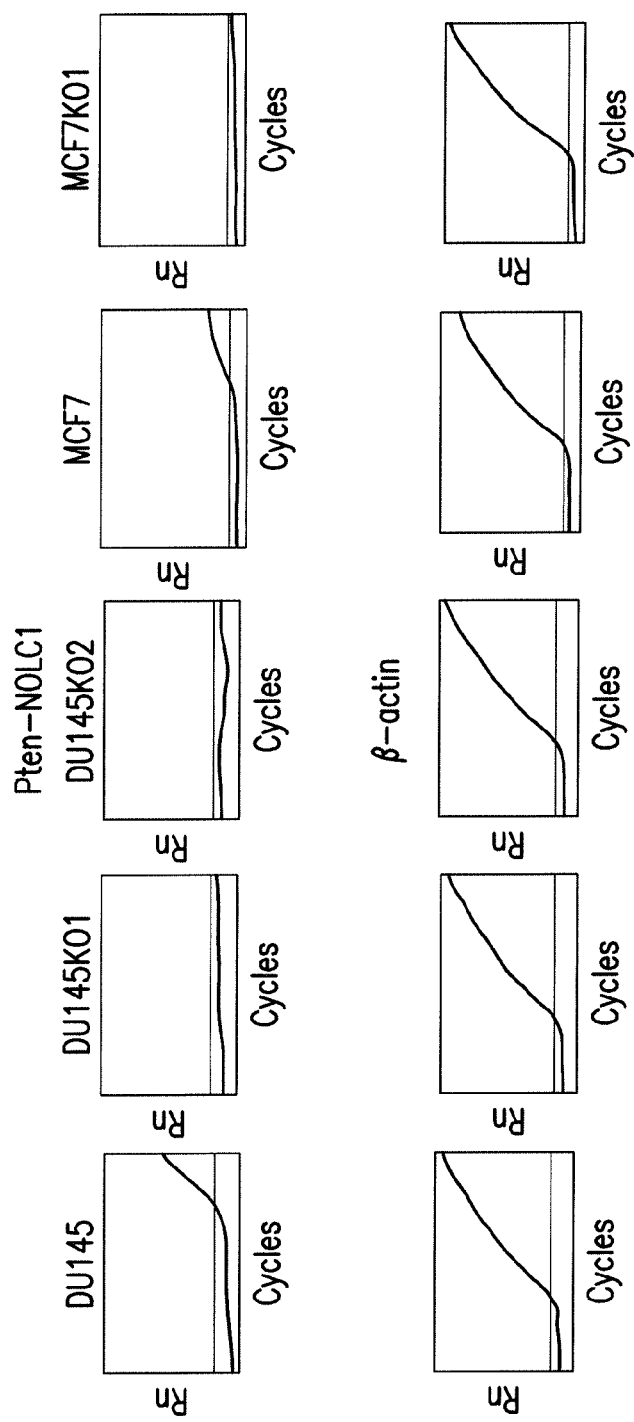

First, Pten-NOLC1 genome knockout in DU145 cells and MCF7 cells were prepared using CRISPR-Cas9$^{D10A}$ approach. As shown in FIG. 23A, the genome breakpoint of Pten-NOLC1 was targeted by two gRNAs flanking the breakpoint. This was followed by gRNA directed Cas9$^{D10A}$ nickase to nick at the target sites (gRNA-Cas9$^{D10A}$ vector) and insertion of a promoterless but ribosome binding site-containing zeocin-mCherry cDNA (donor vector) into the breakpoint through homologous recombination. When both these vectors were transfected into DU145 (prostate cancer cells), MCF7 (breast cancer cells) and other cancer cell lines, the successful interruption of Pten-NOLC1 fusion was indicated by zeocin resistant and display of mCherry fluorescence. Clones of Pten-NOLC1 knockout were obtained through zeocin resistance selection. As shown in FIG. 23B, clones of DU145 and MCF7 were obtained to show knockout of Pten-NOLC1 expression.

Figure 23D:
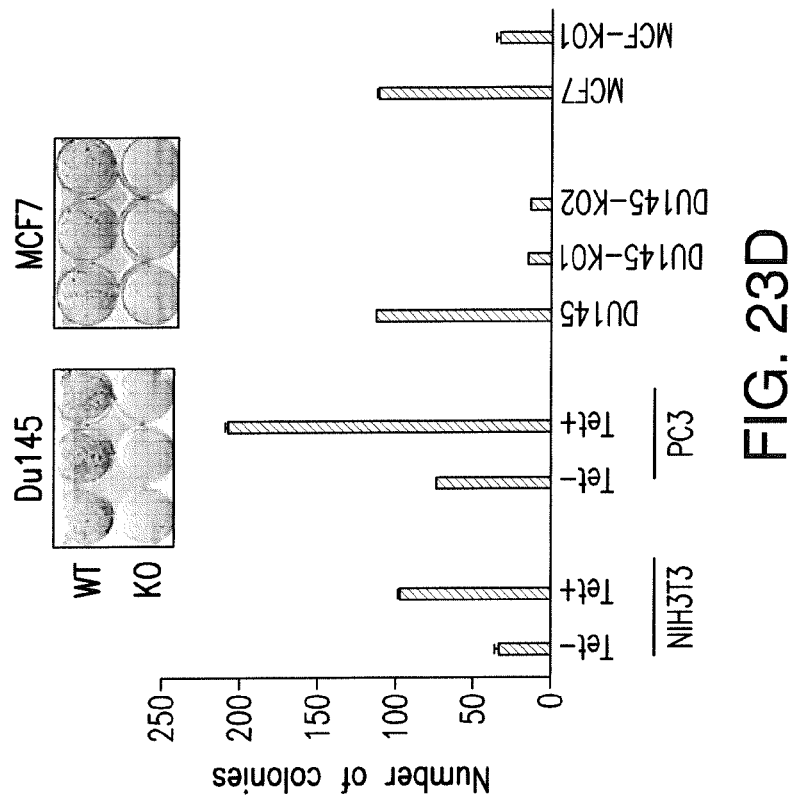
Figure 23C:
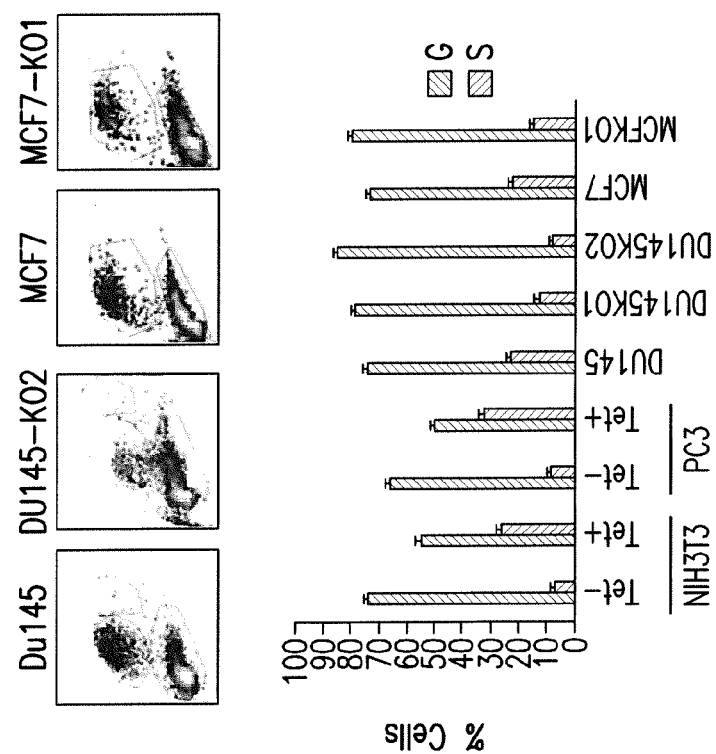
Figure 23E:
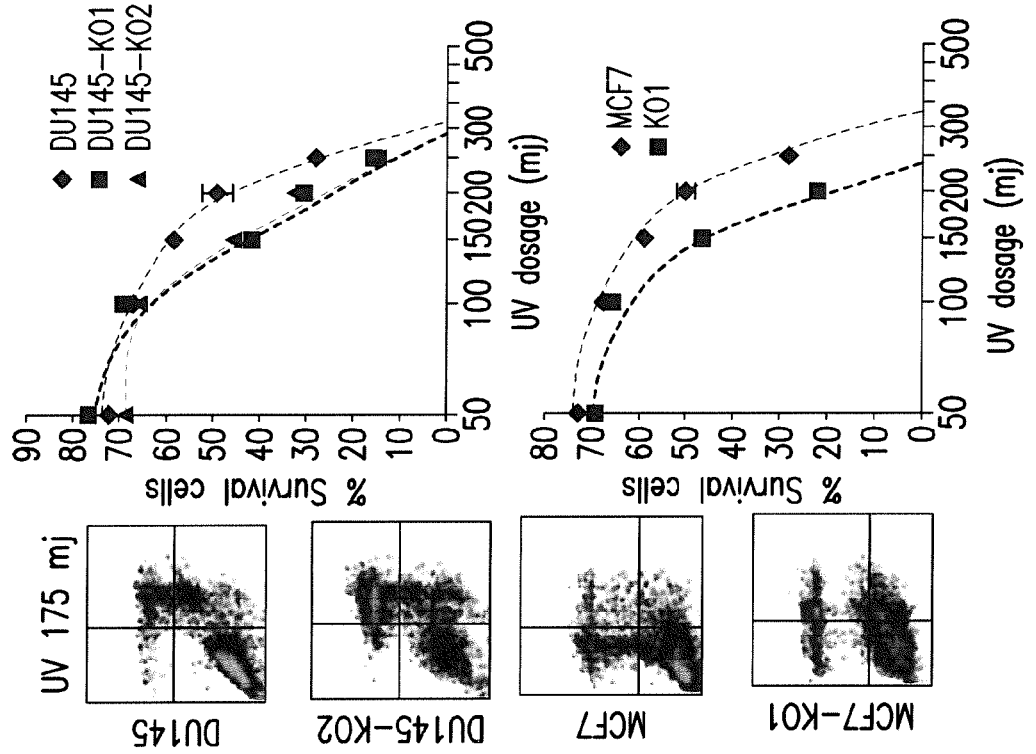
Figure 23G:
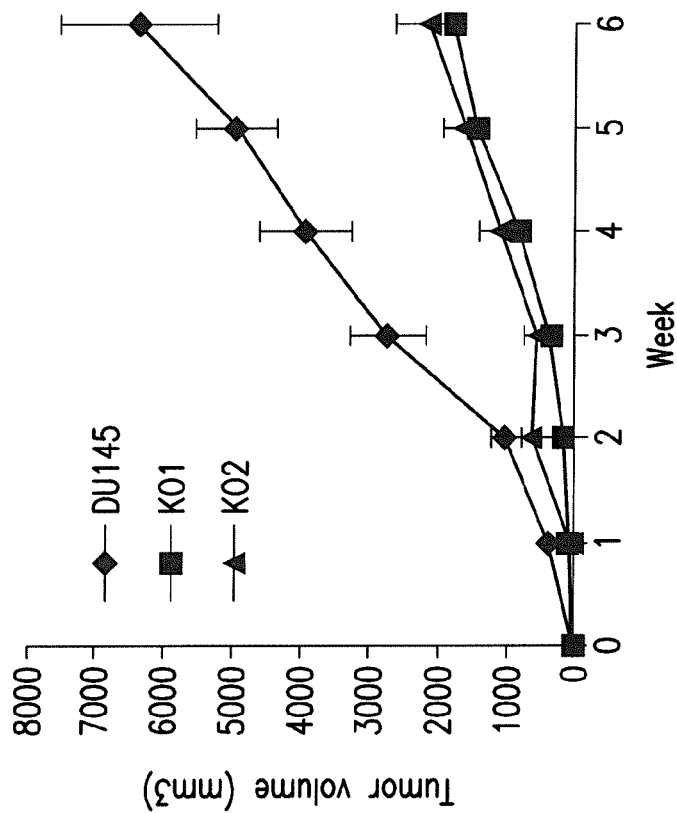
Figure 23F:
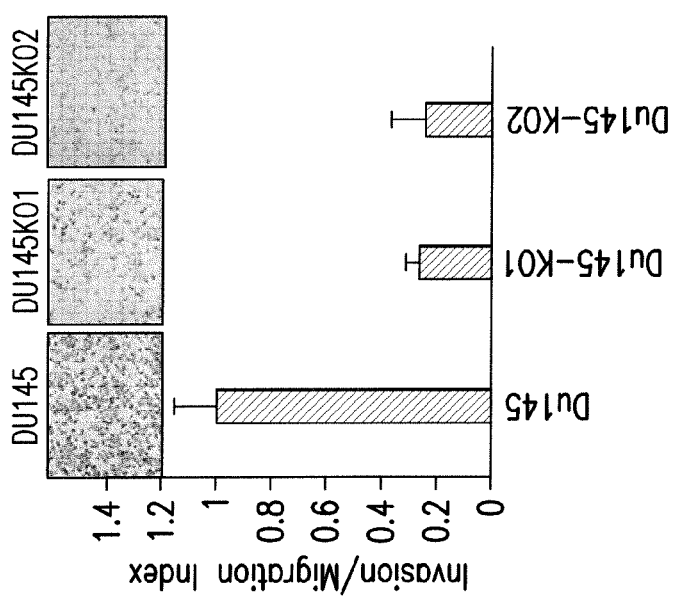
Figure 23I:
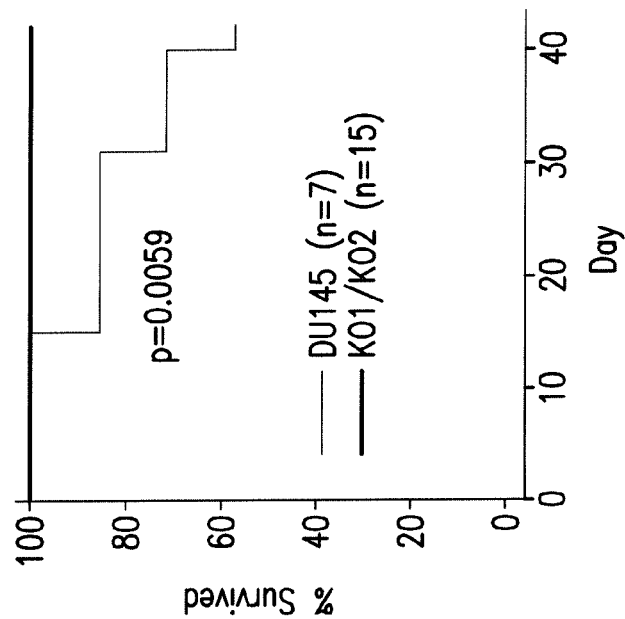
Figure 23H:
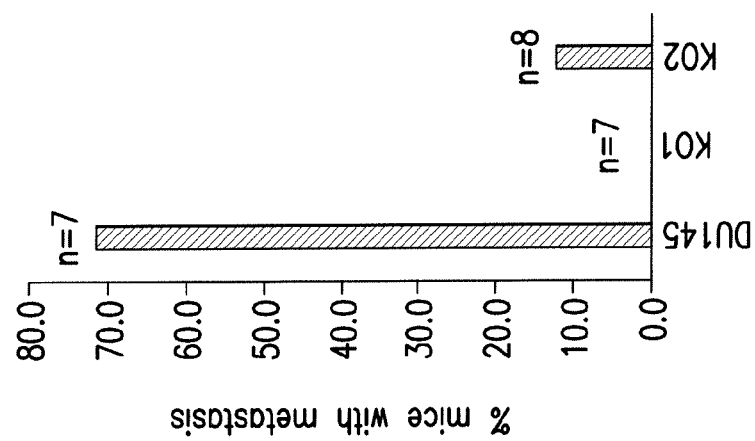

Subsequently, these clones were analyzed for cell cycle characteristics. As shown in FIG. 23C, the cell population in S phase decreased from 23.3% to 13% (p<0.05) and 8% (p<0.05) in Pten-NOLC1 knockout clones DU145KO1 and DU145KO2, respectively, in comparison with their parent DU145 cells, and from 23% to 15% (p<0.05) in MCF7KO1 cells, while the G0/G1 phase of these Pten-NOLC1 knockout cells moderately increased. In contrast, forced expression of Pten-NOLC1 in NIH3T3 and PC3 cells increased the S-phase entry for these cells (7% to 26% for NIH3T3, p<0.05; and 9% to 32% for PC3, p<0.05). Knockout of Pten-NOLC1 produced 8-13 fold decrease (p<0.05) in colony formation for Du145 cells and 2.4 fold drop (p<0.05) for MCF7 cells (FIG. 23D). The finding was reversed if Pten-NOLC1 was forced to express in NIH3T3 (2.83 fold increase, p<0.05) and PC3 (2.8 fold increase, p<0.05) cells. Separately, we performed a UV-induced cell death analysis of these DU145 and MCF7 KO cells, as shown in an example of FACS analysis of Alexa Fluor 488 annexin V binding assays, 36% of the parental DU145 cells treated with 175 mj UV died versus 56% of its knockout counterparts (DU145-KO1;p<0.05), suggesting that the presence of Pten-NOLC1 increases the resistance of cancer cells to UV radiation. Indeed, the removal of Pten-NOLC1 resulted in the cells beoming more sensitive and decreased the ED50 of DU145 cells from 174 mj to 135 mj and ED50 of MCF7 from 175 to 127 mj (FIG. 23E). To investigate the impact of Pten-NOLC1 on cancer invasiveness, matrigel traverse analysis was performed. As shown in FIG. 23F, removal of Pten-NOLC1 in DU145 tumor cells reduced the invasion index by 3.8-4 fold. To test the aggressiveness of these cells in vivo, $5 \times 10^6$ of these cells were subcutaneously grafted in the left flank region of SCID mice. The DU145 tumors grew rapidly and started displaying a visible bump on the flank region in the second week after the grafting and to the end of observation, the bump became almost 35 times of its original size on the second week, while the grafts of two Pten-NOLC1 KO clones of DU145 only became visible at 4th week after the xenografting (FIG. 23G). Most of the mice with DU145 tumor hadmetastatic lesions and ascites, while only one animal from the knockout groups showed such signs (FIG. 23H). All animals xenografted with DU145 cells devoid of Pten-NOLC1 survived the 6-week period of xenografting, while 42% (3/7) SCID mice xenografted with DU145 cell tumor died during the same period. MCF7 cells failed to migrate in the matrigel, and its xenografts did not grow in SCID mice. Taken together, these results indicate that Pten-NOLC1 fusion contributes significantly to the tumor growth and invasion.

Overexpression of c-Met, GAB1 and EGFR are Dependent on Pten-NOLC1.

Figure 28A:
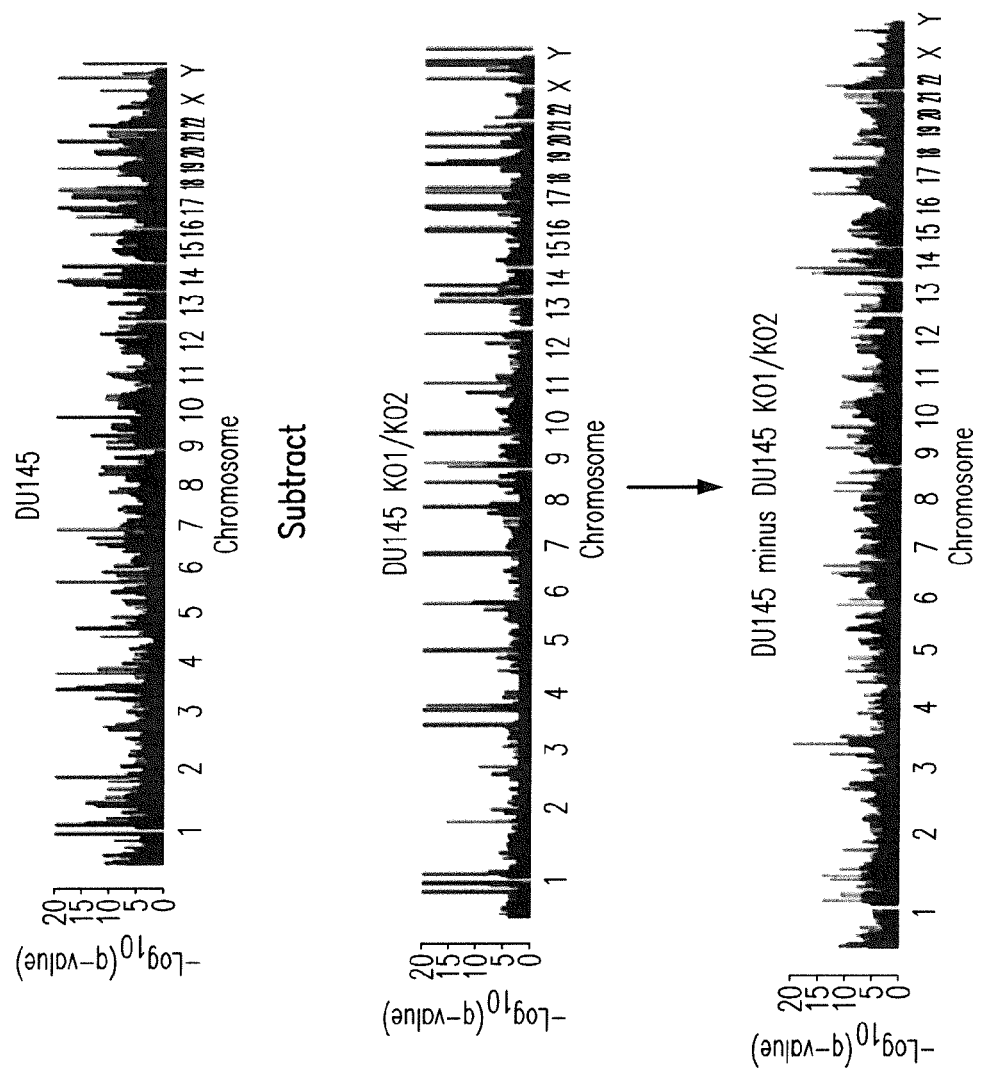
Figure 28A:
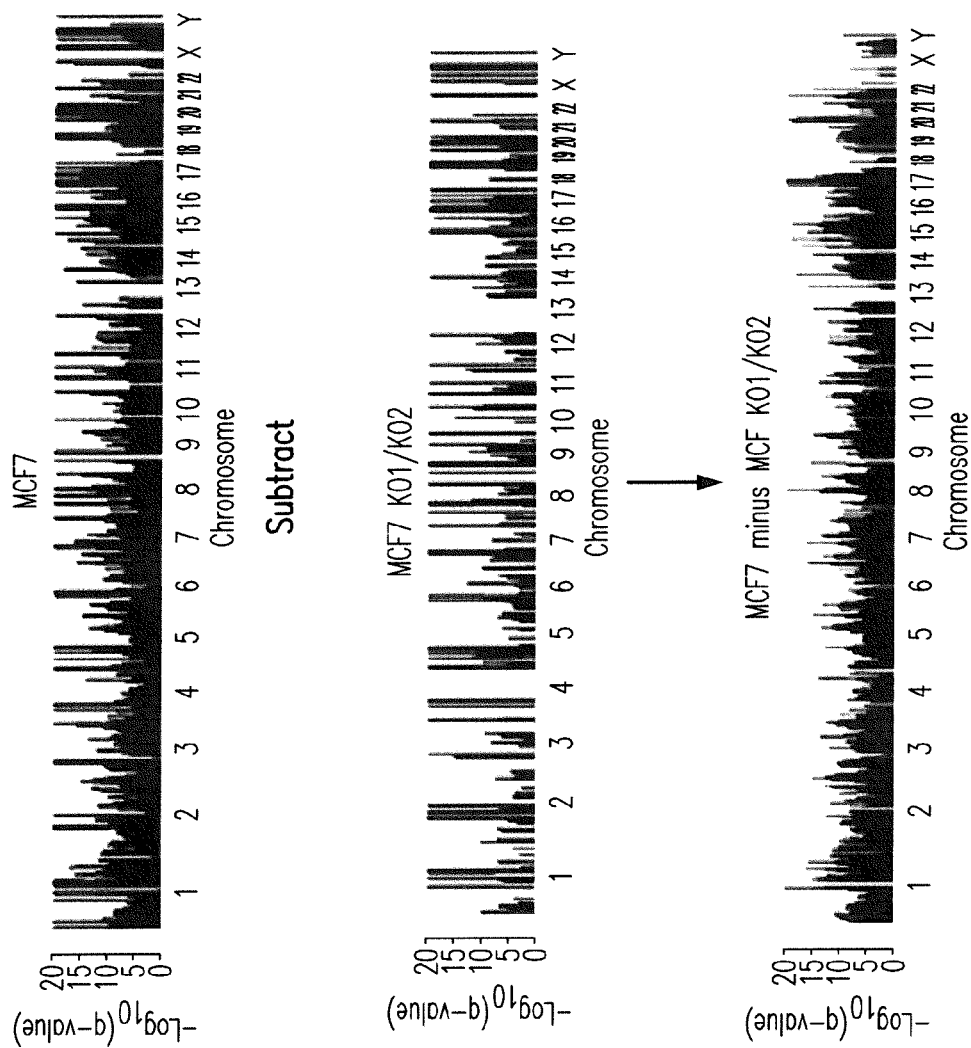
Figure 28B:
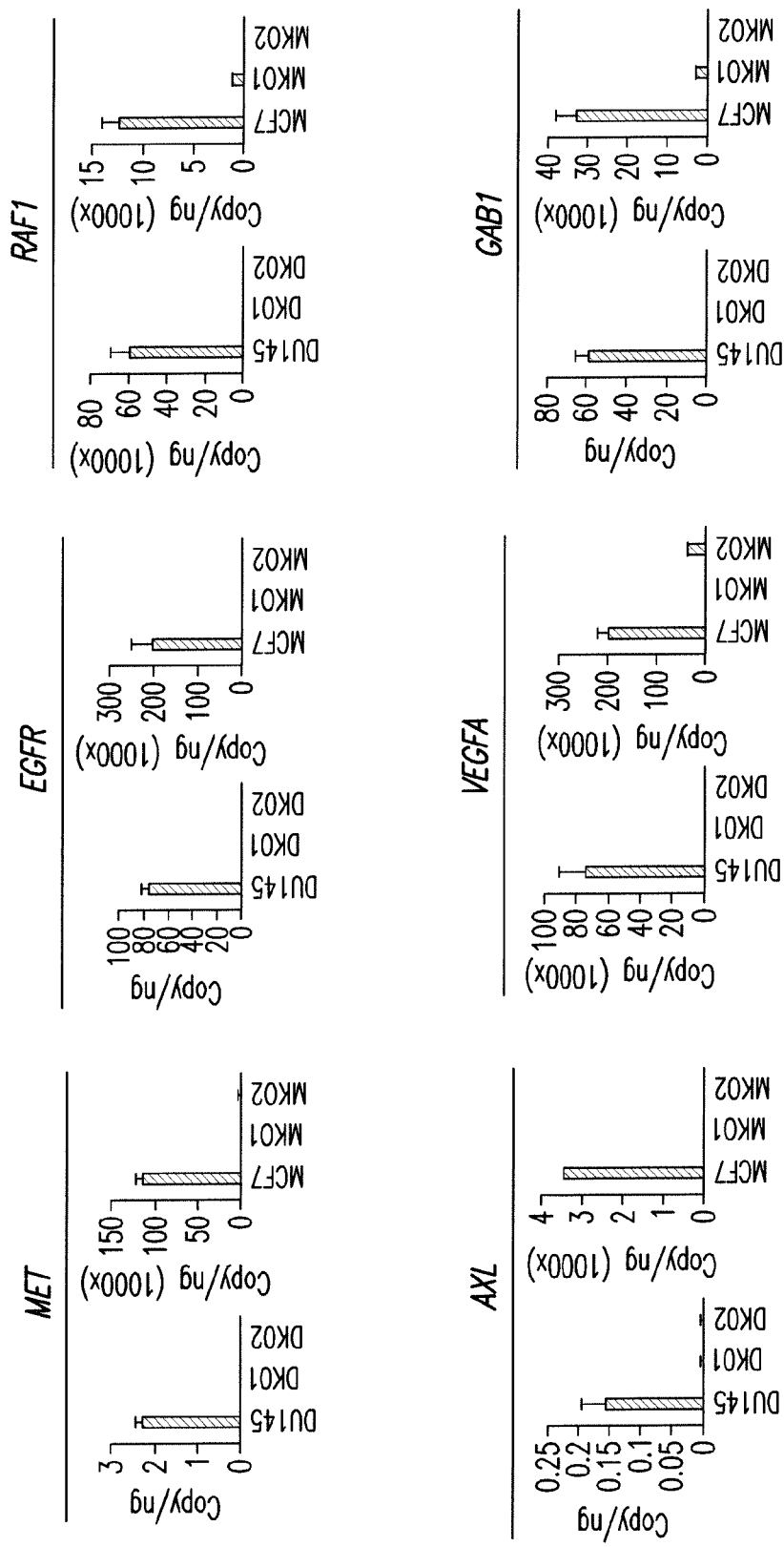

NOLC1 is a cofactor of RNA polymerase 112, and has been implicated as a co-transcription factor (15, 16). To test whether fusion between NOLC1 and Pten may alter its transcription spectrum, DNA fragments of DU145 and MCF7 and their knockout counterparts from chromatin immunoprecipitations using NOLC1 antibodies were sequenced (ChIPseq). As shown in FIG. 28A, 6179 DNA fragment peaks were detected in DU145 cells. The peak events were reduced to 2868 in 2 Pten-NOLC1 knockout clones. Similar results were also identified in MCF7 cells: 4347 peaks in total in MCF7, and 1196 peaks in MKO1 and MKO2. The presence of Pten domain in NOLC1 produced 2.2 to 3.6-fold more genome binding regions, significantly broadening NOLC1 DNA binding activity. To verify whether these DNA binding activities are the direct results of Pten-NOLC1 fusion, Pten-NOLC1-FLAG was forced to express in PC3 and RWPE1 cells, large numbers of DNA peaks were identified in FLAG antibodies-ChIPseq. Many peaks overlapped with those found in DU145 and MCF7 cells. Pathway analysis of these Pten-NOLC1 associated DNA fragments showed that genes from 'HGF signaling' and 'mechanism of cancer' pathways are among the most impacted signals (Table 15). The enrichment includes DNA fragments from the promoter/enhancer regions of MET, EGFR, RAF1, AXL, GAB1 and VEGFA (FIG. 29 and FIG. 28B).

Figure 28C:
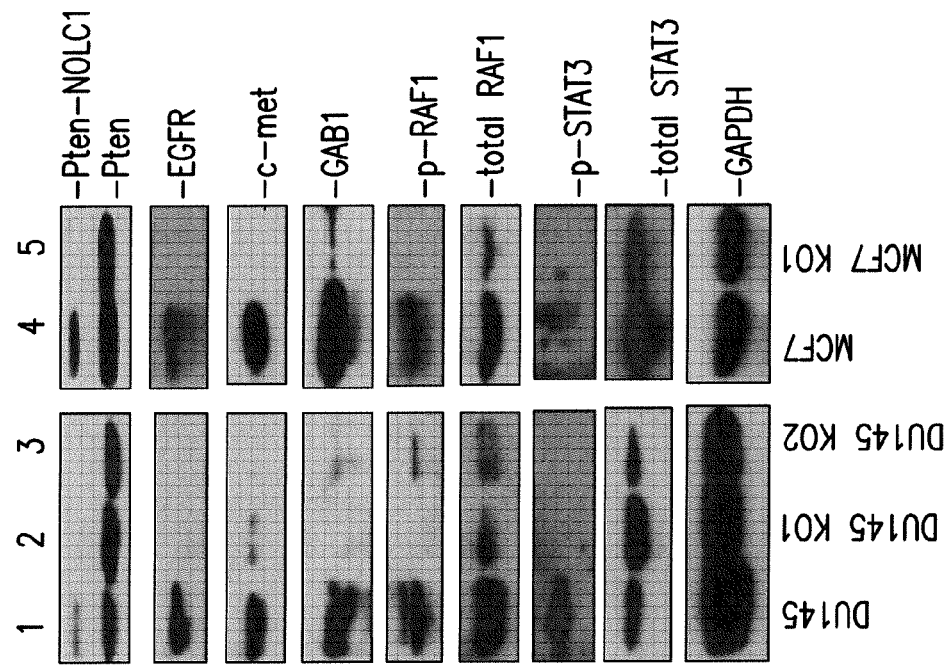
Figure 28D:
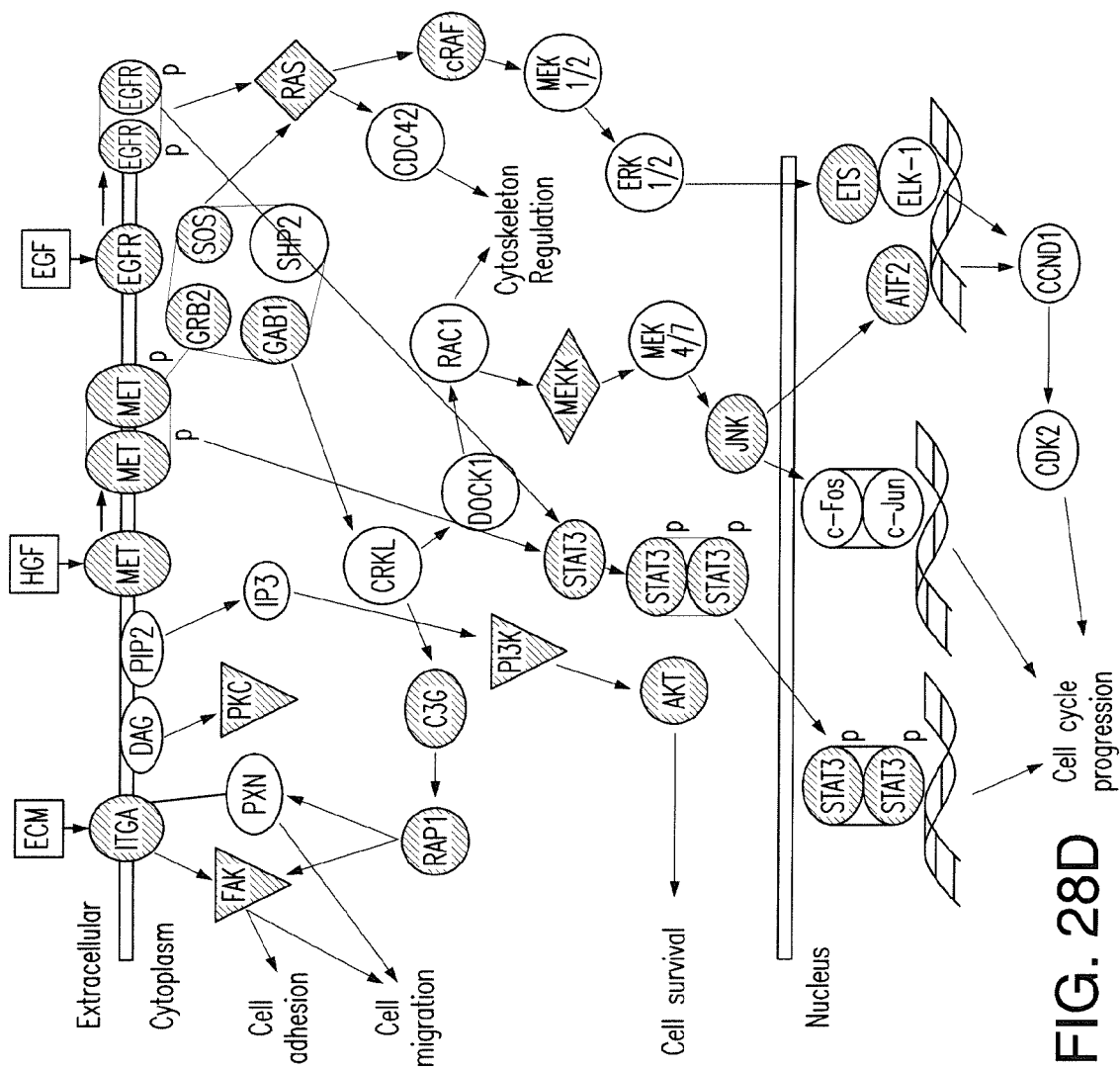

To investigate the impact of removal of Pten-NOLC1 from DU145 cells, gene expression microarray assays were performed performed on DU145 cells and its knockout counterparts. The results showed more than 500 genes and transcripts were down-regulated in both Du145KO1 and Du145KO2 clones in comparison with parent DU145 cells. Among these genes, c-MET was downregulated 2.8-6 fold, EGFR 1.4-1.41 fold, GAB1 1.8-1.9 fold, AXL 1.8-2.3 fold, VEGFA 1.5-1.6 fold (FIG. 24A). Similar down regulations of these gene expressions were also identified using quantitative RT-PCR assay method (FIG. 24B). Interestingly, these findings were similarly identified in MCF7 cells with knockout of Pten-NOLC1 (FIG. 24B). Dramiatic downregulation of MET, EGFR, RAF1, and GAB1 protein expression in DU145KO1, DU145KO2 and MCF7KO1 were identified (FIG. 24C and FIG. 28C). Both RAF1 and STAT3 showed very little phosphorylation. These results suggest that activation of these signaling pathways are largely dependent on the presence of Pten-NOLC1. When combined with ChIPseq/microarray and immunoblot analyses, we found that the expressions of many molecules in the ECM, EGF and HGF signaling pathways are dependent on Pten-NOLC1 (FIG. 28D). Indeed, disruption of Pten-NOLC1 expression in 9 different cancer cell lines including PC3, DU145, SNU479, SNU449, HEP3B, T98G, MCF7, MB231 and H1299 cells by knocking in zeocin-cherry cassette produced large numbers of cell deaths (FIG. 30 and Table 18), in contrast to Pten-NOLC1 negative NIH3T3 cells where the impact is minimal. These results suggest that many cancer cells may addict to Pten-NOLC1 for survival.

TABLE 18

Cell death induced by disruption of Pten-NOLC1

| Cell line | Cas9$^{D10A}$ only % cell death | Cas9$^{D10A}$ + gRNAs % cell death | Cas9$^{D10A}$ + gRNAs + KO cassette % cell death |
| --- | --- | --- | --- |
| MB231 | 17.6 ± 0.50 | 20.0 ± 0.73 | 49.8 ± 0.83 |
| MCF7 | 44.8 ± 2.41 | 44.7 ± 1.25 | 72.7 ± 0.47 |
| PC3 | 11.2 ± 0.34 | 40.7 ± 0.94 | 66.1 ± 0.82 |
| DU145 | 29.8 ± 1.74 | 30.0 ± 0.05 | 57.7 ± 1.25 |
| SNU475 | 10.4 ± 2.41 | 29.5 ± 0.75 | 70.3 ± 0.97 |
| HEP3B | 35.7 ± 0.22 | 42.9 ± 0.25 | 49.6 ± 0.25 |
| SNU449 | 11.7 ± 0.45 | 21.6 ± 0.42 | 49.5 ± 2.31 |
| T98G | 36.4 ± 0.42 | 44.5 ± 0.17 | 55.3 ± 1.08 |

TABLE 18-continued

Cell death induced by disruption of Pten-NOLC1

| Cell line | Cas9$^{D10A}$ only % cell death | Cas9$^{D10A}$ + gRNAs % cell death | Cas9$^{D10A}$ + gRNAs + KO cassette % cell death |
| --- | --- | --- | --- |
| H1299 | 19.3 ± 0.43 | 58.2 ± 0.97 | 73.6 ± 8.38 |
| NIH3T3 | 15.5 ± 0.46 | 16.0 ± 0.21 | 18.9 ± 0.34 |

Pten-NOLC1 Fusion Induced Hepatoma in Mouse.

Figure 25C:
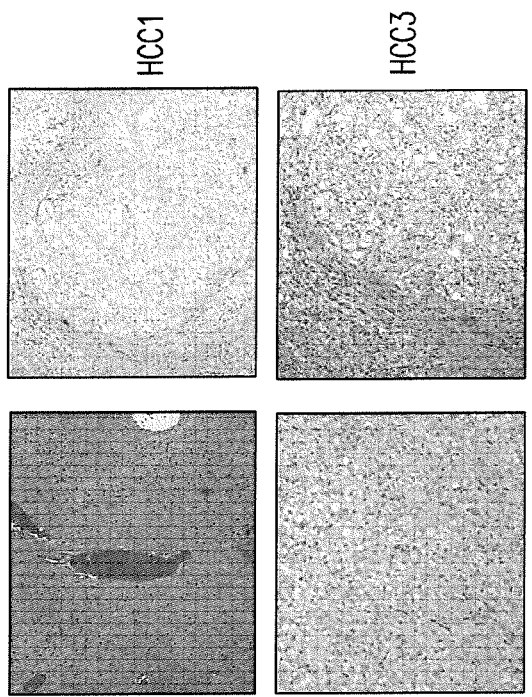
Figure 25B:
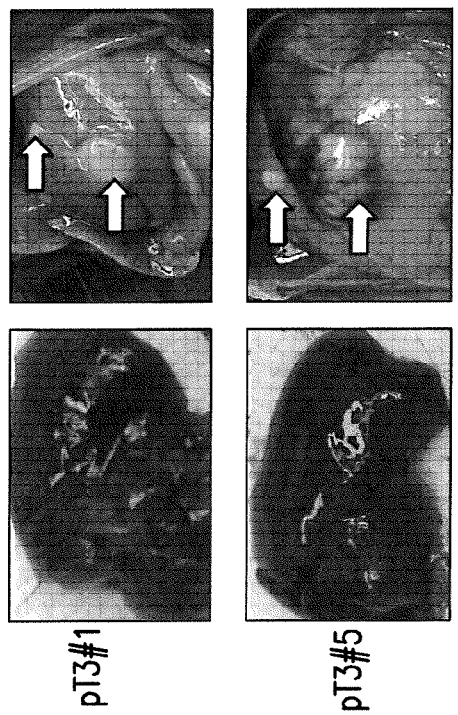
Figure 25A:
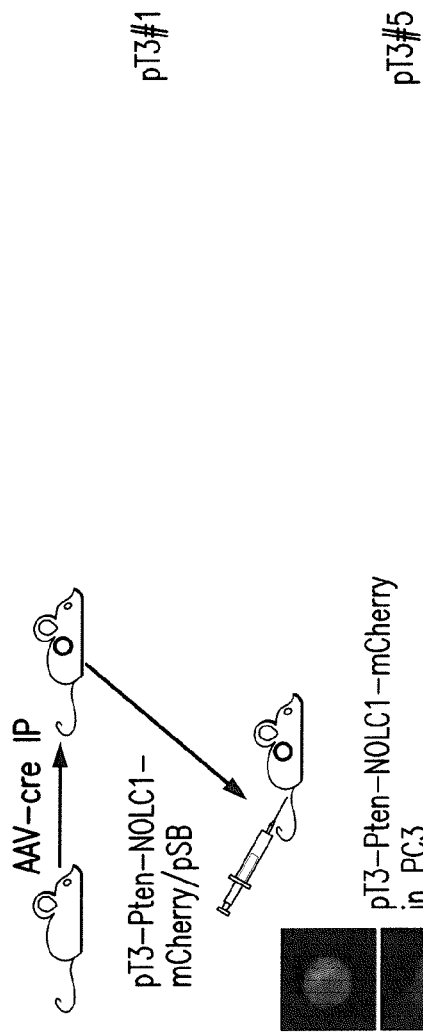
Figure 25E:
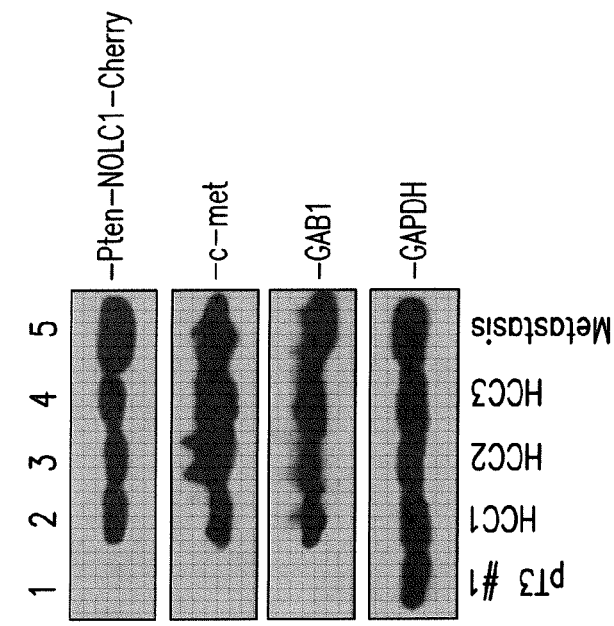
Figure 25D:
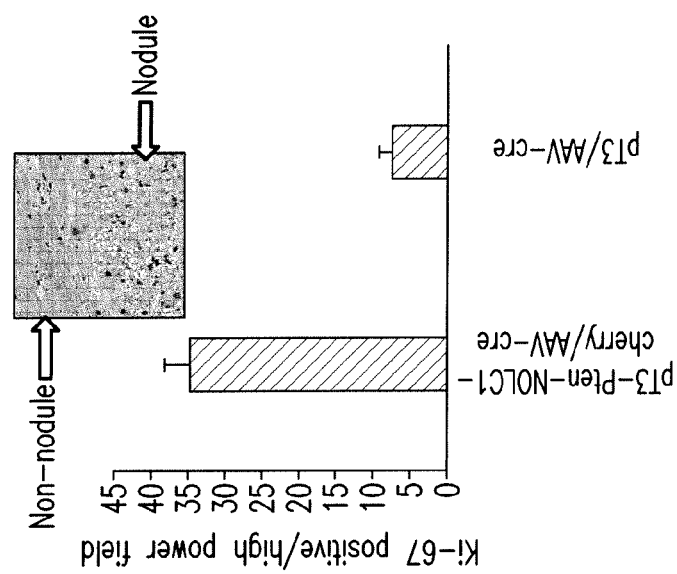

Conversion of Pten to Pten-NOLC1 represents a loss of wild-type Pten and creation of an oncogene in one event. The hypothesis was that this single event may be sufficient to generate cancer in mammals. To test this hypothesis, Pten was somatically knocked out from the liver of C57Bl$^{loxPten+/+}$ mice through intra-peritoneal injection of AAV8-cre. This was followed by hydrodynamic tail vein injection of pT3-Pten-NOLC1-mCherry and pSB so that about 1-5% hepatocytes were transfected with Pten-NOLC1-mCherry gene (FIG. 25A). Within 18 weeks, six of seven mice developed hepatocellular carcinoma, showing distinctive tumor nodules in the liver (FIG. 25B). One mouse developed cancer metastasis in the peritoneal cavity. Two animals have ascites accumulation. In contrast, none of the control mice with somatic Pten knockout and pT3/pSB injection developed sign of tumor in the same period. These tumor cells have large nucleoli and contain significant fatty accumulation in the cytoplasm, probably due to Pten gene knockout. The tumor cells also displayed high frequency of Ki-67 staining, showing 4.6 fold more frequent than that of non-cancerous cells (FIG. 25D). Immunoblot analyses showed Pten-NOLC1-mCherry protein expression in all the cancer samples, which was detected by antibodies specific for Pten or NOLC1, but such protein was absence in pT3/pSB transfected and AAV8-cre treated mouse liver tissues (FIG. 25E). A dramatic up-regulation of c-MET and GAB1 was detected in all the tumor tissues, including the metastatic cancer sample. Thus, these results indicate that a single event of Pten-NOLC1 fusion creation is sufficient to drive the development of spontaneous liver cancer and the oncogenic activity of Pten-NOLC1 is significantly contributed by over-activation of c-MET signaling pathway.

7.4 Discussion

This examples shows that there is a widespread presence of Pten-NOLC1 fusion in human cancers, which suggests a fundamental role of Pten-NOLC1 fusion in cancer development. The positive rate of Pten-NOLC1 in cancer metastasis is even higher, reaching 90% in some types of cancers (FIG. 21). Despite the high frequency of Pten-NOLC1 fusion, to our knowledge, this is the first report to describe such fusion in human cancers. Screening of transcriptome sequencing data sets of 2586 cancer samples covering 17 different cancer types from TCGA, we failed to detect the presence of Pten-NOLC1 fusion transcript. Intrigued by the discrepancies, we investigated the possible differences between the two data sets by comparing the normalized number read alignments for the head or tail exon of Pten or NOLC1 gene. The analysis showed that significantly smaller proportion of mapped reads are aligned to the first exon of either Pten or NOLC1 gene from the TCGA prostate cancer data set in comparison with our data (FIG. 26). Since detection of Pten-NOLC1 requires large number of exon 1 mapped reads for NOLC1, 3' end bias and relatively low sequencing coverage may impede the detection of Pten-NOLC1 fusion transcript.

Creation of Pten-NOLC1 fusion is the result of a large of deletion (14.2 MB) of chromosome 10 sequence spanning between exon 11 of Pten and exon 1 of NOLC1. Such deletion is readily detectable by copy number analysis. Indeed, among 12 Pten-NOLC1 fusion-positive prostate cancer samples that were also analyzed by Affymetrix SNP6.0 array, all showed the similar 14.2 MB spanning deletion between exon 11 of Pten and exon 1 of NOLC1 (FIG. 27). In contrary, 10 prostate cancer samples that are negative for Pten-NOLC1 fusion are found negative for such spanning deletion. Thus, spanning deletion between exon 11 of Pten and exon 1 of NOLC1 may serve as a surrogate indicator for the presence of Pten-NOLC1 fusion. We subsequently applied this analysis to SNP6.0 data sets from TCGA database. Large numbers of cancer samples were found to contain such spanning deletion, ranging from 2% for thyroid cancer data set to 79% from glioblastoma multiforme data set (FIG. 27A-C). The wide presence of Pten-NOLC1 spanning deletion in the cancer genomes suggests the presence of Pten-NOLC1 fusion gene in these cancer samples.

Pten deletion and mutations occur in many human cancers. These mutations result in loss of lipid phosphatase activity and produce genome stability. Here, we identified a Pten derived fusion molecule functionally promotes cancer cell growth through the MET signaling system. Elevated MET is known to facilitate the MET-FAS interactions on the membrane to increase survivals (17). Pten-NOLC1 may increase the survival of cancer cells by elevated the expression level of c-MET such that it abrogates the impact of FAS cell death signaling. This may explain the impact of Pten-NOLC1 induced cell death resistance to UV irradiation. Interestingly, many cancer samples with hemizygous Pten deletion are also positive for Pten-NOLC1 (FIG. 27C). As a result, these cancers are devoid of functional Pten protein, since Pten-NOLC1 is negative for phospholipid phosphatase activity, and is translocated to the nucleus. These cancers may also have over-activated PI3K/Akt signaling due to the lack of deactivation of PIP3(1,4,5). The analysis showed that a single event of creation of Pten-NOLC1 is sufficient to produce spontaneous liver cancer in animals in a short period of time.

Pten-NOLC1 fusion may have significant clinical implication. Clinical trials using drugs targeting at Pten signaling pathway has been initiated (18, 19). Recently, a genome therapy strategy targeting at the chromosomal breakpoint of fusion genes through CRISPR-cas9 system has been developed (20). Using this approach, partial remissions on animals xenografted with cancers positive for fusion gene breakpoints have been achieved. Different from other fusion genes, the breakpoints of Pten-NOLC1 from primary cancer samples or cancer cell lines of different organ origins appear identical, probably due to the utilization of the same anchoring sequence in the chromosome recombination process. This may give significance ease in designing a targeting strategy toward the chromosomal breakpoint of this fusion gene for all the cancers that contain Pten-NOLC1. Thus, the discovery of Pten-NOLC1 fusion gene may lay down an important foundation for future cancer treatment.

TABLE 6 fusionListFilter

| Gene1 | Gene2 | Gene1 | Gene2 | Reads | Distance | Validation |
|---|---|---|---|---|---|---|
| | | | 9916464T | | | |
| ACPP | SEC13 | 3:132047206:+ | 3:10347376:− | 45 | 121699830 | Yes |
| ACPP | SEC13 | 3:132047206:+ | 3:10347376:− | 35 | 121699830 | Yes |
| ACPP | SEC13 | 3:132047175:+ | 3:10346830:− | 28 | 121700345 | No |
| | | | 995772T | | | |
| NAALADL2 | NLGN1 | 3:174577240:+ | 3:173993105:+ | 21 | 584135 | No |
| | | | 997270T | | | |
| HNRNPA2B1 | ETV1 | 7:26235467:− | 7:13978871:− | 5 | 12256596 | reported |
| | | | FB174T | | | |
| LINC00969 | SDHA | 3:195408449:+ | 5:251158:+ | 11 | Inf | No |
| LINC00969 | SDHA | 3:195410736:+ | 5:256449:+ | 11 | Inf | No |
| DOCK7 | OLR1 | 1:62941378:− | 12:10324689:− | 6 | Inf | Yes |
| TARSL2 | TFDP2 | 15:102201915:− | 3:141738778:− | 5 | Inf | No |
| ZNF876P | ZNF141 | 4:247757:+ | 4:366944:+ | 5 | 119187 | No |
| AC004066.3 | PPA2 | 4:106473350:− | 4:106377902:− | 5 | 95448 | No |
| LINC00969 | AC069213.1 | 3:195444620:+ | 3:195343807:+ | 4 | 100813 | No |
| MRPS31P5 | HNRNPA1L2 | 13:52760818:− | 13:53196124:+ | 5 | 435306 | No |
| | | | HB021T | | | |
| EIF4A2 | RPPH1 | 3:186504550:+ | 14:20811534:− | 6 | Inf | No |
| EIF4A2 | RPPH1 | 3:186504582:+ | 14:20811360:− | 6 | Inf | No |
| EIF4A2 | RMRP | 3:186507733:+ | 9:35657969:− | 5 | Inf | No |
| APLP2 | RPPH1 | 11:129987960:+ | 14:20811558:− | 4 | Inf | No |
| NEAT1 | KLK3 | 11:65192786:+ | 19:51362086:+ | 4 | Inf | No |
| RMRP | RPPH1 | 9:35657869:− | 14:20811258:− | 4 | Inf | No |
| RPPH1 | APLP2 | 14:20811405:− | 11:129950317:+ | 4 | Inf | No |
| RPPH1 | APLP2 | 14:20811240:− | 11:129979952:+ | 4 | Inf | No |
| | | | HB207T | | | |
| PCMTD1 | SNTG1 | 8:52758221:− | 8:51085121:+ | 10 | 1673100 | Yes |
| PCMTD1 | SNTG1 | 8:52758221:− | 8:51085121:+ | 6 | 1673100 | Yes |
| PCMTD1 | SNTG1 | 8:52746078:− | 8:51085121:+ | 6 | 1660957 | Yes |

TABLE 6-continued fusionListFilter

| Gene1 | Gene2 | Gene1 | Gene2 | Reads | Distance | Validation |
|---|---|---|---|---|---|---|
| PCMTD1 | SNTG1 | 8:52746078:− | 8:50836062:+ | 5 | 1910016 | Yes |
| PCMTD1 | SNTG1 | 8:52746078:− | 8:50850153:+ | 5 | 1895925 | Yes |
| AC004066.3 | PPA2 | 4:106473350:− | 4:106377902:− | 5 | 95448 | No |
| AC004066.3 | PPA2 | 4:106473350:− | 4:106374799:− | 4 | 98551 | No |
| AC093642.5 | FBXO25 | 2:243081039:+ | 8:381341:+ | 10 | Inf | No |
| AC093642.5 | FBXO25 | 2:243061208:+ | 8:381341:+ | 7 | Inf | No |
| AP000350.6 | KLHL5 | 22:24270137:+ | 4:39077585:+ | 5 | Inf | No |
| AP000350.6 | KLHL5 | 22:24269424:+ | 4:39077582:+ | 5 | Inf | No |
| EIF4A2 | SLC4A4 | 3:186504557:+ | 4:72196359:+ | 4 | Inf | No |
| EIF4A2 | SLC4A4 | 3:186504632:+ | 4:72435346:+ | 4 | Inf | No |
| RPPH1 | EIF4A2 | 14:20811508:− | 3:186505102:+ | 5 | Inf | No |
| RPPH1 | EIF4A2 | 14:20811250:− | 3:186504478:+ | 4 | Inf | No |
| RPPH1 | EIF4A2 | 14:20811274:− | 3:186504592:+ | 4 | Inf | No |
| RPPH1 | EIF4A2 | 14:20811417:− | 3:186504594:+ | 4 | Inf | No |
| SLC4A4 | EIF4A2 | 4:72314022:+ | 3:186505101:+ | 4 | Inf | No |
| SLC4A4 | EIF4A2 | 4:72073964:+ | 3:186504506:+ | 4 | Inf | No |
| SLC4A4 | EIF4A2 | 4:72197333:+ | 3:186504481:+ | 4 | Inf | No |
| ZNF708 | ZNF91 | 19:21474183:− | 19:23545529:− | 10 | 2071346 | No |
| ZNF708 | ZNF91 | 19:21512012:− | 19:23556639:− | 5 | 2044627 | No |
| ZNF91 | ZNF708 | 19:23541604:− | 21:21477031:− | 4 | 2064573 | No |
| | | | HB568T | | | |
| CLTC | ETV1 | 17:57759200:+ | 7:13978871:− | 15 | Inf | Yes |
| CLTC | ETV1 | 17:57759200:+ | 7:13978871:− | 7 | Inf | Yes |
| ETV1 | CLTC | 7:13935567:− | 17:57754475:+ | 5 | Inf | No |
| | | | HB591T | | | |
| RP11-356O9.1 | ETV1 | 14:38033567:+ | 7:13978871:− | 76 | Inf | No |
| RP11-356O9.1 | ETV1 | 14:38033571:+ | 7:13978871:− | 74 | Inf | No |
| RP11-356O9.1 | ETV1 | 14:38033567:+ | 7:13978871:− | 61 | Inf | No |
| RP11-356O9.1 | ETV1 | 14:38033567:+ | 7:13978909:− | 57 | Inf | No |
| RP11-356O9.1 | ETV1 | 14:38034232:+ | 7:13978871:− | 57 | Inf | No |
| EIF4A2 | RPPH1 | 3:186505210:+ | 14:20811371:− | 8 | Inf | No |
| RPPH1 | EIF4A2 | 14:20811316:− | 3:186504501:+ | 8 | Inf | No |
| RPPH1 | EIF4A2 | 14:20811440:− | 3:186504517:+ | 8 | Inf | No |
| EIF4A2 | RMRP | 3:186505209:+ | 9:35657939:− | 4 | Inf | No |
| HDAC1 | RPPH1 | 1:32763305:+ | 14:20811427:− | 4 | Inf | No |
| NEAT1 | NUFIP2 | 11:65205521:+ | 17:27616439:− | 4 | Inf | No |
| NEAT1 | NUFIP2 | 11:65191759:+ | 17:27593971:− | 4 | Inf | No |
| NUFIP2 | NEAT1 | 17:27600224:− | 11:65208796:+ | 4 | Inf | No |
| NUFIP2 | NEAT1 | 17:27617594:− | 11:65208221:+ | 4 | Inf | No |
| NUFIP2 | NEAT1 | 17:27607920:− | 11:65208214:+ | 4 | Inf | No |
| NUFIP2 | NEAT1 | 17:27611691:− | 11:65207094:+ | 4 | Inf | No |
| NUFIP2 | NEAT1 | 17:27612201:− | 11:65207797:+ | 4 | Inf | No |
| NUFIP2 | NEAT1 | 17:27606731:− | 11:65205622:+ | 4 | Inf | No |
| RPPH1 | HDAC1 | 14:20811426:− | 1:32791843:+ | 4 | Inf | No |
| RPPH1 | HDAC1 | 14:20811403:− | 1:32760313:+ | 4 | Inf | No |
| RPPH1 | HDAC1 | 14:20811306:− | 1:32788657:+ | 4 | Inf | No |
| RPPH1 | NEAT1 | 14:20811236:− | 11:65191642:+ | 4 | Inf | No |
| | | | IB483T | | | |
| RP11-356O9.1 | ETV1 | 14:38033567:+ | 7:13978871:− | 6 | Inf | No |
| RP11-356O9.1 | ETV1 | 14:38033571:+ | 7:13978871:− | 4 | Inf | No |
| | | | JB197T | | | |
| AC007238.1 | IK | 2:58688487:− | 5:140037139:+ | 4 | Inf | No |
| DPY19L2 | DPY19L2P2 | 12:64062538:− | 7:102912316:− | 5 | Inf | No |
| DPY19L2 | DPY19L2P2 | 12:64038183:− | 7:102916074:− | 4 | Inf | No |
| DPY19L2 | DPY19L2P2 | 12:63974442:− | 7:102865611:− | 4 | Inf | No |
| | | | KB170T | | | |
| ZMPSTE24 | ZMYM4 | 1:40747199:+ | 1:35879573:+ | 8 | 4867626 | Yes |
| | | | PR375T | | | |
| ABHD2 | ACPP | 15:89660348:+ | 3:132077004:+ | 4 | Inf | No |
| ABHD2 | ACPP | 15:89707817:+ | 3:132076265:+ | 4 | Inf | No |
| EIF4A2 | RPPH1 | 3:186504579:+ | 14:20811554:− | 4 | Inf | No |

TABLE 6-continued fusionListFilter

| Gene1 | Gene2 | Gene1 | Gene2 | Reads | Distance | Validation |
|---|---|---|---|---|---|---|
| | | PR521T | | | | |
| AC022182.2 | NASP | 8:61852325:− | 1:46067927:+ | 4 | Inf | No |
| | | TP09S0420T | | | | |
| LINC00893 | LINC00894 | X:148619647:− | X:149111869:+ | 10 | 492222 | No |
| LINC00893 | LINC00894 | X:148619647:− | X:149112236:+ | 9 | 492589 | No |
| LINC00893 | LINC00894 | X:148620389:− | X:149108930:+ | 7 | 488541 | No |
| AP000350.6 | KLHL5 | 22:24270137:+ | 4:39077585:+ | 5 | Inf | No |
| SAA2-SAA4 | SAA1 | 11:18267456:− | 11:18291265:+ | 5 | 23809 | No |
| ZNF876P | ZNF141 | 4:248538:+ | 4:367464:+ | 5 | 118926 | No |
| AC083862.6 | RNF14 | 7:134813862:+ | 5:141358206:+ | 4 | Inf | No |
| ADAM9 | KIAA0196 | 8:38871562:+ | 8:126075893:− | 7 | 87204331 | No |
| | | TP09S0420T | | | | |
| RP11-356O9.1 | ETV1 | 14:38033567:+ | 7:13978871:− | 46 | Inf | No |
| RP11-356O9.1 | ETV1 | 14:38033571:+ | 7:13978871:− | 40 | Inf | No |
| RP11-356O9.1 | ETV1 | 14:38033567:+ | 7:13978871:− | 38 | Inf | No |
| RP11-356O9.1 | ETV1 | 14:38034232:+ | 7:13978871:− | 34 | Inf | No |
| | | TP09S0420T | | | | |
| TMPRSS2 | ERG | 21:42870046:− | 21:39817544:− | 11 | 3052502 | reported |
| TMPRSS2 | ERG | 21:42880008:− | 21:39956869:− | 9 | 2923139 | reported |
| TMPRSS2 | ERG | 21:42880008:− | 21:39817544:− | 8 | 3062464 | reported |
| TMPRSS2 | ERG | 21:42878372:− | 21:39956869:− | 7 | 2921503 | reported |
| TMPRSS2 | ERG | 21:42879877:− | 21:39956869:− | 6 | 2923008 | reported |
| TMPRSS2 | ERG | 21:42870046:− | 21:39817544:− | 6 | 3052502 | reported |
| NEAT1 | EIF4A2 | 11:65210275:+ | 3:186505152:+ | 4 | Inf | No |
| | | TP12S0918T | | | | |
| RAB3GAP2 | AURKA | 1:220440717:− | 20:54958178:− | 5 | Inf | No |
| RAB3GAP2 | AURKA | 1:220440010:− | 20:54945645:− | 5 | Inf | No |
| | | TP09S0704T | | | | |
| PIK3R1 | BDP1 | 5:67522837:+ | 5:70779669:+ | 12 | 3256832 | No |
| LINC00174 | AC005077.12 | 7:65860866:− | 7:75729274:− | 8 | 9868408 | No |
| AC058791.2 | PRUNE2 | 7:130630479:− | 9:79328637:− | 8 | Inf | No |
| ADSL | SGSM3 | 22:40762502:+ | 22:40796700:+ | 10 | 34198 | No |
| STEAP2 | PDLIM5 | 7:89861798:+ | 4:95577969:+ | 5 | Inf | No |
| UAP1 | DDR2 | 1:162567648:+ | 1:162625001:+ | 5 | 57353 | No |
| | | KB170T | | | | |
| C11orf92 | SAMD4B | 11:111165994:− | 19:39869906:+ | 2 | Inf | No |
| CDK12 | PAPPA2 | 17:37650947:+ | 1:176563660:+ | 4 | Inf | No |
| CDK12 | PAPPA2 | 17:37650947:+ | 1:176563660:+ | 2 | Inf | No |
| FOXJ3 | NEAT1 | 1:42648336:− | 11:65208796:+ | 2 | Inf | No |
| HECTD2 | EIF4A2 | 10:93266631:+ | 3:186505150:+ | 2 | Inf | No |
| NACA | NACAP1 | 12:57106595:− | 8:102381543:+ | 2 | Inf | No |
| NACAP1 | NACA | 8:102381469:+ | 12:57108462:v | 2 | Inf | No |
| NACAP1 | NACA | 8:102381373:+ | 12:57108418:− | 2 | Inf | No |
| RPSA | EIF4A2 | 3:39450005:+ | 3:186504592:+ | 2 | 147054587 | No |
| | | JB426T | | | | |
| RPL7L1 | WAC-AS1 | 6:42854937:+ | 10:28812436:− | 2 | Inf | No |
| | | IB273T | | | | |
| TMPRSS2 | ERG | 21:42880008:− | 21:39817544:− | 3 | 3052502 | reported |
| | | IB112T | | | | |
| ZNF600 | ZNF813 | 19:53268607:− | 19:53995951:+ | 6 | 727344 | No |
| ACPP | EHBP1 | 3:132076846:+ | 2:63180157:+ | 2 | Inf | No |
| ACPP | MRRF | 3:132076601:+ | 9:125037773:+ | 2 | Inf | No |
| AGPAT6 | B2M | 8:41468329:+ | 15:45009805:+ | 2 | Inf | No |
| ARL15 | ENTPD5 | 5:53365216:− | 14:74430404:− | 2 | Inf | No |
| CCDC90B | PPP1CB | 11:82989769:− | 2:29060773:+ | 3 | Inf | No |
| DECR1 | AGR2 | 8:91029397:+ | 7:16844611:− | 2 | Inf | No |
| EIF4A2 | SLC12A2 | 3:186504581:+ | 5:127145034:+ | 2 | Inf | No |
| FAM111A | ATP9A | 11:58922509:+ | 20:50329613:− | 2 | Inf | No |
| GCNT2 | HNRNPF | 6:10629637:+ | 10:43892038:− | 2 | Inf | No |
| MAGT1 | SLC30A4 | X:77118773:− | 15:45775996:− | 2 | Inf | No |
| MRRF | ACPP | 9:125061561:+ | 3:132076997:+ | 2 | Inf | No |
| NEDD4L | PTK2 | 18:56031565:+ | 8:141829119:− | 2 | Inf | No |

TABLE 6-continued

| | | fusionListFilter | | | | |
|---|---|---|---|---|---|---|
| Gene1 | Gene2 | Gene1 | Gene2 | Reads | Distance | Validation |
| NIN | IBTK | 14:51261154:− | 6:82922510:− | 2 | Inf | No |
| PHF14 | AC006465.3 | 7:11149059:+ | 7:7683058:+ | 2 | 3466001 | No |
| PHF14 | RDH11 | 7:11101712:+ | 14:68157138:− | 2 | Inf | No |
| SHROOM2 | ACPP | X:9867303:+ | 3:132071566:+ | 2 | Inf | No |
| TMPRSS2 | ETV1 | 21:42880008:− | 7:13978871:+ | 3 | Inf | Reported |
| U2SURP | AHNAK | 3:142707639:+ | 11:62285721:− | 2 | Inf | No |
| ZCCHC7 | SYNCRIP | 9:37354821:+ | 6:86329135:− | 2 | Inf | No |
| ZNF124 | LRIG1 | 1:247322308:− | 3:66508961:− | 2 | Inf | No |
| ZNF493 | ZNF92 | 19:21608244:+ | 7:64864391:+ | 2 | Inf | No |
| | | HB235T | | | | |
| TMPRSS2 | ERG | 21:42880008:− | 21:39817544:− | 3 | 3052502 | reported |
| | | GB368T | | | | |
| ACPP | ABCC4 | 3:132056398:+ | 13:95830345:− | 2 | Inf | No |
| KLK3 | GNPTAB | 19:51361849:+ | 12:102224596:− | 2 | Inf | No |
| ZNF430 | ZNF91 | 19:21205687:+ | 19:23545527:− | 3 | 2339840 | No |
| ZNF91 | ZNF430 | 19:23556544:− | 19:21216262:+ | 2 | 2340282 | No |
| | | TP12S0943T | | | | |
| MED12 | TBP | X:70361160:+ | 6:170871032:+ | 2 | Inf | No |
| | | TP12S0624T | | | | |
| TMPRSS2 | ERG | 21:42870046:− | 21:39817544:− | 19 | 3052502 | reported |
| TMPRSS2 | ERG | 21:42880008:− | 21:39817544:− | 11 | 3062464 | reported |
| TMPRSS2 | ERG | 21:42870046:− | 21:39795483:− | 5 | 3074563 | reported |
| TMPRSS2 | ERG | 21:42879877:− | 21:39817544:− | 5 | 3062333 | reported |
| KLK2 | CABIN1 | 19:51380552:+ | 22:24569045:+ | 3 | Inf | No |
| PTEN | NOLC1 | 10:89720875:+ | 10:103916776:+ | 4 | 14195901 | Yes |
| | | PR521T | | | | |
| PTEN | NOLC1 | 10:89720875:+ | 10:103916776:+ | 8 | 14195901 | Yes |

TABLE 7

| Prostate | | | | | | | | |
|---|---|---|---|---|---|---|---|---|
| PROSTATE | Pten-NOLC1 | Type | TNM | Margin | Relapse | Relapse fast | Relapse simple | Gleason |
| DB237 | P | T | T2bN0MX | Negative | slow | nf | y | 6.0 |
| FB120 | N | T | T3aN0MX | Negative | slow | nf | y | 7.0 |
| FB174 | P | T | T3aN0MX | Negative | fast | f | y | 7.0 |
| FB183 | N | T | T2cN0MX | Negative | slow | nf | y | 7.0 |
| FB238 | N | T | T3bN0MX | Negative | slow | nf | y | 7.0 |
| FB421 | P | T | T3aN0MX | Negative | fast | f | y | 7.0 |
| FB76 | N | T | T2c N0 MX | Negative | none | nf | n | 7 |
| FB94 | P | T | T2cN0MX | Negative | slow | nf | y | 7.0 |
| GB195 | P | T | T2cN0MX | Negative | slow | nf | y | 7.0 |
| GB368 | P | T | T2c N0 MX | Negative | none | nf | n | 7 |
| GB400 | P | T | T3bN0MX | Negative | fast | f | y | 7.0 |
| HB021 | P | T | T2bN0MX | Negative | fast | f | y | 6.0 |
| HB033 | N | T | T2cN0MX | Negative | none | nf | n | 7.0 |
| HB207 | P | T | T3bN0MX | Negative | fast | f | y | 9.0 |
| HB235 | P | T | T3bN1MX | Negative | slow | nf | y | 9.0 |
| HB261 | P | T | T3aN0MX | Negative | none | nf | n | 7.0 |
| HB303 | N | T | T3a N0 MX | Negative | none | nf | n | 7 |
| HB305 | N | T | T3bN0MX | Negative | fast | f | y | 6.0 |
| HB327 | P | T | T2c N0 MX | Negative | none | nf | n | 8 |
| HB340 | N | T | T2c N0 MX | Negative | none | nf | n | 7 |
| HB466 | P | T | T2aN0MX | Negative | none | nf | n | 7.0 |
| HB48 | P | T | T2aN0MX | Negative | none | nf | n | 6.0 |
| HB492 | N | T | T2c N0 MX | Negative | none | nf | n | 7 |
| HB504 | P | T | T3bN0MX | Positive | fast | f | y | 8.0 |
| HB526 | P | T | T3bN0MX | Positive | fast | f | y | 6.0 |
| HB568 | P | T | T3bN0MX | Negative | fast | f | y | 7.0 |
| HB591 | N | T | T3bN1MX | Negative | fast | f | y | 7.0 |
| HB603 | N | T | T3aN1MX | Negative | slow | nf | y | 7.0 |
| IB112 | P | T | T3aN0MX | Negative | slow | nf | y | 7.0 |
| IB134 | N | T | T3bN0MX | Negative | none | nf | n | 9.0 |
| IB136 | P | T | T3bN1MX | Negative | fast | f | y | 8.0 |
| IB273 | N | T | T2bN0MX | Negative | fast | f | y | 7.0 |
| IB289 | N | T | T2a N0 MX | Negative | none | nf | n | 7 |

TABLE 7-continued

| | | | Prostate | | | | | |
|---|---|---|---|---|---|---|---|---|
| IB298 | P | T | T3bN0MX | Negative | slow | nf | y | 7.0 |
| IB362 | P | T | p3aN0MX | Negative | fast | f | y | 7.0 |
| IB483 | P | T | T2bN0MX | Negative | fast | f | y | 7.0 |
| JB154 | P | T | T3aN0MX | Negative | fast | f | y | 9.0 |
| JB197 | P | T | T3bN0MX | Positive | fast | f | y | 7.0 |
| JB426 | P | T | T2cN0MX | Negative | fast | f | y | 7 |
| JB770 | N | T | T2cN0MX | Negative | fast | f | y | 8 |
| PR018 | N | T | T3aN0MX | Positive | slow | nf | y | 7 |
| PR079 | P | T | T3aN0MX | Positive | slow | nf | y | 7.0 |
| PR236 | P | T | T3bN0MX | Negative | fast | f | y | 10.0 |
| PR300 | P | T | T3bN1MX | Negative | fast | f | y | 7.0 |
| PR303 | P | T | T3bN0MX | Negative | slow | nf | y | 6.0 |
| PR306 | N | T | T3bN0MX | Positive | slow | nf | y | 7.0 |
| PR310 | N | T | T3bN0MX | Negative | fast | f | y | 7.0 |
| PR434 | P | T | T3aN0MX | Negative | slow | nf | y | 7.0 |
| PR521 | N | T | T2bN0MX | Negative | slow | nf | y | 7.0 |
| PR534 | N | T | T2b N0 MX | Negative | none | nf | n | 6 |
| PR79 | P | T | T3aN0MX | Positive | slow | nf | y | 7.0 |
| TP08-S0226 | N | T | T4N1MX | Negative | fast | f | y | 9.0 |
| TP08-S0530 | P | T | T3bN0MX | Negative | fast | f | y | 7.0 |
| TP08-S0542 | N | T | T2cN0MX | Negative | fast | f | y | 7.0 |
| TP08-S0721 | P | T | T3bN1MX | Negative | fast | f | y | 10 |
| TP09-S0006 | P | T | T3bN1MX | Negative | fast | f | y | 8 |
| TP09-S0420 | P | T | T3bN1MX | Negative | fast | f | y | 7 |
| TP09-S0704 | N | T | T4 N1 MX | Negative | fast | f | y | 9 |
| TP09-S0721 | P | T | T3bN1MX | Negative | fast | f | y | 10.0 |
| TP10-S0564 | P | T | T3aN1MX | Negative | fast | f | y | 7.0 |
| TP10-S0565 | N | T | T3bN1MX | Negative | fast | f | y | 9 |
| TP10-S0638 | P | T | T3bN1MX | Negative | fast | f | y | 10 |
| TP10-S0640 | N | T | T3bN1MX | Negative | fast | f | y | 10 |
| TP10-S0703 | P | T | T3bN1MX | Negative | slow | nf | y | 8.0 |
| TP10-S0704 | N | T | T3aN1MX | Negative | slow | nf | y | 9 |
| TP10-S093 | N | T | T3aN0MX | Negative | slow | nf | y | 7 |
| TP10-S0964 | P | T | T3bN1MX | Negative | slow | nf | y | 9 |
| TP10-S1113 | P | T | T3aN1MX | Negative | fast | nf | y | 9.0 |
| TP11-S0155 | P | T | T3bN1MX | Negative | slow | nf | y | 8.0 |
| TP11-S0272 | P | T | T3aN1MX | Negative | slow | nf | y | 7.0 |
| TP11-S0354 | P | T | T3aN1MX | Negative | slow | nf | y | 8.0 |
| TP11-S0463 | P | T | T3bN1MX | Negative | slow | nf | y | 7.0 |
| TP13-0666 | P | T | T2a N0 MX | Negative | fast | nf | n | 6 |
| TP12-S1030 | P | T | T2c N0 MX | Negative | none | nf | n | 7 |
| TP12-S1060 | P | T | T2c N0 MX | Negative | none | nf | n | 7 |
| TP12-S0048 | P | T | T3a N0 MX | Negative | none | nf | n | 8 |
| TP12-S0102 | P | T | T3a N1 MX | Negative | none | nf | n | 7 |
| TP12-S0114 | P | T | T3bN1MX | Negative | fast | f | y | 8.0 |
| TP12-S0246 | P | T | T2c N1 MX | Negative | none | nf | n | 7 |
| TP12-S0337 | N | T | T2a N1 MX | Negative | none | nf | n | 7 |
| TP12-S0340 | P | T | T3b N1 MX | Negative | none | nf | n | 9 |
| TP12-S0373 | N | T | T3aN1MX | Negative | slow | nf | y | 7.0 |
| TP12-S0456 | P | T | T3a N1 MX | Negative | none | nf | n | 8 |
| TP12-S0608 | N | T | T3a N1 MX | Negative | fast | f | y | 8 |
| TP12-S0624 | P | T | T3b N1 MX | Negative | none | nf | n | 7 |
| TP12-S0765 | N | T | T3a N0 MX | Prostate | none | nf | n | 7 |
| TP12-S0786 | P | T | T3b N1 MX | Negative | fast | f | y | 7 |
| TP12-S0790 | N | T | T3a N0 MX | Negative | slow | nf | y | 7 |
| TP12-S0795 | P | T | T3a N0 MX | Negative | none | nf | n | 7 |
| TP12-S0805 | P | T | T3a N1 MX | Negative | none | nf | n | 7 |
| TP12-S0816 | P | T | T3a N0 MX | Negative | none | nf | n | 7 |
| TP12-S0914 | P | T | T2a N1 MX | Negative | none | nf | n | 7 |
| TP12-S0915 | P | T | T3a NX MX | Negative | none | nf | n | 7 |
| TP12-S0928 | N | T | T3a N0 MX | Negative | none | nf | n | 7 |
| TP12-S0943 | P | T | T3a N1 MX | Negative | slow | nf | y | 9 |
| TP12-S0954 | P | T | T3b N0 MX | Negative | fast | f | y | 7 |
| TP12-S0967 | P | T | T3a N0 MX | Negative | none | nf | n | 7 |
| TP12-S0981 | N | T | T3b N0 MX | Negative | none | nf | n | 7 |
| TP12-S1032 | P | T | T3a N0 MX | Negative | none | nf | n | 7 |
| TP12-S1059 | P | T | T3a N0 MX | Negative | fast | f | y | 8 |
| TP12-S1189 | N | T | T2c N0 MX | Negative | none | nf | n | 7 |
| TP12-S1197 | P | T | T2c N0 MX | Negative | none | nf | n | 7 |
| TP12-S1224 | P | T | T2c N0 MX | Negative | none | nf | n | 7 |
| TP12-S1303 | N | T | T3b N1 MX | Negative | fast | f | y | 9 |
| Tp12-S1308 | P | T | T3a N1 MX | Negative | slow | nf | y | 9 |
| TP12-S1309 | P | T | T3a N1 MX | Negative | none | nf | n | 9 |
| TP12-SO048 | P | T | T3a N0 MX | Negative | none | nf | n | 8 |
| TP12-SO246 | P | T | T2c N1 MX | Negative | none | nf | n | 7 |
| TP12-SO337 | N | T | T2a N1 MX | Negative | fast | f | y | 7 |
| TP12-SO340 | N | T | T3b N1 MX | Negative | slow | nf | y | 9 |
| TP12-SO466 | P | T | T3b N1 MX | Negative | fast | f | y | 8 |

TABLE 7-continued

| | | | Prostate | | | | | |
|---|---|---|---|---|---|---|---|---|
| TP12-SO608 | N | T | T3a N1 MX | Negative | fast | f | y | 8 |
| TP13-S0035 | P | T | T3b N1 MX | Negative | none | nf | n | 7 |
| TP13-S0043 | P | T | pT3a N0 MX | Negative | fast | f | y | 8 |
| TP13-S0109 | N | T | pT3b N1 MX | Negative | fast | f | y | 8 |
| TP13-S0248 | P | T | pT3b N1 MX | Negative | fast | f | y | 8 |
| TP13-S0314 | N | T | pT3a N0 MX | Negative | fast | f | y | 7 |
| TP13-S0370 | P | T | pT3a N1 MX | Negative | none | nf | n | 8 |
| TP13-S0438 | P | T | pT3a N1 MX | Negative | none | nf | n | 9 |
| TP13-S0456 | P | T | pT3a N0 MX | Negative | fast | f | y | 9 |
| TP13-S0464 | P | T | pT3b N1 MX | Negative | fast | f | y | 9 |
| TP13-S0546 | P | T | T3b N1 MX | Negative | fast | f | y | 7 |
| TP13-S0571 | N | T | T3b N1 MX | Negative | fast | f | y | 9 |
| TP13-S0573 | P | T | T3b N1 MX | Negative | fast | f | y | 8 |
| TP13-S0582 | P | T | T2c N1 MX | Negative | slow | nf | y | 8 |
| TP13-S0657 | P | T | T3b N1 MX | Negative | fast | f | y | 8 |
| TP13-S0686 | P | T | T3b N1 MX | Negative | slow | nf | y | 9 |
| TP13-S0698 | P | T | T4 N1 MX | Negative | fast | f | y | 9 |
| TP14-S0008 | P | T | T3a N1 MX | Negative | fast | f | y | 7 |
| TP14-S0087 | P | T | T3b N1 MX | Negative | fast | f | y | 7 |
| TP14-S0093 | P | T | T3b N1 MX | Negative | fast | f | y | 9 |
| TP14-S0128 | P | T | T3a N1 MX | Negative | slow | nf | y | 9 |
| TP14-S0145 | P | T | T3a N1 MX | Negative | none | nf | n | 7 |
| TP14-S0159 | P | T | T2c N0 MX | Negative | fast | f | y | 9 |
| TP14-S0221 | P | T | T3a N1 MX | Negative | slow | nf | y | 8 |
| TP14-S0228 | P | T | T3a N1 MX | Negative | slow | nf | y | 7 |
| TP13-S0570 | P | T | T3b N1 MX | Negative | fast | f | y | 9 |
| 99-7270 | P | T | T3BN1MX | Negative | none | nf | n | 9.0 |
| 99-678 | P | T | T3bN0MX | Negative | none | nf | n | 9 |
| TP12-S0996 | P | T | T3aN1MX | Negative | fast | f | y | 7 |
| IB179 | P | T | T3bN1MX | Negative | slow | nf | y | 9 |
| TP10-S0371 | P | T | T3bN1MX | Negative | fast | f | y | 8 |
| TP12-S0466 | N | T | T3bN1MX | Negative | fast | f | y | 8 |
| TP12-S0786 | P | T | T3bN1MX | Negative | fast | f | y | 7 |
| TP12-S0996 | P | T | T3aN1MX | Negative | fast | f | y | 7 |
| TP13-S0034 | N | T | T3bN1MX | Negative | slow | nf | y | 9 |
| KB170 | P | T | T3bN1MX | | fast | f | y | 7 |

| | | Stanford cohort | | | | |
|---|---|---|---|---|---|---|
| Sample number | Pten-NOLC1 | TNM | Relapse | Gleason g: | PSA pre-operative | Month | PSADT |
| 100 | 85/100 | T2a-T4 N0-N1 MX | 50/100 | 6 to 10 | N/A | N/A | N/A |

| U of Wisconsin | iPten-NOLC1 | TNM | Relapse | ison grade | PSA pre-operative | Month | PSADT |
|---|---|---|---|---|---|---|---|
| 163 | 123/163 | T2a-T4 N0-N1 MX | N/A | 6 to 10 | N/A | N/A | N/A |

TABLE 8

Colon Cancer
Part 1

| colon name | Pten-NOLC1 status | Sex | Age at Diagnosis | Grade/Differentiation-Desc | pT | pN | pM | Path Stg Grp | Rx Code-Desc | Surv (months) | Vital Status-Desc | Primary Site-Descc |
|---|---|---|---|---|---|---|---|---|---|---|---|---|
| K301 4D | N | M | 51 | Grade II: Mod diff, mod well diff, | 2 | 2 | 0 | 3C | Chemotherapy, multiple agents (combination regimen | 68 | Alive | Colon, splenic fl |
| KB071 H | N | M | 62 | Grade II: Mod diff, mod well diff, | 2 | 2 | 0 | 3C | Chemotherapy, multiple agents (combination regimen | 89 | Alive | Colon, overlappin |
| RS08-032 1C | N | F | 56 | Grade II: Mod diff, mod well diff, | 3 | 2 | X | 99 | Chemotherapy, multiple agents (combination regimen | 77 | Dead | Colon, descending |
| RS08-074 2D | N | M | 52 | Grade III: Poorly differentiated, d | 3 | 2 | X | 99 | Chemotherapy, multiple agents (combination | 75 | Alive | Sigmoid, NOS |

TABLE 8-continued

Colon Cancer
Part 1

| colon name | Pten-NOLC1 status | Sex | Age at Diagnosis | Grade/Differentiation-Desc | pT | pN | pM | Path Stg Grp | Rx Code-Desc | Surv (months) | Vital Status-Desc | Primary Site-Descc |
|---|---|---|---|---|---|---|---|---|---|---|---|---|
| TB15-012 1C | P | M | 52 | Grade I: Well differentiated, diffe | 3 | 2 | 0 | 3C | Chemotherapy, multiple agents (combination regimen | 78 | Alive | Colon, hepatic fl |
| TB15-013 1F | P | M | 72 | Grade II: Mod diff, mod well diff, | 3 | 1 | X | 99 | Radiation therapy to alleviate symptoms; no attemp | 57 | Dead | Cecum |
| TB15-014 1C | P | M | 55 | Grade II: Mod diff, mod well diff, | 3 | 1 | 0 | 3B | Chemotherapy, multiple agents (combination regimen | 64 | Dead | Cecum |
| TB15-015 1C | N | M | 50 | Grade II: Mod diff, mod well diff, | 2 | 1 | 0 | 3A | Chemotherapy, multiple agents (combination regimen | 73 | Alive | Sigmoid, NOS |
| TB15-016 H | P | M | 90 | Grade II: Mod diff, mod well diff, | 3 | 1 | X | 99 | Partial colectomy, but less than hemicolectomy; se | 83 | Alive | Cecum |
| TB15-017 2B | P | F | 52 | Grade II: Mod diff, mod well diff, | 2 | 1 | X | 99 | Chemotherapy, multiple agents (combination regimen | 74 | Alive | Sigmoid, NOS |
| TB15-018 C | N | F | 71 | Grade III: Poorly differentiated, d | 4 | 1 | 0 | 3B | Partial colectomy, but less than hemicolectomy; se | 60 | Alive | Colon, Transverse |
| TB15-019 C | N | M | 84 | Grade II: Mod diff, mod well diff, | 3 | 1 | 0 | 3B | Hemicolectomy or greater but < total; right/left c | 78 | Dead | Colon, ascending |
| TB15-020 E | P | F | 55 | Grade II: Mod diff, mod well diff, | 3 | 2 | 0 | 3C | Chemotherapy, multiple agents (combination regimen | 72 | Alive | Colon, ascending |
| TB15-021 G | N | F | 84 | Grade II: Mod diff, mod well diff, | 3 | 2 | 0 | 3C | Hemicolectomy or greater but < total; right/left c | 57 | Alive | Colon, Transverse |
| TB15-022 D | N | M | 81 | Grade II: Mod diff, mod well diff, | 3 | 1 | X | 99 | Chemotherapy, multiple agents (combination regimen | 77 | Alive | Cecum |
| TB15-023 1C | N | M | 61 | Grade II: Mod diff, mod well diff, | 3 | 1 | X | 99 | Hemicolectomy or greater but < total; right/left c | 77 | Alive | Colon, descending |
| TB15-052 J T | P | M | 74 | Grade II: Mod diff, mod well diff, | 2 | 1 | X | 99 | Chemotherapy, multiple agents (combination regimen | 83 | Alive | Colon, transverse |
| TB15-053 D T | P | M | 68 | Grade II: Mod diff, mod well diff, | 3 | 2 | X | 99 | Chemotherapy, multiple agents (combination regimen | 75 | Alive | Colon, ascending |
| TB15-054 1D T | P | M | 57 | Grade II: Mod diff, mod well diff, | 3 | 1 | 0 | 3B | Chemotherapy, multiple agents (combination regimen | 29 | Dead | Sigmoid NOS |
| TB15-055 2E T | P | F | 73 | Grade II: Mod diff, mod well diff, | 4 | 2 | 0 | 3C | Chemotherapy, multiple agents (combination regimen | 74 | Alive | Cecum |
| TB15-056 6C T | P | M | 66 | Grade III: Poorly differentiated, d | 3 | 2 | X | 99 | Chemotherapy, multiple agents (combination regimen | 31 | Dead | Cecum |
| TB15-057 1F T | P | F | 57 | Grade II: Mod diff, mod well diff, | 3 | 1 | 1 | 4 | Chemotherapy, multiple agents (combination regimen | 31 | Dead | Colon, overlappin |
| TB15-058 D T | P | M | 67 | Grade III: Poorly differentiated, d | 3 | 2 | 0 | 3C | Chemotherapy, single agent | 6 | Dead | Colon, hepatic fl |

TABLE 8-continued

Colon Cancer
Part 1

| colon name | Pten-NOLC1 status | Sex | Age at Diagnosis | Grade/Differentiation-Desc | pT | pN | pM | Path Stg Grp | Rx Code-Desc | Surv (months) | Vital Status-Desc | Primary Site-Descc |
|---|---|---|---|---|---|---|---|---|---|---|---|---|
| TB15-059 C T | P | M | 46 | Grade II: Mod diff, mod well diff, | 3 | 1 | 0 | 3B | Hemicolectomy or greater but < total; right/left c | 58 | Alive | Colon, descending |
| TP08-S00292 B | P | F | 73 | Grade II: Mod diff, mod well diff, | 3 | 1 | | 99 | Chemotherapy, NOS | 81 | Dead | Cecum |
| TP08-S00620 2C | N | F | 71 | Grade II: Mod diff, mod well diff, | 3 | 1 | X | 99 | Chemotherapy, multiple agents (combination regimen | 75 | Alive | Sigmoid, NOS |
| TP08-S00673 1E | P | F | 69 | Grade II: Mod diff, mod well diff, | 3 | 1 | X | 99 | Hemicolectomy or greater but < total; right/left c | 72 | Alive | Colon, ascending |
| TP08-S00678 D | P | M | 78 | Grade II: Mod diff, mod well diff, | 3 | 1 | X | 99 | Total colectomy | 64 | Dead | Cecum |
| TP09-P317 C | P | F | 82 | Grade II: Mod diff, mod well diff, | 2 | 1 | 0 | 3A | Chemotherapy, single agent | 69 | Alive | Cecum |
| TP09-S0551 E | P | M | 63 | Grade II: Mod diff, mod well diff, | 2 | 1 | X | 99 | Chemotherapy, multiple agents (combination regimen | 56 | Alive | Sigmoid, NOS |

TABLE 8

Colon Cancer
Part 2

| Colon Non/met | Pten | Sex | Age at Diagnosis | Grade/Differentiation-Desc | pT | pN | pM | Path Stg Grp | Rx Code-Desc | Surv (months) | Vital Status-Desc | Primary Site-Desc |
|---|---|---|---|---|---|---|---|---|---|---|---|---|
| TB15-041 IE | P | M | 72 | Grade II: Mod diff, mod well diff, | 2 | 0 | 0 | 1 | Hemicolectomy or greater but < total; right/left c | 63 | Alive | Sigmoid, NOS |
| TB15-035 1J | P | M | 59 | Grade II: Mod diff, mod well diff, | 3 | 0 | 0 | 2A | Chemotherapy, NOS | 60 | Alive | Sigmoid, NOS |
| TB15-039 E | P | M | 70 | Grade II: Mod diff, mod well diff, | 2 | 0 | 0 | 1 | Hemicolectomy or greater but < total; right/left c | 57 | Alive | Cecum |
| TB15-040 E | P | F | 50 | Grade II: Mod diff, mod well diff, | 3 | 0 | 0 | 2A | Chemotherapy, multiple agents (combination regimen | 72 | Alive | Sigmoid, NOS |
| TB15-026 C | P | F | 48 | Grade II: Mod diff, mod well diff, | 3 | 0 | 0 | 2A | Hemicolectomy or greater but < total; right/left c | 62 | Alive | Colon, transverse |
| TB15-025 E | P | M | 74 | Grade II: Mod diff, mod well diff, | 2 | 0 | 0 | 1 | Partial colectomy, but less than hemicolectomy; se | 75 | Dead | Colon, hepatic fl |
| TB15-034 D | N | M | 64 | Grade II: Mod diff, mod well diff, | 3 | 0 | X | 99 | Subtotal colectomy plus resection contiguous organ | 74 | Dead | Colon, descending |
| TB15-033 1H | P | F | 75 | Grade II: Mod diff, mod well diff, | 3 | 0 | 0 | 2A | Total proctocolectomy | 58 | Dead | Colon, ascending |
| TB15-037 1H | P | M | 76 | Grade II: Mod diff, mod well diff, | 3 | 0 | 0 | 2A | Partial colectomy, but less than hemicolectomy; se | 58 | Alive | Sigmoid, NOS |
| TB15-029 I | N | F | 51 | Grade II: Mod diff, mod well diff, | 3 | 0 | 0 | 2A | Chemotherapy, multiple agents (combination regimen | 62 | Alive | Colon, ascending |
| TB15-024 2H | P | M | 53 | Grade II: Mod diff, mod well diff, | 3 | 0 | 0 | 2A | Chemotherapy, multiple agents (combination regimen | 62 | Alive | Sigmoid, NOS |
| TB15-036 2C | P | F | 50 | Grade II: Mod diff, mod well diff, | 3 | 0 | 0 | 2A | Chemotherapy, multiple agents (combination regimen | 63 | Alive | Colon, splenic fl |
| TB15-028 2E | P | F | 42 | Grade II: Mod diff, mod well diff, | 3 | 0 | 0 | 2A | Chemotherapy, multiple agents (combination regimen | 61 | Alive | Colon, transverse |
| TB15-027 F | P | F | 85 | Grade II: Mod diff, mod well diff, | 1 | 0 | X | 99 | Hemicolectomy or greater but < total; right/left c | 63 | Alive | Colon, ascending |

TABLE 8-continued

Colon Cancer
Part 2

| Colon Non/met | Pten | Sex | Age at Diagnosis | Grade/Differentiation-Desc | pT | pN | pM | Path Stg Grp | Rx Code-Desc | Surv (months) | Vital Status-Desc | Primary Site-Desc |
|---|---|---|---|---|---|---|---|---|---|---|---|---|
| TB15-031 D | P | F | 78 | Grade II: Mod diff, mod well diff, | 3 | 0 | X | 99 | Hemicolectomy or greater but < total; right/left c | 74 | Alive | Cecum |
| TB15-032 2C | P | M | 50 | Grade II: Mod diff, mod well diff, | 3 | 0 | 0 | 2A | Chemotherapy, multiple agents (combination regimen | 57 | Alive | Sigmoid, NOS |
| TB15-030 C | P | M | 59 | Grade II: Mod diff, mod well diff, | 2 | 0 | 0 | 1 | Hemicolectomy or greater but < total; right/left c | 71 | Alive | Colon, hepatic fl |
| TB15-044 2B | P | M | 71 | Grade III: Poorly differentiated, d | 3 | 0 | X | 99 | Hemicolectomy or greater but < total; right/left c | 67 | Alive | Cecum |
| TB15-043 1C | P | F | 58 | Grade III: Poorly differentiated, d | 3 | 2 | X | 99 | Chemotherapy, multiple agents (combination regimen | 104 | Alive | Colon, descending |
| TB15-042 D | P | M | 62 | Grade II: Mod diff, mod well diff, | 3 | 0 | 0 | 2A | Hemicolectomy or greater but < total; right/left c | 59 | Alive | Colon, ascending |
| TB15-047 1F | P | F | 51 | Grade II: Mod diff, mod well diff, | 2 | 0 | 0 | 1 | Hemicolectomy or greater but < total; right/left c | 59 | Alive | Cecum |
| TB15-048 1F | N | F | 79 | Grade II: Mod diff, mod well diff, | 3 | 0 | 0 | 2A | Hemicolectomy or greater but < total; right/left c | 62 | Alive | Colon, ascending |
| TB15-049 1F | P | M | 64 | Grade II: Mod diff, mod well diff, | 2 | 0 | X | 99 | Partial colectomy, but less than hemicolectomy; se | 62 | Alive | Sigmoid, NOS |
| TB15-046 2F | P | M | 93 | Grade III: Poorly differentiated, d | 3 | 0 | 0 | 2A | Hemicolectomy or greater but < total; right/left c | 59 | Alive | Colon, ascending |
| TB15-050 E | P | F | 80 | Grade II: Mod diff, mod well diff, | 3 | 0 | X | 99 | Subtotal colectomy plus resection contiguous organ | 59 | Dead | Colon, ascending |
| TB15-051 C | N | M | 50 | Grade II: Mod diff, mod well diff, | 3 | 0 | 0 | 2A | Chemotherapy, multiple agents (combination regimen | 66 | Alive | Colon, descending |
| TB15-045 D | P | F | 66 | Grade I: Well differentiated, diffe | 1 | 0 | 0 | 1 | Hemicolectomy or greater but < total; right/left c | 56 | Alive | Colon, ascending |
| TB15-038 1E | P | F | 92 | Grade III: Poorly differentiated, d | 3 | 0 | X | 99 | Hemicolectomy or greater but < total; right/left c | 65 | Dead | Cecum |
| TB15-075 1L | P | F | 66 | Grade II: Mod diff, mod well diff, | 3 | 0 | X | 99 | Colectomy/-proct w/en bloc resect'n othr NOS; Pelv | 80 | Alive | Colon, sigmoid |
| TB15-098 E | P | F | 68 | Grade II: Mod Diff, mod well diff, | 3 | 0 | x | 99 | Hemicolectomny or greater but < total right/left c | 89 | Alive | Colon, ascending |

TABLE 9

Liver Cancer

| GNT code | Pten-NOLC1 status | Sex | Age at Op. | Primary Cause of Death | Evidence for recurrent malignancy No (0), Yes (1) or unknown (Blank) | Patient Survival Days |
|---|---|---|---|---|---|---|
| 90 | P | M | 81 | Unknown Cause | 0 | 426 |
| 120 | P | M | 51 | Sepsis | 0 | 998 |
| 122 | P | | | N/A | N/A | N/A |
| 92 | P | M | 78 | Graft Failure, Recurrent Disease | 0 | 1577 |
| 119 | P | M | 55 | N/A | N/A | 3894 |
| 121 | P | M | 51 | Malignancy, Specify | 1 | 968 |
| 163 | P | F | 68 | Cardiac | 0 | 3519 |
| 162 | P | M | 86 | Other, Specify | 0 | 28 |
| 112 | P | F | 44 | Malignancy, Recurrent, Specify | 1 | 492 |

TABLE 9-continued

Liver Cancer

| GNT code | Pten-NOLC1 status | Sex | Age at Op. | Primary Cause of Death | Evidence for recurrent malignancy No (0), Yes (1) or unknown (Blank) | Patient Survival Days |
|---|---|---|---|---|---|---|
| 113 | P | M | 79 | Infection, Fungal | 0 | 43 |
| 135 | P | F | 74 | Cerebrovascular, Embolic Stroke | 0 | 4037 |
| 95 | P | M | 76 | Malignancy, Recurrent, Specify | 1 | 927 |
| 94 | P | M | 88 | Malignancy, Recurrent, Specify | 1 | 900 |
| 117 | P | M | 60 | Malignancy, Recurrent, Specify | 1 | 515 |
| 140 | P | M | 85 | Malignancy, Recurrent, Specify | 1 | 740 |
| 110 | P | M | 73 | Malignancy, Recurrent, Specify | 1 | 1802 |
| 111 | N | M | 66 | Malignancy, Recurrent, Specify | 1 | 1115 |
| 134 | P | F | 39 | Malignancy, Recurrent, Specify | 1 | 199 |
| 136 | P | M | 89 | Malignancy, Recurrent, Specify | 1 | 173 |
| 138 | P | F | 70 | N/A | N/A | 7485 |
| 114 | P | M | 76 | Malignancy, Recurrent, Specify | 1 | 194 |
| 141 | N | M | 84 | Malignancy, Specify | 1 | 1396 |
| 142 | P | M | 41 | Infection, Fungal | 0 | 28 |
| 137 | N | M | 61 | N/A | N/A | 9311 |
| 139 | N | M | 83 | Cardiovascular, Myocardial Infarct | 0 | 878 |
| 96 | P | M | 83 | Infection, Bacterial Sepsis | 0 | 28 |
| 165 | N | M | 82 | Malignancy, Recurrent, Specify | 1 | 482 |
| 164 | P | M | 87 | Pulmonary Infection/Pneumonia | 0 | 214 |
| 109 | P | F | 59 | Malignancy, Recurrent, Specify | 1 | 756 |
| 159 | P | M | 76 | Malignancy, Recurrent, Specify | 1 | 1431 |
| 160 | P | M | 78 | Malignancy, Specify | 1 | 139 |
| 108 | N | M | 75 | Malignancy, Recurrent, Specify | 1 | 1416 |
| 152 | P | F | 75 | Malignancy, Recurrent, Specify | 1 | 276 |
| 115 | P | M | 66 | N/A | N/A | 8783 |
| 146 | P | M | 85 | Pulmonary Infection/Pneumonia | 0 | 45 |
| 156 | P | M | 70 | Graft Failure, Recurrent Disease | 0 | 489 |
| 157 | N | M | 84 | Unknown Cause | 0 | 2954 |
| 151 | N | M | 80 | Malignancy, Recurrent, Specify | 1 | 265 |
| 149 | P | F | 67 | Malignancy, Recurrent, Specify | 1 | 1014 |
| 148 | N | M | 82 | Infection, Fungal | 0 | 19 |
| 81 | P | F | 81 | N/A | N/A | 6737 |
| 154 | P | M | 78 | Malignancy, Recurrent, Specify | 1 | 394 |
| 178 | N | M | 61 | Malignancy, Recurrent, Specify | 1 | 856 |
| 153 | P | M | 83 | Liver Dis, Ascending Cholangitis | 0 | 176 |
| 169 | P | M | 71 | Malignancy, Specify | 1 | 1776 |
| 88 | P | M | 82 | N/A | N/A | 6326 |
| 89 | P | F | 63 | Graft Failure, Infection | 0 | 227 |
| 168 | P | M | 81 | Malignancy, Recurrent, Specify | 1 | 381 |
| 85 | P | M | 56 | Malignancy, Recurrent, Specify | 1 | 638 |
| 173 | P | M | 71 | Malignancy, Recurrent, Specify | 1 | 2435 |
| 87 | P | M | 69 | Unknown Cause | 0 | 174 |
| 86 | P | F | 77 | Cardiovascular, Cardiac Arrest | 0 | 3376 |
| 182 | P | M | 64 | Bile Duct Problem | 0 | 40 |
| 179 | P | F | 84 | Cardiovascular, Other, Specify | 0 | 3019 |
| 99 | P | M | 77 | Infection, Fungal | 0 | 61 |

TABLE 9-continued

Liver Cancer

| GNT code | Pten-NOLC1 status | Sex | Age at Op. | Primary Cause of Death | Evidence for recurrent malignancy No (0), Yes (1) or unknown (Blank) | Patient Survival Days |
|---|---|---|---|---|---|---|
| 98 | P | M | 78 | Cardiovascular, Myocardial Infarct | 0 | 3190 |
| 102 | P | M | 67 | N/A | N/A | 4960 |
| 97 | P | M | 74 | Malignancy, Recurrent, Specify | 1 | 1695 |
| 177 | P | M | 70 | Multiple Organ Failure | 0 | 3835 |
| 2 | P | M | 63 | | N/A | 1500 |
| 184 | P | M | 66 | Malignancy, Recurrent, Specify | 1 | 678 |
| 7 | P | M | 56 | N/A | N/A | N/A |
| 27 | P | F | 66 | N/A | N/A | N/A |
| 6 | P | M | 74 | | N/A | 1473 |
| 12 | P | F | 67 | N/A | N/A | N/A |
| 10 | P | M | 58 | N/A | N/A | N/A |
| 23 | P | F | 67 | N/A | N/A | 1317 |
| 17 | P | M | 57 | N/A | N/A | 1365 |
| 28 | P | M | 54 | N/A | N/A | |
| 71 | P | M | 51 | N/A | N/A | 792 |

TABLE 10

Lung Cancer

Part 1

| Case Number | Pten-NOLC1 status | Sex | age_c | clinstage_reg | path_t_reg | path_n_reg | path_m_reg | os_months |
|---|---|---|---|---|---|---|---|---|
| 1 | N | Female | 78 | | 2 | 0 | 0 | 107.9333333 |
| 2 | N | Male | 80 | 4 | 2 | 0 | 0 | 72.53333333 |
| 3 | P | Female | 58 | | 2 | 0 | 0 | 14.13333333 |
| 4 | P | Male | 74 | | 2 | 0 | 0 | 148.2 |
| 5 | P | Female | 70 | | 2 | 2 | 0 | 7.033333333 |
| 6 | P | Female | 76 | 1A | 1 | 0 | 0 | 75.83333333 |
| 7 | N | Female | 74 | 3A | 3 | 0 | 0 | 55.93333333 |
| 8 | P | | | | | | | |
| 9 | P | Male | 80 | 2B | 3 | 0 | 0 | 7.7 |
| 10 | P | Female | 71 | 1B | 2 | 0 | 0 | 138.7333333 |
| 11 | P | Female | 82 | 1A | 1 | 0 | | 128.3666667 |
| 12 | N | Male | 75 | 2B | 2 | 0 | 0 | 17.46666667 |
| 13 | N | Male | 81 | | 2 | 0 | 0 | 19.73333333 |
| 14 | N | Male | 80 | | 2 | 1 | | 20 |
| 15 | P | Male | 72 | 2B | 2 | 1 | 0 | 74.2 |
| 16 | N | Male | 52 | 1B | 2 | 0 | 0 | 8.033333333 |
| 17 | N | Female | 71 | 1B | 2 | 0 | | 9.633333333 |
| 18 | P | Male | 71 | | 2 | 1 | 0 | 19.8 |
| 19 | N | Female | 71 | 1A | 2 | 0 | 0 | 21.9 |
| 20 | N | Male | 65 | 1A | 1 | 2 | 0 | 7.333333333 |
| 21 | P | Male | 69 | | 2 | 0 | | 20.23333333 |
| 22 | P | Male | 73 | 1B | 2 | 1 | | 100 |
| 23 | N | Female | 75 | 1B | 2 | 0 | 0 | 72 |
| 24 | P | Male | 71 | 2B | 2 | 1 | | 99.83333333 |
| 25 | P | Male | 74 | | 2 | 1 | 0 | 96.36666667 |
| 26 | P | | | | | | | |
| 27 | P | Male | 67 | | 2 | 0 | 0 | 67.13333333 |
| 28 | P | Female | 62 | | 2 | 0 | 0 | 0.7 |
| 29 | P | Male | 82 | | 2 | 1 | 0 | 8.133333333 |
| 30 | P | Male | 67 | | 2 | 1 | | 13.9 |
| 31 | P | Male | 74 | | 2 | 0 | 0 | 2.233333333 |
| 32 | P | Male | 59 | | 2 | 0 | 1 | 6.766666667 |
| 33 | N | Male | 83 | 1B | 2 | | | 10.43333333 |
| 34 | P | Male | 64 | | 2 | 0 | 0 | 101.6666667 |
| 35 | P | Female | 68 | | 2 | 0 | 0 | 139.3666667 |
| 36 | P | Male | 73 | 1B | 2 | 1 | 0 | 4.833333333 |
| 37 | P | Male | 73 | 1B | 2 | 1 | 0 | 4.833333333 |
| 38 | P | Female | 76 | | 1 | 0 | 0 | 62.46666667 |
| 39 | P | Female | 60 | | 2 | 1 | 0 | 18.26666667 |
| 40 | N | Female | 56 | 3A | 1 | 2 | 0 | 23 |
| 41 | P | Male | 56 | | 2 | 2 | 0 | 5.9 |
| 42 | P | Female | 74 | | 2 | 0 | | 37.23333333 |
| 43 | N | Female | 77 | 1A | 1 | 0 | 0 | 67.7 |

TABLE 10-continued

| Lung Cancer ||||||||| |
|---|---|---|---|---|---|---|---|---|
| 44 | P | Female | 49 |    | 2  | 0 | 0 | 14.23333333 |
| 45 | P | Female | 73 |    | 2  | 1 |   | 92.4 |
| 46 | P | Female | 65 | 1B | 2  | 1 | 0 | 107.1 |
| 47 | N | Male   | 84 |    | 1  | 0 | 0 | 119.2333333 |
| 48 | P | Male   | 78 |    | 2  | 1 | 0 | 5.5 |
| 49 | N | Female | 69 |    | 4  | 0 |   | 17.83333333 |
| 50 | P | Female | 71 |    | 1  | 0 | 0 | 94.76666667 |
| 51 | P | Female | 79 | 3A | 2  | 0 | 0 | 107.9666667 |
| 52 | P | Female | 61 |    | 1  | 0 | 0 | 80.1 |
| 53 | N | Male   | 56 |    | 4  |   |   | 43.8 |
| 54 | N | Female | 63 | 1A | 1  | 0 | 0 | 3.2 |
| 55 | N | Female | 61 | 3B | 1  | 0 | 0 | 64.13333333 |
| 56 | N | Female | 60 |    | 4  | 1 | 0 | 7 |
| 57 | P | Male   | 76 | 3B | 4  | 0 | 0 | 50.3 |
| 58 | N | Male   | 65 | 3A | 3  | 2 |   | 19.16666667 |
| 59 | P | Female | 68 | 1B | 2  | 0 |   | 100.6666667 |
| 60 | N | Male   | 76 |    | 4  | 1 | 0 | 30.86666667 |
| 61 | N | Male   | 75 | 1B | 2A | 0 |   | 54.36666667 |
| 62 | P | Male   | 68 | 1A | 1A | 0 | 0 | 61.6 |
| 63 | N | Female | 75 | 1A | 1  | 0 | 0 | 62.8 |
| 64 | N | Male   | 66 | 3A | 1  | 2 |   | 32.06666667 |
| 65 | N |        |    |    |    |   |   |   |
| 66 | N | Male   | 84 | 1B | 2  | 1 | 0 | 41.7 |
| 67 | N | Female | 55 | 1B | 4  | 1 | 0 | 60.83333333 |
| 68 | N | Female | 66 | 1B | 2  | 1 | 0 | 54.16666667 |
| 69 | P | Male   | 84 | 1B | 2  | 0 |   | 21.96666667 |
| 70 |   | Male   | 56 |    | 2  | 1 | 0 | 15.36666667 |

| Part 2 ||||||||||
|---|---|---|---|---|---|---|---|---|---|
| Case No. | Pten-NOLC1 status | age | male/female | t_stage | n_stage | m_stage | clinstage | castatusdesc | OS_tumor_size_registry |
| 71 | P | 53 | F | T1 | N2 | MX | 3a | No evidence of this tumor | 16 |
| 72 | P | 66 | F | T1 | N0 | MX | 1a | Evidence of this tumor | 15 |
| 73 | N | 57 | F | T2 | N0 | MX | 1b | No evidence of this tumor | 35 |
| 74 | P |    |   |    |    |    |    |   |    |
| 75 | P | 64 | M | T4 | N2 | MX | 3b | Evidence of this tumor | 30 |
| 76 | P | 52 | M | T2 | N0 | MX | 1b | No evidence of this tumor | 35 |
| 77 | P | 74 | M | T2 | N2 | MX | 3a | Evidence of this tumor | 45 |
| 78 | P | 44 | F | T1 | N2 | MX | 3a | Evidence of this tumor | 30 |
| 79 | P | 57 | M | T3 | N0 | MX | 2b | Evidence of this tumor | 27 |
| 80 | P | 80 | M | T2 | N1 | MX | 2a | No evidence of this tumor | 40 |
| 81 | N | 60 | M | T1 | N1 | MX | 2a | Evidence of this tumor | 21 |
| 82 | P | 74 | M | T2 | N0 | MX | 1b | Evidence of this tumor | 110 |
| 83 | P | 65 | F | T1 | N1 | MX | 2a | No evidence of this tumor | 25 |
| 84 | P | 44 | M | T1 | N0 | MX | 1a | No evidence of this tumor | 15 |
| 85 | N | 82 | F | T2 | N2 | MX | 3a | Evidence of this tumor | 40 |
| 86 | P | 56 | F | T2 | N0 | MX | 1b | No evidence of this tumor | 25 |

TABLE 10-continued

Lung Cancer

| 87 | P | 76 | M | T2 | N2 | MX | 3a | No evidence of this tumor | 15 |
| 88 | P | 63 | M | T2 | N0 | MX | 1b | No evidence of this tumor | 35 |
| 89 | P | 57 | M | T2 | N1 | MX | 2b | No evidence of this tumor | 18 |
| 90 | P | 67 | M | T1 | N0 | MX | 1a | No evidence of this tumor | 18 |
| 91 | P | 41 | F | T2 | N0 | MX | 1b | No evidence of this tumor | 9 |
| 92 | P | 51 | F | T4 | N0 | MX | 3b | No evidence of this tumor | 19 |
| 93 | N | 75 | M | T2 | N1 | MX | 2b | No evidence of this tumor | 33 |
| 94 | N | 69 | F | T2 | N1 | MX | 2b | No evidence of this tumor | 32 |
| 95 | P | 68 | F | T1 | N0 | MX | 1a | Evidence of this tumor | 15 |
| 96 | P | 65 | F | T2 | N1 | MX | 2b | No evidence of this tumor | 24 |
| 97 | P | 58 | M | T1 | N0 | MX | 1a | No evidence of this tumor | 28 |
| 98 | P | 65 | M | T3 | N1 | M1 | 3a | Evidence of this tumor | 40 |
| 99 | P | 60 | F | T2 | N0 | MX | 1b | No evidence of this tumor | 25 |
| 100 | P | 50 | F | T4 | N0 | MX | 3b | Evidence of this tumor | 19 |
| 101 | P | 65 | M | T1 | N0 | MX | 1a | No evidence of this tumor | 10 |
| 102 | N | 75 | M | T4 | N0 | MX | 3b | Evidence of this tumor | 35 |

University of Kansas samples

| Patient Code | Tumor tissue code | Stage | | Type | to grann-NOLC1 |
|---|---|---|---|---|---|
| 1089 | 5A8.22 | PT1 | Squamous | 4 | |
| 1106 | 5A8.44 | PT1 | Adenocarcinoma | 2 | P |
| 1153 | 5A8.63 | PT1 | Adenocarcinoma | 1 | P |
| 1175 | 5A8.64 | PT2 | Adenocarcinoma | 2 | P |
| 1187 | 5A9.40 | PT2 | Adenocarcinoma | 4 | |
| 1233 | 5A9.32 | PT2 | Adenocarcinoma | 4 | P |
| 1363 | 5A10.7 | PT2 | Adenocarcinoma | 2 | P |
| 1385 | 5A10.54 | PT2 | Adenocarcinoma | 2 | P |
| 1398 | 5A10.65 | PT2 | Squamous | 4 | |
| 1406 | 5A10.74 | PT2 | Squamous | 2 | P |
| 1412 | 5A11.13 | | Squamous | 2 | P |
| 1452 | 5A11.12 | PT1 | Squamous | 2 | P |
| 1475 | 5A11.28 | PT2 | Adenocarcinoma | 2 | |
| 1525 | 5A11.48 | PT2 | Mixed Squamous | 4 | P |
| 1586 | 5A12.3 | PT2 | Squamous | 4 | P |
| 1648 | 5A11.14 | PT1 | Adenocarcinoma | 4 | P |

University of Iowa

| Code | Sex | Age | Grade | History | Stage | Pten-NOLC1 |
|---|---|---|---|---|---|---|
| LP-001 | M | 60 | n/a | Adenocarcinoma | pT3N | P |
| LP-002 | M | 65 | G2: M | Adenocarcinoma | pT1a | P |
| LP-003 | F | 67 | n/a | Well-diff | T3N0 | N |

TABLE 10-continued

| | | | Lung Cancer | | | |
|---|---|---|---|---|---|---|
| LP-004 (same patient) | F | 67 | G2: M | Moderate | pT3N | N |
| LP-005 | F | 65 | n/a | Adenocarcinoma | T1N0 | P |
| LP-006 (same patient) | F | 65 | n/a | meta | T1N0 | P |
| LP-007 | F | 62 | n/a | Adenocarcinoma | pT1a | N |
| LP-008 | F | 59 | n/a | Poor | pT2a | P |
| LP-009 | F | 77 | G2: M | Invas | T2aN | P |
| LP-010 | M | 75 | n/a | Adenocarcinoma | pT1a | P |
| LP-011B3 | M | 74 | G2: M | Moderate | T3N1 | N |
| LP-011B4 | | | | | | P |
| LP-011B5 | | | | | | P |
| LP-011B6 | | | | | | P |
| LP-011B7 | | | | | | P |
| LP-012 | M | 80 | G2: M | Adenocarcinoma | T2aN | P |
| LP-013 | M | 63 | | Adenocarcinoma | Stage | N |
| LP-014 | F | 70 | | Moderate | Stage | P |
| LP-015 | F | 82 | G3: F | Sarc | T3N0 | P |
| LP-016F3 | M | 72 | G2: | Invas | T1bN | N |
| LP-017A6 | F | 70 | G2: | Invas | T2bN | P |
| LP-018C7 | M | 70 | G2: | Pulm | T3N2 | P |
| LP-019B3 | F | 70 | G2: | aden | T2aN | P |
| LP-020D6 | M | 62 | n/a | Invase | T1aN | N |
| LP-021A5 | F | 59 | G2: | aden | T2aN | P |
| LP-022 D2 | M | 83 | n/a | aden | T4N | P |
| LP-023A4 | F | 41 | G2: | Aden | T1aN | P |
| LP-024 A2 | F | 77 | G2: | Aden | T2aN | N |

1 = well defferentiated
2 = moderate defferentiated
3 = moderate to poorly defferentiated
4 = poorly defferentiated
5 = un-defferentiated

TABLE 11

Breast Cancer

Part 1a

| Lobular mets (T) | Pren-NOLC1 Status | Ageat DX | Histo/Behavior ICD-O-3-Desc | Grade/Differentiation-Desc | Clinical T | Clinical N | Clinical M | Clinical Stage Group | Pathologic T | Pathologic N |
|---|---|---|---|---|---|---|---|---|---|---|
| TB15-092 4G | P | 78 | Lobular carcinoma, NOS | Grade II: Mod diff, mod we | 3 | 0 | 0 | 2B | 3 | 1A |
| TB15-090 4I | N | 43 | Lobular carcinoma, NOS | Grade II: Mod diff, mod we | 3 | 0 | 0 | 2B | 3 | 1A |
| TB15-094 3B | N | 65 | Lobular carcinoma, NOS | Grade II: Mod diff, mod we | 2 | 0 | 0 | 2A | 1C | 2 |
| TB15-095 4O | N | 61 | Lobular carcinoma, NOS | Grade I: Well differentiat | 1C | 0 | 0 | 1 | 1B | 1A |
| TB15-093 1D | N | 51 | Lobular carcinoma, NOS | Grade I: Well differentiat | 1B | 0 | 0 | 1 | 1C | 1A |
| TB15-091 2C | N | 58 | Lobular carcinoma, NOS | Cell type not determined, | 2 | 0 | 0 | 2A | 2 | 2A |
| TB15-097 6QQ | N | 45 | Lobular carcinoma, NOS | Grade II: Mod diff, mod we | 2 | 0 | 0 | 2A | 3 | 1M |
| TB15-088 3D | N | 56 | Lobular carcinoma, NOS | Grade II: Mod diff, mod we | 2 | 0 | 1 | 4 | 2 | 1A |
| TB15-089 3C | N | 79 | Lobular carcinoma, NOS | Grade II: Mod diff, mod we | 1C | 0 | 0 | 1 | 2 | 1A |
| TB15-096 6D | N | 73 | Infiltrating lobular mixed w/other type | Grade III: Poorly differen | X | 0 | 0 | 2A | 0 | 0 |
| TB15-124 | P | 48 | Lobular carcinoma in situ, NOS | Cell type not determined, not state | IS | 0 | 0 | 0 | IS | 0 |
| TB15-123 | P | 65 | Lobular carcinoma, NOS | Grade II: Mod diff, mod we | 4 | | | 99 | | |
| TB15-121 | P | 55 | Lobular carcinoma, NOS | Grade II: Mod diff, mod we | 2 | 0 | 0 | 2A | 2 | 2A |
| TB15-122 | P | 49 | Lobular carcinoma, NOS | Grade III: Poorly differen | 2 | 1 | 0 | 2B | 1B | 2A |
| TB15-119 | N | 64 | Lobular carcinoma, NOS | Grade II: Mod diff, mod we | 1C | 0 | 0 | 1 | 1C | 1M |
| TB15-105 | P | 47 | Lobular carcinoma, NOS | Grade II: Mod diff, mod we | 1B | 0 | 0 | 1 | 1B | 0 |
| TB15-106 | P | 43 | Lobular carcinoma, NOS | Grade II: Mod diff, mod we | 1C | 0 | 0 | 1 | 1C | 0 |
| TB15-108 | P | 49 | Lobular carcinoma, NOS | Grade II: Mod diff, mod we | 2 | 0 | 0 | 2A | 2 | 0 |
| TB15-109 | P | 48 | Lobular carcinoma, NOS | Grade II: Mod diff, mod we | 1C | 0 | 0 | 1 | 1C | 0 |
| TB15-111 | P | 51 | Lobular carcinoma, NOS | Grade II: Mod diff, mod we | IS | 0 | 0 | 0 | 1C | 0 |

TABLE 11-continued

Breast Cancer

| | | | | | | | | | |
|---|---|---|---|---|---|---|---|---|---|
| TB15-110 | P | 78 | Lobular carcinoma, NOS | Grade II: Mod diff, mod we | 1C | 1 | 0 | 1C | 0 |
| TB15-107 | P | 83 | Lobular carcinoma, NOS | Grade II: Mod diff, mod we | 2 | 2A | 0 | 2 | 0 |
| TB15-112 | P | 62 | Lobular carcinoma, NOS | Grade II: Mod diff, mod we | 1 | 1 | 0 | 3 | 1A |
| TB15-113 | P | 59 | Lobular carcinoma, NOS | Grade II: Mod diff, mod we | 2 | 2A | 0 | 2 | 0 |
| TB15-104 | P | 70 | Lobular carcinoma, NOS | Grade II: Mod diff, mod we | 1C | 1 | 0 | 2 | 0 |
| TB15-101 | P | 74 | Lobular carcinoma, NOS | Grade II: Mod diff, mod we | 1 | 1 | 0 | 1C | 0 |
| TB15-103 | P | 81 | Lobular carcinoma, NOS | Grade III: Poorly differen | 1C | 1 | 0 | 2 | 0 |
| TB15-100 | P | 69 | Lobular carcinoma, NOS | Grade II: Mod diff, mod we | 1C | 1 | 0 | 1C | 0 |
| TB15-102 | P | 69 | Lobular carcinoma, NOS | Grade II: Mod diff, mod we | 1C | 1 | 0 | 1C | 0 |
| TB15-099 | P | 62 | Lobular carcinoma, NOS | Grade II: Mod diff, mod we | 1 | 1 | 0 | 1C | 0 |

Part 1b

| Lobular mets (T) | Pathologic M | Pathologic Stage Group | ER Asssay | PR Assay | HER2: Summary Result | Type 1st Recurrence-Desc | Months from Dx To 1st Recurrence | Survival in Months | Vital Status-Desc |
|---|---|---|---|---|---|---|---|---|---|
| TB15-092 4G | X | 99 | Postive/elevated | Postive/elevated | HER-2 negative | Patient became disease-free after treatment and has not had a recurrence. | 0 | 79 | Alive |
| TB15-090 4I | X | 99 | Postive/elevated | Postive/elevated | HER-2 negative | Patient became disease-free after treatment and has not had a recurrence. | 0 | 80 | Alive |
| TB15-094 3B | 0 | 3A | Postive/elevated | Postive/elevated | FISH-negative | Patient became disease-free after treatment and has not had a recurrence. | 0 | 66 | Alive |
| TB15-095 4O | X | 99 | Postive/elevated | Postive/elevated | HER-2 negative | Patient became disease-free after treatment and has not had a recurrence. | 0 | 59 | Alive |
| TB15-093 1D | 0 | 2A | Postive/elevated | Negative/normal | HER-2 negative | Patient became disease-free after treatment and has not had a recurrence. | 0 | 81 | Alive |
| TB15-091 2C | 0 | 2B | Postive/elevated | Postive/elevated | HER-2 negative | Patient became disease-free after treatment and has not had a recurrence. | 0 | 93 | Alive |
| TB15-097 6QQ | | 3A | Postive/elevated | Postive/elevated | HER-2 negative | Patient became disease-free after treatment and has not had a recurrence. | 0 | 57 | Alive |

TABLE 11-continued

Breast Cancer

| | | | | | | | | |
|---|---|---|---|---|---|---|---|---|
| TB15-088 3D | 1 | 4 | Postive/elevated | Postive/elevated | HER-2 negative | Since diagnosis, patient has never been disease-free. This includes cases with distant metastasis at diagnosis, systemic | 0 | 41 | Dead |
| TB15-089 3C | 0 | 2B | Postive/elevated | Postive/elevated | HER-2 negative | Patient became disease-free after treatment and has not had a recurrence. | 0 | 86 | Alive |
| TB15-096 6D | 0 | 0 | Postive/elevated | Postive/elevated | FISH - positive | Patient became disease-free after treatment and has not had a recurrence. | 0 | 12 | Dead |
| TB15-124 | 0 | 0 | Positive/elevated | Positive/Elevated | HER-2 negative | Patient became disease-free after treatment and has not had a recurrence. | 000 | 103 | Alive |
| TB15-123 | 0 | 99 | Postive/elevated | Postive/elevated | HER-2 positive | Patient became disease-free after treatment and has not had a recurrence. | 0 | 73 | Alive |
| TB15-121 | 0 | 3A | Postive/elevated | Postive/elevated | HER-2 negative | Patient became disease-free after treatment and has not had a recurrence. | 0 | 95 | Alive |
| TB15-122 | 0 | 3A | Postive/elevated | Postive/elevated | HER-2 negative | Patient became disease-free after treatment and has not had a recurrence. | 0 | 83 | Alive |
| TB15-119 | X | 99 | Postive/elevated | Postive/elevated | HER-2 negative | Patient became disease-free after treatment and has not had a recurrence. | 0 | 61 | Alive |
| TB15-105 | 0 | 1 | Postive/elevated | Postive/elevated | HER-2 negative | Patient became disease-free after treatment and has not had a recurrence. | 0 | 62 | Alive |
| TB15-106 | 0 | 1 | Negative/normal | Negative/normal | HER-2 negative | Patient became disease-free after treatment and has not had a recurrence. | 0 | 65 | Alive |
| TB15-108 | X | 99 | Postive/elevated | Negative/normal | HER-2 negative | Patient became disease-free after treatment and has not had a recurrence. | 0 | 68 | Alive |
| TB15-109 | 0 | 1 | Postive/elevated | Postive/elevated | HER-2 negative | Patient became disease-free after treatment and has not had a recurrence. | 0 | 65 | Alive |
| TB15-111 | 0 | 1 | Postive/elevated | Postive/elevated | HER-2 negative | Patient became disease-free after treatment and has not had a recurrence. | 0 | 68 | Alive |
| TB15-110 | 0 | 1 | Postive/elevated | Postive/elevated | HER-2 negative | Distant recurrence of an invasive tumor in multiple sites (recurrences that can be coded to more than one category 51-59 | | 73 | Alive |
| TB15-107 | X | 2A | Postive/elevated | Negative/normal | HER-2 negative | Patient became disease-free after treatment and has not had a recurrence. | 0 | 63 | Dead |

TABLE 11-continued

Breast Cancer

| | Pten-NOLC1 Status | Age at Diagnosis | Histo/Behavior ICD-O-3-Desc | Grade/Differentiation-Desc | | | | | |
|---|---|---|---|---|---|---|---|---|---|
| TB15-112 | 0 | 3A | Postive/elevated | HER-2 negative | Patient became disease-free after treatment and has not had a recurrence. | 0 | 66 | Alive | |
| TB15-113 | X | 99 | Postive/elevated | Negative/normal | HER-2 negative | Patient became disease-free after treatment and has not had a recurrence. | 0 | 62 | Alive |
| TB15-104 | 0 | 2A | Postive/elevated | HER-2 negative | Distant recurrence of an invasive tumor in bone only. This includes bones other than the primary site. | 68 | 70 | Alive | |
| TB15-101 | X | 1 | Postive/elevated | HER-2 negative | Patient became disease-free after treatment and has not had a recurrence. | 0 | 80 | Alive | |
| TB15-103 | 0 | 2A | Postive/elevated | HER-2 negative | Patient became disease-free after treatment and has not had a recurrence. | 0 | 75 | Alive | |
| TB15-100 | 0 | 1 | Postive/elevated | HER-2 positive | Patient became disease-free after treatment and has not had a recurrence. | 0 | 79 | Alive | |
| TB15-102 | 0 | 1 | Postive/elevated | HER-2 negative | Patient became disease-free after treatment and has not had a recurrence. | 0 | 72 | Alive | |
| TB15-099 | 0 | 1 | Postive/elevated | HER-2 negative | Patient became disease-free after treatment and has not had a recurrence. | 0 | 89 | Alive | |

Part 2a

| Ductal carcinoma met | Pten-NOLC1 Status | Age at Diagnosis | Histo/Behavior ICD-O-3-Desc | Grade/Differentiation-Desc | Clinical T | Clinical N | Clinical M | Clinical Stage Group | Pathologic T |
|---|---|---|---|---|---|---|---|---|---|
| TB15-060 1B | P | 38 | Infiltrating duct carcinoma, NOS | Grade I: Well differentiated, diffe | 3 | 1 | 0 | 3A | 3 |
| TB15-061 3H | N | 59 | Infiltrating duct carcinoma, NOS | Grade II: Mod diff, mod well diff, | 2 | 1 | 0 | 2B | 1C |
| TB15-072 1F | N | 63 | Infiltrating duct carcinoma, NOS | Grade III: Poorly differentiated, d | 3 | 2 | 0 | 3A | 2 |
| TB15-071 C | P | 41 | Infiltrating duct carcinoma, NOS | Grade III: Poorly differentiated, d | 2 | 1 | 0 | 2B | 3 |
| TB15-062 5A | P | 50 | Infiltrating duct carcinoma, NOS | Grade II: Mod diff, mod well diff, | 2 | 0 | 0 | 2A | 2 |
| TB15-066 1J | P | 55 | Infiltrating duct carcinoma, NOS | Grade II: Mod diff, mod well diff, | 1 | 0 | 0 | 1 | 1C |
| TB15-063 1B | P | 54 | Infiltrating duct carcinoma, NOS | Grade II: Mod diff, mod well diff, | 1C | 0 | 0 | 1 | 1C |
| TB15-070 1E | N | 45 | Infiltrating duct carcinoma, NOS | Grade III: Poorly differentiated, d | 3 | 1 | X | 99 | 3 |
| TB15-068 1D | N | 61 | Infiltrating duct carcinoma, NOS | Grade III: Poorly differentiated, d | 3 | 3 | 0 | 3C | 3 |

TABLE 11-continued

Breast Cancer

| | | | | | | | |
|---|---|---|---|---|---|---|---|
| TB15-065 5L | N | 28 | Infiltrating duct carcinoma, NOS | Grade III: Poorly differentiated, d | 3 | 0 | 2B | 1C |
| TB15-073 1B | N | 79 | Infiltrating duct carcinoma, NOS | Grade III: Poorly differentiated, d | 1C | 0 | 2A | 1C |
| TB15-067 O | P | 64 | Infiltrating duct carcinoma, NOS | Grade II: Mod diff, mod well diff, | 4B | 0 | 3B | 2 |
| TB15-074 5H | N | 27 | Infiltrating duct carcinoma, NOS | Grade III: Poorly differentiated, d | 2 | 0 | 2B | 1A |
| TB15-064 6I | P | 49 | Infiltrating duct carcinoma, NOS | Grade II: Mod diff, mod well diff, | 1C | 0 | 1 | 2 |
| TB15-069 1G | P | 71 | Infiltrating duct carcinoma, NOS | Grade II: Mod diff, mod well diff, | 1A | 0 | 1 | 1B |
| TB15-116 | P | 72 | Infiltrating duct carcinoma, NOS | Grade I: Well differentiated, diffe | 1A | 0 | 1 | 1C |
| TB15-118 | P | 61 | Infiltrating duct carcinoma, NOS | Grade II: Mod diff, mod well diff, | 1 | 0 | 1 | 2 |
| TB15-117 | P | 46 | Infiltrating duct carcinoma, NOS | Grade III: Poorly differentiated, d | 1C | 0 | 1 | 2 |
| TB15-085 | P | 58 | Infiltrating duct carcinoma, NOS | Grade III: Poorly differentiated, d | 1M | 0 | 1 | 2 |
| TB15-086 | P | 52 | Infiltrating duct carcinoma, NOS | Grade I: Well differentiated, diffe | 1 | 0 | 1 | 1C |
| TB15-076 | P | 67 | Infiltrating duct carcinoma, NOS | Grade II: Mod diff, mod well diff, | 1C | 0 | 1 | 1B |
| TB15-087 | P | 50 | Infiltrating duct carcinoma, NOS | Grade II: Mod diff, mod well diff, | 2 | 0 | 2A | 1C |
| TB15-083 | P | 38 | Infiltrating duct carcinoma, NOS | Grade I: Well differentiated, diffe | 3 | 0 | 2B | 2 |
| TB15-082 | P | 45 | Infiltrating duct carcinoma, NOS | Grade II: Mod diff, mod well diff, | 3 | 0 | 2B | X |
| TB15-078 | P | 64 | Infiltrating duct carcinoma, NOS | Grade III: Poorly differentiated, d | 1C | 0 | 1 | 1C |
| TB15-077 | P | 62 | Infiltrating duct carcinoma, NOS | Grade II: Mod diff, mod well diff, | 2 | 0 | 2A | 1A |
| TB15-079 | P | 76 | Infiltrating duct carcinoma, NOS | Grade I: Well differentiated, diffe | 1B | 0 | 1 | 1B |
| TB15-080 | P | 67 | Infiltrating duct carcinoma, NOS | Grade II: Mod diff, mod well diff, | 1B | 0 | 1 | 1B |
| TB15-081 | N | 57 | Infiltrating duct carcinoma, NOS | Grade II: Mod diff, mod well diff, | 1C | 0 | 1 | 1C |
| TB15-084 | N | 68 | Infiltrating duct carcinoma, NOS | Grade I: Well differentiated, diffe | 1C | 0 | 1 | 1B |

TABLE 11-continued

Breast Cancer

Part 2b

| Ductal carcinoma met | Pathologic N | Pathologic M | Pathologic Stage Group | ER Assay | PR Assay | HER2: Summary Result | Type 1st Recurrence-Desc | Months from Dx to 1st Recurrence | Survival In Months | Vital Status-Desc |
|---|---|---|---|---|---|---|---|---|---|---|
| TB15-060 1B | 1 | 0 | 3A | Positive/Elevated | Positive/Elevated | 988 | Patient became disease-free after treatment and has not had a recurrence. | 000 | 067 | Alive |
| TB15-061 3H | 1 | 0 | 2A | Positive/Elevated | Positive/Elevated | 988 | Patient became disease-free after treatment and has not had a recurrence. | 000 | 074 | Alive |
| TB15-072 1F | 1C | X | 99 | Negative, Normal | Negative, Normal | 988 | Distant recurrence of an invasive tumor in a single distant site (51-58) and local, trocar and/or regional recurrence (1 | 013 | 018 | Dead |
| TB15-071 C | 2A | 0 | 3A | Negative, Normal | Negative, Normal | 988 | Distant recurrence of an invasive tumor in multiple sites (recurrences that can be coded to more than one category 51-59 | 020 | 023 | Dead |
| TB15-062 5A | 1M | X | 99 | Positive/Elevated | Positive/Elevated | 988 | Patient became disease-free after treatment and has not had a recurrence. | 000 | 062 | Alive |
| TB15-066 1J | 1A | X | 99 | Positive/Elevated | Negative, Normal | 988 | Patient became disease-free after treatment and has not had a recurrence. | 000 | 059 | Alive |
| TB15-063 1B | 1A | 0 | 2A | Positive/Elevated | Negative, Normal | 988 | Patient became disease-free after treatment and has not had a recurrence. | 000 | 061 | Alive |
| TB15-070 1E | 2A | X | 99 | Negative, Normal | Negative, Normal | 988 | Distant recurrence of an invasive tumor in multiple sites (recurrences that can be coded to more than one category 51-59 | 027 | 037 | Dead |
| TB15-068 1D | 3B | X | 99 | Positive/Elevated | Negative, Normal | 988 | Distant recurrence of an invasive tumor in multiple sites (recurrences that can be coded to more than one category 51-59 | 018 | 028 | Dead |
| TB15-065 5L | 2A | 0 | 3A | Positive/Elevated | Positive/Elevated | 988 | Patient became disease-free after treatment and has not had a recurrence. | 000 | 060 | Alive |
| TB15-073 1B | 1A | 0 | 2A | Negative, Normal | Negative, Normal | 988 | Patient became disease-free after treatment and has not had a recurrence. | 000 | 060 | Alive |
| TB15-067 O | 1A | 0 | 2B | Negative, Normal | Negative, Normal | 988 | Patient became disease-free after treatment and has not had a recurrence. | 000 | 068 | Dead |

TABLE 11-continued

Breast Cancer

| | | | | | | | | |
|---|---|---|---|---|---|---|---|---|
| TB15-074 5H | 1A | 0 | 2A | Positive/Elevated | Positive/Elevated | Negative/Normal | Patient became disease-free after treatment and has not had a recurrence. | 000 | 063 | Alive |
| TB15-064 6I | 1M | 0 | 2B | Positive/Elevated | Positive/Elevated | 988 | Patient became disease-free after treatment and has not had a recurrence. | 000 | 061 | Alive |
| TB15-069 1G | 1A | X | 99 | Positive/Elevated | Positive/Elevated | 988 | Patient became disease-free after treatment and has not had a recurrence. | 000 | 063 | Alive |
| TB15-116 | 0 | 0 | 1 | Positive/Elevated | Positive/Elevated | 988 | Patient became disease-free after treatment and has not had a recurrence. | 000 | 061 | Alive |
| TB15-118 | 0 | X | 99 | Positive/Elevated | Positive/Elevated | 988 | Patient became disease-free after treatment and has not had a recurrence. | 000 | 060 | Alive |
| TB15-117 | 0 | 0 | 2A | Negative/Normal | Negative/Normal | 988 | Patient became disease-free after treatment and has not had a recurrence. | 000 | 063 | Alive |
| TB15-085 | 0 | 0 | 2A | Negative/Normal | Negative/Normal | 988 | Patient became disease-free after treatment and has not had a recurrence. | 000 | 058 | Alive |
| TB15-086 | 0 | 0 | 99 | Positive/Elevated | Positive/Elevated | 988 | Patient became disease-free after treatment and has not had a recurrence. | 000 | 062 | Alive |
| TB15-076 | 0 | 0 | 1 | Positive/Elevated | Positive/Elevated | 988 | Patient became disease-free after treatment and has not had a recurrence. | 000 | 061 | Alive |
| TB15-087 | 0 | X | 99 | Positive/Elevated | Positive/Elevated | 988 | Patient became disease-free after treatment and has not had a recurrence. | 000 | 063 | Alive |
| TB15-083 | 0 | 0 | 2A | Positive/Elevated | Positive/Elevated | 988 | Patient became disease-free after treatment and has not had a recurrence. | 000 | 062 | Alive |

TABLE 11-continued

| | | | | | Breast Cancer | | | |
|---|---|---|---|---|---|---|---|---|
| TB15-082 | X | X | 99 | Positive/Elevated | Positive/Elevated | 988 | Patient became disease-free after treatment and has not had a recurrence. | 000 | 063 | Alive |
| TB15-078 | 0 | 0 | 1 | Negative/Normal | Negative/Normal | 988 | Patient became disease-free after treatment and has not had a recurrence. | 000 | 065 | Alive |
| TB15-077 | 0 | X | 99 | Positive/Elevated | Positive/Elevated | 988 | Patient became disease-free after treatment and has not had a recurrence. | 000 | 064 | Alive |
| TB15-079 | 0 | 0 | 1 | Positive/Elevated | Positive/Elevated | 988 | Patient became disease-free after treatment and has not had a recurrence. | 000 | 060 | Alive |
| TB15-080 | 0 | 0 | 1 | Positive/Elevated | Positive/Elevated | 988 | Patient became disease-free after treatment and has not had a recurrence. | | | |
| TB15-081 | 0 | 0 | 1 | Positive/Elevated | Positive/Elevated | 988 | Patient became disease-free after treatment and has not had a recurrence. | 000 | 058 | Alive |
| TB15-084 | 0 | 0 | 1 | Positive/Elevated | Positive/Elevated | 988 | Patient became disease-free after treatment and has not had a recurrence. | 000 | 060 | Alive |

TABLE 12

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| TB15-127 | P | 90 | Grade I: Well differentiated, diffe | 12 | 00 | 1A | X | 0 | 1A | Patient became disease-free after treatment and has not had a recurrence. | 78 | Dead |
| TB15-128 | N | 59 | Cell type not determined, not state | 14 | 00 | 3B | 0 | 0 | 3B | Patient became disease-free after treatment and has not had a recurrence. | 80 | Alive |
|  |  | 59 | Cell type not determined, not state | 14 | 00 | 3B | 0 | 0 | 3B | Patient became disease-free after treatment and has not had a recurrence. | 80 | Alive |
| TB15-129 | N | 41 | Cell type not determined, not state | 10 | 00 | 1 | 0 | 0 | 1 | Patient became disease-free after treatment and has not had a recurrence. | 81 | Alive |
|  |  | 41 | Cell type not determined, not state | 10 | 00 | 1 | 0 | 0 | 1 | Patient became disease-free after treatment and has not had a recurrence. | 81 | Alive |
| TB15-130 | P | 83 | Grade I: Well differentiated, diffe | 09 | 00 | 2A | 0 | 0 | 2A | Patient became disease-free after treatment and has not had a recurrence. | 85 | Alive |
| TB15-131 | N | 61 | Grade III: Poorly differentiated, d | 21 | 00 | 1C | 0 | 0 | 1C | Patient became disease-free after treatment and has not had a recurrence. | 85 | Alive |
|  |  | 61 | Grade III: Poorly differentiated, d | 21 | 00 | 1C | 0 | 0 | 1C | Patient became disease-free after treatment and has not had a recurrence. | 85 | Alive |
|  |  | 61 | Grade III: Poorly differentiated, d | 21 | 00 | 1C | 0 | 0 | 1C | Patient became disease-free after treatment and has not had a recurrence. | 85 | Alive |
| TB15-132 | N | 70 | Grade III: Poorly differentiated, d | 23 | 00 | 2C | 0 | 0 | 2C | Patient became disease-free after treatment and has not had a recurrence. | 76 | Alive |
|  |  | 70 | Grade III: Poorly differentiated, d | 23 | 00 | 2C | 0 | 0 | 2C | Patient became disease-free after treatment and has not had a recurrence. | 76 | Alive |
| TB15-133 | P | 44 | Grade I: Well differentiated, diffe | 06 | 00 | 1C | 0 | X | 99 | Patient became disease-free after treatment and has not had a recurrence. | 80 | Alive |
|  |  | 44 | Grade I: Well differentiated, diffe | 06 | 00 | 1C | 0 | X | 99 | Patient became disease-free after treatment and has not had a recurrence. | 80 | Alive |
| TB15-134 | N | 42 | Grade III: Poorly differentiated, d | 00 | 20 | 2A | 0 | X | 99 | Patient became disease-free after treatment and has not had a recurrence. | 64 | Alive |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 42 | Grade III: Poorly differentiated, d | 00 | 20 | 2A | 0 | X | 99 | Patient became disease-free after treatment and has not had a recurrence. | 64 | Alive |
| TB15-135 | P | 61 | Grade II: Mod diff, mod well diff, | 25 | 00 | 1C | 0 | 0 | 1C | Patient became disease-free after treatment and has not had a recurrence. | 87 | Alive |
| | | 61 | Grade II: Mod diff, mod well diff, | 25 | 00 | 1C | 0 | 0 | 1C | Patient became disease-free after treatment and has not had a recurrence. | 87 | Alive |
| | | 61 | Grade II: Mod diff, mod well diff, | 25 | 00 | 1C | 0 | 0 | 1C | Patient became disease-free after treatment and has not had a recurrence. | 87 | Alive |
| TB15-136 | N | 57 | Grade II: Mod diff, mod well diff, | 23 | 00 | 1A | 0 | 0 | 1A | Patient became disease-free after treatment and has not had a recurrence. | 60 | Alive |
| | | 57 | Grade II: Mod diff, mod well diff, | 23 | 00 | 1A | 0 | 0 | 1A | Patient became disease-free after treatment and has not had a recurrence. | 60 | Alive |
| TB15-137 | N | 52 | Grade III: Poorly differentiated, d | 21 | 00 | 1C | 0 | 0 | 1C | Distant systemic recurrence of an invasive tumor only. This includes lymphoma, leukemia, bone marrow | 84 | Alive |
| | | 52 | Grade III: Poorly differentiated, d | 21 | 00 | 1C | 0 | 0 | 1C | Distant systemic recurrence of an invasive tumor only. This includes lymphoma, leukemia, bone marrow | 84 | Alive |
| | | 52 | Grade III: Poorly differentiated, d | 21 | 00 | 1C | 0 | 0 | 1C | Distant systemic recurrence of an invasive tumor only. This includes lymphoma, leukemia, bone marrow | 84 | Alive |
| TB15-138 | N | 35 | Grade IV: Undifferentiated, anaplas | 14 | 00 | 1C | 0 | 0 | 1C | Patient became disease-free after treatment and has not had a recurrence. | 83 | Alive |
| | | 35 | Grade IV: Undifferentiated, anaplas | 14 | 00 | 1C | 0 | 0 | 1C | Patient became disease-free after treatment and has not had a recurrence. | 83 | Alive |
| TB15-139 | P | 55 | Grade I: Well differentiated, diffe | 15 | 00 | 3B | 0 | X | 99 | Patient became disease-free after treatment and has not had a recurrence. | 86 | Alive |
| | | 55 | Grade I: Well differentiated, diffe | 15 | 00 | 3B | 0 | X | 99 | Patient became disease-free after treatment and has not had a recurrence. | 86 | Alive |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| TB15-140 | P | 56 | Grade I: Well differentiated, diffe | 14 | 00 | 1C | 0 | X | 99 | Patient became disease-free after treatment and has not had a recurrence. | 84 | Alive |
|  |  | 56 | Grade I: Well differentiated, diffe | 14 | 00 | 1C | 0 | X | 99 | Patient became disease-free after treatment and has not had a recurrence. | 84 | Alive |
| TB15-141 | N | 42 | Grade III: Poorly differentiated, d | 16 | 00 | 1C | 0 | 0 | 1C | Patient became disease-free after treatment and has not had a recurrence. | 58 | Alive |
|  |  | 42 | Grade III: Poorly differentiated, d | 16 | 00 | 1C | 0 | 0 | 1C | Patient became disease-free after treatment and has not had a recurrence. | 58 | Alive |
| TB15-142 | N | 44 | Grade II: Mod diff, mod well diff, | 11 | 00 | 1B | 0 | X | 99 | Patient became disease-free after treatment and has not had a recurrence. | 82 | Alive |
|  |  | 44 | Grade II: Mod diff, mod well diff, | 11 | 00 | 1B | 0 | X | 99 | Patient became disease-free after treatment and has not had a recurrence. | 82 | Alive |
| TB15-143 | P | 58 | Grade III: Poorly differentiated, d | 02 | 00 | 1C | 0 | 0 | 1C | Patient became disease-free after treatment and has not had a recurrence. | 80 | Alive |
|  |  | 58 | Grade III: Poorly differentiated, d | 02 | 00 | 1C | 0 | 0 | 1C | Patient became disease-free after treatment and has not had a recurrence. | 80 | Alive |
| TB15-144 | P | 50 | Cell type not determined, not state | 00 | 98 | 1A | 0 | 0 | 1A | Patient became disease-free after treatment and has not had a recurrence. | 66 | Alive |
|  |  | 50 | Cell type not determined, not state | 00 | 98 | 1A | 0 | 0 | 1A | Patient became disease-free after treatment and has not had a recurrence. | 66 | Alive |
| TB15-145 | P | 45 | Grade IV: Undifferentiated, anaplas | 11 | 00 | 1C | 0 | X | 99 | Patient became disease-free after treatment and has not had a recurrence. | 73 | Alive |
|  |  | 45 | Grade IV: Undifferentiated, anaplas | 11 | 00 | 1C | 0 | X | 99 | Patient became disease-free after treatment and has not had a recurrence. | 73 | Alive |
| TB15-146 | P | 49 | Grade III: Poorly differentiated, d | 15 | 00 | 1C | 0 | 0 | 1C | Patient became disease-free after treatment and has not had a recurrence. | 70 | Alive |
|  |  | 49 | Grade III: Poorly differentiated, d | 15 | 00 | 1C | 0 | 0 | 1C | Patient became disease-free after treatment and has not had a recurrence. | 70 | Alive |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 49 | Grade III: Poorly differentiated, d | 15 | 00 | 1C | 0 | 0 | 1C | Patient became disease-free after treatment and has not had a recurrence. | 70 | Alive |
| TB15-147 | P | 55 | Grade III: Poorly differentiated, d | 18 | 00 | 3B | 0 | 0 | 3B | Patient became disease-free after treatment and has not had a recurrence. | 64 | Alive |
| TB15-148 | P | 44 | Grade III: Poorly differentiated, d | 16 | 00 | 1C | 0 | X | 99 | Patient became disease-free after treatment and has not had a recurrence. | 63 | Alive |
| | | 44 | Grade III: Poorly differentiated, d | 16 | 00 | 1C | 0 | X | 99 | Patient became disease-free after treatment and has not had a recurrence. | 63 | Alive |
| TB15-149 | N | 69 | Grade II: Mod diff, mod well diff, | 18 | 00 | 3B | 0 | | 3B | Patient became disease-free after treatment and has not had a recurrence. | 62 | Alive |
| | | 69 | Grade II: Mod diff, mod well diff, | 18 | 00 | 3B | 0 | | 3B | Patient became disease-free after treatment and has not had a recurrence. | 62 | Alive |
| TB15-150 | N | 63 | Grade III: Poorly differentiated, d | 00 | 98 | 3C | X | X | 99 | Patient became disease-free after treatment and has not had a recurrence. | 75 | Dead |
| | | 63 | Grade III: Poorly differentiated, d | 00 | 98 | 3C | X | X | 99 | Patient became disease-free after treatment and has not had a recurrence. | 75 | Dead |
| TB15-151 | P | 42 | Grade II: Mod diff, mod well diff, | 04 | 00 | 1A | 0 | 0 | 1A | Patient became disease-free after treatment and has not had a recurrence. | 93 | Alive |
| | | 42 | Grade II: Mod diff, mod well diff, | 04 | 00 | 1A | 0 | 0 | 1A | Patient became disease-free after treatment and has not had a recurrence. | 93 | Alive |
| TB15-152 | P | 50 | Grade III: Poorly differentiated, d | 23 | 00 | 1A | 0 | 0 | 1A | Patient became disease-free after treatment and has not had a recurrence. | 90 | Alive |
| | | 50 | Grade III: Poorly differentiated, d | 23 | 00 | 1A | 0 | 0 | 1A | Patient became disease-free after treatment and has not had a recurrence. | 90 | Alive |
| TB15-153 | P | 75 | Grade I: Well differentiated, diffe | 12 | 00 | 1A | 0 | 0 | 1A | Patient became disease-free after treatment and has not had a recurrence. | 91 | Alive |
| TB15-154 | N | 59 | Grade III: Poorly differentiated, d | 10 | 00 | 2A | 0 | 0 | 2A | Patient became disease-free after treatment and has not had a recurrence. | 84 | Alive |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| TB15-155 | | 43 | Grade I: Well differentiated, diffe | 20 | 00 | 1A | 0 | 0 | 1A | Patient became disease-free after treatment and has not had a recurrence. | 89 | |
| | | 43 | Grade I: Well differentiated, diffe | 20 | 00 | 1A | 0 | 0 | 1A | Patient became disease-free after treatment and has not had a recurrence. | 89 | Alive |
| TB15-156 | P | 42 | Grade II: Mod diff, mod well diff, | 09 | 00 | 1C | 0 | 0 | 1C | Patient became disease-free after treatment and has not had a recurrence. | 84 | Alive |
| | | 42 | Grade II: Mod diff, mod well diff, | 09 | 00 | 1C | 0 | 0 | 1C | Patient became disease-free after treatment and has not had a recurrence. | 84 | Alive |
| | | 42 | Grade II: Mod diff, mod well diff, | 09 | 00 | 1C | 0 | 0 | 1C | Patient became disease-free after treatment and has not had a recurrence. | 84 | Alive |
| TB15-157 | P | 50 | Cell type not determined, not state | 22 | 00 | 1C | 0 | 0 | 1C | Patient became disease-free after treatment and has not had a recurrence. | 85 | Alive |
| | | 50 | Cell type not determined, not state | 22 | 00 | 1C | 0 | 0 | 1C | Patient became disease-free after treatment and has not had a recurrence. | 85 | Alive |
| TB15-180 | N | 57 | Cell type not determined, not state | 12 | 02 | 3C | 1 | 0 | 3C | Since diagnosis, patient has never been disease-free. This includes cases with distant metastasis at | 7 | Dead |
| | | 57 | Cell type not determined, not state | 12 | 02 | 3C | 1 | 0 | 3C | Since diagnosis, patient has never been disease-free. This includes cases with distant metastasis at | 7 | Dead |
| | | 57 | Cell type not determined, not state | 12 | 02 | 3C | 1 | 0 | 3C | Since diagnosis, patient has never been disease-free. This includes cases with distant metastasis at | 7 | Dead |
| TB15-181 | P | 56 | Grade III: Poorly differentiated, d | 08 | 07 | 3C | 1 | X | 99 | Since diagnosis, patient has never been disease-free. This includes cases with distant metastasis at | 24 | Dead |
| | | 56 | Grade III: Poorly differentiated, d | 08 | 07 | 3C | 1 | X | 99 | Since diagnosis, patient has never been disease-free. This includes cases with distant metastasis at | 24 | Dead |
| TB15-182 | N | 68 | Cell type not determined, not state | 07 | 04 | 3C | 1 | 0 | 3C | Distant recurrence of an invasive tumor in lymph node only. Refer to the staging scheme for a descri | 39 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 68 | Cell type not determined, not state | 07 | 04 | 3C | 1 | 0 | 3C | Distant recurrence of an invasive tumor in lymph node only. Refer to the staging scheme for a descri | 39 | Dead |
| | | 68 | Cell type not determined, not state | 07 | 04 | 3C | 1 | 0 | 3C | Distant recurrence of an invasive tumor in lymph node only. Refer to the staging scheme for a descri | 39 | Dead |
| TB15-183 | N | 81 | Grade III: Poorly differentiated, d | 13 | 03 | 3C | 1 | 0 | 3C | Since diagnosis, patient has never been disease-free. This includes cases with distant metastasis at | 7 | Dead |
| TB15-184 | P | 51 | Grade III: Poorly differentiated, d | 20 | 20 | 3 | 1 | 1 | 4 | Recurrence of an invasive tumor in regional lymph nodes only. | 75 | Dead |
| | | 51 | Grade III: Poorly differentiated, d | 20 | 20 | 3 | 1 | 1 | 4 | Recurrence of an invasive tumor in regional lymph nodes only. | 75 | Dead |
| | | 51 | Grade III: Poorly differentiated, d | 20 | 20 | 3 | 1 | 1 | 4 | Recurrence of an invasive tumor in regional lymph nodes only. | 75 | Dead |
| | | 51 | Grade III: Poorly differentiated, d | 20 | 20 | 3 | 1 | 1 | 4 | Recurrence of an invasive tumor in regional lymph nodes only. | 75 | Dead |
| | | 51 | Grade III: Poorly differentiated, d | 20 | 20 | 3 | 1 | 1 | 4 | Recurrence of an invasive tumor in regional lymph nodes only. | 75 | Dead |
| | | 51 | Grade III: Poorly differentiated, d | 20 | 20 | 3 | 1 | 1 | 4 | Recurrence of an invasive tumor in regional lymph nodes only. | 75 | Dead |
| TB15-185 | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| | | 51 | Grade II: Mod diff, mod well diff, | 19 | 15 | 3C | 1 | 1 | 4 | Since diagnosis, patient has never been disease-free. This includes cases with distant metastasis at | 80 | Alive |
| TB15-186 | N | 57 | Grade III: Poorly differentiated, d | 00 | 98 | 3C | X | 1 | 4 | Since diagnosis, patient has never been disease-free. This includes cases with distant metastasis at | 9 | Dead |
| | | 57 | Grade III: Poorly differentiated, d | 00 | 98 | 3C | X | 1 | 4 | Since diagnosis, patient has never been disease-free. This includes cases with distant metastasis at | 9 | Dead |
| | | 57 | Grade III: Poorly differentiated, d | 00 | 98 | 3C | X | 1 | 4 | Since diagnosis, patient has never been disease-free. This includes cases with distant metastasis at | 9 | Dead |
| | | 57 | Grade III: Poorly differentiated, d | 00 | 98 | 3C | X | 1 | 4 | Since diagnosis, patient has never been disease-free. This includes cases with distant metastasis at | 9 | Dead |
| | | 57 | Grade III: Poorly differentiated, d | 00 | 98 | 3C | X | 1 | 4 | Since diagnosis, patient has never been disease-free. This includes cases with distant metastasis at | 9 | Dead |
| | | 57 | Grade III: Poorly differentiated, d | 00 | 98 | 3C | X | 1 | 4 | Since diagnosis, patient has never been disease-free. This includes cases with distant metastasis at | 9 | Dead |
| TB15-187 | P | 41 | Grade III: Poorly differentiated, d | 20 | 01 | 3C | 1 | 0 | 3C | Patient became disease-free after treatment and has not had a recurrence. | 74 | Alive |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 41 | Grade III: Poorly differentiated, d | 20 | 01 | 3C | 1 | 0 | 3C | Patient became disease-free after treatment and has not had a recurrence. | 74 | Alive |
| TB15-188 | N | 70 | Grade III: Poorly differentiated, d | 00 | 98 | 3C | X | 1 | 4 | Since diagnosis, patient has never been disease-free. This includes cases with distant metastasis at | 58 | Dead |
| | | 70 | Grade III: Poorly differentiated, d | 00 | 98 | 3C | X | 1 | 4 | Since diagnosis, patient has never been disease-free. This includes cases with distant metastasis at | 58 | Dead |
| | | 70 | Grade III: Poorly differentiated, d | 00 | 98 | 3C | X | 1 | 4 | Since diagnosis, patient has never been disease-free. This includes cases with distant metastasis at | 58 | Dead |
| | | 70 | Grade III: Poorly differentiated, d | 00 | 98 | 3C | X | 1 | 4 | Since diagnosis, patient has never been disease-free. This includes cases with distant metastasis at | 58 | Dead |
| | | 70 | Grade III: Poorly differentiated, d | 00 | 98 | 3C | X | 1 | 4 | Since diagnosis, patient has never been disease-free. This includes cases with distant metastasis at | 58 | Dead |
| | | 70 | Grade III: Poorly differentiated, d | 00 | 98 | 3C | X | 1 | 4 | Since diagnosis, patient has never been disease-free. This includes cases with distant metastasis at | 58 | Dead |
| TB15-189 | P | 66 | Grade IV: Undifferentiated, anaplas | 14 | 03 | 3C | 1 | 0 | 3C | Distant recurrence, to a site not listed in 46-62 or there is insufficient information available to | 57 | Dead |
| | | 66 | Grade IV: Undifferentiated, anaplas | 14 | 03 | 3C | 1 | 0 | 3C | Distant recurrence, to a site not listed in 46-62 or there is insufficient information available to | 57 | Dead |
| | | 66 | Grade IV: Undifferentiated, anaplas | 14 | 03 | 3C | 1 | 0 | 3C | Distant recurrence, to a site not listed in 46-62 or there is insufficient information available to | 57 | Dead |
| TB15-190 | P | 65 | Grade III: Poorly differentiated, d | 09 | 05 | 3C | 1 | 0 | 3C | Patient became disease-free after treatment and has not had a recurrence. | 78 | Alive |
| | | 65 | Grade III: Poorly differentiated, d | 09 | 05 | 3C | 1 | 0 | 3C | Patient became disease-free after treatment and has not had a recurrence. | 78 | Alive |
| TB15-191 | P | 61 | Grade III: Poorly differentiated, d | 07 | 00 | 3C | 0 | 1 | 4 | Distant recurrence of an invasive tumor in multiple sites | 34 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 61 | Grade III: Poorly differentiated, d | 07 | 00 | 3C | 0 | 1 | 4 | (recurrences that can be coded to more tha Distant recurrence of an invasive tumor in multiple sites (recurrences that can be coded to more tha | 34 | Dead |
| TB15-192 | P | 52 | Cell type not determined, not state | 02 | 00 | 3C | 0 | 1 | 4 | Since diagnosis, patient has never been disease-free. This includes cases with distant metastasis at | 3 | Dead |
| | | 52 | Cell type not determined, not state | 02 | 00 | 3C | 0 | 1 | 4 | Since diagnosis, patient has never been disease-free. This includes cases with distant metastasis at | 3 | Dead |
| | | 52 | Cell type not determined, not state | 02 | 00 | 3C | 0 | 1 | 4 | Since diagnosis, patient has never been disease-free. This includes cases with distant metastasis at | 3 | Dead |
| | | 52 | Cell type not determined, not state | 02 | 00 | 3C | 0 | 1 | 4 | Since diagnosis, patient has never been disease-free. This includes cases with distant metastasis at | 3 | Dead |
| | | 52 | Cell type not determined, not state | 02 | 00 | 3C | 0 | 1 | 4 | Since diagnosis, patient has never been disease-free. This includes cases with distant metastasis at | 3 | Dead |
| TB15-193 | P | 70 | Grade III: Poorly differentiated, d | 03 | 00 | 3C | 0 | 0 | 3C | Distant recurrence of an invasive tumor in lymph node only. Refer to the staging scheme for a descri | 38 | Dead |
| | | 70 | Grade III: Poorly differentiated, d | 03 | 00 | 3C | 0 | 0 | 3C | Distant recurrence of an invasive tumor in lymph node only. Refer to the staging scheme for a descri | 38 | Dead |
| TB15-194 | N | 50 | Grade IV: Undifferentiated, anaplas | 08 | 01 | 3C | 1 | 0 | 3C | Patient became disease-free after treatment and has not had a recurrence. | 76 | Alive |
| | | 50 | Grade IV: Undifferentiated, anaplas | 08 | 01 | 3C | 1 | 0 | 3C | Patient became disease-free after treatment and has not had a recurrence. | 76 | Alive |
| TB15-195 | P | 69 | Grade III: Poorly differentiated, d | 01 | 00 | 3C | 0 | 0 | 3C | Distant recurrence of an invasive tumor in multiple sites (recurrences that can be coded to more tha | 9 | Dead |
| | | 69 | Grade III: Poorly differentiated, d | 01 | 00 | 3C | 0 | 0 | 3C | Distant recurrence of an invasive tumor in multiple sites (recurrences that can be coded to more tha | 9 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 69 | Grade III: Poorly differentiated, d | 01 | 00 | 3C | 0 | 0 | 3C | Distant recurrence of an invasive tumor in multiple sites (recurrences that can be coded to more tha | 9 | Dead |
| TB15-196 | N | 57 | Grade III: Poorly differentiated, d | 07 | 07 | 3C | 1 | 0 | 3C | Recurrence of an invasive tumor in regional lymph nodes only. | 70 | Alive |
| | | 57 | Grade III: Poorly differentiated, d | 07 | 07 | 3C | 1 | 0 | 3C | Recurrence of an invasive tumor in regional lymph nodes only. | 70 | Alive |
| | | 57 | Grade III: Poorly differentiated, d | 07 | 07 | 3C | 1 | 0 | 3C | Recurrence of an invasive tumor in regional lymph nodes only. | 70 | Alive |
| TB15-197 | N | 61 | Grade III: Poorly differentiated, d | 16 | 02 | 3C | 1 | 0 | 3C | Recurrence of an invasive tumor in adjacent tissue or organ(s) only. | 58 | Dead |
| | | 61 | Grade III: Poorly differentiated, d | 16 | 02 | 3C | 1 | 0 | 3C | Recurrence of an invasive tumor in adjacent tissue or organ(s) only. | 58 | Dead |
| | | 61 | Grade III: Poorly differentiated, d | 16 | 02 | 3C | 1 | 0 | 3C | Recurrence of an invasive tumor in adjacent tissue or organ(s) only. | 58 | Dead |
| TB15-198 | P | 48 | Grade III: Poorly differentiated, d | 16 | 07 | 3C | 1 | 0 | 3C | Since diagnosis, patient has never been disease-free. This includes cases with distant metastasis at | 16 | Dead |
| | | 48 | Grade III: Poorly differentiated, d | 16 | 07 | 3C | 1 | 0 | 3C | Since diagnosis, patient has never been disease-free. This includes cases with distant metastasis at | 16 | Dead |
| TB15-199 | N | 78 | Grade III: Poorly differentiated, d | 01 | 01 | 3C | 1 | 1 | 4 | Regional recurrence, and there is insufficient information available to code to 21-27. | 30 | Dead |
| | | 78 | Grade III: Poorly differentiated, d | 01 | 01 | 3C | 1 | 1 | 4 | Regional recurrence, and there is insufficient information available to code to 21-27. | 30 | Dead |
| | | 78 | Grade III: Poorly differentiated, d | 01 | 01 | 3C | 1 | 1 | 4 | Regional recurrence, and there is insufficient information available to code to 21-27. | 30 | Dead |
| | | 78 | Grade III: Poorly differentiated, d | 01 | 01 | 3C | 1 | 1 | 4 | Regional recurrence, and there is insufficient information available to code to 21-27. | 30 | Dead |
| | | 78 | Grade III: Poorly differentiated, d | 01 | 01 | 3C | 1 | 1 | 4 | Regional recurrence, and there is insufficient information available to code to 21-27. | 30 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| TB15-207 | P | 64 | Grade II: Mod diff, mod well diff, | 04 | 00 | 3C | 0 | 1 | 4 | Since diagnosis, patient has never been disease-free. This includes cases with distant metastasis at | 10 | Dead |
|  |  | 64 | Grade II: Mod diff, mod well diff, | 04 | 00 | 3C | 0 | 1 | 4 | Since diagnosis, patient has never been disease-free. This includes cases with distant metastasis at | 10 | Dead |
|  |  | 64 | Grade II: Mod diff, mod well diff, | 04 | 00 | 3C | 0 | 1 | 4 | Since diagnosis, patient has never been disease-free. This includes cases with distant metastasis at | 10 | Dead |
| TB15-208 | P | 52 | Grade III: Poorly differentiated, d | 10 | 06 | 3C | 1 | 1 | 4 | Since diagnosis, patient has never been disease-free. This includes cases with distant metastasis at | 2 | Dead |
|  |  | 52 | Grade III: Poorly differentiated, d | 10 | 06 | 3C | 1 | 1 | 4 | Since diagnosis, patient has never been disease-free. This includes cases with distant metastasis at | 2 | Dead |
| TB15-209 | P | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
|  |  | 66 | Grade III: Poorly differentiated, d | 20 | 00 | 3C | 0 | 0 | 3C | Recurrence of an invasive tumor in regional lymph nodes only. | 81 | Dead |
| TB15-210 | N | 71 | Grade III: Poorly differentiated, d | 04 | 04 | 3C | 1 | 0 | 3C | Since diagnosis, patient has never been disease-free. This includes cases with distant metastasis at | 30 | Dead |
|  |  | 71 | Grade III: Poorly differentiated, d | 04 | 04 | 3C | 1 | 0 | 3C | Since diagnosis, patient has never been disease-free. | 30 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| TB15-211 | N | 78 | Grade III: Poorly differentiated, d | 06 | 00 | 3C |  | 1 | 3C | This includes cases with distant metastasis at Since diagnosis, patient has never been disease-free. | 27 | Dead |
|  |  | 78 | Grade III: Poorly differentiated, d | 06 | 00 | 3C |  | 1 | 3C | This includes cases with distant metastasis at Since diagnosis, patient has never been disease-free. | 27 | Dead |
|  |  | 78 | Grade III: Poorly differentiated, d | 06 | 00 | 3C |  | 1 | 3C | This includes cases with distant metastasis at Since diagnosis, patient has never been disease-free. | 27 | Dead |
|  |  | 78 | Grade III: Poorly differentiated, d | 06 | 00 | 3C |  | 1 | 3C | This includes cases with distant metastasis at Since diagnosis, patient has never been disease-free. | 27 | Dead |
|  |  | 78 | Grade III: Poorly differentiated, d | 06 | 00 | 3C |  | 1 | 3C | This includes cases with distant metastasis at Since diagnosis, patient has never been disease-free. | 27 | Dead |
| TB15-212 | N | 79 | Grade III: Poorly differentiated, d | 01 | 01 | 3C | 1 | 1 | 4 | This includes cases with distant metastasis at Since diagnosis, patient has never been disease-free. | 78 | Dead |
|  |  | 79 | Grade III: Poorly differentiated, d | 01 | 01 | 3C | 1 | 1 | 4 | This includes cases with distant metastasis at Since diagnosis, patient has never been disease-free. | 78 | Dead |
|  |  | 79 | Grade III: Poorly differentiated, d | 01 | 01 | 3C | 1 | 1 | 4 | This includes cases with distant metastasis at Since diagnosis, patient has never been disease-free. | 78 | Dead |
|  |  | 79 | Grade III: Poorly differentiated, d | 01 | 01 | 3C | 1 | 1 | 4 | This includes cases with distant metastasis at Since diagnosis, patient has never been disease-free. | 78 | Dead |
|  |  | 79 | Grade III: Poorly differentiated, d | 01 | 01 | 3C | 1 | 1 | 4 | This includes cases with distant metastasis at Since diagnosis, patient has never been disease-free. | 78 | Dead |
|  |  | 79 | Grade III: Poorly differentiated, d | 01 | 01 | 3C | 1 | 1 | 4 | This includes cases with distant metastasis at Since diagnosis, patient has never been disease-free. | 78 | Dead |
|  |  | 79 | Grade III: Poorly differentiated, d | 01 | 01 | 3C | 1 | 1 | 4 | This includes cases with distant metastasis at Since diagnosis, patient has never been disease-free. | 78 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 79 | Grade III: Poorly differentiated, d | 01 | 01 | 3C | 1 | 1 | 4 | This includes cases with distant metastasis at Since diagnosis, patient has never been disease-free. | 78 | Dead |
| TB15-213 | P | 77 | Grade III: Poorly differentiated, d | 00 | 98 | 3C | X | 1 | 4 | This includes cases with distant metastasis at Since diagnosis, patient has never been disease-free. | 25 | Dead |
| | | 77 | Grade III: Poorly differentiated, d | 00 | 98 | 3C | X | 1 | 4 | This includes cases with distant metastasis at Since diagnosis, patient has never been disease-free. | 25 | Dead |
| TB15-214 | P | 72 | Grade III: Poorly differentiated, d | 05 | 01 | 3C | 1 | 0 | 3C | Recurrence of an invasive tumor in adjacent tissue or organ(s) only. | 11 | Dead |
| | | 72 | Grade III: Poorly differentiated, d | 05 | 01 | 3C | 1 | 0 | 3C | Recurrence of an invasive tumor in adjacent tissue or organ(s) only. | 11 | Dead |
| | | 72 | Grade III: Poorly differentiated, d | 05 | 01 | 3C | 1 | 0 | 3C | Recurrence of an invasive tumor in adjacent tissue or organ(s) only. | 11 | Dead |
| TB15-215 | N | 68 | Grade III: Poorly differentiated, d | 01 | 00 | 3C | 0 | 1 | 4 | Since diagnosis, patient has never been disease-free. This includes cases with distant metastasis at | 32 | Dead |
| | | 68 | Grade III: Poorly differentiated, d | 01 | 00 | 3C | 0 | 1 | 4 | Since diagnosis, patient has never been disease-free. This includes cases with distant metastasis at | 32 | Dead |
| | | 68 | Grade III: Poorly differentiated, d | 01 | 00 | 3C | 0 | 1 | 4 | Since diagnosis, patient has never been disease-free. This includes cases with distant metastasis at | 32 | Dead |
| TB15-216 | N | 69 | Cell type not determined, not state | 12 | 09 | 3C | 1 | 0 | 3C | Distant recurrence of an invasive tumor in multiple sites (recurrences that can be coded to more tha | 85 | Dead |
| | | 69 | Cell type not determined, not state | 12 | 09 | 3C | 1 | 0 | 3C | Distant recurrence of an invasive tumor in multiple sites (recurrences that can be coded to more tha | 85 | Dead |
| | | 69 | Cell type not determined, not state | 12 | 09 | 3C | 1 | 0 | 3C | Distant recurrence of an invasive tumor in multiple sites (recurrences that can be coded to more tha | 85 | Dead |

TABLE 12-continued

Ovarian Cancer

Part 1

| Anon# | Pten-NOLC1 Status | Age at Diagnosis | Grade/Differentiation-Desc | Reg Nodes Exam | Regl Nodes Positive | pT | pN | pM | Path Stg Grp | Type 1st Recurrence | Surv (Months) | Vital Status |
|---|---|---|---|---|---|---|---|---|---|---|---|---|
| | | 69 | Cell type not determined, not state | 12 | 09 | 3C | 1 | 0 | 3C | Distant recurrence of an invasive tumor in multiple sites (recurrences that can be coded to more tha | 85 | Dead |
| | | 69 | Cell type not determined, not state | 12 | 09 | 3C | 1 | 0 | 3C | Distant recurrence of an invasive tumor in multiple sites (recurrences that can be coded to more tha | 85 | Dead |
| | | 69 | Cell type not determined, not state | 12 | 09 | 3C | 1 | 0 | 3C | Distant recurrence of an invasive tumor in multiple sites (recurrences that can be coded to more tha | 85 | Dead |

TABLE 13

Esophagus

| Cancer sample | Pten-NOLC1 status |
|---|---|
| 994,995 TE | N |
| 15995 TE | P |
| 16115 TE | P |
| 18787 TE | N |
| 41791 TE | N |
| 40320 TE | P |
| 40498 TE | P |
| 41081 TE | P |
| 15938 TE | P |
| 16806 TE | P |
| 18734 TE | P |
| 19061 TE | P |
| 43526 TE | P |
| 44636 TE | P |
| 43872 TE | P |
| 43888 TE | P |
| 41285 TE | P |
| 41701 TE | P |
| 41744 TE | P |
| 42709 TE | P |
| 44231 TE | P |
| 44014 TE | P |
| 44267 TE | P |
| 43075 TE | P |
| 40776 TE | P |
| 40371 TE | P |
| 19487 TE | P |
| 40449 TE | P |
| 40107 TE | P |
| 41032 TE | P |
| 11913 TE | N |
| 14020 TE | P |
| 11836 TE | N |
| 13516 TE | P |

TABLE 14

(Glioblastoma)

| Sample | Pten-HOLC1 | area | dx | sex | age at dx | date of de. | survival day |
|---|---|---|---|---|---|---|---|
| 2 | N | fr, r | gbm | f | 43.22466 | 39592 | 250 |
| 5 | P | occ, l | gbm | m | 42.72877 | 38631 | 261 |
| 7 | P | temp, r | gbm | m | 56.28496 | 39639 | 588 |
| 10 | P | fr, l | gbm | m | 47.24932 | 40152 | 642 |
| 11 | N | temp-par, | gbm | m | 45.39726 | 39057 | 677 |
| 12 | P | temp, l | gbm | m | 42.63562 | 42358 | 690 |
| 13 | P | temp, r | gbm | f | 53.13699 | 40024 | 1106 |
| 15 | P | par, r | gbm | f | 44.57534 | 41335 | 2805 |
| 17 | N | x | gbm | f | 77.08496 | 42552 | 2977 |
| 18 | N | x | gbm | f | 65.21096 | 42157 | 398 |
| 19 | N | x | gbm | f | 69.95616 | 39773 | 660 |
| 21 | N | x | gbm, r/r | f | 63.72877 | 40012 | 458 |
| 22 | P | x | gbm | m | 78.35616 | 39626 | 71 |
| 24 | P | x | gbm | m | 56.19726 | 39896 | 315 |
| 27 | N | x | gbm | f | 85.03288 | 39943 | 360 |
| 29 | P | x | gbm | f | 60.35068 | 42552 | 2914 |
| 32 | P | x | gbm | m | 63.48767 | 42131 | 485 |

TABLE 14-continued (Glioblastoma)

| Sample | Pten-HOLC1 | area | dx | sex | age at dx | date of de. | survival day |
|---|---|---|---|---|---|---|---|
| 39 | N | temp, r | gbm | m | 55.30685 | 38280 | 11 |
| 40 | P | occ, r | gbm | f | 69.27945 | 38300 | 362 |
| 46 | P | x | gbm | m | 65.76164 | 38057 | 113 |
| 50 | N | x | gbm | m | 42.80822 | 38041 | 96 |
| 53 | N | temp, r | gbm | f | 61.97534 | 38493 | 373 |
| 54 | N | temp, l | gbm | m | 69.16986 | 38494 | 348 |
| 60 | P | x | gbm | m | 48.31781 | 38493 | 316 |
| 62 | P | x | gbm | m | 43.35616 | 38501 | 236 |
| 65 | P | fr, l | gbm | m | 70.54247 | 38306 | 39 |
| 66 | P | tem-par, l | gbm | m | 64.46301 | 39278 | 1003 |
| 67 | P | x | gbm, r/r | m | 57.19726 | 38445 | 152 |
| 71 | N | temp, l | gbm | m | 53.35616 | 40680 | 2303 |
| 78 | P | par, r | gbm | f | 75.75616 | 39057 | 679 |
| 79 | P | temp, r | gbm | m | 50.99178 | 38830 | 436 |
| 80 | P | x | gbm, r/r | m | 67.80548 | 38475 | 67 |
| 82 | N | x | gbm, r/r | f | 46.44384 | 38543 | 103 |
| 83 | P | par, r | gbm | m | 37.30411 | 39448 | 1007 |
| 84 | P | fr, l | gbm | f | 69.83288 | 38668 | 205 |
| 86 | P | fr, l | gbm | m | 73.86027 | 38977 | 447 |
| 87 | P | par-occ, r | gbm | f | 78.1863 | 38898 | 344 |
| 95 | P | x | gbm | m | 33.4411 | 38922 | 349 |
| 96 | P | x | gbm | f | 78.3589 | 42552 | 3937 |
| 98 | P | x | gbm, r/r | m | 58.12329 | 38798 | 173 |
| 99 | P | temp, l | gbm | m | 65.86849 | 38747 | 108 |
| 100 | P | par, l | gbm | f | 69.53973 | 41122 | 2443 |
| 102 | P | x | gbm | f | 60.40548 | 39363 | 675 |
| 103 | P | temp, l | gbm | f | 75.66027 | 39004 | 302 |
| 104 | P | temp, l | gbm, r/r | m | 64.83014 | 40257 | 1550 |
| 105 | P | fr, l | gbm | f | 62.4411 | 38925 | 188 |
| 106 | P | temp, l | gbm | m | 44.36438 | 39179 | 442 |
| 115 | P | x | gbm | m | 44.4274 | 39313 | 514 |
| 117 | P | x | gbm | m | 52.15342 | 38978 | 96 |
| 119 | P | x | gbm | f | 56.73151 | 39377 | 436 |
| 122 | P | x | gbm | m | 56.77808 | 39076 | 116 |
| 123 | P | x | gbm | m | 75.72055 | 39033 | 73 |
| 124 | P | x | gbm, r/r | m | 55.65479 | 39041 | 74 |
| 125 | P | x | gbm | m | 55.70411 | 39139 | 143 |
| 127 | P | x | gbm | f | 75.72055 | 39352 | 346 |
| 128 | P | x | gbm | f | 43.70137 | 39214 | 208 |
| 131 | P | x | gbm | f | 81.33699 | 39031 | 18 |
| 132 | P | x | gbm | m | 48.61096 | 39180 | 166 |
| 135 | P | x | gbm, r/r | f | 38.23014 | 39735 | 713 |
| 136 | P | x | gbm | m | 78.61644 | 39304 | 281 |
| 137 | P | x | gbm | f | 74.37534 | 39241 | 205 |
| 138 | P | x | gbm, r/r | f | 72.97808 | 39112 | 75 |
| 139 | P | x | gbm | f | 25.93973 | 42552 | 3483 |
| 142 | P | x | gbm | f | 82.20274 | 39269 | 190 |
| 143 | P | x | gbm | m | 72.67671 | 39140 | 36 |
| 146 | P | x | gbm | m | 68.38904 | 39638 | 532 |
| 147 | N | x | gbm | m | 72.6274 | 39332 | 220 |
| 150 | P | x | gbm | f | 75.72055 | 39547 | 428 |
| 154 | P | x | meningiom | f | 32.87123 | 39477 | 357 |
| 159 | P | x | gbm, r/r | m | 60.43014 | 39189 | 69 |
| 160 | P | x | gbm, r/r | f | 63.53151 | 39352 | 161 |
| 165 | P | x | gbm | f | 69.4274 | 39466 | 257 |
| 166 | P | x | gbm | m | 60.32603 | 39728 | 517 |
| 167 | P | x | gbm, r/r | m | 45.72055 | 39498 | 257 |
| 168 | P | x | gbm | m | 61.04658 | 39429 | 167 |
| 170 | P | x | gbm, r/r | f | 58.25753 | 39550 | 262 |
| 172 | N | x | gbm | m | 77.70685 | 39498 | 202 |
| 173 | P | x | gbm, giant | f | 62.86575 | 39394 | 91 |
| 174 | P | x | gbm from | f | 82.0411 | 39925 | 575 |
| 175 | P | x | gbm | m | 58.03836 | 39650 | 286 |
| 176 | P | x | gbm | f | 55.89863 | 39925 | 495 |
| 177 | P | x | gbm | m | 65.11507 | 40198 | 700 |
| 178 | N | x | gbm | m | 80.86575 | 39659 | 149 |
| 179 | P | x | gbm | m | 54.41096 | 39631 | 93 |
| 180 | P | x | gbm, sm c | m | 61.66301 | 40372 | 820 |
| 181 | P | x | gbm | f | 60.57534 | 39565 | 15 |
| 182 | N | x | gbm | f | 44.08219 | 42552 | 2991 |
| 183 | N | x | gbm | f | 51.92055 | 40541 | 940 |
| 184 | N | x | gbm, r/r | m | 61.83562 | 41396 | 1793 |
| 185 | P | x | gbm | m | 58.80822 | 40433 | 830 |
| 186 | N | x | gbm, r/r | f | 60.43288 | 40126 | 516 |
| 187 | N | x | gbm | m | 71.24384 | 39806 | 142 |

TABLE 14-continued (Glioblastoma)

| Sample | Pten-HOLC1 | area | dx | sex | age at dx | date of de. | survival day |
|---|---|---|---|---|---|---|---|
| 188 | P | x | gbm | m | 65.62466 | 39997 | 329 |
| 189 | P | x | gbm | f | 56.66301 | 40510 | 835 |
| 190 | N | x | gbm | m | 55.95342 | 40354 | 669 |
| 191 | P | x | gbm | m | 84.60274 | 39984 | 276 |
| 192 | P | x | gliosarc | f | 71.88493 | 40088 | 365 |
| 193 | N | temp, r | gbm | m | 28.32329 | 41940 | 2163 |
| 194 | N | x | gbm | m | 73.0411 | 40015 | 237 |
| 195 | N | x | gbm | f | 73.74247 | 39838 | 58 |
| 196 | P | x | gbm | m | 80.53425 | 40007 | 180 |
| 197 | P | x | gbm | m | 84.04384 | 40008 | 35 |
| 198 | P | x | gbm | f | 61.06575 | 42049 | 2054 |
| 199 | P | x | gbm | m | 72.20822 | 40087 | 23 |
| 200 | P | x | gbm | m | 51.73425 | 42552 | 2095 |
| 201 | P | x | gbm | m | 58.34521 | 42552 | 2025 |
| 202 | P | x | gbm, r/r | m | 44.24658 | 40831 | 221 |
| 203 | P | x | gbm | f | 53.74795 | 41097 | 459 |
| 204 | N | x | gbm | m | 75.04658 | 40722 | 61 |
| 205 | P | x | gbm | f | 38.71507 | 41336 | 625 |
| 212 | P | x | gbm | m | 49.85205 | 41518 | 768 |
| 219 | P | par, l | aa | f | 60.80274 | 41620 | 344 |
| 220 | P | temp, l | gbm | m | 61.18082 | 41615 | 333 |
| 226 | P | temp, l | gbm | m | 60.32603 | 42552 | 1267 |
| 227 | P | x | gbm, r/r | m | 74.30685 | 41367 | 29 |
| 231 | P | front, l | gbm | m | 89.71507 | 41678 | 32 |
| 233 | P | temp, l | gliosarc | m | 80.50959 | 41733 | 87 |
| 236 | P | par, r | gbm | f | 82.38356 | 41697 | 37 |
| 239 | P | par, l | gbm | f | 58.62466 | 41816 | 146 |
| 241 | P | temp, l | gbm | m | 60.86027 | 42552 | 873 |
| 242 | P | x | gbm | f | 79.13151 | 42000 | 321 |
| 245 | P | temp, r | gbm | f | 54.4411 | 42335 | 657 |
| 250 | P | fr, r | gbm | f | 75.58356 | 41890 | 201 |
| 251 | P | x | gbm | f | 43.48027 | 42552 | 856 |
| 252 | P | x | gbm | m | 59.30959 | 41711 | 10 |
| 253 | P | fr, r | gbm | m | 56.84932 | 42552 | 848 |
| 257 | P | fr, r | gbm | m | 66.87671 | 41788 | 72 |
| 259 | N | fr, l | gbm | m | 56.83562 | 42331 | 607 |
| 260 | P | x | gbm | f | 72.16438 | 42208 | 482 |
| 263 | P | par-occ, r | gbm | f | 50.42466 | 42552 | 821 |
| 264 | P | occ, l | gbm | f | 81.90137 | 41853 | 122 |
| 265 | P | x | gbm | f | 64.53151 | 42552 | 804 |
| 267 | P | x | gbm | m | 58.28767 | 42552 | 791 |
| 268 | P | x | gbm | f | 59.30411 | 42384 | 619 |
| 269 | P | fr, l | gbm | f | 74.08219 | 42177 | 410 |
| 270 | P | fr, l | gbm | m | 57.97534 | 42552 | 784 |
| 284 | P | par, r | gbm | f | 72.99726 | 42058 | 290 |
| 288 | P | fr, l | gbm | f | 72.07671 | 41992 | 192 |
| 293 | P | par, r | gbm | f | 74.63288 | 41880 | 80 |
| 301 | P | x | gbm | m | 87.73973 | 42200 | 383 |
| 303 | P | fr, r | gbm | f | 43.22466 | 39592 | 250 |
| 304 | P | occ, l | gbm | m | 42.72877 | 38631 | 261 |
| 306 | P | temp, r | gbm | m | 56.28493 | 39639 | 588 |
| 310 | P | fr, l | gbm | m | 47.24932 | 40152 | 642 |
| 320 | N | temp-par, | gbm | m | 45.39726 | 39057 | 677 |
| 323 | N | temp, l | gbm | m | 42.63562 | 42358 | 690 |
| 330 | P | temp, r | gbm | f | 53.13699 | 40024 | 1106 |
| 331 | P | par, r | gbm | f | 44.57534 | 41335 | 2805 |
| 332 | P | temp, l | gliosarc | m | 80.50959 | 41733 | 87 |
| 333 | P | par, r | gbm | f | 82.38356 | 41697 | 135 |

TABLE 15

| Ingenuity Canonical Pathways | −log10(p-value) | −log10(B-H) p-va | Ratio |
|---|---|---|---|
| Role NFAT in Cardiac Hypertrophy | 10.7 | 7.93 | 0.374 |
| Molecular Mechanisms of Cancer | 8.21 | 5.85 | 0.292 |
| GNRH Signaling | 8.1 | 5.85 | 0.386 |
| Axonal Guidance Signaling | 6.89 | 4.84 | 0.27 |
| HGF Signaling | 6.86 | 4.84 | 0.377 |
| Protein Kinase A Signaling | 6.67 | 4.72 | 0.276 |
| Renin-Angiotensin Signaling | 6.03 | 4.16 | 0.355 |
| PTEN Signaling | 5.39 | 3.57 | 0.345 |
| CREB Signaling in Neurons | 5.25 | 3.49 | 0.306 |

TABLE 15-continued

| Ingenuity Canonical Pathways | −log10(p-value) | −log10(B-H) p-va | Ratio |
|---|---|---|---|
| Ephrin Receptor Signaling | 5.1 | 3.38 | 0.308 |
| G Beta Gamma Signaling | 4.89 | 3.23 | 0.364 |
| RANK Signaling in Osetoclasts | 4.87 | 3.23 | 0.35 |
| Cardiac Hypertrophy Signaling | 4.81 | 3.22 | 0.283 |
| α-Adrenergic Signaling | 4.79 | 3.22 | 0.365 |
| Dopamine-DARPP32 Feedback in cAMP Signaling | 4.77 | 3.22 | 0.308 |
| FGF Signaling | 4.67 | 3.15 | 0.356 |
| NGF Signaling | 4.59 | 3.12 | 0.328 |
| Glioma Signaling | 4.57 | 3.12 | 0.333 |
| Corticotropin Releasing Hormone Signaling | 4.56 | 3.12 | 0.336 |
| P2Y Purigenic Receptor Signaling Pathway | 4.54 | 3.12 | 0.318 |
| Nitric Oxide Signaling in the Cardiovascular System | 4.46 | 3.06 | 0.333 |
| Integrin Signaling | 4.43 | 3.05 | 0.283 |
| ErbB Signaling | 4.34 | 2.98 | 0.34 |
| fMLP Signaling in Neutrophils | 4.32 | 2.97 | 0.32 |
| Neuropathic Pain Signaling in Dorsal Horn Neurons | 4.29 | 2.96 | 0.325 |
| CDK5 Signaling | 4.24 | 2.94 | 0.337 |
| IL-3 Signaling | 4.13 | 2.85 | 0.349 |
| NF-κB Activation by Viruses | 4.13 | 2.85 | 0.345 |
| Rac Signaling | 4.11 | 2.84 | 0.319 |
| EGF Signaling | 4.05 | 2.8 | 0.368 |
| IL-1 Signaling | 4.03 | 2.8 | 0.337 |
| Regulation of the Epithelial-Mesenchymal Transition | 4 | 2.8 | 0.283 |
| B Cell Receptor Signaling | 4 | 2.8 | 0.283 |
| Thrombin Signaling | 3.97 | 2.78 | 0.279 |
| Synaptic Long Term Potentiation | 3.93 | 2.77 | 0.314 |
| Non-Small Cell Lung Cancer Signaling | 9.92 | 2.77 | 0.351 |
| p70S6K Signaling | 3.92 | 2.77 | 0.305 |
| Erythropoietin Signaling | 3.92 | 2.77 | 0.346 |
| ERK/MAPK Signaling | 3.88 | 2.75 | 0.278 |
| Tec Kinase Signaling | 3.78 | 2.66 | 0.286 |
| LPS-stimulated MAPK Signaling | 3.72 | 2.61 | 0.333 |
| Growth Hormone Signaling | 3.71 | 2.61 | 0.337 |
| AMPK Signaling | 3.63 | 2.55 | 0.272 |
| Breast Cancer Regulation by Stathmin1 | 3.63 | 2.55 | 0.272 |
| HER-2 Signaling in Breast Cancer | 3.62 | 2.55 | 0.33 |
| IGF-1 Signaling | 3.51 | 2.45 | 0.311 |
| PPARα/RXRα Activation | 3.48 | 2.43 | 0.28 |
| FAK Signaling | 3.47 | 2.43 | 0.316 |
| nNOS Signaling in Neurons | 3.46 | 2.43 | 0.391 |
| HIPPO signaling | 3.42 | 2.41 | 0.326 |
| Relaxin Signaling | 3.42 | 2.41 | 0.285 |
| FLT3 Signaling in Hematopoeitic Progenitor Cells | 3.41 | 2.41 | 0.329 |
| Chronic Myeloid Leukemia Signaling | 3.41 | 2.41 | 0.311 |
| ErbB4 Signaling | 3.38 | 2.39 | 0.343 |
| Production of Nitric Oxide and Reactive Oxygen Sp | 3.35 | 2.37 | 0.269 |
| Huntingon's Disease Signaling | 3.34 | 2.36 | 0.258 |
| Calcium Signaling | 3.29 | 2.33 | 0.275 |
| Gap Junction Signaling | 3.26 | 2.3 | 0.275 |
| UVA-induced MAPK Signaling | 3.24 | 2.29 | 0.305 |
| Role of Osteoblasts, Osteoclasts, and Chondrocytes | 3.23 | 2.28 | 0.259 |
| Melanocyte Development and Pigmentation Signali | 3.19 | 2.26 | 0.309 |
| Colorectal Cancer Metastasis Signaling | 3.19 | 2.26 | 0.255 |
| CNTF Signaling | 3.17 | 2.24 | 0.35 |
| Virus Entry via Endocytic Pathways | 3.14 | 2.23 | 0.304 |
| Small Cell Lung Cancer Signaling | 3.13 | 2.23 | 0.318 |
| GPCR-Mediated Nutrient Sensing in Enteroendocri | 3.13 | 2.23 | 0.318 |
| Role of Tissue Factor in Cancer | 3.1 | 2.21 | 0.292 |
| Angiopoietin Signaling | 3.1 | 2.21 | 0.325 |
| Oncostatin M Signaling | 3.07 | 2.19 | 0.412 |
| PDGF Signaling | 3.07 | 2.19 | 0.311 |
| Thrombopoietin Signaling | 3.06 | 2.19 | 0.338 |
| Superpathway of Inositol Phosphate Compounds | 3.04 | 2.17 | 0.256 |
| Telomerase Signaling | 3.01 | 2.15 | 0.296 |
| G-Protein Coupled Receptor Signaling | 3 | 2.15 | 0.247 |
| Cellular Effects of Sildenafil (Viagra) | 2.99 | 2.15 | 0.286 |
| BMP signaling pathway | 2.99 | 2.15 | 0.324 |
| Prolactin Signaling | 2.94 | 2.11 | 0.313 |
| IL-8 Signaling | 2.93 | 2.11 | 0.26 |
| Phospholipase C Signaling | 2.93 | 2.11 | 0.252 |
| Pancreatic Adenocarcinoma Signaling | 2.93 | 2.11 | 0.288 |
| RAR Activation | 2.91 | 2.09 | 0.262 |
| P13K/AKT Signaling | 2.89 | 2.08 | 0.285 |
| IL-17 Signaling | 2.77 | 1.97 | 0.306 |
| Leptin Signaling in Obesity | 2.77 | 1.97 | 0.306 |
| Renal Cell Carcinoma Signaling | 2.75 | 1.95 | 0.309 |
| Role of NFAT in Regulation of the Immune Response | 2.73 | 1.94 | 0.26 |
| 14-3-3-mediated Signaling | 2.73 | 1.94 | 0.277 |

TABLE 15-continued

| Ingenuity Canonical Pathways | −log10(p-value) | −log10(B-H) p-va | Ratio |
|---|---|---|---|
| Role of Macrophages, Fibroblasts and Endothelial ( | 2.72 | 1.94 | 0.238 |
| Type II Diabetes Mellitus Signaling | 2.69 | 1.92 | 0.278 |
| Basal Cell Carcinoma Signaling | 2.68 | 1.91 | 0.319 |
| ERK5 Signaling | 2.66 | 1.9 | 0.313 |
| Cardiac β-adrenergic Signaling | 2.64 | 1.89 | 0.272 |
| NF-κB Signaling | 2.64 | 1.89 | 0.258 |
| CXCR4 | 2.63 | 1.89 | 0.262 |
| Role of PKR in Interferon Induction and Antiviral Re | 2.63 | 1.89 | 0.366 |
| Chondroitin Sulfate Biosynthesis | 2.63 | 1.89 | 0.34 |
| Wnt/β-catenin Signaling | 2.61 | 1.88 | 0.26 |
| PEDF Signaling | 2.61 | 1.88 | 0.299 |
| Melatonin Signaling | 2.59 | 1.87 | 0.314 |
| Insulin Receptor Signaling | 2.58 | 1.86 | 0.27 |
| UVB-Induced MAPK Signaling | 2.57 | 1.85 | 0.318 |
| Paxillin Signaling | 2.55 | 1.84 | 0.282 |
| eNOS Signaling | 2.54 | 1.83 | 0.261 |
| VEGF Family Ligand-Receptor Interactions | 2.54 | 1.83 | 0.295 |
| Epithelial Adherens Junction Signaling | 2.5 | 1.8 | 0.266 |
| Ceramide Signaling | 2.49 | 1.8 | 0.29 |
| Mitotic Roles of Polo-Like Kinase | 2.46 | 1.77 | 0.317 |
| IL-15 Signaling | 2.45 | 1.76 | 0.303 |
| Dermatan Sulfate Biosynthesis | 2.43 | 1.75 | 0.327 |
| Folate Polyglutamylation | 2.42 | 1.75 | 0.6 |
| Xenobiotic Metabolism Signaling | 2.42 | 1.75 | 0.237 |
| Glucocorticoid Receptor Signaling | 2.42 | 1.74 | 0.235 |
| CCR3 Signaling in Eosinophils | 2.41 | 1.74 | 0.27 |
| PI3K Signaling in B Lymphocytes | 2.41 | 1.74 | 0.27 |
| April Mediated Signaling | 2.4 | 1.74 | 0.359 |
| CDP-diacylglycerol Biosynthesis I | 2.38 | 1.72 | 0.417 |
| Cyclins and Cell Cycle Regulation | 2.37 | 1.72 | 0.299 |
| Germ Cell-Sertoli Cell Junction Signaling | 2.37 | 1.72 | 0.254 |
| Neuregulin Signaling | 2.36 | 1.71 | 0.291 |
| IL-4 Signaling | 2.36 | 1.71 | 0.291 |
| IL-6 Signaling | 2.29 | 1.65 | 0.266 |
| STAT3 Pathway | 2.27 | 1.63 | 0.297 |
| Sphingosine-1-phosphate Signaling | 2.26 | 1.62 | 0.266 |
| Regulation of IL-2 Expression in Activated and Anei | 2.22 | 1.59 | 0.291 |
| Natural Killer Cell Signaling | 2.22 | 1.59 | 0.267 |
| Chondroitin Sulfate Biosynthesis (Late Stages) | 2.19 | 1.57 | 0.333 |
| mTOR Signaling | 2.19 | 1.57 | 0.244 |
| B Cell Activating Factor Signaling | 2.18 | 1.57 | 0.341 |
| Glioblastoma Multiforme Signaling | 2.16 | 1.56 | 0.252 |
| Gaq Signaling | 2.16 | 1.55 | 0.252 |
| Human Embryonic Stem Cell Pluripotency | 2.15 | 1.55 | 0.257 |
| 3-phosphoinositide Biosynthesis | 2.15 | 1.55 | 0.244 |
| Factors Promoting Cardiogenesis in Vertebrates | 2.15 | 1.55 | 0.281 |
| Apoptosis Signaling | 2.15 | 1.55 | 0.281 |
| CCR5 Signaling in Macrophages | 2.13 | 1.54 | 0.299 |
| Lymphotoxin β Receptor Signaling | 2.13 | 1.54 | 0.299 |
| Prostate Cancer Signaling | 2.12 | 1.54 | 0.277 |
| D-myc-inositol-5-phosphate Metabolism | 2.12 | 1.54 | 0.252 |
| Amyloid Processing | 2.11 | 1.53 | 0.32 |
| Synaptic Long Term Depression | 2.1 | 1.53 | 0.255 |
| Phosphatidylglycerol Biosynthesis II (Non-plastidic) | 2.09 | 1.51 | 0.385 |
| GPCR-Mediated Integration of Enteroendocrine Sig | 2.08 | 1.51 | 0.292 |
| Estrogen-Dependent Breast Cancer Signaling | 2.05 | 1.48 | 0.286 |
| VEGF Signaling | 2.03 | 1.47 | 0.27 |
| Endothelin-1 Signaling | 2.03 | 1.47 | 0.242 |
| Fc Epsilon RI Signaling | 2.01 | 1.46 | 0.261 |
| Actin Cytoskeleton Signaling | 2.01 | 1.46 | 0.235 |
| Mouse Embryonic Stem Cell Pluripotency | 2.01 | 1.46 | 0.267 |
| Chondroitin and Dermatan Biosynthesis | 2.01 | 1.46 | 0.667 |
| Ovarian Cancer Signaling | 2 | 1.46 | 0.252 |
| TGF-β Signaling | 1.98 | 1.44 | 0.276 |
| IL-17A Signaling in Airway Cells | 1.98 | 1.44 | 0.282 |
| Cholecystokinin/Gastrin-mediated Signaling | 1.97 | 1.44 | 0.267 |
| Netrin Signaling | 1.96 | 1.43 | 0.333 |
| Role of NANOG in Mammalian Embryonic Stem Ce | 1.96 | 1.43 | 0.258 |
| Sertoli Cell-Sertoli Cell Junction Signaling | 1.96 | 1.43 | 0.243 |
| D-myo-inositol (1,4,5)-Trisphosphate Biosynthesis | 1.96 | 1.43 | 0.37 |
| JAK/Stat Signaling | 1.95 | 1.42 | 0.277 |
| p53 Signaling | 1.94 | 1.42 | 0.261 |
| TNFR1 Signaling | 1.91 | 1.39 | 0.312 |
| Myo Mediated Apoptosis Signaling | 1.91 | 1.39 | 0.286 |
| CTLA4 Signaling in Cytotoxic T Lymphocytes | 1.88 | 1.36 | 0.265 |
| SAPK/JNK Signaling | 1.86 | 1.35 | 0.262 |
| IL-22 Signaling | 1.84 | 1.34 | 0.375 |
| T Cell Receptor Signaling | 1.84 | 1.34 | 0.259 |

TABLE 15-continued

| Ingenuity Canonical Pathways | −log10(p-value) | −log10(B-H) p-va | Ratio |
|---|---|---|---|
| Macropinocytosis Signaling | 1.78 | 1.28 | 0.272 |
| Uracil Degradation II (Reductive) | 1.75 | 1.25 | 0.75 |
| Thymine Degradation | 1.75 | 1.25 | 0.75 |
| Chemokine Signaling | 1.73 | 1.24 | 0.279 |
| Gαi Signaling | 1.72 | 1.23 | 0.25 |
| GM-CSF Signaling | 1.71 | 1.22 | 0.274 |
| Bladder Cancer Signaling | 1.7 | 1.21 | 0.264 |
| Reelin Signaling in Neurons | 1.69 | 1.21 | 0.261 |
| Acute Myeloid Leukemia Signaling | 1.69 | 1.21 | 0.261 |
| CD40 Signaling | 1.68 | 1.21 | 0.269 |
| cAMP-mediated signaling | 1.68 | 1.21 | 0.227 |
| nNOS Signaling in Skeletal Muscle Cells | 1.66 | 1.18 | 0.429 |
| Leukocyte Extravasation Signaling | 1.64 | 1.17 | 0.228 |
| 3-phosphoinositide Degradation | 1.64 | 1.17 | 0.238 |
| Heparan Sulfate Biosynthesis | 1.63 | 1.16 | 0.277 |
| Glutamate Receptor Signaling | 1.63 | 1.16 | 0.286 |
| D-myo-inositol (1,4,5,)-triphosphate Degradation | 1.62 | 1.15 | 0.389 |
| UVC-Induced MAPK Signaling | 1.6 | 1.14 | 0.302 |
| ILK Signaling | 1.6 | 1.14 | 0.229 |
| Aldosterone Signaling in Epithelial Cells | 1.6 | 1.14 | 0.234 |
| CD27 Signaling in Lymphocytes | 1.59 | 1.14 | 0.288 |
| PKCΘ Signaling in T Lymphocytes | 1.57 | 1.12 | 0.242 |
| tRNA Splicing | 1.57 | 1.12 | 0.308 |
| Wnt/Ca+ pathway | 1.56 | 1.11 | 0.281 |
| Cell Cycle Regulation by BTG Family Proteins | 1.54 | 1.1 | 0.314 |
| GDP-L-fucose Biosynthesis I (from GDP-D-mannos | 1.53 | 1.09 | 1 |
| Neurotrophin/TRK Signaling | 1.52 | 1.09 | 0.263 |
| G Protein Signaling Mediated by Tubby | 1.52 | 1.08 | 0.323 |
| Agrin Interactions at Neuromuscular Junction | 1.5 | 1.07 | 0.269 |
| Androgen Signaling | 1.5 | 1.07 | 0.245 |
| Sperm Motility | 1.49 | 1.06 | 0.242 |
| Heparan Sulfate Biosynthesis (Late Stages) | 1.49 | 1.06 | 0.276 |
| Signaling by Rho Family GTPases | 1.47 | 1.05 | 0.219 |
| Histidine Degradation III | 1.47 | 1.04 | 0.5 |
| Cell Cycle: G1/S Checkpoint Regulation | 1.46 | 1.04 | 0.27 |
| HIF1α Signaling | 1.45 | 1.03 | 0.241 |
| IL-9 Signaling | 1.44 | 1.03 | 0.289 |
| GABA Receptor Signaling | 1.44 | 1.03 | 0.265 |
| Hereditary Breast Cancer Signaling | 1.44 | 1.03 | 0.234 |
| Inhibition of Angiogenesis by TSP1 | 1.43 | 1.02 | 0.312 |
| Myo-inositol Biosynthesis | 1.41 | 1 | 0.6 |
| Role of IL-17F in Allergic Inflammatory Airway Dise | 1.41 | 1 | 0.293 |
| Endometrial Cancer Signaling | 1.4 | 1 | 0.266 |
| Pyridoxal 5'-phosphate Salvage Pathway | 1.4 | 1 | 0.266 |
| Fcγ Receptor-mediated Phagocytosis in Macrophag | 1.39 | 0.985 | 0.247 |
| Melanoma Signaling | 1.38 | 0.985 | 0.273 |
| Role of JAK1, JAK2, and TYK2 in Interferon Signalir | 1.38 | 0.982 | 0.333 |
| Hepatic Cholestasis | 1.37 | 0.975 | 0.228 |
| DNA Methylation and Transcriptional Repression Si | 1.36 | 0.973 | 0.35 |
| Extrinsic Prothrombin Activation Pathway | 1.36 | 0.973 | 0.375 |
| Osteoarthritis Pathway | 1.34 | 0.949 | 0.22 |
| Dermatan Sulfate Biosynthesis (Late Stages) | 1.33 | 0.947 | 0.286 |
| p38 MAPK Signaling | 1.32 | 0.94 | 0.235 |
| Sonic Hedgehog Signaling | 1.31 | 0.926 | 0.31 |
| Amyotrophic Lateral Sclerosis Signaling | 1.28 | 0.904 | 0.236 |
| Role of JAK family kinases in IL-6-type Cytokine Sig | 1.28 | 0.903 | 0.32 |
| Docosahexaenoic Acid (DHA) Signaling | 1.28 | 0.903 | 0.269 |
| GDNF Family Ligand-Receptor Interactions | 1.27 | 0.895 | 0.25 |
| Dopamine Receptor Signaling | 1.27 | 0.895 | 0.25 |
| Phagosome Formation | 1.24 | 0.873 | 0.233 |
| RhoGDI Signaling | 1.24 | 0.872 | 0.221 |
| FcγRIIB Signaling in B Lymphocytes | 1.22 | 0.851 | 0.264 |
| D-myo-inositol (1,4,5,6)-Tetrakisphosphate Biosynt | 1.21 | 0.85 | 0.226 |
| D-myo-inositol (3,4,5,6)-tetrakisphosphate Biosynth | 1.21 | 0.85 | 0.226 |
| Adipogenesis pathway | 1.21 | 0.849 | 0.227 |
| CD28 Signaling in T Helper Cells | 1.21 | 0.848 | 0.228 |
| PPAR Signaling | 1.2 | 0.848 | 0.239 |
| iNOS Signaling | 1.2 | 0.84 | 0.273 |
| PXR/RXR Activation | 1.19 | 0.837 | 0.254 |
| Cancer Drug Resistance By Drug Efflux | 1.17 | 0.823 | 0.265 |
| Regulation of eIF4 and p70S6K Signaling | 1.16 | 0.807 | 0.221 |
| Role of IL-17A in Arthritis | 1.13 | 0.783 | 0.246 |
| Salvage Pathways of Pyrimidine Ribonucleotides | 1.12 | 0.773 | 0.234 |
| Assembly of RNA Polymerase II Complex | 1.11 | 0.771 | 0.26 |
| D-glucuronate Degradation I | 1.1 | 0.764 | 0.667 |
| Thyroid Hormone Biosynthesis | 1.1 | 0.764 | 0.667 |
| Calcium-induced T Lymphocyte Apoptosis | 1.09 | 0.757 | 0.25 |
| Ephrin A Signaling | 1.09 | 0.757 | 0.25 |

TABLE 15-continued

| Ingenuity Canonical Pathways | −log10(p-value) | −log10(B-H) p-va | Ratio |
|---|---|---|---|
| Glioma Invasiveness Signaling | 1.08 | 0.748 | 0.243 |
| PAK Signaling | 1.08 | 0.748 | 0.23 |
| Toll-like Receptor Signaling | 1.08 | 0.748 | 0.24 |
| 4-1BB Signaling in T Lymphocytes | 1.07 | 0.738 | 0.281 |
| Actin Nucleation by ARP-WASP Complex | 1.05 | 0.721 | 0.25 |
| Notch Signaling | 1.04 | 0.716 | 0.27 |
| Role of PI3K/AKT Signaling in the Pathogenesis of | 1.03 | 0.71 | 0.237 |
| 1D-myo-inositol Hexakisphosphate Biosynthesis II( | 1.03 | 0.708 | 0.316 |
| Death Receptor Signaling | 0.997 | 0.676 | 0.228 |
| Ceramide Biosynthesis | 0.985 | 0.666 | 0.429 |
| Superpathway of D-myo-inositol (1,4,5)-trisphosoha | 0.983 | 0.665 | 0.292 |
| UDP-N-acetyl-D-galactosamine Biosynthesis II | 0.979 | 0.663 | 0.364 |
| Hepatic Fibrosis/Hepatic Stellate Cell Activation | 0.975 | 0.661 | 0.21 |
| TR/RXR Activation | 0.963 | 0.651 | 0.224 |
| Ephrin B Signaling | 0.948 | 0.637 | 0.233 |
| TWEAK Signaling | 0.932 | 0.623 | 0.265 |
| Thyroid Cancer Signaling | 0.919 | 0.612 | 0.256 |
| IL-17A Signaling in Gastric Cells | 0.906 | 0.601 | 0.28 |
| IL-10 Signaling | 0.904 | 0.601 | 0.232 |
| Role of JAK1 and JAK3 in yc Cytokine Signaling | 0.904 | 0.601 | 0.232 |
| IL-2 Signaling | 0.902 | 0.601 | 0.234 |
| Parkinson's Signaling | 0.9 | 0.601 | 0.312 |
| NRF2-mediated Oxidative Stress Response | 0.881 | 0.583 | 0.205 |
| IL-17A Signaling in Fibroblasts | 0.871 | 0.575 | 0.257 |
| Role of CHK Proteins in Cell Cycle Checkpoint Con | 0.856 | 0.564 | 0.236 |
| Pentose Phosphate Pathway (Oxidative Branch) | 0.856 | 0.564 | 0.5 |
| N-acetylglucosamine Degradation II | 0.856 | 0.564 | 0.5 |
| Sumoylation Pathway | 0.852 | 0.562 | 0.219 |
| Regulation of Actin-based Motility by Rho | 0.839 | 0.551 | 0.221 |
| IL-12 Signaling and Production in Macrophages | 0.831 | 0.544 | 0.208 |
| Caveolar-mediated Endocytosis Signaling | 0.823 | 0.538 | 0.225 |
| Clathrin-mediated Endocytosis Signaling | 0.819 | 0.536 | 0.202 |
| Activation of IRF by Cytosolic Pattern Recognition F | 0.814 | 0.533 | 0.23 |
| Mechanisms of Viral Exit from Host Cells | 0.81 | 0.53 | 0.244 |
| Semaphorin Signaling in Neurons | 0.765 | 0.499 | 0.231 |
| Histidine Degradation VI | 0.764 | 0.499 | 0.308 |
| Methylthiopropionate Biosynthesis | 0.764 | 0.499 | 1 |
| S-methyl-5'-thioadenosine Degradation II | 0.764 | 0.499 | 1 |
| Thiamin Salvage III | 0.764 | 0.499 | 1 |
| Methylglyoxal Degradation VI | 0.764 | 0.499 | 1 |
| L-cysteine Degradation II | 0.764 | 0.499 | 1 |
| Adenine and Adenosine Salvage VI | 0.764 | 0.499 | 1 |
| Phosphatidylethanolamine Biosynthesis III | 0.764 | 0.499 | 1 |
| Role of JAK2 in Hormone-like Cytokine Signaling | 0.763 | 0.499 | 0.25 |
| Gα12/13 Signaling | 0.751 | 0.488 | 0.206 |
| Acute Phase Response Signaling | 0.742 | 0.481 | 0.201 |
| ErbB2-ErbB3 Signaling | 0.741 | 0.481 | 0.221 |
| Valine Degradation I | 0.733 | 0.474 | 0.278 |
| Leucine Degradation I | 0.719 | 0.463 | 0.333 |
| Folate Transformations I | 0.719 | 0.463 | 0.333 |
| IL-15 Production | 0.711 | 0.457 | 0.25 |
| Gustation Pathway | 0.706 | 0.453 | 0.205 |
| Estrogen Receptor Signaling | 0.69 | 0.439 | 0.203 |
| Creatine-phosphate Biosynthesis | 0.685 | 0.439 | 0.4 |
| Tetrahydrofolate Salvage from 5,10-methenyltetrah | 0.685 | 0.439 | 0.4 |
| CMP-N-acetylneuraminate Biosynthesis I (Eukaryo | 0.685 | 0.439 | 0.4 |
| dTMP De Novo Biosynthesis | 0.685 | 0.439 | 0.4 |
| Triacylglycerol Biosynthesis | 0.668 | 0.424 | 0.227 |
| D-myo-inositol (1,3,4)-triphosphate Biosynthesis | 0.662 | 0.421 | 0.263 |
| DNA damage-induced 14-3-3σSignaling | 0.662 | 0.421 | 0.263 |
| TNFR2 Signaling | 0.656 | 0.416 | 0.241 |
| Gas Signaling | 0.65 | 0.412 | 0.204 |
| Regulation of Cellular Mechanics by Calpain Protea | 0.643 | 0.407 | 0.218 |
| Assembly of RNA Polymerase I Complex | 0.62 | 0.386 | 0.3 |
| Calcium Transport I | 0.62 | 0.386 | 0.3 |
| HMGB1 Signaling | 0.617 | 0.385 | 0.198 |
| Coagulation System | 0.611 | 0.38 | 0.229 |
| Antiproliferative Role of Somatostatin Receptor 2 | 0.605 | 0.377 | 0.208 |
| Hypoxia Signaling in the Cardiovascular System | 0.605 | 0.377 | 0.208 |
| Role of BRCA1 in DNA Damage Response | 0.596 | 0.359 | 0.205 |
| Pyrimidine Ribonucleotides Interconversion | 0.577 | 0.351 | 0.22 |
| Selenocysteine Biosynthesis II (Archaea and Eukar | 0.559 | 0.336 | 0.333 |
| Purine Ribonucleosides Degradation to Ribose-1-pl | 0.559 | 0.336 | 0.333 |
| ATM Signaling | 0.558 | 0.336 | 0.203 |
| Cysteine Biosynthesis III (mammalia) | 0.541 | 0.325 | 0.238 |
| iCOS-iCOSL Signaling in T Helper Cells | 0.54 | 0.325 | 0.195 |
| Role of RIG1-like Receptors in Antiviral Innate Imm | 0.538 | 0.325 | 0.214 |
| Role of p14/p19ARF in Tumor Suppression | 0.538 | 0.325 | 0.214 |

TABLE 15-continued

| Ingenuity Canonical Pathways | −log10(p-value) | −log10(B-H) p-va | Ratio |
| --- | --- | --- | --- |
| Glycogen Degradation II | 0.537 | 0.325 | 0.273 |
| Purine Nucleotides De Novo Biosynthesis II | 0.537 | 0.325 | 0.273 |
| Granzyme B Signaling | 0.536 | 0.325 | 0.25 |
| Mismatch Repair in Eukaryotes | 0.536 | 0.325 | 0.25 |
| Nur77 Signaling in T Lymphocytes | 0.527 | 0.318 | 0.208 |
| Retinoic acid Mediated Apoptosis Signaling | 0.509 | 0.313 | 0.203 |
| TREM1 Signaling | 0.505 | 0.313 | 0.2 |
| Role of MAPK Signaling in the Pathogenesis of Infl | 0.505 | 0.313 | 0.2 |
| UDP-D-xylose and UDP-D-glucuronate Biosynthesi | 0.502 | 0.313 | 0.5 |
| Dolichol and Dolichyl Phosphate Biosynthesis | 0.502 | 0.313 | 0.5 |
| Epoxysqualene Biosynthesis | 0.502 | 0.313 | 0.5 |
| Spermine Biosynthesis | 0.502 | 0.313 | 0.5 |
| L-DOPA Degradation | 0.502 | 0.313 | 0.5 |
| Taurine Biosynthesis | 0.502 | 0.313 | 0.5 |
| Spermidine Biosynthesis I | 0.502 | 0.313 | 0.5 |
| Anandamide Degradation | 0.502 | 0.313 | 0.5 |
| Glycine Degradation (Creatine Biosynthesis) | 0.502 | 0.313 | 0.5 |
| Cysteine Biosynthesis/Homocysteine Degradation | 0.502 | 0.313 | 0.5 |
| Putrescine Biosynthesis III | 0.502 | 0.313 | 0.5 |
| Glycine Biosynthesis I | 0.502 | 0.313 | 0.5 |
| Pyrimidine ribonucleotides De Novo Biosynthesis | 0.501 | 0.313 | 0.209 |
| Unfolded protein response | 0.495 | 0.308 | 0.204 |
| Circadian Rhythm Signaling | 0.473 | 0.287 | 0.212 |
| BER pathway | 0.466 | 0.282 | 0.25 |
| Superpathway of Serine and Glycine Biosynthesis I | 0.462 | 0.282 | 0.286 |
| Thioredoxin Pathway | 0.462 | 0.282 | 0.286 |
| Phosphatidylcholine Biosynthesis I | 0.462 | 0.282 | 0.286 |
| Glycoaminoglycan-protein Linkage Region Biosyntl | 0.462 | 0.282 | 0.286 |
| Dendritic Cell Maturation | 0.454 | 0.275 | 0.185 |
| Role of Wnt/GSK-3β Signaling in the Pathogenesis | 0.428 | 0.251 | 0.192 |
| Chondroitin Sulfate Degradation (Metazoa) | 0.406 | 0.232 | 0.231 |
| Choline Biosynthesis III | 0.406 | 0.232 | 0.231 |
| Glycogen Degradation III | 0.406 | 0.232 | 0.231 |
| Tumoricidal Function of Hepatic Natural Killer Cells | 0.4 | 0.229 | 0.208 |
| Estrogen-mediated S-phase Entry | 0.4 | 0.229 | 0.208 |
| Role of Pattern Recognition Receptors in Recogniti | 0.396 | 0.226 | 0.183 |
| Sucrose Degradation V (Mammalian) | 0.385 | 0.219 | 0.25 |
| Phosphatidylethanolamine Biosynthesis II | 0.385 | 0.219 | 0.25 |
| GDP-glucose Biosynthesis | 0.385 | 0.219 | 0.25 |
| Tight Junction Signaling | 0.383 | 0.217 | 0.181 |
| Cardiomyocyte Differentiation via BMP Receptors | 0.379 | 0.217 | 0.211 |
| Methionine Degradation I (to Homocysteine) | 0.379 | 0.217 | 0.211 |
| PCP pathway | 0.375 | 0.217 | 0.188 |
| Protein Ubiquitination Pathway | 0.374 | 0.217 | 0.178 |
| Diphthamide Biosynthesis | 0.364 | 0.217 | 0.333 |
| S-methyl-5-thio-α-D-ribose 1-phosphate Degradatio | 0.364 | 0.217 | 0.333 |
| Glutathione Biosynthesis | 0.364 | 0.217 | 0.333 |
| Tetrahydrobiopterin Biosynthesis I | 0.364 | 0.217 | 0.333 |
| Inosine-5′-phosphate Biosynthesis II | 0.364 | 0.217 | 0.333 |
| Glycerol-3-phosphate Shuttle | 0.364 | 0.217 | 0.333 |
| 1D-myo-inositol Hexakisphosphate Biosynthesis V | 0.364 | 0.217 | 0.333 |
| Oxidized GTP and dGTP Detoxification | 0.364 | 0.217 | 0.333 |
| Tetrahydrobiopterin Biosynthesis II | 0.364 | 0.217 | 0.333 |
| S-adenosyl-L-methionine Biosynthesis | 0.364 | 0.217 | 0.333 |
| N-acetylglucosamine Degradation I | 0.364 | 0.217 | 0.333 |
| Serotonin Receptor Signaling | 0.359 | 0.213 | 0.19 |
| DNA Double-Strand Break Repair by Homologous | 0.354 | 0.213 | 0.214 |
| DNA Double-Strand Break Repair by Non-Homolog | 0.354 | 0.213 | 0.214 |
| Isoleucine Degradation I | 0.354 | 0.213 | 0.214 |
| Colanic Acid Building Blocks Biosynthesis | 0.354 | 0.213 | 0.214 |
| VDR/RXR Activation | 0.341 | 0.2 | 0.182 |
| Maturity Onset Diabetes of Young (MODY) Signaling | 0.338 | 0.198 | 0.2 |
| Cdc42 Signaling | 0.336 | 0.198 | 0.178 |
| Antiproliferative Role of TOB in T Cell Signaling | 0.327 | 0.192 | 0.192 |
| Cell Cycle: G2/M DNA Damage Checkpoint Regula | 0.325 | 0.192 | 0.184 |
| Sphingosine and Sphingosine-1-phosphate Metabo | 0.323 | 0.192 | 0.222 |
| Glucose and Glucose-1-phosphate Degradation | 0.323 | 0.192 | 0.222 |
| Prostanoid Biosynthesis | 0.323 | 0.192 | 0.222 |
| Heme Biosynthesis II | 0.323 | 0.192 | 0.222 |
| Th1 Pathway | 0.321 | 0.191 | 0.177 |
| Type I Diabetes Mellitus Signaling | 0.319 | 0.19 | 0.178 |
| Histamine Degradation | 0.309 | 0.182 | 0.2 |
| Vitamin-C Transport | 0.309 | 0.182 | 0.2 |
| Endoplasmic Reticulum Stress Pathway | 0.301 | 0.175 | 0.19 |
| Heme Degradation | 0.276 | 0.158 | 0.25 |
| Branched-chain α-keto acid Dehydrogenase Compl | 0.276 | 0.158 | 0.25 |
| Heme Biosynthesis from Uroporphyrinogen-III I | 0.276 | 0.158 | 0.25 |
| Spermine and Spermidine Degradation I | 0.276 | 0.158 | 0.25 |

TABLE 15-continued

| Ingenuity Canonical Pathways | −log10(p-value) | −log10(B-H) p-va | Ratio |
|---|---|---|---|
| Trans, trans-farnesyl Diphosphate Biosynthesis | 0.276 | 0.158 | 0.25 |
| L-cysteine Degradation I | 0.276 | 0.158 | 0.25 |
| Phenylalanine Degradation I (Aerobic) | 0.276 | 0.158 | 0.25 |
| Oleate Biosynthesis II (Animals) | 0.272 | 0.158 | 0.2 |
| NAD Phosphorylation and Dephosphorylation | 0.272 | 0.158 | 0.2 |
| Pentose Phosphate Pathway | 0.272 | 0.158 | 0.2 |
| Pregnenolone Biosynthesis | 0.272 | 0.158 | 0.2 |
| Superpathway of Methionine Degradation | 0.265 | 0.153 | 0.176 |
| Cell Cycle Control of Chromosomal Replication | 0.263 | 0.153 | 0.175 |
| Transcriptional Regulatory Network in Embryonic S | 0.263 | 0.153 | 0.175 |
| Pyrimidine Deoxyribonucleotides De Novo Biosynth | 0.24 | 0.131 | 0.174 |
| TCA Cycle II (Eukaryotic) | 0.24 | 0.131 | 0.174 |
| Ubiquinol-10 Biosynthesis (Eukaryotic) | 0.237 | 0.131 | 0.176 |
| γ-linolenate Biosynthesis II (Animals) | 0.237 | 0.131 | 0.176 |
| Mitochondrial L-carnitine Shuttle Pathway | 0.237 | 0.131 | 0.176 |
| Trehalose Degradation II (Trehalase) | 0.214 | 0.116 | 0.2 |
| Serine Biosynthesis | 0.214 | 0.116 | 0.2 |
| Tetrapyrrole Biosynthesis II | 0.214 | 0.116 | 0.2 |
| Glycerol Degradation I | 0.214 | 0.116 | 0.2 |
| Rapoport-Leubering Glycolytic Shunt | 0.214 | 0.116 | 0.2 |
| Lactose Degradation III | 0.214 | 0.116 | 0.2 |
| Tyrosine Degradation I | 0.214 | 0.116 | 0.2 |

TABLE 16

Primer sequence for nested PCR to identify Pten-NOLC1 breakpoint (SEQ ID NOs: 230-250, in order)

| Pten Forward Primer | Sequence |
|---|---|
| Pten_intr_F1 (AAG-15 bp) | 5' CATTTTGTGGGGTTGTTGACTTG |
| Pten_intr_F2 (AAG-224 bp) | 5' TTGCTGAAATCTGGGCAAAGGTG |
| Pten_intr_F3 (AAG-480 bp) | 5' AGGCCCAGCATAATTTAGCACAGG |
| Pten_intr_F4 (AAG-963 bp) | 5' TTCCCCTGTTCATTCACCACACTC |
| Pten_intr_F4.5 | 5' ATTCACCACACTCGTTTCTTTCTC |
| Pten_intr_F4.7 | 5' TCACCTGTAATCCCAGCACTTTGG |
| Pten_intr_F5 (AAG-1338 bp) | 5' GGCAACAGAGCAAGACTCTGTCTTA |
| Pten_intr_F6 (AAG-2431 bp) | 5' CAGAGTGGACAAGAAAACCAGTCC |
| Pten_intr_F7 (AAG-3211 bp) | 5' ACTAAGGAGTTTGAGACCAGCCTG |

| NOLC1 Reverse Primer | Sequence |
|---|---|
| NOLC_exo_R1 | 5' TAAGAGGGAAGAGGCATTGGCATC (GATGCCAATGCCTCTTCCCTCTTA) |
| NOLC_Intr_R2 (−119 bp) | 5' TTTTGCTACGTGCATAAATCAGGAG (CTCCTGATTTATGCACGTAGCAAAA) |
| NOLC_Intr_R3 (−198 bp) | 5' CTATGTTTGCGGCACCATCTAACC (GGTTAGATGGTGCCGCAAACATAG) |
| NOLC_Intr_R4 (−231 bp) | 5' CCTGCCTGCCAATCTATATTGATC (GATCAATATAGATTGGCAGGCAGG) |
| NOLC_Intr_R5 (−305 bp) | 5' TGCTTGTAATCCCAGCACTTTGGG (CCCAAAGTGCTGGGATTACAAGCA) |
| NOLC_Intr_R6 (−348 bp) | 5' AAGAGGTCAGGAGTTCAAGACCAG (CTGGTCTTGAACTCCTGACCTCTT) |

TABLE 17

Primer and Probe sequence for Taqman quantitative PCR (SEQ ID NO: 251-271, in order from left to right)

| Gene and location | F | R | probe |
|---|---|---|---|
| MET +233 | GCCCCTTTCAGATCCAGTAC | AGCAGTCAGGTCTCTTAGGG | AAGAAAGCAGAACCCCTGAGGCG |
| MET −195 | GGACTAGGGGACGGACAG | AGGCGACCAGACTAGG | CGAGGCAGACAGACACGTGCT |
| EGFR −824 | TTTCCCTGGCATTTCTCCTG | CCGTGGAGGTGCTTTTAGAG | CCCACTGCCCCTGTAGCTCC |
| RAF1 −91 | CGCCATTTCGAAGCTGAAGAG | TTCTCGATTACCGAGTGCCTC | TAGGCGACGCTGACTTGCTTT |
| RAF1 −678 | GATTAATAGGAAACTGGTTAAGAGAACG | ACTATCTAGTTCATTCTTGGATGGATG | TGCTACACATCCAATCTGGGTTG |
| AXL −651 | GATCTGTGTCTCCCCAAGTAAG | GATTCCTGGAGAAACCTCAGAG | CCCAGCCGTGTCCTCCTGTC |

TABLE 17 -continued

Primer and Probe sequence for
Taqman quantitative PCR (SEQ ID NO: 251-271,
in order from left to right)

| Gene and location | F | R | probe |
|---|---|---|---|
| VEGFA-308 | AACCTCACTTTCCTGCTCC | TGAAAATTACCCATCCGCCC | TCTGTCCAGAGACACGCGCC |

7.5 References

1. Li J, Yen C, Liaw D, Podsypanina K, Bose S, Wang S I, Puc J, Miliaresis C, Rodgers L, McCombie R, Bigner S H, Giovanella B C, Ittmann M, Tycko B, Hibshoosh H, Wigler M H, Parsons R: PTEN, a putative protein tyrosine phosphatase gene mutated in human brain, breast, and prostate cancer. Science (New York, N.Y. 1997, 275:1943-7.
2. Steck P A, Pershouse M A, Jasser S A, Yung W K, Lin H, Ligon A H, Langford L A, Baumgard M L, Hattier T, Davis T, Frye C, Hu R, Swedlund B, Teng D H, Tavtigian S V: Identification of a candidate tumour suppressor gene, MMAC1, at chromosome 10q23.3 that is mutated in multiple advanced cancers. Nature genetics 1997, 15:356-62.
3. Myers M P, Pass I, Batty I H, Van der Kaay J, Stolarov J P, Hemmings B A, Wigler M H, Downes C P, Tonks N K: The lipid phosphatase activity of PTEN is critical for its tumor supressor function. Proceedings of the National Academy of Sciences of the United States of America 1998, 95:13513-8.
4. Maehama T, Dixon J E: The tumor suppressor, PTEN/MMAC1, dephosphorylates the lipid second messenger, phosphatidylinositol 3,4,5-trisphosphate. The Journal of biological chemistry 1998, 273:13375-8.
5. Sansal I, Sellers W R: The biology and clinical relevance of the PTEN tumor suppressor pathway. J Clin Oncol 2004, 22:2954-63.
6. McCubrey J A, Steelman L S, Abrams S L, Lee J T, Chang F, Bertrand F E, Navolanic P M, Terrian D M, Franklin R A, D'Assoro A B, Salisbury J L, Mazzarino M C, Stivala F, Libra M: Roles of the RAF/MEK/ERK and PI3K/PTEN/AKT pathways in malignant transformation and drug resistance. Adv Enzyme Regul 2006, 46:249-79.
7. Baker S J: PTEN enters the nuclear age. Cell 2007, 128:25-8.
8. Trotman L C, Wang X, Alimonti A, Chen Z, Teruya-Feldstein J, Yang H, Pavletich N P, Carver B S, Cordon-Cardo C, Erdjument-Bromage H, Tempst P, Chi S G, Kim H J, Misteli T, Jiang X, Pandolfi P P: Ubiquitination regulates PTEN nuclear import and tumor suppression. Cell 2007, 128:141-56.
9. Shen W H, Balajee A S, Wang J, Wu H, Eng C, Pandolfi P P, Yin Y: Essentialrole for nuclear PTEN in maintaining chromosomal integrity. Cell 2007, 128:157-70.
10. Han B, Mehra R, Lonigro R J, Wang L, Suleman K, Menon A, Palanisamy N, Tomlins S A, Chinnaiyan A M, Shah R B: Fluorescence in situ hybridization study shows association of PTEN deletion with ERG rearrangement during prostate cancer progression. Mod Pathol 2009, 22:1083-93.
11. Yin Y, Shen W H: PTEN: a new guardian of the genome. Oncogene 2008, 27:5443-53.
12. Chen H K, Pai C Y, Huang J Y, Yeh N H: Human Nopp140, which interacts with RNA polymerase I: implications for rRNA gene transcription and nucleolar structural organization. Molecular and cellular biology 1999, 19:8536-46.
13. Pai C Y, Chen H K, Sheu H L, Yeh N H: Cell-cycle-dependent alterations of a highly phosphorylated nucleolar protein p130 are associated with nucleologenesis. Journal of cell science 1995, 108 (Pt 5):1911-20.
14. Vlietstra R J, van Alewijk D C, Hermans K G, van Steenbrugge G J, Trapman J: Frequent inactivation of PTEN in prostate cancer cell lines and xenografts. Cancer research 1998, 58:2720-3.
15. Lee Y M, Miau L H, Chang C J, Lee S C: Transcriptional induction of the alpha-1 acid glycoprotein (AGP) gene by synergistic interaction of two alternative activator forms of AGP/enhancer-binding protein (C/EBP beta) and NF-kappaB or Nopp140. Molecular and cellular biology 1996, 16:4257-63.
16. Hwang Y C, Lu T Y, Huang D Y, Kuo Y S, Kao C F, Yeh N H, Wu H C, Lin C T: NOLC1, an enhancer of nasopharyngeal carcinoma progression, is essential for TP53 to regulate MDM2 expression. The American journal of pathology 2009, 175:342-54.
17. Wang X, DeFrances M C, Dai Y, Pediaditakis P, Johnson C, Bell A, Michalopoulos G K, Zamegar R: A mechanism of cell survival: sequestration of Fas by the HGF receptor Met. Mol Cell 2002, 9:411-21.
18. Cloughesy T F, Yoshimoto K, Nghiemphu P, Brown K, Dang J, Zhu S, Hsueh T, Chen Y, Wang W, Youngkin D, Liau L, Martin N, Becker D, Bergsneider M, Lai A, Green R, Oglesby T, Koleto M, Trent J, Horvath S, Mischel P S, Mellinghoff I K, Sawyers C L: Antitumor activity of rapamycin in a Phase I trial for patients with recurrent PTEN-deficient glioblastoma. PLoS medicine 2008, 5:e8.
19. Courtney K D, Corcoran R B, Engelman J A: The PI3K pathway as drug target in human cancer. J Clin Oncol 2010, 28:1075-83.
20. Zhang-Hui Chen, Yan P. Yu, Ze-Hua Zuo, Joel B. Nelson, George K. Michalopoulos, Satdatshan Monga, Silvia Liu, Tseng G, Luo J-H: Targeting genomic rearrangements in tumor cells using Cas9-mediated insertion of a suicide gene Nature biotechnology 2017, in press.
21. Y. P. Yu et al., *Am J Pathol* (Oct. 7, 2013).
22. J. H. Luo et al., *Am J Pathol* 182, 2028 (June, 2013).
23. Y. P. Yu et al., *Am J Pathol* 180, 2240 (June, 2012).
24. H. Edgren et al., Genome Biol 12, R6.
25. T. Prakash et al., PLoS One 5, e13284 (2010).
26. C.-W. F. Wei Zeng, Stefan Muller Arisona, Huamin Qu, Computer Graphics Forum, 271 (2013).

Various references are cited in this document, which are hereby incorporated by reference in their entireties herein.

What is claimed is:

1. A method of treating a subject, comprising (i) determining that at least one fusion gene is present in a sample obtained from a subject; wherein the at least one fusion gene is selected from the group consisting of TRMT11-GRIK2, SLC45A2-AMACR, MTOR-TP53BP1, LRRC59-FLJ60017, TMEM135-CCDC67, KDM4B-AC011523.2, MAN2A1-FER, PTEN-NOLC1, CCNH-C5orf30, ZMPSTE24-ZMYM4, CLTC-ETV1, ACPP-SEC13, DOCK7-OLR1, PCMTD1-SNTG1 and a combination thereof; and (ii) then performing a CRISPR/Cas genome editing technique targeting the one or more fusion genes within one or more cells of the subject to achieve an anti-neoplastic effect or an anti-cancer effect, wherein the CRISPR/Cas system uses a Cas9 endonuclease, wherein the subject does not have prostate cancer.

2. The method of claim 1, wherein the subject has a pre-malignant or a neoplastic condition.

3. The method of claim 1, wherein the subject has cancer.

4. The method of claim 3, wherein the cancer is breast cancer, liver cancer, lung cancer, cervical cancer, endometrial cancer, pancreatic cancer, ovarian cancer, gastric cancer, thyroid cancer, glioblastoma multiforme, colorectal cancer, diffuse large B cell-lymphoma, sarcoma, acute and chronic lymphocytic leukemia, Hodgkin's lymphoma, non-Hodgkin's lymphoma, or esophageal adenocarcinoma.

5. The method of claim 1, wherein the at least one fusion gene is detected by FISH analysis or by reverse transcription polymerase chain reaction.

6. The method of claim 1, wherein the CRISPR/Cas system cleaves a sequence within the fusion gene genomic sequence to insert a nucleic acid within the at least one fusion gene to induce cell death.

7. The method of claim 1, wherein the genome editing technique comprises: transducing the one or more cells with (i) a vector comprising a nucleic acid encoding a Cas9 protein and two guide RNAs (gRNA) and (ii) a vector comprising a donor nucleic acid and one or more targeting sequences.

8. The method of claim 7, wherein one of the gRNAs is complementary to a region within a first gene of the at least one fusion gene and the other gRNA is complementary to a region within a second gene of the at least one fusion gene.

9. The method of claim 7, wherein the donor nucleic acid encodes HSV-1 thymidine kinase.

10. The method of claim 7, wherein the method further comprises administering to the subject a therapeutically effective amount of ganciclovir or valganciclovir.

11. The method of claim 7, wherein one of the gRNAs is complementary to a region within a MAN2A1 gene of a MAN2A1-FER fusion gene and the other gRNA can be complementary to a region within a FER gene.

12. The method of claim 7, wherein one of the gRNAs is complementary to a region within a TMEM135 gene of a TMEM135-CCDC67 fusion gene and the other gRNA can be complementary to a region within a CCDC67 gene.

13. The method of claim 12, wherein the one or more cells of the subject are cancer cells.

14. The method of claim 13, wherein the cancer cells are breast cancer, liver cancer, lung cancer, cervical cancer, endometrial cancer, pancreatic cancer, ovarian cancer, gastric cancer, thyroid cancer, glioblastoma multiforme, colorectal cancer, diffuse large B cell lymphoma, sarcoma, acute and chronic lymphocytic leukemia, Hodgkin's lymphoma, non-Hodgkin's lymphoma or esophageal adenocarcinoma cells.

15. The method of claim 3, wherein the cancer is not lung adenocarcinoma, glioblastoma multiforme or hepatocellular carcinoma.

* * * * *

SEQUENCE LISTING

<160> NUMBER OF SEQ ID NOS: 278

<210> SEQ ID NO 1
<211> LENGTH: 60
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 1
gcaaatacta tttcagaaac agcctatgag ggaaattttg gtgaagtata taagggcaca    60

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
cagccuauga gggaaauuuu gguga                                          25

<210> SEQ ID NO 3
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucaccaaaau uucccucaua ggcuguu                                        27

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccactacca tgccctcttc acaggtgtca tggagaaact ccagctgggc ccagaga       57

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ugcccucuuc acagguguca uggag                                          25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuccaugaca ccugugaaga gggcaug                                        27
```

```
<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtcagaatc caagtcaagt caggattcct tgttctggga atgtcagtgg aatctgctcc    60
tgc                                                                 63

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gucaggauuc cuuguucugg gaaug                                         25

<210> SEQ ID NO 9
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cauucccaga acaaggaauc cugacuu                                       27

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttttaagact caccaagggc aaataagaag ccaactccaa caggtggaag agtacca      57

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
gacucaccaa gggcaaauaa gaagc                                         25

<210> SEQ ID NO 12
<211> LENGTH: 27
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
gcuucuuauu ugcccuuggu gagucuu                                          27

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgtcacagtt actagatata atgaaaatac ctggagtaga acagaaaaat tattatgtct      60

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
augaaaauac cuggaguaga acaga                                            25

<210> SEQ ID NO 15
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ucuguucuac uccagguauu uucauua                                          27

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aactacctgc actttgggga gcctaagtcc tggacagtaa gcaagcctgg atctgagaga      60

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gagccuaagu ccuggacagu aagca                                            25
```

<210> SEQ ID NO 18
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugcuuacugu ccaggacuua ggcuccc                                          27

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agcatctgga gttccgcctg ccggtggtat ttttgaatat gtggaatctg gcccaatggg      60
agctg                                                                  65

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
ccgccugccg gugguauuuu ugaat                                            25

<210> SEQ ID NO 21
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auucaaaaau accaccggca ggcggaa                                          27

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgcttggat gagaagcagt gtaagcagtg tgcaaacaag gtgactggaa gcacctgctc      60
aatggctg                                                               68

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic

```
                              oligonucleotide
<220> FEATURE:
<223> OTHER INFORMATION: Description of Combined DNA/RNA Molecule:
      Synthetic oligonucleotide

<400> SEQUENCE: 23
acaaggugac uggaagcacc ugcuc                                          25

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gagcaggugc uuccagucac cuuguuu                                        27

<210> SEQ ID NO 25
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagccaaccg atacttttct ccaaatttta agacacagca ggatgccaat gcctcttccc    60
tcttagac                                                             68

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cuccaaauuu uaagacacag cagga                                          25

<210> SEQ ID NO 27
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uccugcugug ucuuaaaauu uggagaa                                        27

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcccatatat ggagttccgc g                                              21
```

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tctggcaagc tatctaaccc c                                            21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcccattgac acctttccca c                                            21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaggcttcc aggtacaaca g                                            21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcccagttgc agaaaggaat g                                            21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttgattttc agtggcaggc c                                            21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gactacgtct catgcctttc c                                            21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ttctcatcag gctggtcctt c        21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gatgtggtgg aatatgccaa gg        22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aaatccatgt gctgtggcac c        21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cgcaatgagg aagaagggaa c        21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cataaatctg gaatagggct cag        23

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
taaaagctaa agttaaatac ctgtttgaaa atggta        36

<210> SEQ ID NO 41

```
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcactcataa agaagagctt gaatttggaa atgac                              35

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atagctttga taaactgctc tccagaatgt tg                                 32

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gccaactcac ccagattggc tgcaatgccg tcag                               34

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgccaatact agtgtggctt ttcatggcct gccac                              35

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcagaaacag cctatgaggg aaattttggt ga                                 32

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gactcaccaa gggcaaataa gaagccaact ccaacag                            37

<210> SEQ ID NO 47
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taagcagtgt gcaaacaagg tgactggaag cacctgctca at                    42

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcatctggag ttccgcctgc cggtggtatt tttgaatatg                       40

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccagtcagtc aggattcctt gttctgggaa tgtcagtgg                        39

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gttactagat ataatgaaaa tacctggagt agaacagaaa                       40

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccactaccat gccctcttca caggtgtcat ggagaaactc ca                    42

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aactacctgc actttgggga gcctaagtcc tggacagtaa gcaagcc               47

<210> SEQ ID NO 53
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 53
aatgtttaaa tttggaacgt ggactttggg gcaggt                              36

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
taataatgaa cctagctacc ctaaactcct                                     30

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tctcattatg ttgccgaagg ggatatcacc acca                                34

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttttctccaa attttaagag acagcaggat gccaa                               35

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aaatttggaa cgtggacttt ggg                                            23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagaccatct tactggaagt tcc                                            23

<210> SEQ ID NO 59
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 59
tggtactctt ccacctgttg g                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttggcatgat agaccagtcc c                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagcaccaag ggaatgtgta g                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcgctgtcgt gtacccttaa c                                              21

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggtaagggta gtattgggta gc                                             22

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccagggctgg aattactatg g                                              21

<210> SEQ ID NO 65
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 65
aagcaccagt ctgcacaatc c                                          21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ttgatgtctg ctcccatcag g                                          21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgatatcgtg gccagctaac c                                          21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aacacgccct acctgtactt c                                          21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctgagcaaag acagcaacac c                                          21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggaagttca agtcagcgca g                                          21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
gctgtctttg tgtgcaaact cc                                           22

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgactgctt ggatgagaag c                                            21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccagcatgca gcttttctga g                                            21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agtaggcgcg agctaagcag g                                            21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggacagtct gaatcatgtc c                                            21

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tcaagatcat tgctcctcct gagc                                         24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgctgtcacc ttcaccgttc cagt                                          24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aacctgagtc tgccaaggac tagc                                          24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ttccacacac cactggccat cttc                                          24

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acagaagtct gggatgtgga                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcccaaaaag acagacagaa                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gatcccaagc tcttcctctt                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 83
acgtttgtgt gtgcatctgt                                           20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gggtgatttt cctctttggt                                           20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgattccaat catagccaca                                           20

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgtcatagtt tagaacgaac taacg                                     25

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ctgaggtatc aaaaactcag agg                                       23

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtgggctgaa aagctcccga ttat                                      24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
```
attcaaaggg tatctgggct ctgg                                          24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
actggcacag aacaggcact tagg                                          24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggaggaactg ggaaccacac aggt                                          24

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccctagtgga tgataagaat aatcagtatg                                    30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggacagatga taaatacata ggatggatgg                                    30

<210> SEQ ID NO 94
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtactcacgt aagctttcgc caccatggtg agcaagg                            37

<210> SEQ ID NO 95
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

```
gactcagatg ggcgcccttg tacagctcgt ccatgcc                              37

<210> SEQ ID NO 96
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gactcagatg gcggccgcct gtattctttg ttttacagat ttgctgtcag gggttagata    60
gcttgccag                                                            69

<210> SEQ ID NO 97
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gtactcacgt aagcttgagc taacattacc aatgaggc                            38

<210> SEQ ID NO 98
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gactcagatg gctagcagtt cactgagtgt gccatgc                             37

<210> SEQ ID NO 99
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gtactcacgt gaattcctat tctgcctgct tgcatacctt ttgttttggt tgcagtatag    60
tgggctgag                                                            69

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gactcagatg aagcttaaga gcatgggctt tggagtc                             37

<210> SEQ ID NO 101
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 101
gtactcacgt tctagactgg aatctaggac tcttggc                                    37

<210> SEQ ID NO 102
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gactcagatg gcggccgcga acatcagaac tgggagagg                                  39

<210> SEQ ID NO 103
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gtactcacgt aagcttcagg agaatcactt gaacccg                                    37

<210> SEQ ID NO 104
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
taatgttggt tttaccaaaa atataaatgg tttgcctctc agtagataac atttatcttt           60
aataaattcc cttccctatc ttttaaagat ctcttttcga gcacatat                       108

<210> SEQ ID NO 105
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
taatatgtgc tcgaaaagag atctttaaaa gatagggaag ggaatttatt aaagataaat           60
gttatctact gagaggcaaa ccatttatat ttttggtaaa accaacat                       108

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
taataatgaa cctagctacc ctaaactcct                                            30

<210> SEQ ID NO 107
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 107
gtgaattcat tcatcataaa                                                    20

<210> SEQ ID NO 108
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggccagtgaa ttgtaatacg actcactata gggaggcggt agcattaagg gcccctaag         60 ttttagagct agaaatagca ag                                                 82

<210> SEQ ID NO 109
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ggccagtgaa ttgtaatacg actcactata gggaggcgga tagctagaag gtggatcacg        60
ttttagagct agaaatagca ag                                                 82

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tctttgcact ttctgcatgt cccc                                               24

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gtccatcacg atgccagtgg tac                                                23

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cactcactga gctctttgcc                                                    20

<210> SEQ ID NO 113
```

```
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cctgtgaatt cattcatcat aaaataataa tgaacctagc taccctaaac tccttttaca    60
ctcactgagc tctttgcctg g                                              81

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gcccatatat ggagttccgc g                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aggcaaagag ctcagtgagt g                                              21

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tgcctcattg gtaatgttag ctc                                            23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ggcgaattgg gtacacttac c                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
actcacgggg atttccaagt c                                              21
```

```
<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aagtcgtgct gcttcatgtg g                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tgttctagcc aagaggctga g                                              21

<210> SEQ ID NO 121
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gactcagatg gaattcaagg tggaacacag aaggagg                             37

<210> SEQ ID NO 122
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtactcacgt gaattcgatt actttaaata actcacttgg cttcttgcag aggtagagct    60
gagagaag                                                             68

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
agcacagaga cccagaaggt c                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aggaggagga ggaggagaaa g                                              21
```

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
atgatgatat cgccgcgctc                                               20

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cacgatggag gggaagacg                                                19

<210> SEQ ID NO 127
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aggggcatca gctaccctta agtccagagc catttc                             36

<210> SEQ ID NO 128
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggcattggca tcctgctgtg tcttaaaatt tggagaaaag ta                      42

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129 tactttctc caaattttaa gacacagcag gatgccaatg cc                       42

<210> SEQ ID NO 130
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
accgaagatg gcctctctag actcgctgtc aaactt                             36

```
<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aggggcatca gctaccctta agtccagagc catttc                              36

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
accgaagatg gcctctctag actcgctgtc aaactt                              36

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cttaaaattt ggagatctag atcggttggc tttgtc                              36

<210> SEQ ID NO 134
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
accgaagatg gcctctctag agacttttgt aatttgtgta tgctgatc                 48

<210> SEQ ID NO 135
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tcagctaccc ttaagcggta gtgacgcgta ttgc                                34

<210> SEQ ID NO 136
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
accgaagatg gcctctctag actcgctgtc aaactt                              36

<210> SEQ ID NO 137
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gtgggatcca catgacagcc atcatcaaag ag                                      32

<210> SEQ ID NO 138
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
catacacaaa ttacaaaagt ctgaggatcc ccaggaattc ccgggtcgac tc                 52

<210> SEQ ID NO 139
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gtgggatcca catgacagcc atcatcaaag ag                                      32

<210> SEQ ID NO 140
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cgagtcgacc cgggaattcc tggggatcct cactcgctgt caaacttaat ag                 52

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gagcgtgcag ataatgacaa gg                                                 22

<210> SEQ ID NO 142
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gccagaagct atagatgtct aagag                                              25

<210> SEQ ID NO 143
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ccaccttcta gctattgagt agcattaa                                            28

<210> SEQ ID NO 144
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tccaccttct agctattgag tagcat                                              26

<210> SEQ ID NO 145
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
accccgtgat ccaccttcta gctattgagt agcattaagg gccccctaag ggtt              54

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gtgatccacc ttctagcta                                                      19

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gtagcattaa gggccccct a                                                    21

<210> SEQ ID NO 148
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttttctccaa attttaagac acagcaggat gccaa                                    35

<210> SEQ ID NO 149
<211> LENGTH: 28
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 149
atacaaaaat tagctgggac tacagaca                28

<210> SEQ ID NO 150
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
tcactcataa agaagagctt gaatttggaa atgac           35

<210> SEQ ID NO 151
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
atagctttga taaactgctc tccagaatgt tg              32

<210> SEQ ID NO 152
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
gccaactcac ccagattggc tgcaatgccg tcag            34

<210> SEQ ID NO 153
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
taaaagctaa agttaaatac ctgtttgaaa atggta          36

<210> SEQ ID NO 154
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
tgccaatact agtgtggctt ttcatggcct gccac           35

<210> SEQ ID NO 155
<211> LENGTH: 31
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 155
actcagttag taaatgaagg agctggaaca t                                          31

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
actcagttag taaaaggagc tggaacat                                              28

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gactgaatgc acatgccacc acacccggct                                           30

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gactgaacat gccaccacac ccggct                                               26

<210> SEQ ID NO 159
<211> LENGTH: 20
<212> TYPE: DNA
<213> ORGANISM: Homo sapiens

<400> SEQUENCE: 159
cactcactga gctctttgcc                                                      20

<210> SEQ ID NO 160
<211> LENGTH: 20
<212> TYPE: DNA
<213> ORGANISM: Homo sapiens

<400> SEQUENCE: 160
cactgactga gctctctgac                                                      20

<210> SEQ ID NO 161
<211> LENGTH: 20
<212> TYPE: DNA
<213> ORGANISM: Homo sapiens

<400> SEQUENCE: 161
cactcactgt cctctttgcc                                                      20

<210> SEQ ID NO 162
```

-continued

```
<211> LENGTH: 20
<212> TYPE: DNA
<213> ORGANISM: Homo sapiens

<400> SEQUENCE: 162
aactcagcga gctctttgcc                                               20

<210> SEQ ID NO 163
<211> LENGTH: 20
<212> TYPE: DNA
<213> ORGANISM: Homo sapiens

<400> SEQUENCE: 163
cactcactga gatctgtgcc                                               20

<210> SEQ ID NO 164
<211> LENGTH: 20
<212> TYPE: DNA
<213> ORGANISM: Homo sapiens

<400> SEQUENCE: 164
gactcactga actctttggc                                               20

<210> SEQ ID NO 165
<211> LENGTH: 20
<212> TYPE: DNA
<213> ORGANISM: Homo sapiens

<400> SEQUENCE: 165
ccctgaatga gctctttgcc                                               20

<210> SEQ ID NO 166
<211> LENGTH: 20
<212> TYPE: DNA
<213> ORGANISM: Mus sp.

<400> SEQUENCE: 166
cactgactca gttctttgcc                                               20

<210> SEQ ID NO 167
<211> LENGTH: 20
<212> TYPE: DNA
<213> ORGANISM: Mus sp.

<400> SEQUENCE: 167
cactccatca gctctttgcc                                               20

<210> SEQ ID NO 168
<211> LENGTH: 20
<212> TYPE: DNA
<213> ORGANISM: Mus sp.

<400> SEQUENCE: 168
cactcactgg cccctttgcc                                               20

<210> SEQ ID NO 169
<211> LENGTH: 20
<212> TYPE: DNA
<213> ORGANISM: Mus sp.

<400> SEQUENCE: 169
tacccactga gctctttccc                                               20
```

```
<210> SEQ ID NO 170
<211> LENGTH: 20
<212> TYPE: DNA
<213> ORGANISM: Mus sp.

<400> SEQUENCE: 170
cactcactga gcactgtgtc                                               20

<210> SEQ ID NO 171
<211> LENGTH: 20
<212> TYPE: DNA
<213> ORGANISM: Mus sp.

<400> SEQUENCE: 171
cactgactga gtcctttgcc                                               20

<210> SEQ ID NO 172
<211> LENGTH: 20
<212> TYPE: DNA
<213> ORGANISM: Homo sapiens

<400> SEQUENCE: 172
tagcattaag ggcccccctaa                                              20

<210> SEQ ID NO 173
<211> LENGTH: 20
<212> TYPE: DNA
<213> ORGANISM: Homo sapiens

<400> SEQUENCE: 173
tagcactgaa ggcccccctaa                                              20

<210> SEQ ID NO 174
<211> LENGTH: 20
<212> TYPE: DNA
<213> ORGANISM: Homo sapiens

<400> SEQUENCE: 174
tagcattaag ggcccacttg                                               20

<210> SEQ ID NO 175
<211> LENGTH: 20
<212> TYPE: DNA
<213> ORGANISM: Homo sapiens

<400> SEQUENCE: 175
tagcactgag ggcccccaaa                                               20

<210> SEQ ID NO 176
<211> LENGTH: 20
<212> TYPE: DNA
<213> ORGANISM: Homo sapiens

<400> SEQUENCE: 176
tagtattcag ggcccactaa                                               20

<210> SEQ ID NO 177
<211> LENGTH: 20
<212> TYPE: DNA
<213> ORGANISM: Homo sapiens

<400> SEQUENCE: 177
tgggattagg ggcccccctaa                                              20
```

```
<210> SEQ ID NO 178
<211> LENGTH: 20
<212> TYPE: DNA
<213> ORGANISM: Mus sp.

<400> SEQUENCE: 178
tagctttaag tgcctcctaa                                               20

<210> SEQ ID NO 179
<211> LENGTH: 20
<212> TYPE: DNA
<213> ORGANISM: Mus sp.

<400> SEQUENCE: 179
taccattaag tgcccccaaa                                               20

<210> SEQ ID NO 180
<211> LENGTH: 20
<212> TYPE: DNA
<213> ORGANISM: Mus sp.

<400> SEQUENCE: 180
tggcattaag ggcccattaa                                               20

<210> SEQ ID NO 181
<211> LENGTH: 20
<212> TYPE: DNA
<213> ORGANISM: Mus sp.

<400> SEQUENCE: 181
ttgcattcag ggtcccctaa                                               20

<210> SEQ ID NO 182
<211> LENGTH: 20
<212> TYPE: DNA
<213> ORGANISM: Mus sp.

<400> SEQUENCE: 182
tagcattaag tgccctctta                                               20

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cccacaaaaa gggtacatgc c                                             21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tttggattca gcacagtggc c                                             21

<210> SEQ ID NO 185
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aggaggacca tgccatttcc c                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
agaggctcca gacgcattgt g                                              21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tcagtgccct gctcaaaaca g                                              21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ctcagtcagt atccctgcca g                                              21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tgggaaggaa ttggagggaa g                                              21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gctgtcatct acagcatcct g                                              21

<210> SEQ ID NO 191
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 191
cagggaagct gctttagaat g                                              21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tgaaatccct gacccccaat c                                              21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cagactggac aaggtgctgc g                                              21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cacagagtat gctaggggaa g                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gtgaatgccc tctctctttg c                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
agggtattgt ggaggtcaca g                                              21

<210> SEQ ID NO 197
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 197
cttactactt aagccgccca g                                             21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
atcatctaag gggagtcttg g                                             21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cagctcctcg cccttgctca c                                             21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gacagtctgg cagagttatg c                                             21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gagcacggga ggcaaataaa c                                             21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
gtgaagggca cactcttcca g                                             21

<210> SEQ ID NO 203
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 203
ggaggaggta ttggagggtt g                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aaggcatcac tcaccacact g                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tctatgatgt agcctcagct c                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gtggcatttg cttaccctgg a                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
atggggctgt atgtgaagag g                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ctgcatcttc acagggtcgt c                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 209
agagctttca ggtgtgctgt c                                             21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ttgcccacct gcgactagag a                                             21

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgggttgatc tagctgatgg ag                                            22

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ctcaaccaac ctctaatact gtac                                          24

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gtctgctccc taaacgagat g                                             21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ccaaaccaaa gagtggtgga g                                             21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
aagggatgct acagcctgtc c                                         21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tgggcacgga gataggttgt c                                         21

<210> SEQ ID NO 217
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
gcttctgtta gggctttcat gc                                        22

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
cacagcatag ccaaacttat gg                                        22

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
cagctcctcg cccttgctca c                                         21

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
gcctcattgg taatgttagc tc                                        22

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 221
agcatggcac actcagtgaa c                                            21

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ctcctgaccc cgtgatccac ct                                           22

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
aaaccataat catgctgact g                                            21

<210> SEQ ID NO 224
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ctccggactc tagcgtcgac acttaagtcc agagcc                            36

<210> SEQ ID NO 225
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
atggtgatgg tgatggcggc cgcttaacta gatccgg                           37

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
attcaccaca ctcgtttctt tctc                                         24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
```
cctgcctgcc aatctatatt gatc                                          24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
cggttatacc gctttgggat caaa                                          24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
caccgagatg gggtttcacc atgt                                          24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
cattttgtgg gggttgttga cttg                                          24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ttgctgaaat ctggggcaaa ggtg                                          24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
aggcccagca taatttagca cagg                                          24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ttcccctgtt cattcaccac actc                                          24

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
attcaccaca ctcgtttctt tctc                                          24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tcacctgtaa tcccagcact ttgg                                          24

<210> SEQ ID NO 236
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ggcaacagag caagactctg tctta                                         25

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
cagagtggac aagaaaacca gtcc                                          24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
actaaggagt ttgagaccag cctg                                          24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
taagagggaa gaggcattgg catc                                          24

```
<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gatgccaatg cctcttccct ctta                                          24

<210> SEQ ID NO 241
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ttttgctacg tgcataaatc aggag                                         25

<210> SEQ ID NO 242
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ctcctgattt atgcacgtag caaaa                                         25

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ctatgtttgc ggcaccatct aacc                                          24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
ggttagatgg tgccgcaaac atag                                          24

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
cctgcctgcc aatctatatt gatc                                          24
```

<210> SEQ ID NO 246
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gatcaatata gattggcagg cagg                                          24

<210> SEQ ID NO 247
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
tgcttgtaat cccagcactt tggg                                          24

<210> SEQ ID NO 248
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
cccaaagtgc tgggattaca agca                                          24

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
aagaggtcag gagttcaaga ccag                                          24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
ctggtcttga actcctgacc tctt                                          24

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gccccttcca gatccagtac                                               20

```
<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
agcagtcagg tctcttaggg                                              20

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
aagaaagcag aacccctgag gcg                                          23

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
ggactagggg acggacag                                                18

<210> SEQ ID NO 255
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
aggcgaccag actgagg                                                 17

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
cgaggcagac agacacgtgc t                                            21

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tttccctggc atttctcctg                                              20

<210> SEQ ID NO 258
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
ccgtggaggt gcttttagag                                                   20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
cccactgccc ctgtagctcc                                                   20

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
cgccatttcg aagctgaaga g                                                 21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
ttctcgatta ccgagtgcct c                                                 21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
taggcgacgc tgacttgctt t                                                 21

<210> SEQ ID NO 263
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
gattaatagg aaactggtta agagaacg                                          28

<210> SEQ ID NO 264
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
actatctagt tcattcttgg atggatg                                           27

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
tgctacacat ccaatctggg ttg                                               23

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
gatctgtgtc tccccaagta ag                                                22

<210> SEQ ID NO 267
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
gattcctgga gaaacctcag ag                                                22

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
cccagccgtg tcctcctgtc                                                   20

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
aacctcactt tcctgctcc                                                    19

<210> SEQ ID NO 270
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 270
tgaaaattac ccatccgccc                                            20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
tctgtccaga gacacgcgcc                                            20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gccaatatgg cgaaaccta                                             20

<210> SEQ ID NO 273
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
cagccggcca atatggcgaa acccta                                     26

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gagatggggt ttcaccatgt tgg                                        23

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gagatggggt ttcaccatgt                                            20

<210> SEQ ID NO 276
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 276
ccctgtttta catatgagga aac                                               23

<210> SEQ ID NO 277
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
aatgcctctt ccc                                                          13

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ggcgaattgg gtacacttac c                                                 21
```